(12) United States Patent
Zhao et al.

(10) Patent No.: US 11,905,274 B2
(45) Date of Patent: Feb. 20, 2024

(54) RECEPTOR INHIBITORS, PHARMACEUTICAL COMPOSITIONS COMPRISING THE SAME AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Gong Li, Beijing (CN); Xiang Li, Beijing (CN); Yuanyuan Jiang, Beijing (CN); Yeming Wang, Beijing (CN); Huai Huang, Beijing (CN); Liying Zhou, Beijing (CN); Yanan Liu, Beijing (CN); Ning Shao, Beijing (CN); Fengping Xiao, Beijing (CN); Zhenguang Zou, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 220 days.

(21) Appl. No.: 16/971,702

(22) PCT Filed: Feb. 22, 2019

(86) PCT No.: PCT/CN2019/075862
§ 371 (c)(1),
(2) Date: Aug. 21, 2020

(87) PCT Pub. No.: WO2019/161781
PCT Pub. Date: Aug. 29, 2019

(65) Prior Publication Data
US 2021/0395231 A1    Dec. 23, 2021

(30) Foreign Application Priority Data

Feb. 23, 2018    (CN) .......................... 201810154610.5

(51) Int. Cl.
| | |
|---|---|
| C07D 403/06 | (2006.01) |
| C07D 295/215 | (2006.01) |
| C07D 403/14 | (2006.01) |
| C07D 409/12 | (2006.01) |
| C07D 413/06 | (2006.01) |
| C07D 417/06 | (2006.01) |

(52) U.S. Cl.
CPC ....... C07D 403/06 (2013.01); C07D 295/215 (2013.01); C07D 403/14 (2013.01); C07D 409/12 (2013.01); C07D 413/06 (2013.01); C07D 417/06 (2013.01)

(58) Field of Classification Search
CPC .................................................. C07D 403/06
See application file for complete search history.

(56) References Cited

U.S. PATENT DOCUMENTS 5,543,311 A * 8/1996 Brummond .......... G01N 33/535
                                                                               435/7.93
5,672,611 A    9/1997 Doll et al.
2006/0223741 A1    10/2006 Smith et al.

FOREIGN PATENT DOCUMENTS

| CN | 101087619 | 12/2012 |
|---|---|---|
| FR | 1192168 | 10/1959 |
| JP | H10511980 | 11/1998 |
| JP | H11503157 | 3/1999 |
| JP | H11236372 | 8/1999 |
| JP | 2007531729 | 11/2007 |
| WO | 9220661 | 11/1992 |
| WO | 1992020661 | 11/1992 |
| WO | 9500498 | 1/1995 |
| WO | 2005056524 | 6/2005 |
| WO | 2017165822 | 9/2017 |

OTHER PUBLICATIONS

PubChem CID 114328253, National Center for Biotechnology Information. PubChem Compound Summary for CID 114328253. https://pubchem.ncbi.nlm.nih.gov/compound/114328253. Accessed Jul. 5, 2022, create date Jan. 29, 2016. (Year: 2016).*
Chemical Abstracts Registry No. 438472-79-8, indexed in the Registry file on STN CAS Online Jul. 12, 2002. (Year: 2002).*
Toldy et al., Acta Chimica Academiae Scientiarum Hungaricae (1971), 70(1-2), pp. 101-122. (Year: 1971).*
An English translation of Toldy et al., Acta Chimica Academiae Scientiarum Hungaricae (1971), 70(1-2), pp. 101-122. (Year: 1971).*
PubChem CID 1114009, National Center for Biotechnology Information. PubChem Compound Summary for CID 1114009. https://pubchem.ncbi.nlm.nih.gov/compound/1114009. Accessed Oct. 31, 2022, create date Jul. 10, 2005. (Year: 2005).*
Berenguer et al., Inst. "Lopez-Neyra" Parasitol., Granada, Spain Source: Revista Iberica de Parasitologia (1973), 33(1), 81-106. (Year: 1973).*
Chemical Abstracts Registry No. 334500-65-1, indexed in the Registry file on STN CAS Online May 3, 2001. (Year: 2001).*
Jain S, Yadav A. "An Ab Initio Study of At2 Antagonists." Chemical biology & drug design. Mar. 2008;71(3):271-7.

(Continued)

*Primary Examiner* — Laura L Stockton
(74) *Attorney, Agent, or Firm* — Robin L. Teskin; Baker, Donelson, Bearman, Caldwell & Berkowitz, PC

(57) ABSTRACT

The present invention discloses a receptor inhibitor of formula (I), a composition comprising the same and the usage thereof.

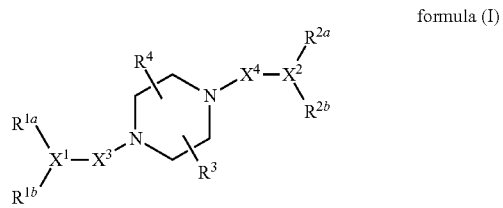

formula (I)

44 Claims, No Drawings

(56) References Cited

OTHER PUBLICATIONS

Wu et al. "Synthesis and structure-activity relationships of a novel series of non-peptide AT2-selective angiotensin II receptor antagonists." Bioorganic & Medicinal Chemistry Letters. Oct. 1, 1993;3(10):2023-8.

Berellini et al. "Pharmacophore, drug metabolism, and pharmacokinetics models on non-peptide AT1, AT2, and AT1/AT2 angiotensin II receptor antagonists." Journal of medicinal chemistry. Jun. 30, 2005;48(13):4389-99.

* cited by examiner

RECEPTOR INHIBITORS, PHARMACEUTICAL COMPOSITIONS COMPRISING THE SAME AND USE THEREOF

CROSS-REFERENCE TO RELATED APPLICATIONS

This application is a U.S. National Phase application of Int'l Appl. No. PCT/CN2019/075862, filed Feb. 22, 2019, which claims priority to Int'l Appl. No. CN 201810154610.5, filed Feb. 23, 2018, each of which are incorporated herein by reference in their entireties.

FIELD OF THE INVENTION

The present invention relates to an angiotensin II type 2 ($AT_2$) receptor inhibitor, a pharmaceutical composition comprising the same, and its use for the prophylaxis or the treatment of an $AT_2$ receptor-mediated disorder or a symptom associated therewith.

BACKGROUND OF THE INVENTION

There are two known subtypes of angiotensin II (A-II) receptors, namely $AT_1$ and $AT_2$ subtypes. In rat brain, A-II receptors are mainly of $AT_2$ subtypes. $AT_2$-specific inhibitors are valuable in the treatment of various cerebrovascular, cognitive, and central nervous system (CNS) diseases. In addition, $AT_2$ receptors are found in neuronal tumor cells and transformed human nerve cells.

$AT_2$ receptors have also been implicated in the differentiation and regeneration of neuronal tissue, and the maintenance of bone mass.

In some studies, $AT_2$ receptor antagonism is associated with the treatment of pain, particularly inflammatory pain and neuropathic pain, two types of pain which are difficult to treat or relieve. Impaired nerve conduction velocity is also associated with nerve damage and has been implicated in peripheral neuropathies, Carpal Tunnel Syndrome, ulnar neuropathy, Guillain-Barre Syndrome, fascioscapulohumeral muscle dystrophy and spinal disc herniation. Impaired nerve conduction velocity may lead to diminished reflex responses and altered peripheral sensation, such as parasthesia and in some cases pain. $AT_2$ receptor inhibitors have been shown to restore nerve conduction velocity.

Cell proliferation and angiogenesis are important biological functions in normal tissue. However, uncontrolled cell proliferation and angiogenesis may lead to a tumor and other proliferative disorders. $AT_2$ receptor inhibitors have been shown to have anti-proliferative activity.

Osteoporosis is a significant problem in older populations, especially in postmenopausal women. The current therapies for osteoporosis rely on calcium supplementation. However, the control the bone formation and bone resorption is complex. $AT_2$ receptor inhibitors have been shown to increase bone mass.

The role of the $AT_2$ receptors in modulating neuronal outgrowth and the associated effects of $AT_2$ receptor inhibitors on reducing neuronal outgrowth, indicates that $AT_2$ receptor inhibitors may be useful therapeutics in diseases characterized by aberrant nerve regeneration.

$AT_2$ receptors are also found in the reproductive organs of female mammals, including uterus and ovaries. The role of angiotensin II in the processes leading to ovulation has been reported.

SUMMARY OF THE INVENTION

The present invention provides a compound for use as an $AT_2$ receptor inhibitor, which exhibits excellent inhibitory activity on $AT_2$ receptors and excellent properties such as better physicochemical properties (e.g., solubility, physical and/or chemical stability), improved pharmacokinetic properties (e.g., improved bioavailability, proper half-life and duration of action), and improved safety (low toxicity and/or less side effects, wide therapeutic window). More particularly, the compound of the present invention has selective inhibitory activity on $AT_2$ receptors, compared to $AT_1$ receptors.

An aspect of the present invention provides a compound or a pharmaceutically acceptable salt, ester, stereoisomer, polymorph, solvate, N-oxide, isotopically labeled compound, metabolite or prodrug thereof, wherein the compound has a structure of formula (I):

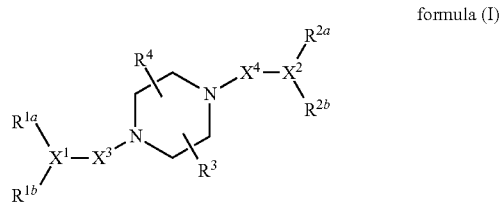

formula (I)

wherein:
$R^{1a}$, $R^{1b}$, $X^1$, $R^{2a}$, $R^{2b}$ and $X^2$ have the definitions described in the following Meaning (1), (2), (3) or (4):
(1) $R^{1a}$, $R^{1b}$ and $X^1$ together represent:
(i)

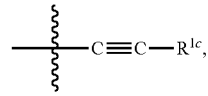

(ii)

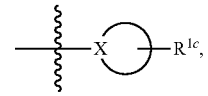

wherein:
the ring

is a saturated or partially unsaturated $C_{3-10}$ cyclic hydrocarbyl group, or a saturated or partially unsaturated 3- to 10-membered heterocyclic group;
X is C, $CR^{10}$ or N;
$R^{1c}$ is selected from the group consisting of saturated or partially unsaturated $C_{3-10}$ cyclic hydrocarbyl group, saturated or partially unsaturated 3- to 10-membered heterocyclic group, $C_{6-10}$ aryl and 5- to 14-membered heteroaryl, —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group, —$C_{1-6}$ alkylene-$C_{6-10}$ aryl and —$C_{1-6}$ alkylene-(5- to 14-membered heteroaryl);

$X^2$ is $CR^{10}$ or N;

$R^{2a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{2b}$ is selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

wherein, optionally, when $R^{2a}$ and $R^{2b}$ are each independently the $C_{3-10}$ cyclic hydrocarbyl group, 3- to 10-membered heterocyclic group, $C_{6-10}$ aryl, or 5- to 14-membered heteroaryl, an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

or (2) $R^{1a}$, $R^{2a}$, $R^{1b}$ and $R^{2b}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$ or N;

$X^2$ is $CR^{15}$;

$R^{15}$ is selected from the group consisting of halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—C(=O)$R^{12}$, —$NR^{11}$—C(=O)$OR^{12}$, —$NR^{11}$—S(=O)$_yR^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_xR^{11}$, —$C_{1-6}$ alkylene-S(=O)$_yOR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_yR^{12}$, —$C_{1-6}$ alkylene-$NR^{11}$—C(=O)$NR^{11}R^{12}$, —$C_{1-6}$ alkylene-OS(=O)$_yR^{11}$, —$C_{1-6}$, alkylene-OS(=O)$_yNR^{11}R^{12}$, —$C_{1-6}$ alkylene-S(=O)$_yNR^{11}R^{12}$, —$C_{1-6}$ alkylene-$NR^{11}$—S(=O)$_yNR^{11}R^{12}$, —$C_{1-6}$ alkylene-$NR^{11}R^{12}$ and —O—$C_{1-6}$ alkylene-$NR^{11}R^{12}$;

or (3) $R^{1a}$ is selected from the group consisting of —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group and —$C_{1-6}$ alkylene-(5- to 14-membered heteroaryl);

$R^{1b}$, $R^{2a}$ and $R^{2b}$ are each independently selected from the group consisting of OH; $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$, N, O or S; provided that: when $X^1$ is O or S, $R^{1b}$ does not exist;

$X^2$ is $CR^{10}$ or N;

or (4) $X^1$ and $X^2$ are each independently $CR^{10}$ or N;

$R^{1a}$ and $R^{2a}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{1b}$ and $R^{2b}$ are each independently selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

provided that:

$R^{1a}$ and $R^{1b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{1a}$ is connected to an available ring atom on $R^{1b}$ through Y group, such that $R^{1a}$ and $R^{1b}$ together with $X^1$ to which they are attached form an optionally substituted saturated or partially unsaturated fused ring system $Q^1$ containing 3 or more rings; and/or $R^{2a}$ and $R^{2b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

wherein, when $R^{1a}$, $R^{1b}$, $X^1$, $R^{2a}$, $R^{2b}$ and $X^2$ have the definitions described in any one of the Meanings (1), (2), (3) and (4), Y and Z me each independently selected from the group consisting of a single bond; $NR^{10}$; $C_{1-3}$ alkylene, wherein 1 or 2 $CH_2$ moieties me optionally replaced with a group independently selected from O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene me each optionally substituted by 1, 2, 3 or more groups selected from the group consisting of halogen, OH, $-NR^{11}R^{12}$, cyano, nitro, $C_{1-6}$ alkyl, $C_{1-6}$ alkyl-O—, epoxy and oxo;

$X^3$ and $X^4$ me each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ me connected to $X^1$ or $X^2$; preferably, $X^3$ and $X^4$ me each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)$OR^{11}$, —C(=O)$NR^{11}$—OH, —C(=O)$NR^{11}R^{12}$, —C(=O)$NR^{11}$S(=O)$_y$$NR^{11}R^{12}$, —C(=O)$NR^{11}$S(=O)$_y$$R^{12}$, —S(=O)$_y$$R^{11}$, —S(=O)$_y$$OR^{11}$, —S(=O)$_y$$NR^{11}R^{12}$, —S(=O)$_y$$NR^{11}$S(=O)$_z$$OR^{12}$, —S(=O)$_y$$NR^{11}$C(=O)$R^{12}$, —S(=O)$_y$$NR^{11}$C(=O)$OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_x$$R^{11}$, —$C_{1-6}$ alkylene-S(=O)$_y$$OR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_y$$R^{12}$, —$C_{1-6}$ alkylene-$NR^{11}$—C(=O)$NR^{11}R^{12}$, —$C_{1-6}$ alkylene-OS(=O)$_y$$R^{11}$, —$C_{1-6}$ alkylene-OS(=O)$_y$$NR^{11}R^{12}$, —$C_{1-6}$ alkylene-S(=O)$_y$$NR^{11}R^{12}$, —$C_{1-6}$ alkylene-$NR^{11}$—S(=O)$_y$$NR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)$OR^{11}$, —C(=O)$NR^{11}R^{12}$, —C(=O)$NR^{11}$S(=O)$_y$$NR^{11}R^{12}$, —C(=O)$NR^{11}$S(=O)$_y$$R^{12}$, —S(=O)$_y$$R^{11}$, —S(=O)$_y$$OR^{11}$, —S(=O)$_y$$NR^{11}R^{12}$, —S(=O)$_y$$NR^{11}$S(=O)$_z$$OR^{12}$, —S(=O)$_y$$NR^{11}$C(=O)$R^{12}$, —S(=O)$_y$$NR^{11}$C(=O)$OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_x$$R^{11}$, —$C_{1-6}$ alkylene-S(=O)$_y$$OR^{11}$. —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_y$$R^{12}$, —$C_{1-6}$ alkylene-$NR^{11}$—C(=O)$NR^{11}R^{12}$, —$C_{1-6}$ alkylene-OS(=O)$_y$$R^{11}$, —$C_{1-6}$ alkylene-OS(=O)$_y$$NR^{11}R^{12}$, —$C_{1-6}$ alkylene-S(=O)$_y$$NR^{11}R^{12}$, —$C_{1-6}$ alkylene-$NR^{11}$—S(=O)$_y$$NR^{11}R^{12}$, —$C_{1-6}$ alkylene-$NR^{11}R^{12}$ and —O—$C_{1-6}$ alkylene-$NR^{11}R^{12}$; and wherein the alkyl, alkylene, cyclic hydrocarbyl group, heterocyclic group, aryl, heteroaryl and aralkyl as defined for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2; and provided that:

in the case that $R^{1a}$, $R^{1b}$, $X^1$, $R^{2a}$, $R^{2b}$ and $X^2$ have the definitions described in the Meaning (4), when $R^{1a}$ and $R^{1b}$ are each independently $C_{1-8}$ alkyl, Z is not —$CH_2$—, —$CH_2$—$CH_2$— or —$CH_2$—$CH_2$—$CH_2$—; or when $R^{2a}$ and $R^{2b}$ are each independently $C_{1-8}$ alkyl, Y is not —$CH_2$—, —$CH_2$—$CH_2$— or —$CH_2$—$CH_2$—$CH_2$—.

Another aspect of the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof, and one or more pharmaceutically acceptable carriers, and the pharmaceutical composition is preferably in the form of a solid, semi-solid, liquid, or gas preparation.

Another aspect of the present invention provides use of the compound of the present invention or a pharmaceutically acceptable salt, ester, stereoisomer, polymorph, solvate, N-oxide, isotopically labeled compound, metabolite or prodrug thereof, or the pharmaceutical composition of the present invention in the manufacture of a medicament for use as an $AT_2$ receptor inhibitor.

Another aspect of the present invention provides the compound of the present invention or a pharmaceutically acceptable salt, ester, stereoisomer, polymorph, solvate, N-oxide, isotopically labeled compound, metabolite or prodrug thereof, or the pharmaceutical composition of the present invention for use as an AT$_2$ receptor inhibitor.

Another aspect of the present invention provides a method for the prophylaxis or the treatment of an AT$_2$ receptor-mediated disorder or a symptom associated therewith, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

Another aspect of the present invention provides a method for regulating a reproductive function associated with AT$_2$ receptors in a female patient, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

DETAILED DESCRIPTION OF THE INVENTION

Definitions

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, particularly 1-8 ("$C_{1-8}$ alkyl") carbon atoms, e.g., 1-6 ("$C_{1-6}$ alkyl"), 1-4 ("$C_{1-4}$ alkyl") carbon atoms, more particularly, 1, 2, 3, 4, 5, 6, 7 or 8 carbon atoms. For example, as used herein, the term "$C_{1-8}$ alkyl" refers to a linear or branched group having 1-8 carbon atoms (such as methyl, ethyl, n-propyl, isopropyl, n-butyl, isobutyl, sec-butyl, tert-butyl, n-pentyl, isopentyl, neopentyl, or 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl), which is optionally substituted with one or more (e.g., 1 to 3) suitable substituents such as halogen (in which case the group may be referred to as "halogenated alkyl") (e.g., $CH_2F$, $CHF_2$, $CF_3$, $CCl_3$, $C_2F_5$, $C_2Cl_5$, $CH_2CF_3$, $CH_2Cl$ or —$CH_2CH_2CF_3$ etch. The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-8 carbon atoms ("$C_{2-8}$ alkenyl", such as "$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, heptenyl and octenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5, 6, 7 or 8 carbon atoms, e.g., ethynyl, 1-propynyl, 2-propynyl, 2-butynyl, 3-butynyl, 2-pentynyl, 3-pentynyl, 4-pentynyl, 2-hexynyl, 3-hexynyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6, such as 5-6 or 5-7) ring carbon atoms, including but not limited to cyclopropyl(ene) (ring), cyclobutyl(ene) (ring), cyclopentyl(ene) (ring), cyclohexyl(ene) (ring), cycloheptyl (ene) (ring), cyclooctyl(ene) (ring), cyclononyl(ene) (ring), cyclohexenyl(ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) monocyclic or bicyclic group having e.g. 3-10 (suitably having 3-8, and more suitably having 3-6; or suitably having 8-10, and more suitably having 9 or 10) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated monocyclic or bicyclic heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of monocyclic heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Bicyclic heterocyclylene, heterocyclyl and heterocycle include spiro ring systems, fused (e.g., benzo-fused) systems, or bridged systems. The benzo-fused heterocyclylene, heterocyclyl and heterocycle refer to the above-mentioned monocyclic heterocyclylene, heterocyclyl and heterocycle fused to benzene, for example, a benzo derivative of a saturated or partially unsaturated monocyclic group with 3-6 (suitably with 4-6, more suitably 5-6) ring atoms, in which 1, 2, 3 or 4 ring atoms are heteroatoms selected from N, O and S and the remaining ring atoms are C (i.e., "7- to 10-membered benzo fused heterocyclylene, heterocyclyl and heterocycle"), including for example 2,3-dihydrobenzofuranyl (ene)

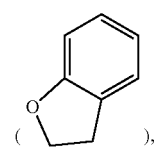

1,3-dihydroisobenzofuranyl(ene)
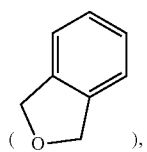
2,3-dihydrobenzo[c]thienyl(ene)
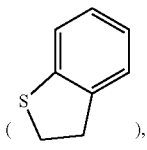
1,3-dihydrobenzo[c]thienyl(ene)
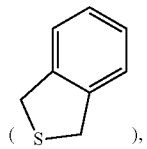
dihydroindolyl(ene)
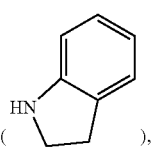
dihydroisoindolyl(ene)
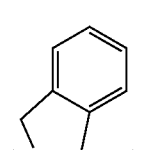
benzo[d][1,3]dioxolyl(ene)
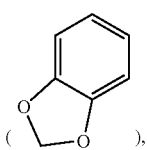
benzo[d][1,3]dithiolyl(ene)
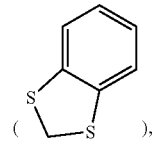
benzo[d][1,3]oxathiolyl(ene)
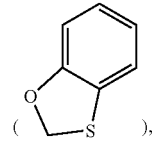
3H-benzo[c][1,2]oxathiolyl(ene)
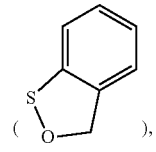
3H-benzo[d][1,2]oxathiolyl(ene)
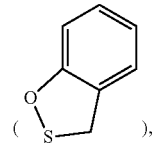
2,3-dihydrobenzo[d]oxazolyl(ene)
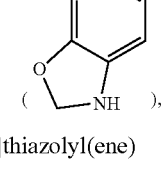
2,3-dihydrobenzo[d]thiazolyl(ene)
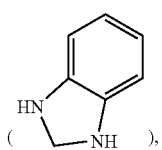
2,3-dihydro-1H-benzo[d]imidazolyl(ene)

2,3-dihydrobenzo[d]isoxazolyl(ene)

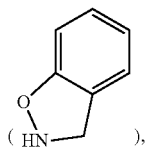

2,3-dihydrobenzo[d]isothiazolyl(ene)

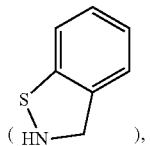

1,3-dihydrobenzo[c]isoxazolyl(ene)

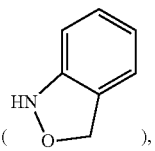

1,3-dihydrobenzo[c]isothiazolyl(ene)

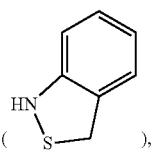

2,3-dihydro-1H-indazolyl(ene)

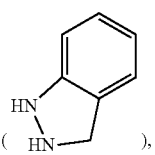

chromanyl(ene)

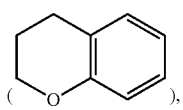

2H-chromenyl(ene)

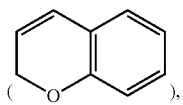

4H-chromanyl(ene)

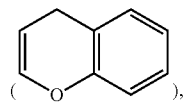

dihydrobenzothiopyranyl(ene)

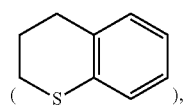

2H-thiochromenyl(ene) (2H-thiochromene,

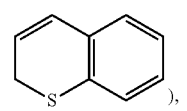

4H-benzothiopyranyl(ene) (4H-thiochromene,

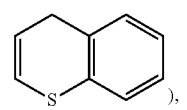

1,2,3,4,4a,8a-hexahydroquinolinyl(ene)

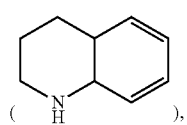

1,2,4a,8a-tetrahydroquinolinyl(ene)

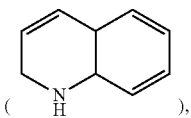

1,4,4a,8a-tetrahydroquinolinyl(ene)

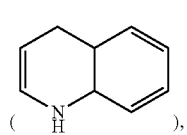

1,2,3,4,4a,8a-hexahydroisoquinolinyl(ene)

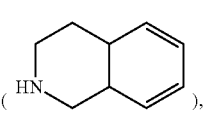

1,2,3,4,4a,8a-hexahydroquinoxalinyl(ene)

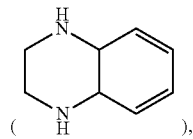

1,4,4a,8a-tetrahydroquinoxalinyl(ene)

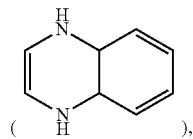

1,2,3,4,4a,8a-hexahydroquinazolinyl(ene)

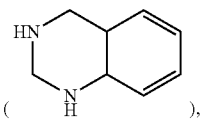

2,4,4a,8a-tetrahydro-1H-benzo[d][1,3]oxazinyl(ene)

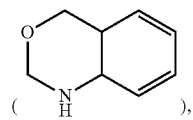

3,4,4a,8a-tetrahydro-2H-benzo[b][1,4]oxazinyl(ene)

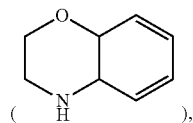

3,4,4a,8a-tetrahydro-2H-benzo[e][1,3]oxazinyl(ene)

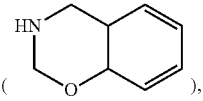

2,4,4a,8a-tetrahydro-1H-benzo[d][1,3]thiazinyl(ene)

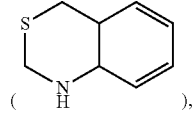

3,4,4a,8a-tetrahydro-2H-benzo[b][1,4]thiazinyl(ene)

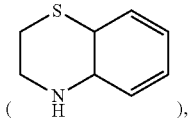

3,4,4a,8a-tetrahydro-2H-benzo[e][1,3]thiazinyl(ene)

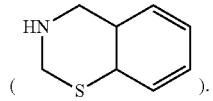

The bridged systems also include for example 8-azaspiro[4.5]decane, 3,9-diazaspiro[5.5]undecane, 2-azabicyclo[2.2.2]octane. Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —NO₂, and $C_{1-6}$ alkyl, etch.

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene) (e.g., 1-pyrazolyl, 3-pyrazolyl, 4-pyrazolyl and 5-pyrazolyl), isoxazolyl(ene), isothiazolyl(ene), oxadiazolyl(ene), triazolyl(ene), tetrazolyl(ene) (e.g. 1-tetrazolyl or 5-tetrazolyl), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may optionally further comprise one or more (e.g., one, two, three or four) ring members selected from the group consisting of N, O, C=O, S, S=O and S(=O)₂. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more from a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced with an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drag and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The carbon-carbon bonds of the compound of the present invention may be depicted herein using a solid line (———), a solid wedge (━━■), or a dotted wedge (∙∙∙∙∙∙∙∙∙∙∙). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hyperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

SPECIFIC EMBODIMENTS

Compound

In general, the present invention provides a compound or a pharmaceutically acceptable salt, ester, stereoisomer, polymorph, solvate, N-oxide, isotopically labeled compound, metabolite or prodrug thereof, wherein the compound has a structure of formula (I):

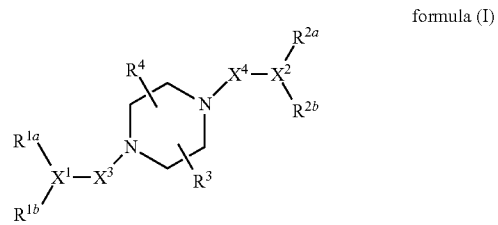

formula (I)

wherein:
$R^{1a}$, $R^{1b}$, $X^1$, $R^{2a}$, $R^{2b}$ and $X^2$ have the definitions described in the following Meaning (1), (2), (3) or (4):
(1) $R^{1a}$, $R^{1b}$ and $X^1$ together represent:
(i)

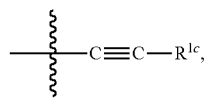

(ii)

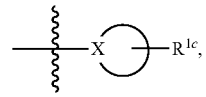

wherein:

the ring

is a saturated or partially unsaturated $C_{3-10}$ cyclic hydrocarbyl group, or a saturated or partially unsaturated 3- to 10-membered heterocyclic group;

X is C, $CR^{10}$ or N;

$R^{1c}$ is selected from the group consisting of saturated or partially unsaturated $C_{3-10}$ cyclic hydrocarbyl group, saturated or partially unsaturated 3- to 10-membered heterocyclic group, $C_{6-10}$ aryl and 5- to 14-membered heteroaryl, —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group, —$C_{1-6}$ alkylene-$C_{6-10}$ aryl and —$C_{1-6}$ alkylene-(5- to 14-membered heteroaryl);

$X^2$ is $CR^{10}$ or N;

$R^{2a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{2b}$ is selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

wherein, optionally, when $R^{2a}$ and $R^{2b}$ are each independently the $C_{3-10}$ cyclic hydrocarbyl group, 3- to 10-membered heterocyclic group, $C_{6-10}$ aryl, or 5- to 14-membered heteroaryl, an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

or (2) $R^{1a}$, $R^{2a}$, $R^{1b}$ and $R^{2b}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$ or N;

$X^2$ is $CR^{15}$;

$R^{15}$ is selected from the group consisting of halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_y$—$NR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_y$—$NR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—C$(=O)R^{12}$, —$NR^{11}$—C$(=O)OR^{12}$, —$NR^{11}$—S$(=O)_y$—$R^{12}$, —$NR^{11}$—C$(=O)$—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—$S(=O)_yR^{12}$, —$C_{1-6}$ alkylene-$NR^{11}$—$C(=O)NR^{11}R^{12}$, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—$S(=O)_yNR^{11}R^{12}$, —$C_{1-6}$ alkylene-$NR^{11}R^{12}$ and —$O$—$C_{1-6}$ alkylene-$NR^{11}R^{12}$;

or (3) $R^{1a}$ is selected from the group consisting of —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group and —$C_{1-6}$ alkylene-(5- to 14-membered heteroaryl);

$R^{1b}$, $R^{2a}$ and $R^{2b}$ are each independently selected from the group consisting of OH; $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$, N, O or S; provided that: when $X^1$ is O or S, $R^{1b}$ does not exist;

$X^2$ is $CR^{10}$ or N;

or (4) $X^1$ and $X^2$ are each independently $CR^{10}$ or N;

$R^{1a}$ and $R^{2a}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{1b}$ and $R^{2b}$ are each independently selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

provided that:

$R^{1a}$ and $R^{1b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{1a}$ is connected to an available ring atom on $R^{1b}$ through Y group, such that $R^{1a}$ and $R^{1b}$ together with $X^1$ to which they are attached form an optionally substituted saturated or partially unsaturated fused ring system $Q^1$ containing 3 or more rings; and/or $R^{2a}$ and $R^{2b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

wherein, when $R^{1a}$, $R^{1b}$, $X^1$, $R^{2a}$, $R^{2b}$ and $X^2$ have the definitions described in any one of the Meanings (1), (2), (3) and (4), Y and Z are each independently selected from the group consisting of a single bond; $NR^{10}$; $C_{1-3}$ alkylene, wherein 1 or 2 $CH_2$ moieties are optionally replaced with a group independently selected from O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene are each optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo;

$X^3$ and $X^4$ are each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^1$ or $X^2$; preferably, $X^3$ and $X^4$ are each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—$C(=O)R^{12}$, —$NR^{11}$—$C(=O)OR^{12}$, —$NR^{11}$—$S(=O)_y$—$R^{12}$, —$NR^{11}$—$C(=O)$—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—$S(=O)_yR^{12}$, —$C_{1-6}$ alkylene-$NR^{11}$—$C(=O)NR^{11}R^{12}$, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—$S(=O)_yNR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—$C(=O)R^{12}$, —$NR^{11}$—$C(=O)OR^{12}$, —$NR^{11}$—$S(=O)_y$—$R^{12}$, —$NR^{11}$—$C(=O)$—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—$S(=O)_yR^{12}$, —$C_{1-6}$ alkylene-$NR^{11}$—$C(=O)NR^{11}R^{12}$, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—$S(=O)_yNR^{11}R^{12}$, —$C_{1-6}$ alkylene-$NR^{11}R^{12}$ and —O—$C_{1-6}$ alkylene-$NR^{11}R^{12}$; and wherein the alkyl, alkylene, cyclic hydrocarbyl group, heterocyclic group, aryl, heteroaryl and aralkyl recited for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2; and provided that:

in the case that $R^{1a}$, $R^{1b}$, $X^1$, $R^{2a}$, $R^{2b}$ and $X^2$ have the definitions described in the Meaning (4), when $R^{1a}$ and $R^{1b}$ are each independently $C_{1-8}$ alkyl, Z is not —$CH_2$—, —$CH_2$—$CH_2$— or —$CH_2$—$CH_2$—$CH_2$—; or when $R^{2a}$ and $R^{2b}$ are each independently $C_{1-8}$ alkyl, Y is not —$CH_2$—, —$CH_2$—$CH_2$— or —$CH_2$—$CH_2$—$CH_2$—.

The first aspect of the embodiments of the compound according to the present invention relates to the abovementioned compound having the structure of formula (I), or the pharmaceutically acceptable salt, ester, stereoisomer, polymorph, solvate, N-oxide, isotopically labeled compound, metabolite, or prodrug thereof, wherein $R^{1a}$, $R^{1b}$, $X^1$, $R^{2a}$, $R^{2b}$ and $X^2$ have the definitions described in the abovementioned Meaning (4).

As such, the first aspect of the compound of the present invention relates to the compound having the structure of formula (I), or a pharmaceutically acceptable salt, ester, stereoisomer, polymorph, solvate, N-oxide, isotopically labeled compound, metabolite or prodrug thereof, wherein:

$X^1$ and $X^2$ are each independently $CR^{10}$ or N;

$R^{1a}$ and $R^{2a}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{1b}$ and $R^{2b}$ are each independently selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

provided that:

$R^{1a}$ and $R^{1b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{1a}$ is connected to an available ring atom on $R^{1b}$ through Y group, such that $R^{1a}$ and $R^{1b}$ together with $X^1$ to which they are attached form an optionally substituted saturated or partially unsaturated fused ring system $Q^1$ containing 3 or more rings; and/or $R^{2a}$ and $R^{2b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

wherein,

Y and Z are each independently selected from the group consisting of a single bond; $NR^{10}$; $C_{1-3}$ alkylene, wherein 1 or 2 $CH_2$ moieties are optionally replaced with a group independently selected from O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene are each optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo;

$X^3$ and $X^4$ are each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^1$ or $X^2$; preferably, $X^3$ and $X^4$ are each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)$OR^{11}$, —C(=O)$NR^{11}$—OH, —C(=O)$NR^{11}R^{12}$, —C(=O)$NR^{11}$S(=O)$_y$$NR^{11}R^{12}$, —C(=O)$NR^{11}$S(=O)$_y$$R^{12}$, —S(=O)$_y$$R^{11}$, —S(=O)$_y$$OR^{11}$, —S(=O)$_y$$NR^{11}R^{12}$, —S(=O)$_y$$NR^{11}$S(=O)$_z$$OR^{12}$, —S(=O)$_y$$NR^{11}$C(=O)$R^{12}$, —S(=O)$_y$$NR^{11}$C(=O)$OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_x$$R^{11}$, —$C_{1-6}$ alkylene-S(=O)$_y$$OR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_y$$R^{12}$, —$C_{1-6}$ alkylene-$NR^{11}$—C(=O)$NR^{11}R^{12}$, —$C_{1-6}$ alkylene-OS(=O)$_y$$R^{11}$, —$C_{1-6}$ alkylene-OS(=O)$_y$$NR^{11}R^{12}$, —$C_{1-6}$ alkylene-S(=O)$_y$$NR^{11}R^{12}$, —$C_{1-6}$ alkylene-$NR^{11}$—S(=O)$_y$$NR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)$OR^{11}$, —C(=O)$NR^{11}R^{12}$, —C(=O)$NR^{11}$S(=O)$_y$$NR^{11}R^{12}$, —C(=O)$NR^{11}$S(=O)$_y$$R^{12}$, —S(=O)$_y$$R^{11}$, —S(=O)$_y$$OR^{11}$, —S(=O)$_y$$NR^{11}R^{12}$, —S(=O)$_y$$NR^{11}$S(=O)$_z$$OR^{12}$, —S(=O)$_y$$NR^{11}$C(=O)$R^{12}$, —S(=O)$_y$$NR^{11}$C(=O)$OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_x$$R^{11}$, —$C_{1-6}$ alkylene-S(=O)$_y$$OR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_y$$R^{12}$, —$C_{1-6}$ alkylene-$NR^{11}$—C(=O)$NR^{11}R^{12}$, —$C_{1-6}$ alkylene-OS(=O)$_y$$R^{11}$, —$C_{1-6}$, alkylene-OS(=O)$_y$$NR^{11}R^{12}$, —$C_{1-6}$ alkylene-S(=O)$_y$$NR^{11}R^{12}$, —$C_{1-6}$ alkylene-$NR^{11}$—S(=O)$_y$$NR^{11}R^{12}$, —$C_{1-6}$ alkylene-$NR^{11}R^{12}$ and —O—$C_{1-6}$ alkylene-$NR^{11}R^{12}$; and wherein the alkyl, alkylene, cyclic hydrocarbyl group, heterocyclic group, aryl, heteroaryl and aralkyl recited for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2; and provided that:

when $R^{1a}$ and $R^{1b}$ are each independently $C_{1-8}$ alkyl, Z is not —$CH_2$—, —$CH_2$—$CH_2$— or —$CH_2$—$CH_2$—$CH_2$—; or when $R^{2a}$ and $R^{2b}$ are each independently $C_{1-8}$ alkyl, Y is not —$CH_2$—, —$CH_2$—$CH_2$— or —$CH_2$—$CH_2$—$CH_2$—.

The embodiments of the compound according to the first aspect are described further below.

In some embodiments, the present invention provides the above-mentioned compound having the structure of formula (I), or a pharmaceutically acceptable salt, ester, stereoisomer, polymorph, solvate, N-oxide, isotopically labeled compound, metabolite or prodrug thereof, wherein:

$X^1$ and $X^2$ are each independently $CR^{10}$ or N;

$R^{1a}$ and $R^{2a}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{1b}$ and $R^{2b}$ are each independently selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

provided that:

$R^{1a}$ and $R^{1b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{1a}$ is connected to an available ring atom on $R^{1b}$ through Y group, such that $R^{1a}$ and $R^{1b}$ together with $X^1$ to which they are attached form an optionally substituted saturated or partially unsaturated fused ring system containing 3 or more rings; and/or $R^{2a}$ and $R^{2b}$ are each independently the $C_{3-10}$ cyclic hydrocarbyl group, 3- to 10-membered heterocyclic group, $C_{6-10}$ aryl or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system containing 3 or more rings;

Y and Z are each independently selected from the group consisting of a single bond; $NR^{10}$; $C_{1-3}$ alkylene, wherein 1 or 2 $CH_2$ moieties are optionally replaced with a group independently selected from O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene are each optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo;

preferably, Y and Z are each independently selected from the group consisting of $NR^{10}$; $C_{1-3}$ alkylene replaced with 1, 2 3 or more epoxy or oxo groups; $C_{1-3}$ alkylene, in which 1 or 2 $CH_2$ are replaced with a group independently selected from O, S, or $NR^{10}$; and wherein the $C_{1-3}$ alkylene is optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo; and $C_{2-3}$ alkenylene, in which any one of the CH moieties forming a C=C double bond is optionally replaced with N; and wherein the $C_{2-3}$ alkenylene is optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo;

$X^3$ and $X^4$ are each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^1$ or $X^2$; preferably, $X^3$ and $X^4$ are each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_yOR^{12}$, —$S(=O)_yNR^{11}C(=O)R^{12}$, —$S(=O)_yNR^{11}C(=O)OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_xR^{11}$, —$C_{1-6}$ alkylene-S(=O)$_yOR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_yR^{12}$, —$C_{1-6}$ alkylene-$NR^{11}$—C(=O)$NR^{11}R^{12}$, —$C_{1-6}$ alkylene-OS(=O)$_yR^{11}$, —$C_{1-6}$ alkylene-OS(=O)$_yNR^{11}R^{12}$, —$C_{1-6}$ alkylene-S(=O)$_yNR^{11}R^{12}$, —$C_{1-6}$ alkylene-$NR^{11}$—S(=O)$_yNR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)O$R^{11}$, —C(=O)NR$^{11}R^{12}$, —C(=O)NR$^{11}$S(=O)$_y$NR$^{11}R^{12}$, —C(=O)NR$^{11}$S(=O)$_y R^{12}$, —S(=O)$_y R^{11}$, —S(=O)$_y OR^{11}$, —S(=O)$_z NR^{11}R^{12}$, —S(=O)$_y NR^{11}$S(=O)$_z OR^{12}$, —S(=O)$_y NR^{11}$C(=O)$R^{12}$, —S(=O)$_y NR^{11}$C(=O)$OR^{12}$, —NR$^{11}R^{12}$, —NR$^{11}$—C(=O)$R^{12}$, —NR$^{11}$—C(=O)$OR^{12}$, —NR$^{11}$—S(=O)$_y$—$R^{12}$, —NR$^{11}$—C(=O)—NR$^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_x R^{11}$, —$C_{1-6}$ alkylene-S(=O)$_y OR^{11}$, —$C_{1-6}$ alkylene-OC(=O)NR$^{11}R^{12}$, —$C_{1-6}$ alkylene-C(=O)NR$^{11}R^{12}$, —$C_{1-6}$ alkylene-C(=O)NR$^{11}$—S(=O)$_y R^{12}$, —$C_{1-6}$ alkylene-NR$^{11}$—C(=O)NR$^{11}R^{12}$, —$C_{1-6}$ alkylene-OS(=O)$_y R^{11}$, —$C_{1-6}$ alkylene-OS(=O)$_y NR^{11}R^{12}$, —$C_{1-6}$ alkylene-S(=O)$_y NR^{11}R^{12}$, —$C_{1-6}$ alkylene-NR$^{11}$—S(=O)$_y NR^{11}R^{12}$, —$C_{1-6}$ alkylene-NR$^{11}R^{12}$ and —O—$C_{1-6}$ alkylene-NR$^{11}R^{12}$; and wherein the alkyl, alkylene, cyclic hydrocarbyl group, heterocyclic group, aryl, heteroaryl and aralkyl as defined for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2;

y and z, at each occurrence, are each independently 1 or 2; and provided that:

when $R^{1a}$ and $R^{1b}$ are each independently $C_{1-8}$ alkyl, Z is not —$CH_2$—, —$CH_2$—$CH_2$— or —$CH_2$—$CH_2$—$CH_2$—; or when $R^{2a}$ and $R^{2b}$ are each independently $C_{1-8}$ alkyl, Y is not —$CH_2$—, —$CH_2$—$CH_2$— or —$CH_2$—$CH_2$—$CH_2$—.

In some embodiments, the compound of formula (I) further meets the following condition: when $R^{1a}$ and $R^{1b}$ are independently phenyl optionally substituted by 1, 2, 3 or more $R^{13}$, Z is not —$CH_2$—, —$CH_2$—$CH_2$— or —$CH_2$—$CH_2$—$CH_2$—; or when $R^{2a}$ and $R^{2b}$ are each independently phenyl optionally substituted by 1, 2, 3, or more $R^{13}$, Y is not —$CH_2$—, —$CH_2$—$CH_2$— or —$CH_2$—$CH_2$—$CH_2$—.

Preferably, in any of the embodiments described above, the compound of formula (I) has a structure of formula (II):

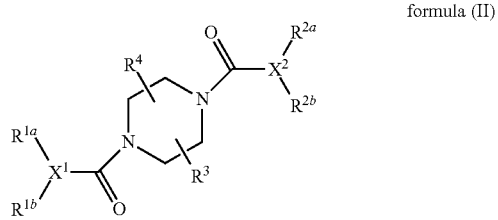

formula (II)

wherein $R^{1b}$ and $R^{2b}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl).

In some further embodiments, $R^{1a}$ and $R^{1b}$ are each independently, or $R^{2a}$ and $R^{2b}$ are each independently selected from the group consisting of $C_{1-6}$ alkyl, such as methyl, ethyl, n-propyl, isopropyl, n-butyl, isobutyl, sec-butyl, tert-butyl, n-pentyl, isopentyl, neopentyl, 1-hexyl, 1-heptyl, 1-octyl;

$C_{2-6}$ alkenyl, such as vinyl, 1-propenyl, 2-propenyl, 2-butenyl, 3-butenyl, 2-pentenyl, 3-pentenyl, 4-pentenyl, 2-hexenyl;

$C_{2-6}$ alkynyl, such as ethynyl, 1-propynyl, 2-propynyl, 2-butynyl, 3-butynyl, 2-pentynyl, 3-pentynyl, 4-pentynyl, 2-hexynyl, 3-hexynyl;

$C_{3-7}$ cyclic hydrocarbyl group, such as $C_{5-7}$ cyclic hydrocarbyl group, such as cyclopropyl, cyclopentyl, cyclohexyl;

5- to 7-membered monocyclic heterocyclic group;

8- to 10-membered benzo-fused heterocyclic group, such as

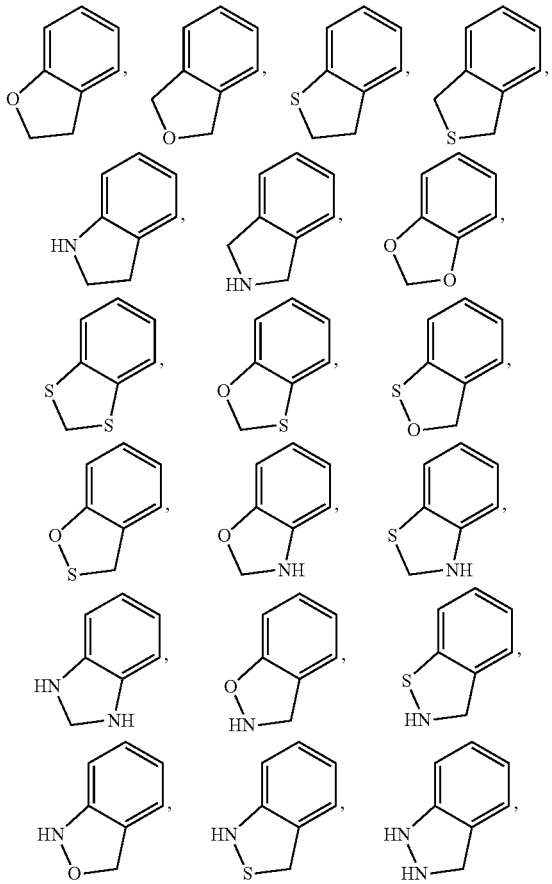

-continued

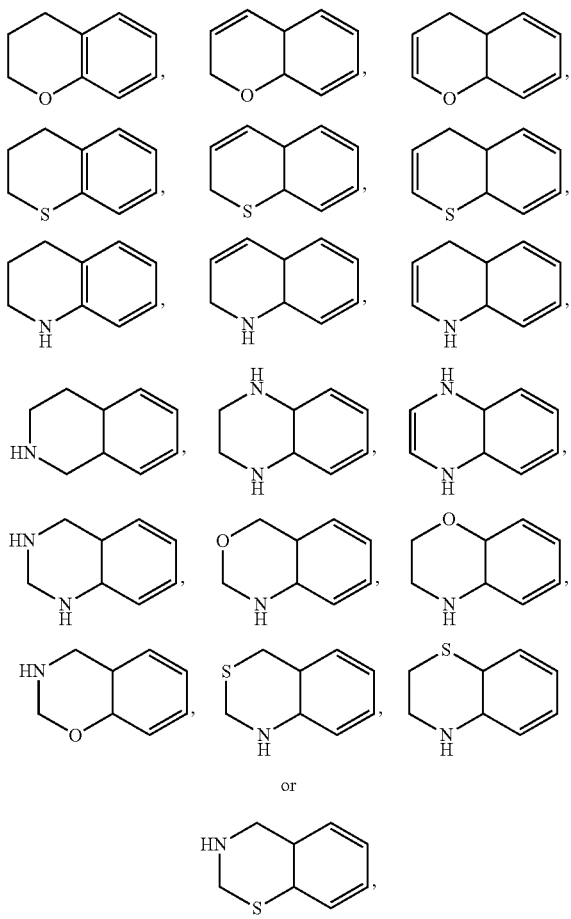

preferably

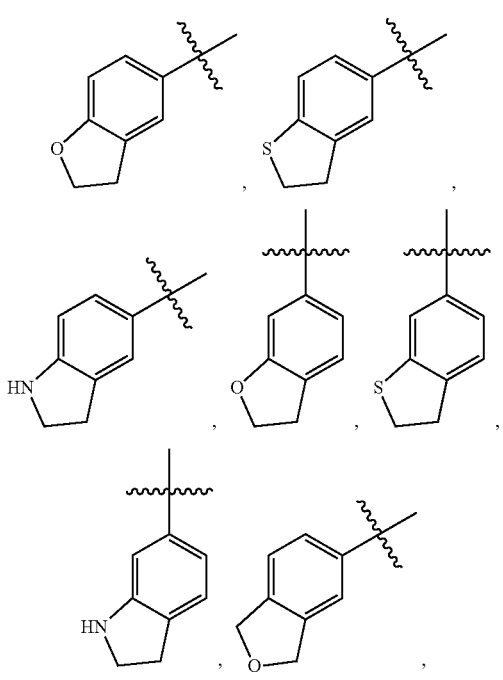

or

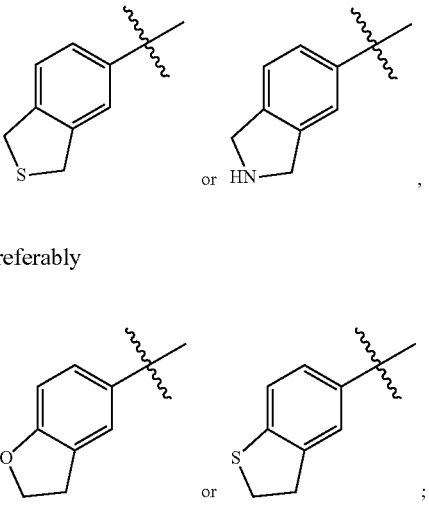

more preferably phenyl; and 5- to 6-membered heteroaryl, such as thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl, more preferably thienyl or furyl, more preferably thienyl;

the above alkyl, alkenyl, alkynyl, cyclic hydrocarbyl group, heterocyclic group, aryl and heteroaryl, at each occurrence, are each optionally substituted by 1, 2 or 3 $R^{13}$.

In other further embodiments, $R^{1a}$ and $R^{1b}$ are each independently, or $R^{2a}$ and $R^{2b}$ are each independently selected from the group consisting of —$C_{1-6}$ alkylene-$C_{6-10}$ aryl, preferably —$C_{1-4}$ alkylene-$C_{6-10}$ aryl, more preferably phenylmethylene- or phenylethylene-; and —$C_{1-6}$ alkylene-(5- to 14-membered heteroaryl), preferably —$C_{1-4}$ alkylene-(5- to 10-membered heteroaryl), more preferably -methylene-(5- to 10-membered heteroaryl) and -ethylene-(5- to 10-membered heteroaryl), wherein the heteroaryl is preferably selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl and its benzo derivatives, more preferably selected from the group consisting of thienyl and furanyl and its benzo derivatives, more preferably selected from the group consisting of thienyl and its benzo derivatives; and the above alkylene, aryl and heteroaryl, at each occurrence, are each optionally substituted by 1, 2 or 3 $R^{13}$.

In some further embodiments, $R^{1a}$ and $R^{1b}$ are each independently, or $R^{2a}$ and $R^{2b}$ are each independently selected from the group consisting of methyl, ethyl, n-propyl, n-pentyl, cyclopropyl, cyclopentyl, cyclohexyl, phenyl,

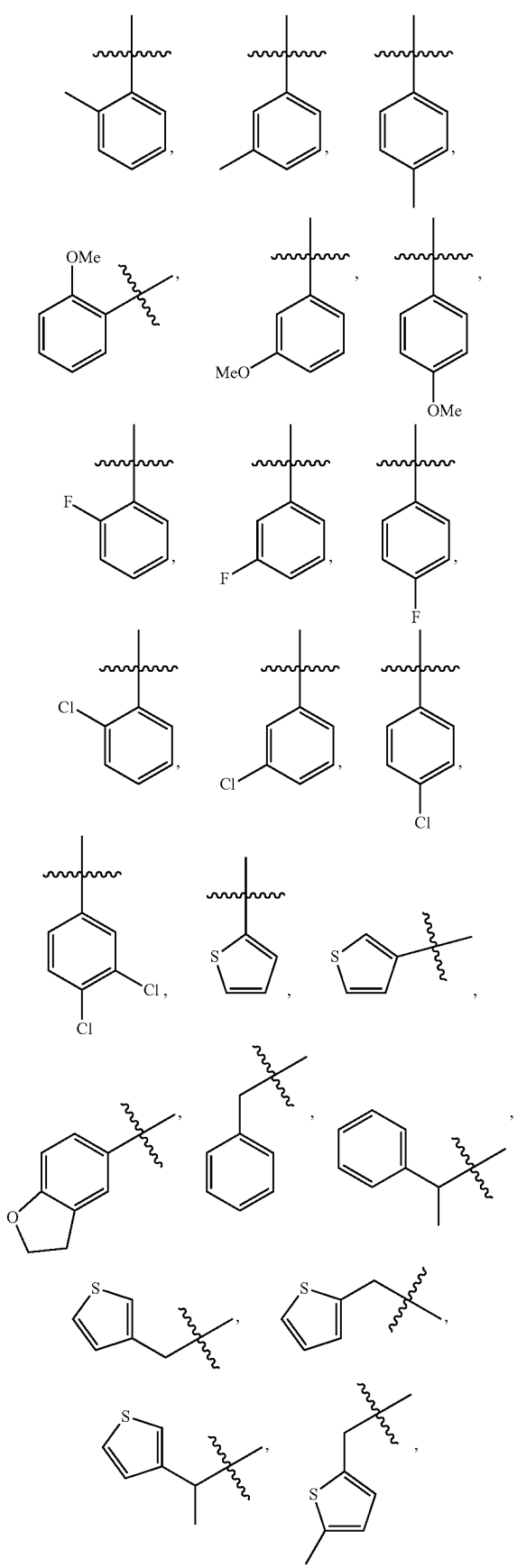

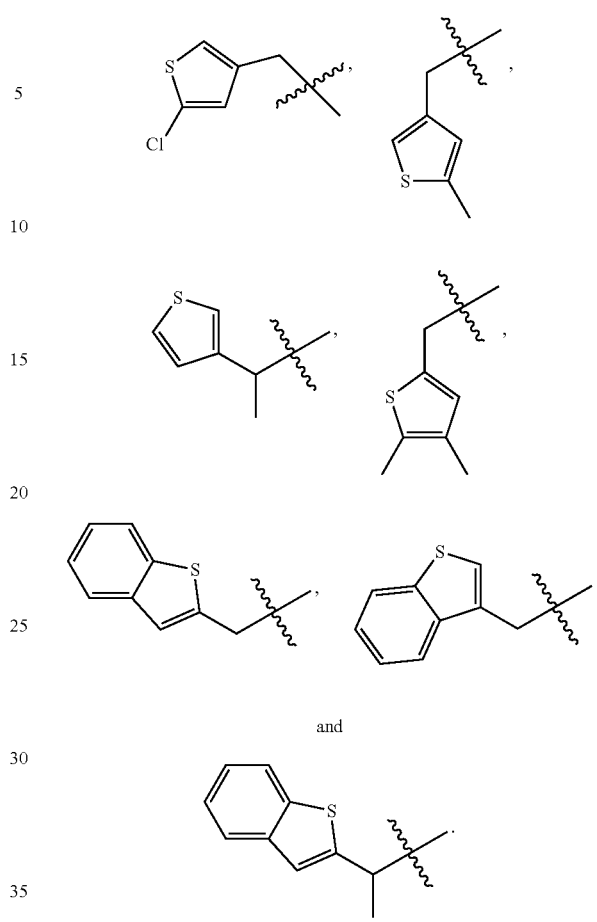

and

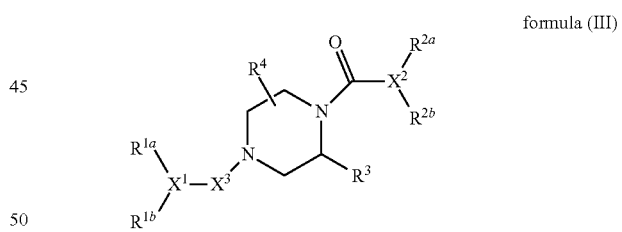

In other embodiments, the compound of formula (I) has a structure of formula (III):

formula (III)

wherein $R^{1b}$ is H; and $X^3$ is the —O—C(=O)—, —S—C(=O)—, —O—S(=O)$_y$—, —NR$^{10}$—C(=O)— or —NR$^{10}$—S(=O)$_y$—, preferably the —O—C(=O)— or —NR$^{10}$—C(=O)—; and $R^{1a}$, $X^1$, $R^{2a}$, $R^{2b}$, $X^2$, $R^3$ and $R^4$ are as defined in any of the embodiments described above.

In some further embodiments, $X^1$ is CH; and/or $R^{1a}$ is $C_{5-7}$ cyclic hydrocarbyl group, 5- to 7-membered monocyclic heterocyclic group, phenyl, or 5- to 6-membered heteroaryl, preferably phenyl.

Preferably, in any of the embodiments described above, the fused ring system $Q^1$ has a structure of formula (a):

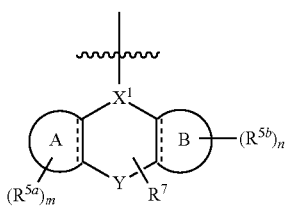

formula (a)

wherein:
ring A and ring B are each independently $C_{3-10}$ cyclic hydrocarbyl group, 3- to 10-membered heterocyclic group, $C_{6-10}$ aryl or 5- to 14-membered heteroaryl, preferably $C_{5-7}$ cyclic hydrocarbyl group (such as cyclopentyl or cyclohexyl), 5- to 7-membered monocyclic heterocyclic group, phenyl or 5- to 6-membered heteroaryl;

----- means a single bond or a double bond.

More preferably, the fused ring system $Q^1$ with the structure of formula (a) is a group having a structure of formula (1) or formula (2):

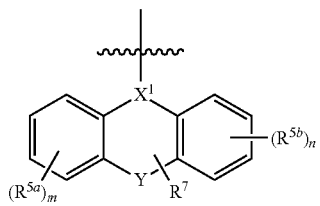

formula (1)

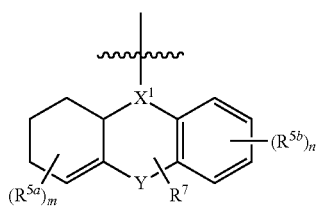

formula (2)

wherein
$R^{5a}$ and $R^{5b}$, at each occurrence, are each independently $R^{10}$;
$R^7$ is absent or is $R^{10}$;
$X^1$, $R^{10}$ and Y are as defined in any of the embodiments described above;
m and n are each independently 0, 1, 2 or 3.

Preferably, in any of the embodiments described above, the fused ring system $Q^2$ has a structure of formula (b):

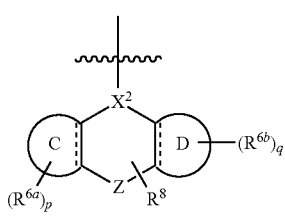

formula (b)

wherein:
ring C and ring D are each independently $C_{3-10}$ cyclic hydrocarbyl group, 3- to 10-membered heterocyclic group, $C_{6-10}$ aryl or 5- to 14-membered heteroaryl, preferably $C_{5-7}$ cyclic hydrocarbyl group, 5- to 7-membered monocyclic heterocyclic group (such as cyclopentyl or cyclohexyl), phenyl or 5- to 6-membered heteroaryl;

----- means a single bond or a double bond.

More preferably, the fused ring system $Q^2$ with the structure of formula (b) is a group having a structure of formula (3) or formula (4):

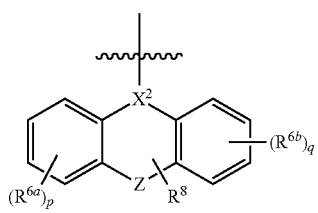

formula (3)

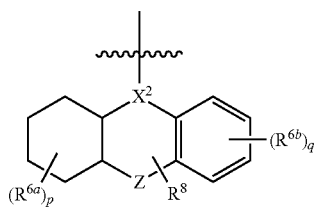

formula (4)

wherein
$R^{6a}$ and $R^{6b}$, at each occurrence, are each independently $R^{10}$;
$R^8$ is absent or is $R^{10}$;
$X^2$, $R^{10}$ and Z are as defined in any of the embodiments described above;
p and q are each independently 0, 1, 2 or 3.

In some further embodiments, Y and Z, at each occurrence, are independently selected from the group consisting of a single bond; $NR^{10}$; O; S; and methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo, particularly from the group consisting of F, Cl, $C_{1-4}$ alkyl-O— (such as $CH_3$—O—), epoxy and oxo; preferably, Y and Z, at each occurrence, are each independently selected from the group consisting of $NR^{10}$; O; S; methylene and ethylene which are optionally substituted by 1, 2, 3 or more epoxy or oxo groups; and —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo, and particularly from the group consisting of F, Cl, $C_{1-4}$ alkyl-O— (such as $CH_3$—O—), epoxy and oxo.

In some preferred embodiments, the group of formula (1) has a structure selected from:

formula (1a-1)
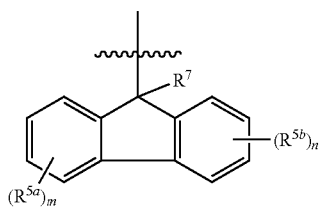
formula (1a-2)
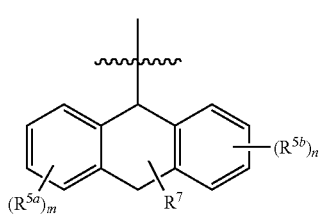
formula (1a-3)
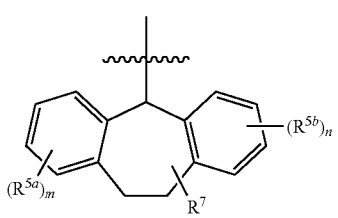
formula (1a-4)
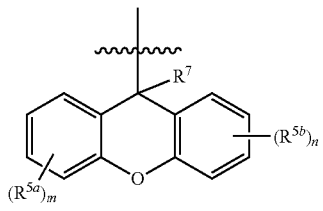
formula (1a-5)
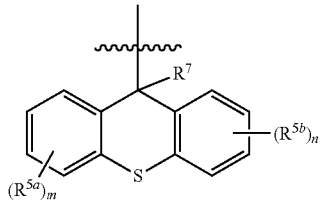
formula (1a-6)
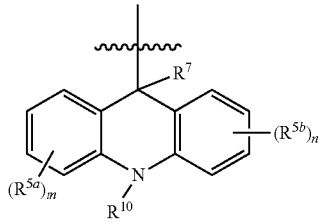
formula (1a-7)
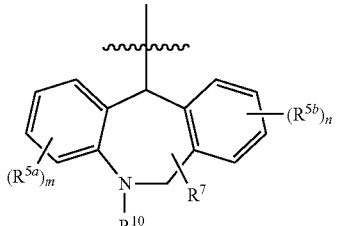
-continued
formula (1a-8)
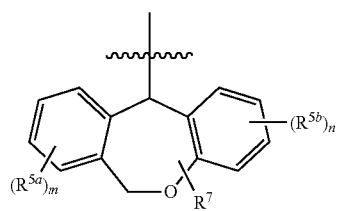
formula (1a-9)
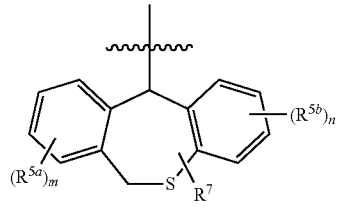
formula (1a-10)
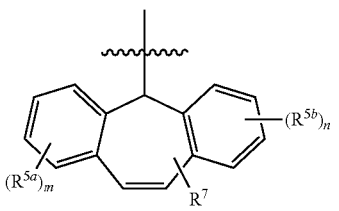
formula (1a-11)
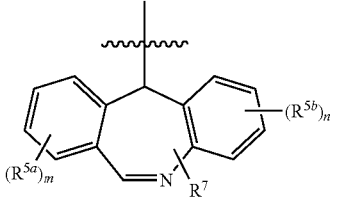
formula (1a-12)
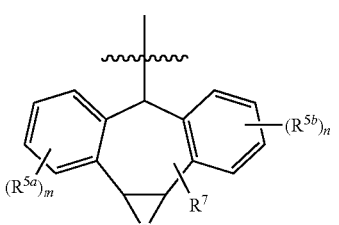
formula (1a-13)
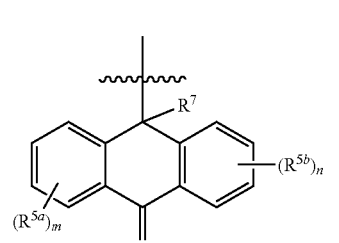
formula (1a-14)
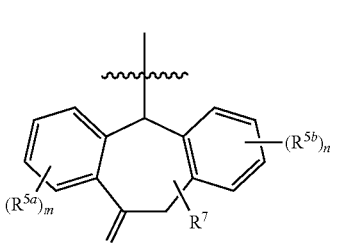

-continued formula (1a-15)

formula (1a-16)

formula (1a-17)

formula (1b-1)

formula (1b-2)

formula (1b-3)

formula (1b-4)

formula (1b-5)

formula (1b-6)

formula (1b-7)

formula (1b-8)

formula (1b-9)

formula (1b-10)

formula (1b-11)

-continued
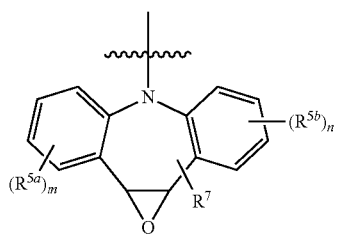
formula (1b-12)
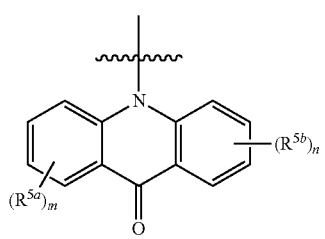
formula (1b-13)
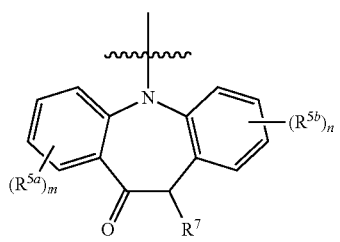
formula (1b-14)
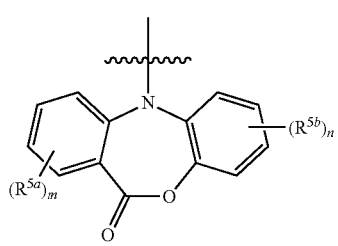
formula (1b-15)
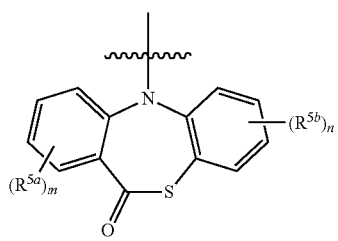
formula (1b-16)
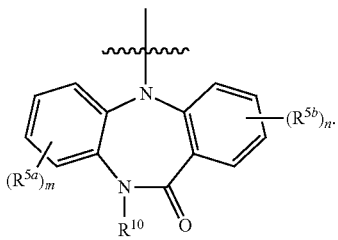
formula (1b-17)
In some preferred embodiments, the group of formula (2) has a structure selected from:
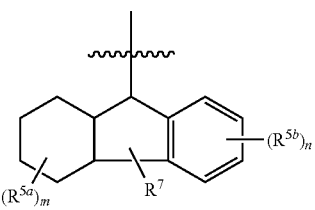
formula (2a-1)
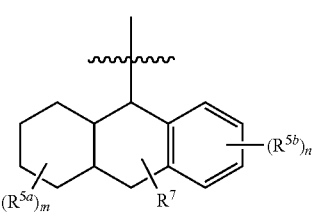
formula (2a-2)
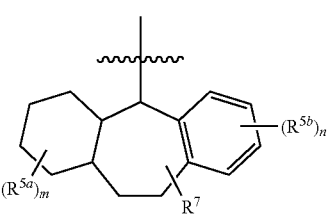
formula (2a-3)
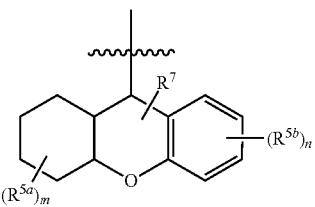
formula (2a-4)
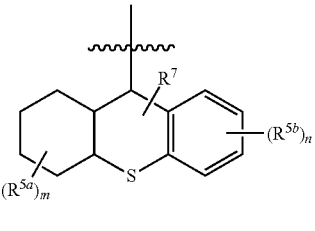
formula (2a-5)
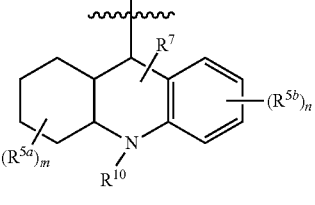
formula (2a-6)
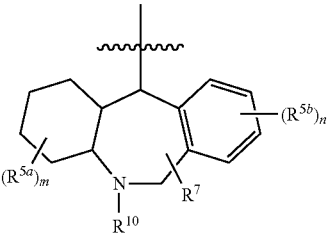
formula (2a-7)

41
-continued
formula (2a-8)
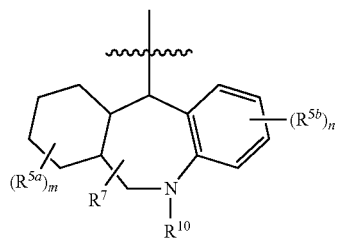
formula (2a-9)
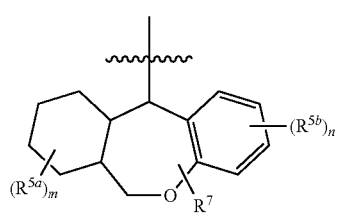
formula (2a-10)
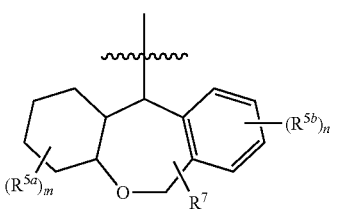
formula (2a-11)
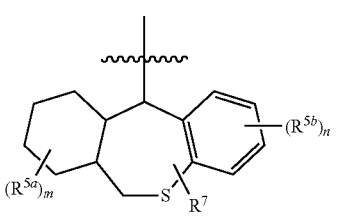
formula (2a-12)
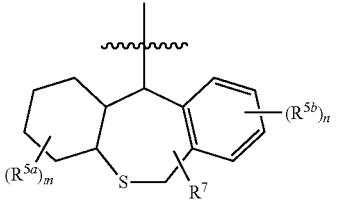
formula (2a-13)
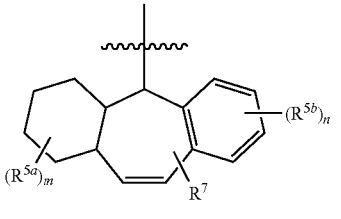
formula (2a-14)
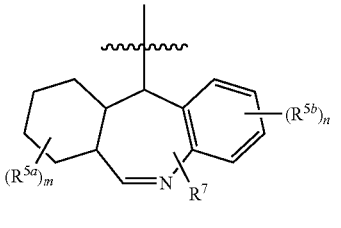
42
-continued
formula (2a-15)
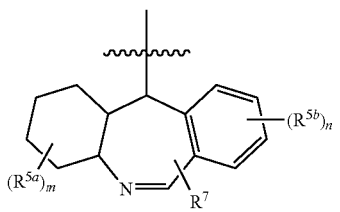
formula (2a-16)
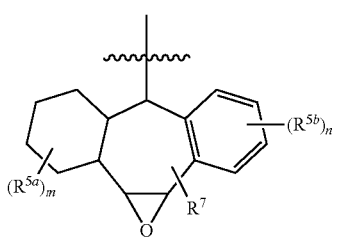
formula (2a-17)
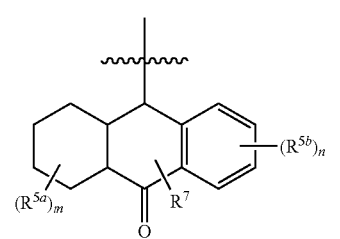
formula (2a-18)
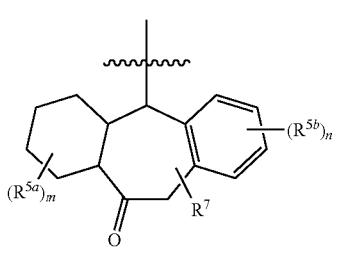
formula (2a-19)
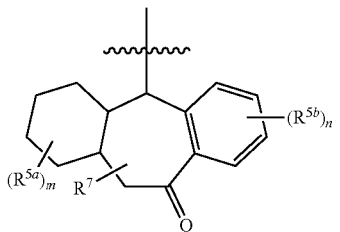
formula (2a-20)
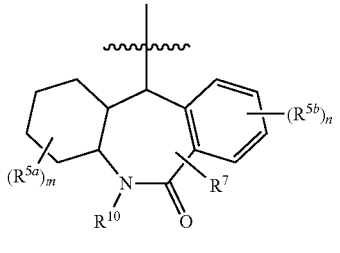

-continued
formula (2a-21)
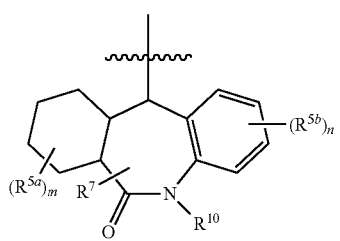
formula (2a-22)
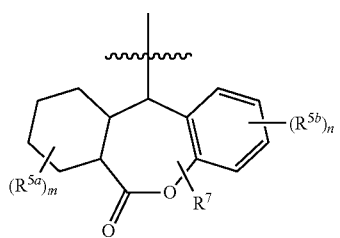
formula (2a-23)
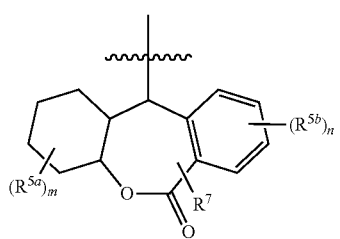
formula (2a-24)
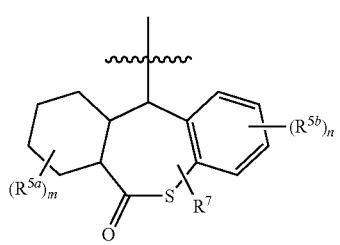
formula (2a-25)
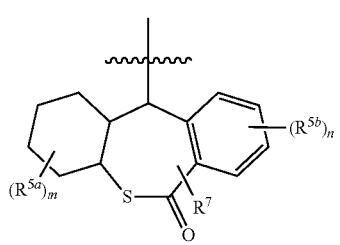
formula (2b-1)
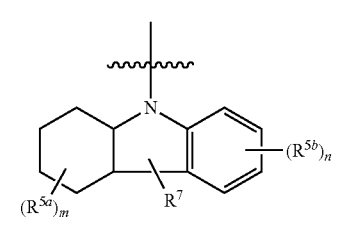
formula (2b-2)
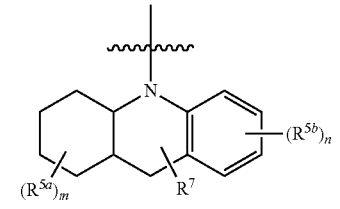
formula (2b-3)
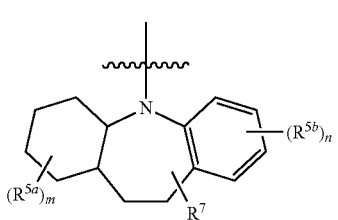
formula (2b-4)
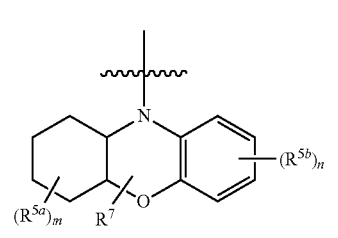
formula (2b-5)
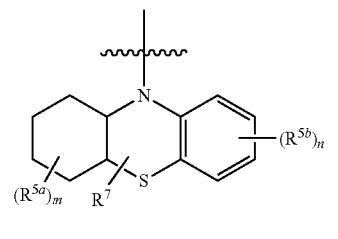
formula (2b-6)
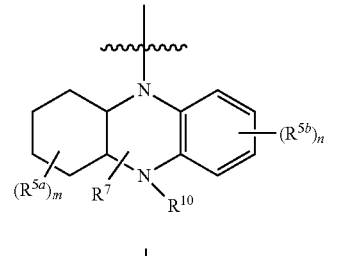
formula (2b-7)
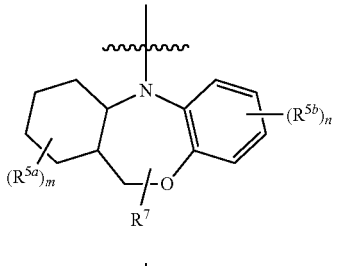
formula (2b-8)
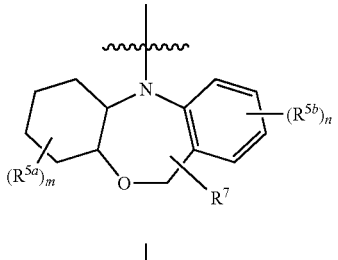
formula (2b-9)
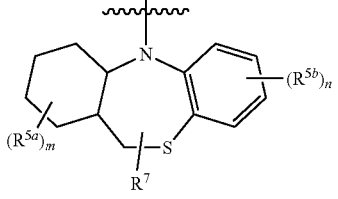

formula (2b-10)
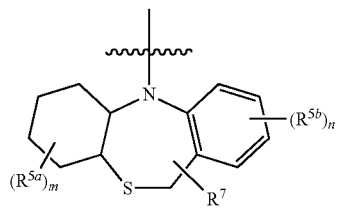
formula (2b-11)
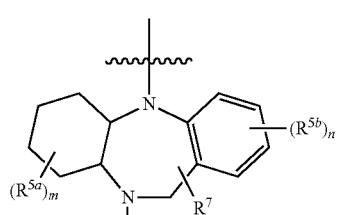
formula (2b-12)
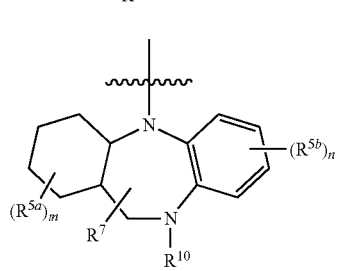
formula (2b-13)
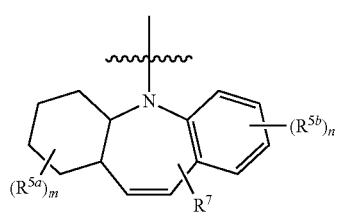
formula (2b-14)
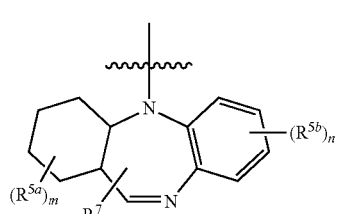
formula (2b-15)
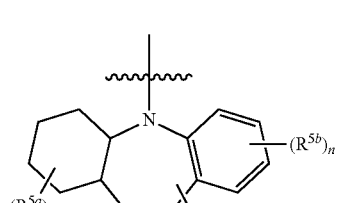
formula (2b-16)
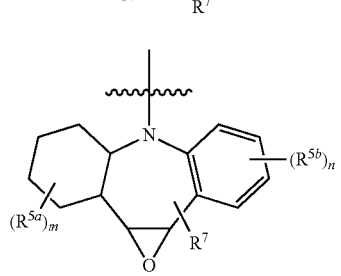
formula (2b-17)
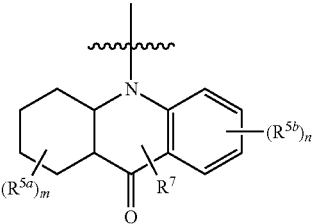
formula (2b-18)
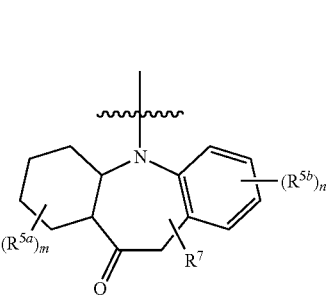
formula (2b-19)
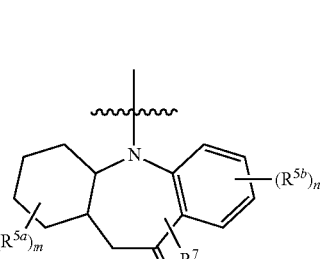
formula (2b-20)
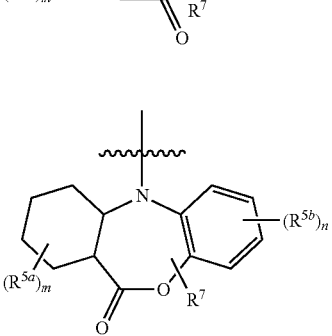
formula (2b-21)
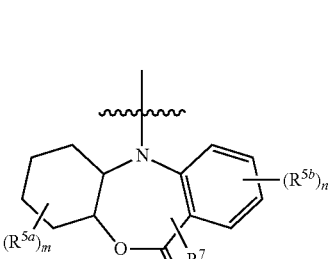
formula (2b-22)
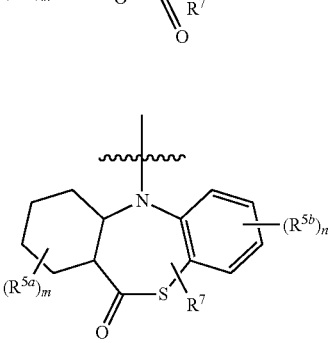

formula (2b-23)
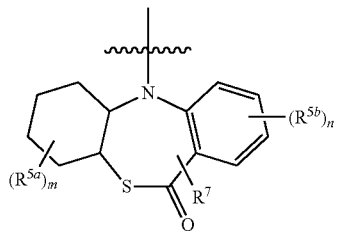
formula (2b-24)
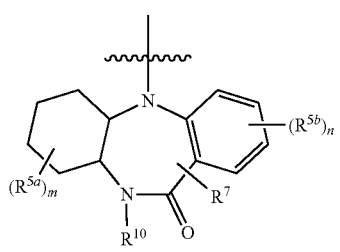
formula (2b-25)
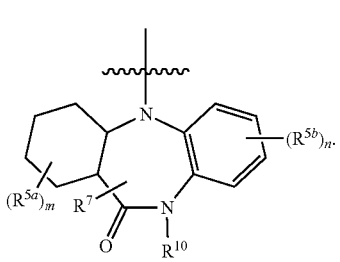
In some preferred embodiments, the group of formula (3) has a structure selected from:
formula (3a-1)
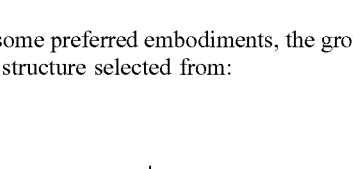
formula (3a-2)
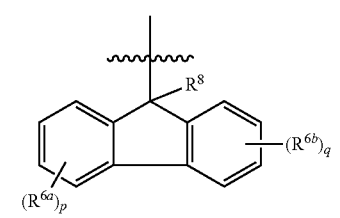
formula (3a-3)
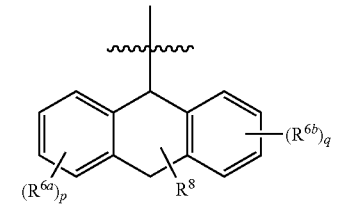
formula (3a-4)
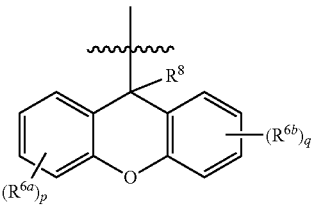
formula (3a-5)
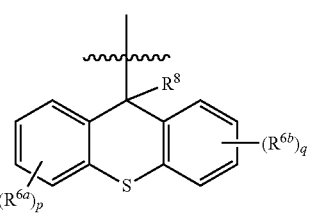
formula (3a-6)
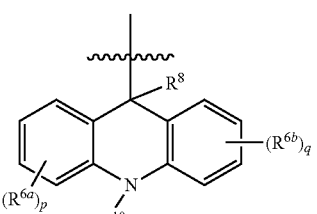
formula (3a-7)
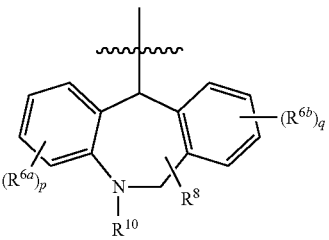
formula (3a-8)
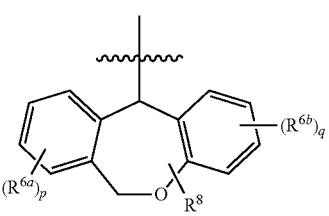
formula (3a-9)
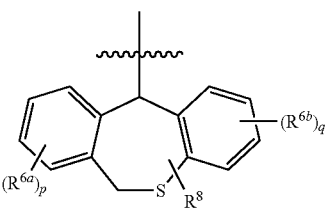
formula (3a-10)
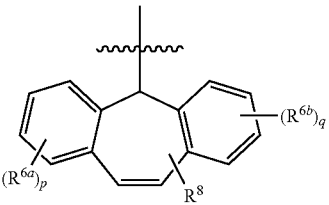

formula (3a-11)
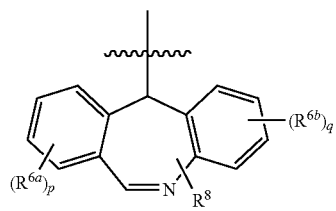
formula (3a-12)
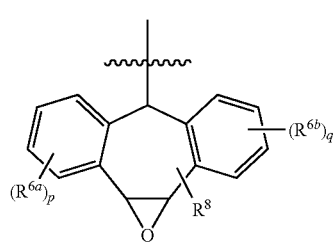
formula (3a-13)
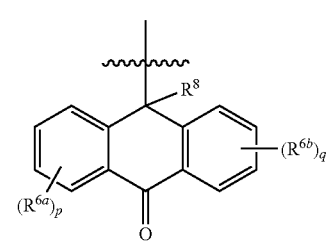
formula (3a-14)
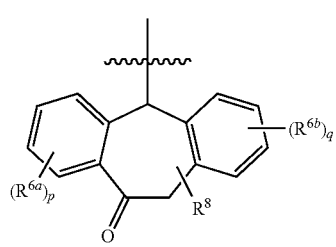
formula (3a-15)
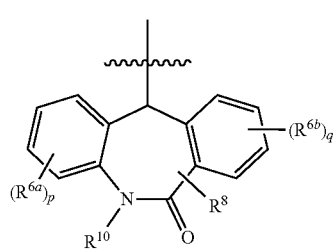
formula (3a-16)
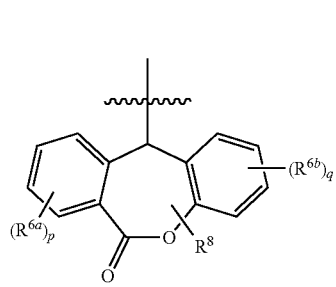
formula (3a-17)
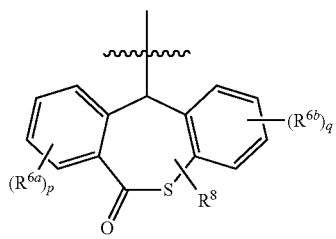
formula (3b-1)
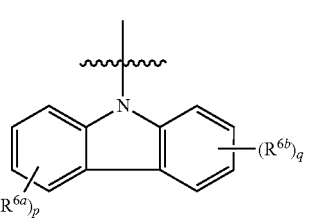
formula (3b-2)
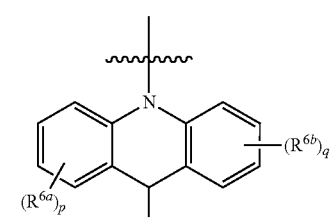
formula (3b-3)
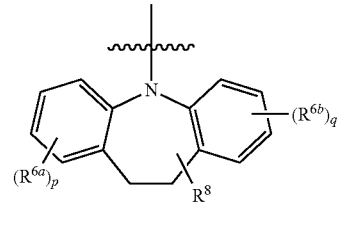
formula (3b-4)
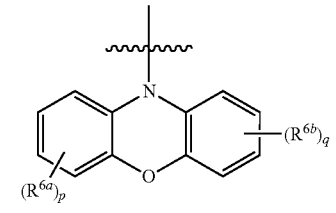
formula (3b-5)
formula (3b-6)
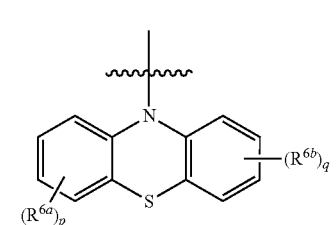

formula (3b-7)
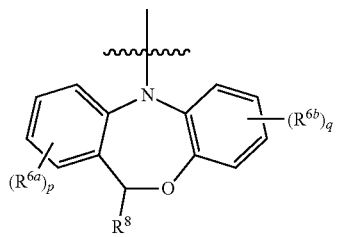
formula (3b-8)
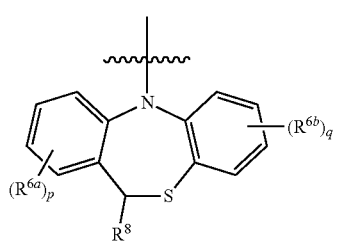
formula (3b-9)
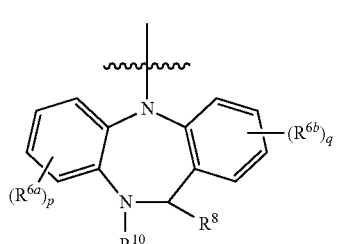
formula (3b-10)
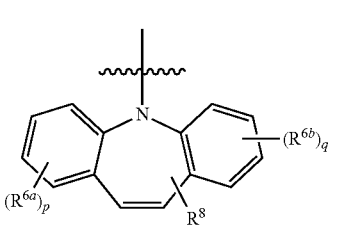
formula (3b-11)
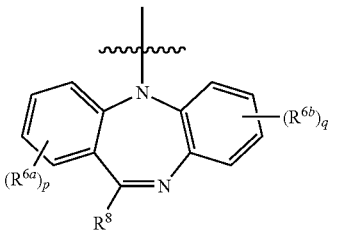
formula (3b-12)
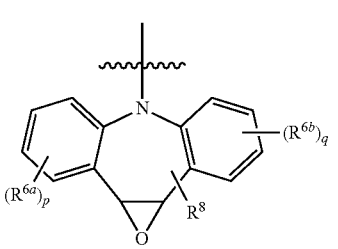
formula (3b-13)
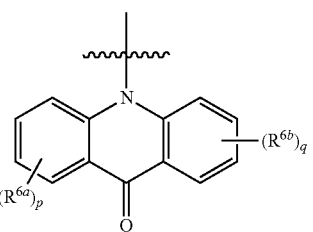
formula (3b-14)
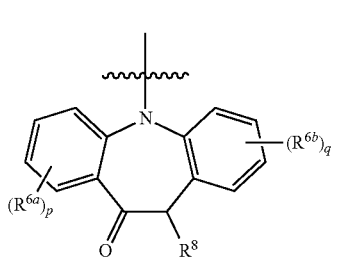
formula (3b-15)
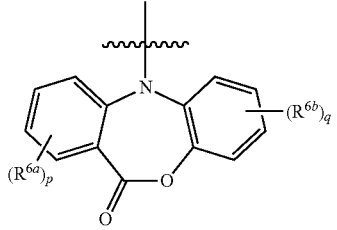
formula (3b-16)
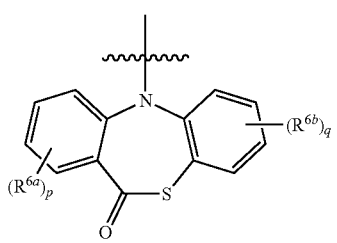
formula (3b-17)
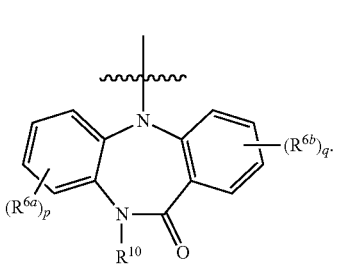
In some preferred embodiments, the group of formula (4) has a structure selected from:
formula (4a-1)
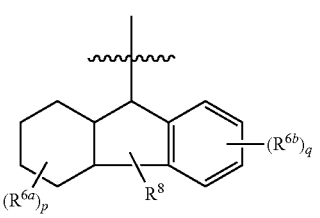

formula (4a-2)
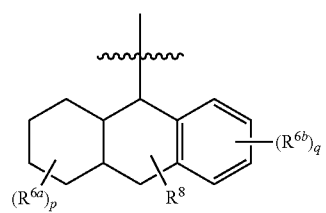
formula (4a-3)
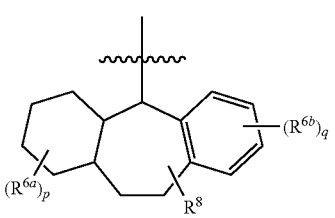
formula (4a-4)
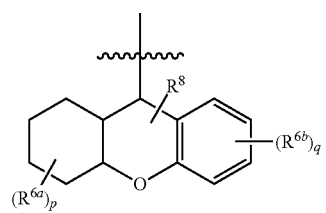
formula (4a-5)
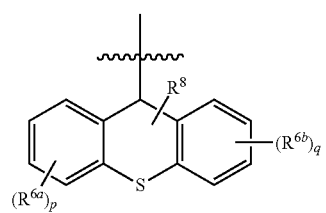
formula (4a-6)
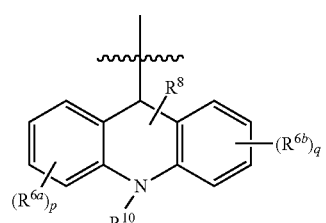
formula (4a-7)
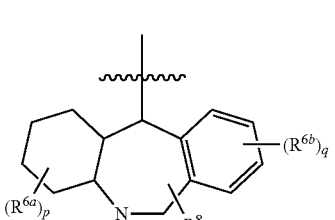
formula (4a-8)
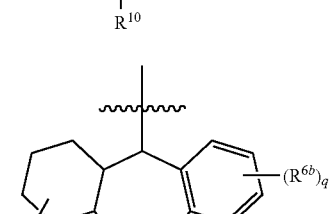
formula (4a-9)
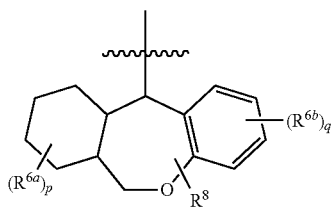
formula (4a-10)
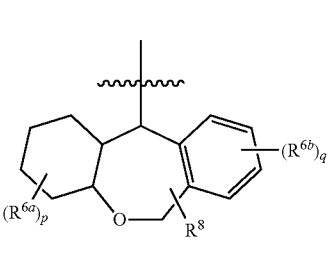
formula (4a-11)
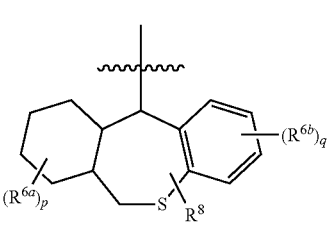
formula (4a-12)
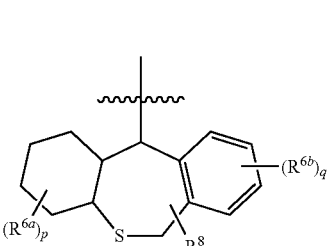
formula (4a-13)
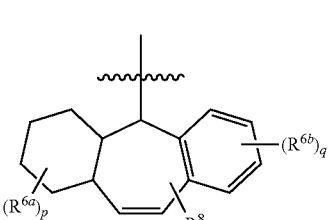
formula (4a-14)
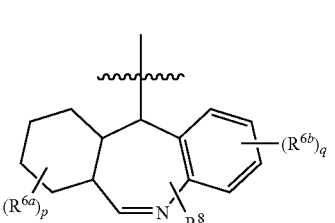
formula (4a-15)
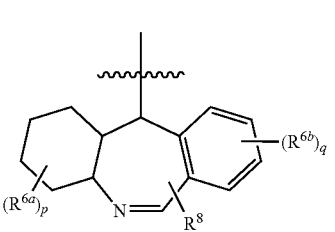

-continued
formula (4a-16)
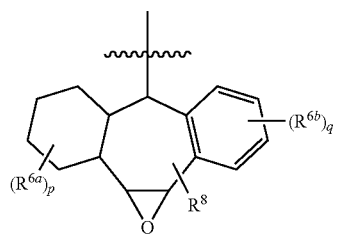
formula (4a-17)
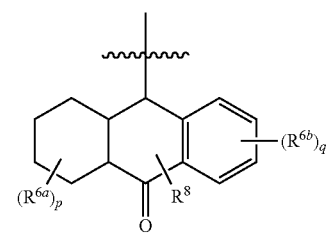
formula (4a-18)
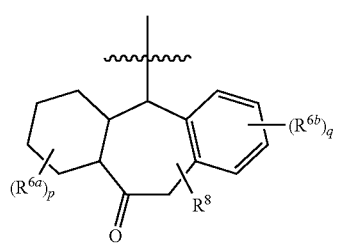
formula (4a-19)
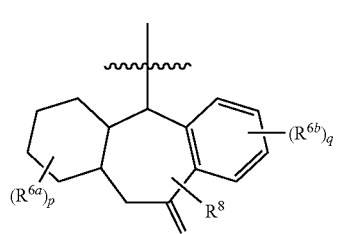
formula (4a-20)
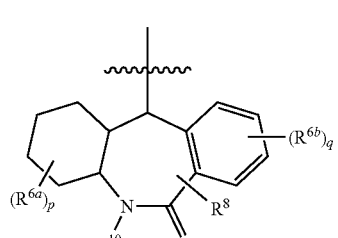
formula (4a-21)
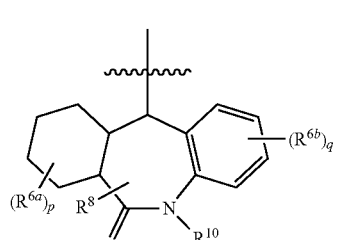
-continued
formula (4a-22)
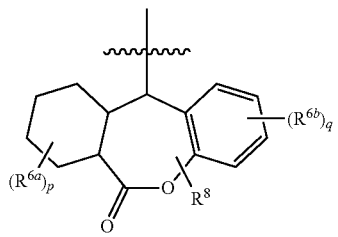
formula (4a-23)
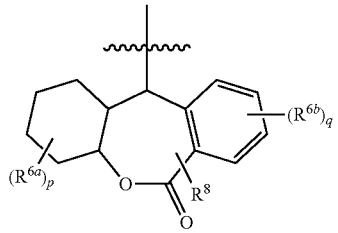
formula (4a-24)
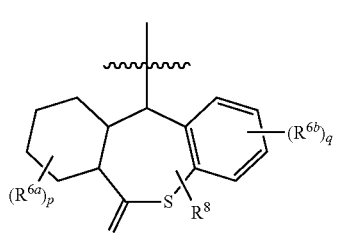
formula (4a-25)
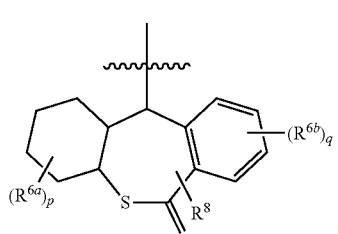
formula (4b-1)
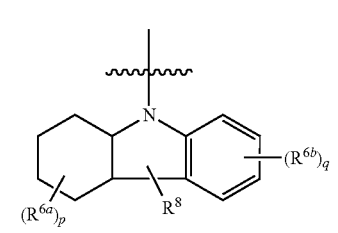
formula (4b-2)
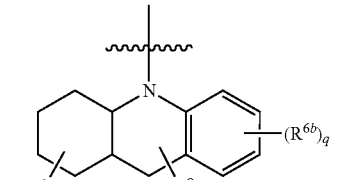
formula (4b-3)
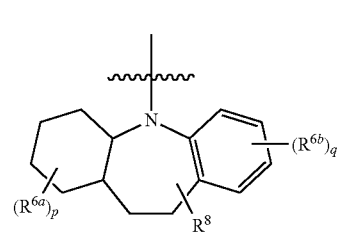

-continued
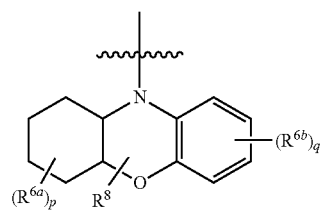
formula (4b-4)
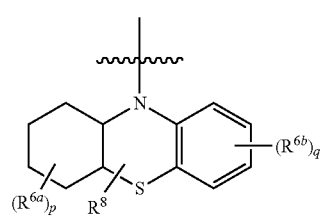
formula (4b-5)
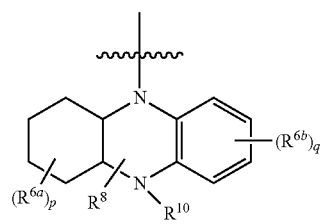
formula (4b-6)
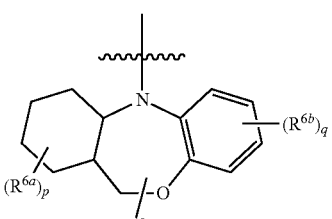
formula (4b-7)
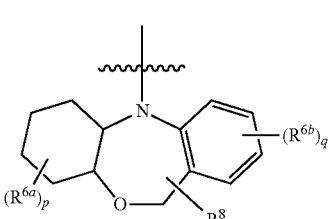
formula (4b-8)
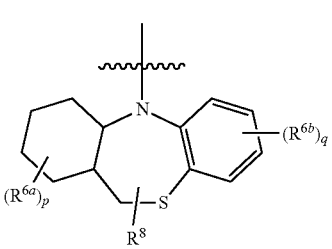
formula (4b-9)
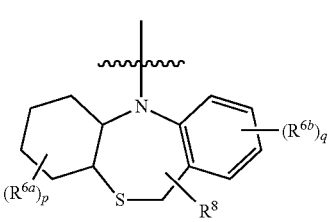
formula (4b-10)
-continued
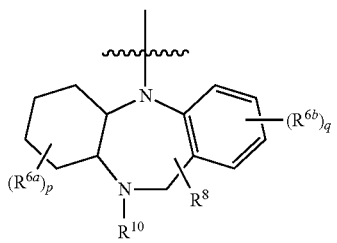
formula (4b-11)
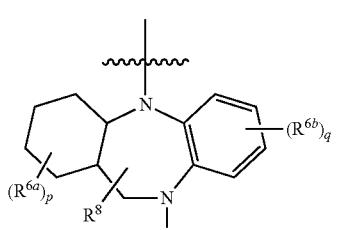
formula (4b-12)
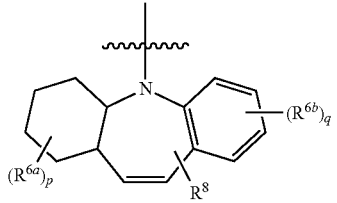
formula (4b-13)
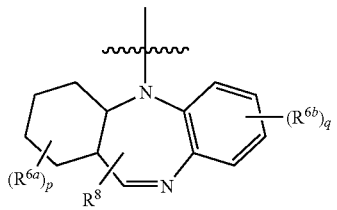
formula (4b-14)
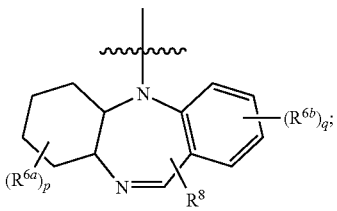
formula (4b-15)
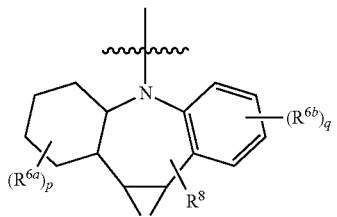
formula (4b-16)
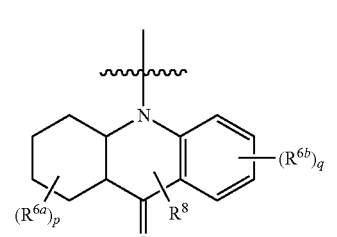
formula (4b-17)

formula (4b-18)
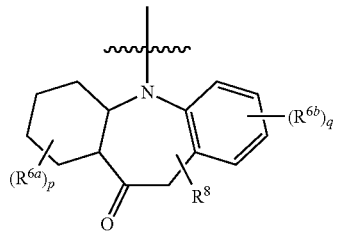
formula (4b-19)
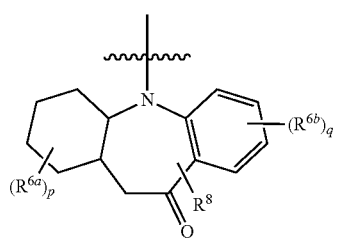
formula (4b-20)
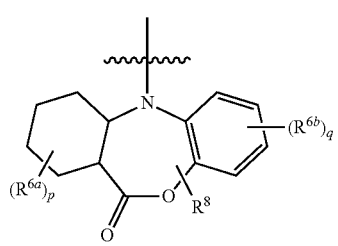
formula (4b-21)
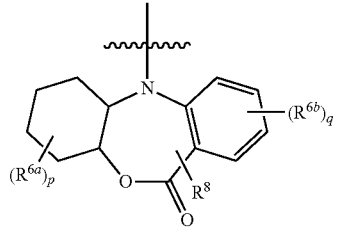
formula (4b-22)
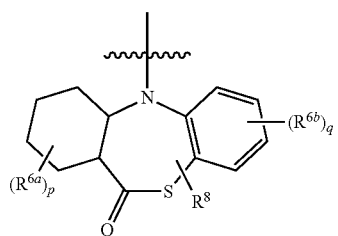
formula (4b-23)
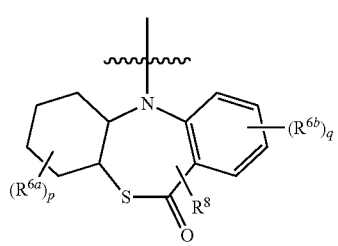
formula (4b-24)
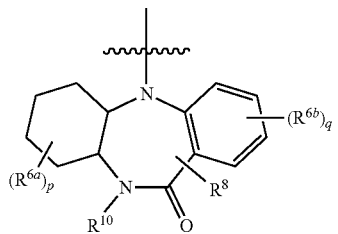
formula (4b-25)
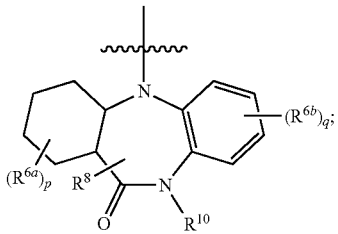
wherein $R^{5a}$, $R^{5b}$, $R^{6a}$, $R^{6b}$, $R^7$, $R^8$, $R^{10}$, m, n, p and q, at each occurrence, are each independently as defined in any of the embodiments described above.
Preferably, the group of formula (1) and the group of formula (3) each have a structure selected from
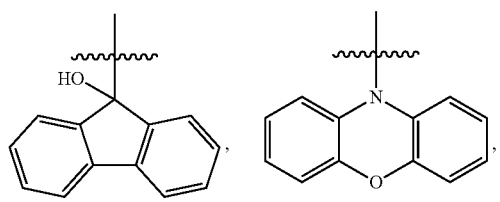
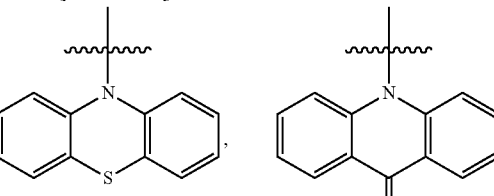

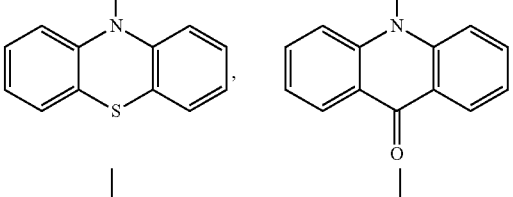

-continued
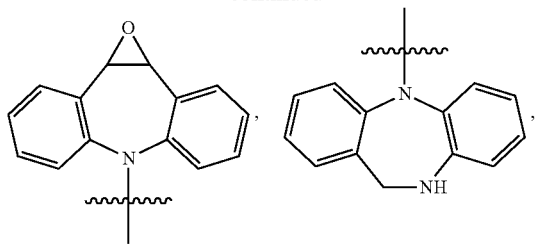
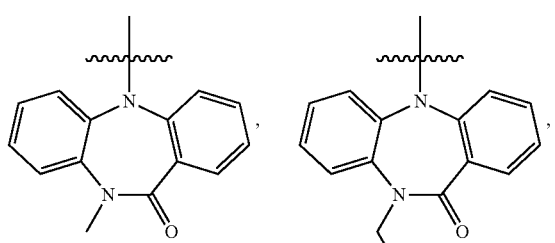
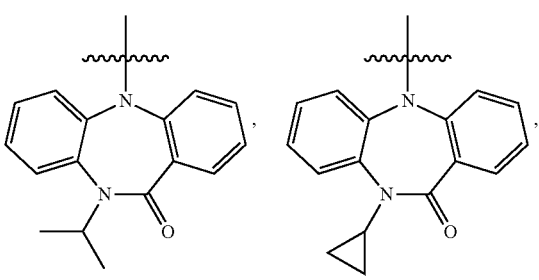
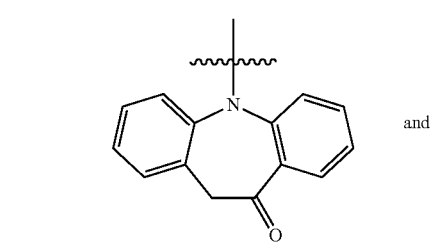
and
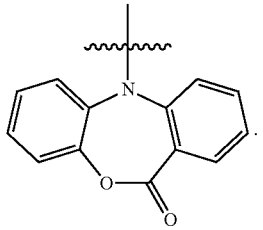
Preferably, the group of formula (2) and the group of formula (4) each have a structure selected from
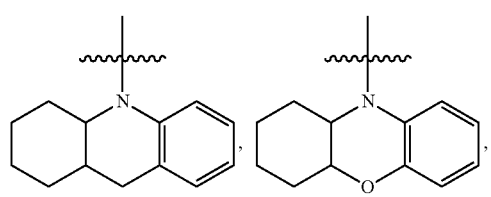
-continued
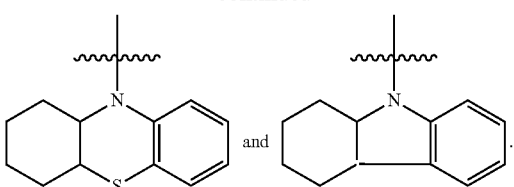
and
In other preferred embodiments, the group of formula (1) has a structure selected from
formula (1a-18)
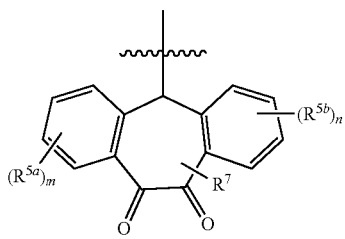
formula (1a-19)
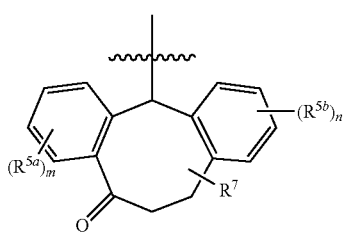
formula (1a-20)
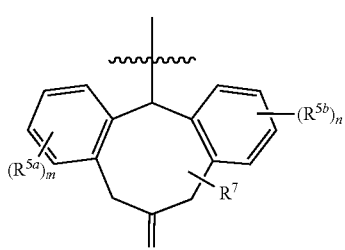
formula (1a-21)
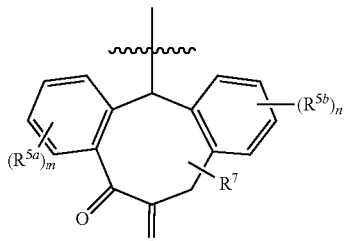
formula (1a-22)
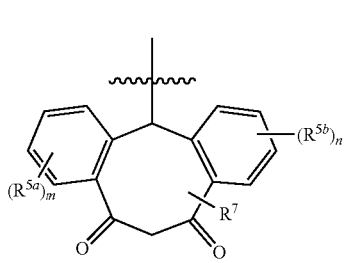

-continued
formula (1b-18)
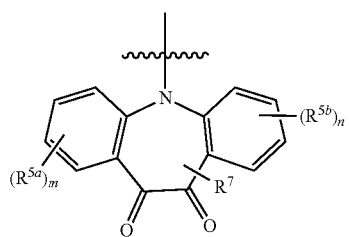
formula (1b-19)
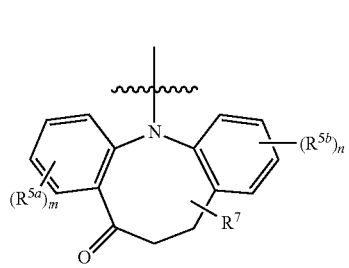
formula (1b-20)
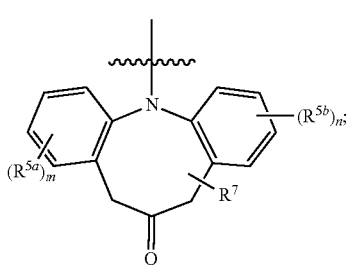
formula (1b-21)
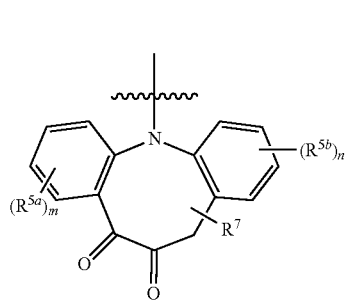
formula (1b-22)
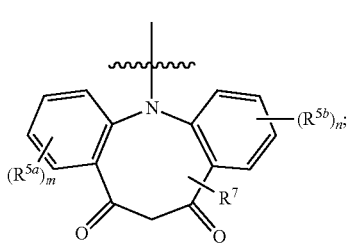
in other preferred embodiments, the group of formula (2) has a structure selected from
formula (2a-26)
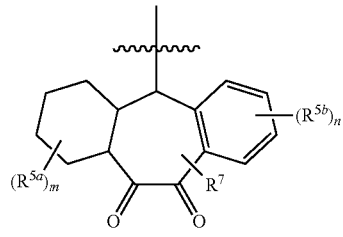
formula (2a-27)
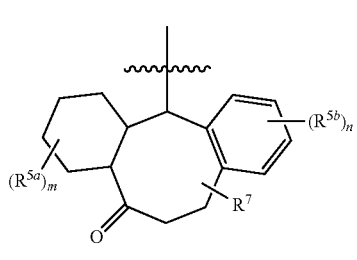
formula (2a-28)
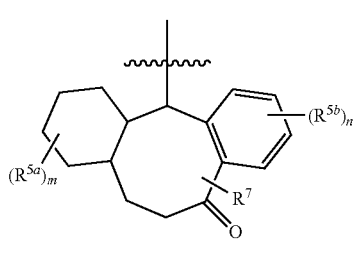
formula (2a-29)
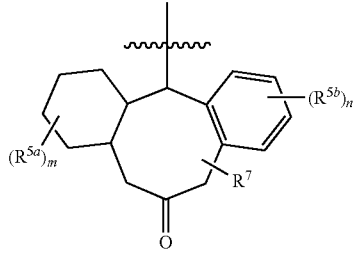
formula (2a-30)
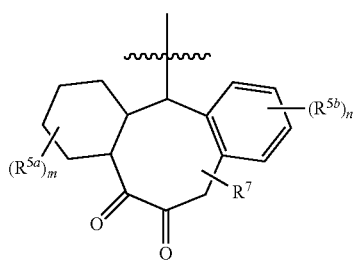
formula (2a-31)
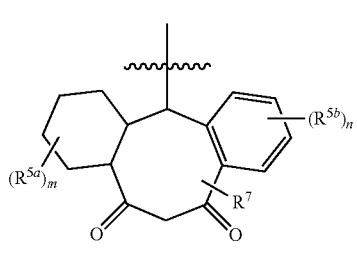

formula (2a-32)
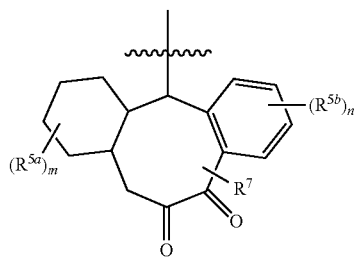
formula (2b-26)
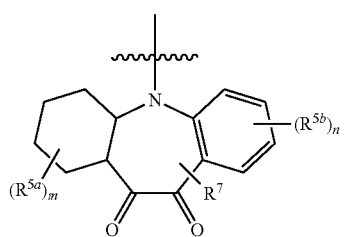
formula (2b-27)
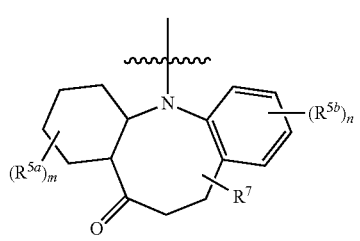
formula (2b-28)
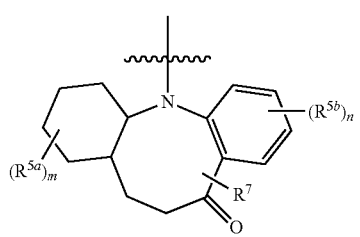
formula (2b-29)
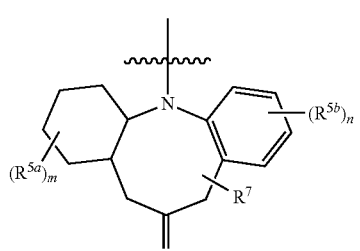
formula (2b-30)
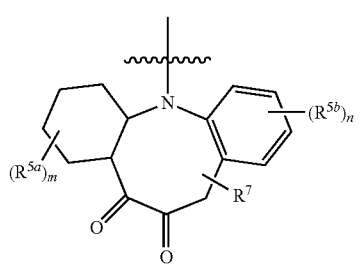
formula (2b-31)
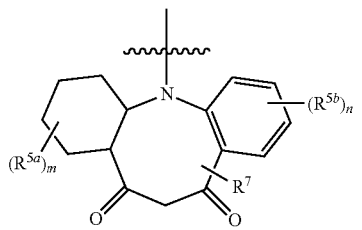
formula (2b-32)
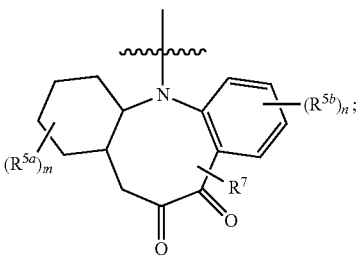
in other preferred embodiments, the group of formula (3) has a structure selected from
formula (3a-18)
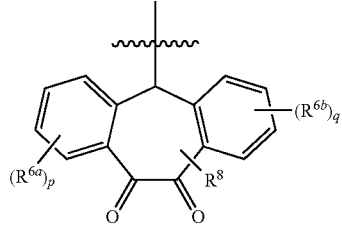
formula (3a-19)
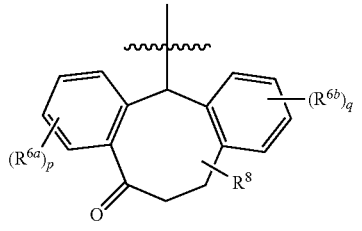
formula (3a-20)
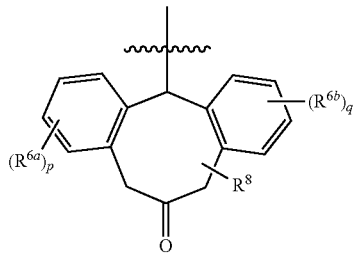
formula (3a-21)
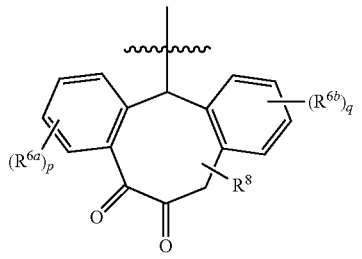

formula (3a-22)
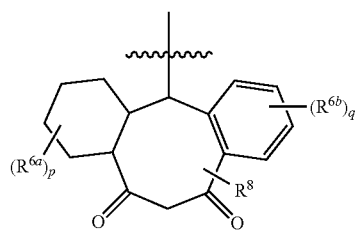
formula (3b-18)
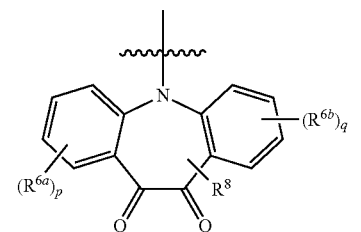
formula (3b-19)
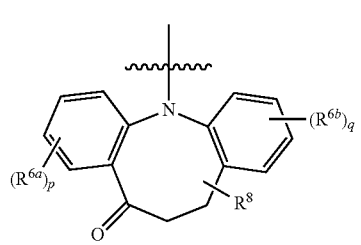
formula (3b-20)
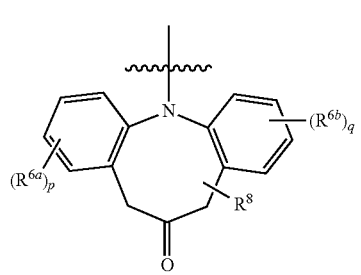
formula (3b-21)
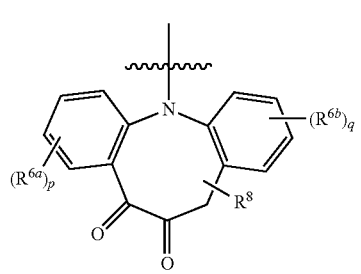
formula (3b-22)
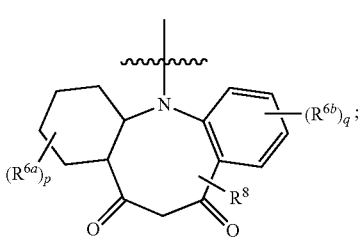
in other preferred embodiments, the group of formula (4) has a structure selected from
formula (4a-26)
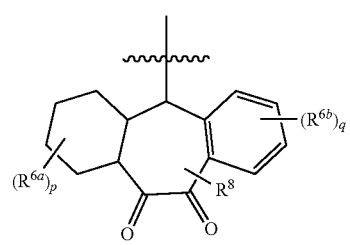
formula (4a-27)
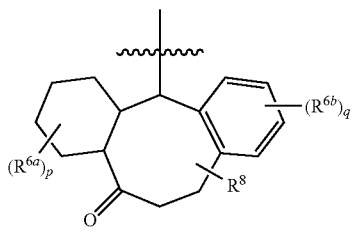
formula (4a-28)
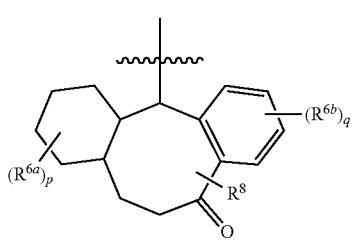
formula (4a-29)
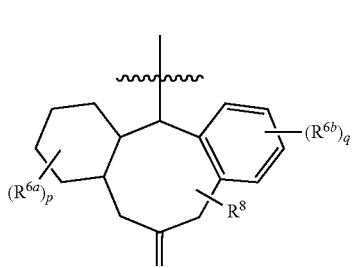
formula (4a-30)
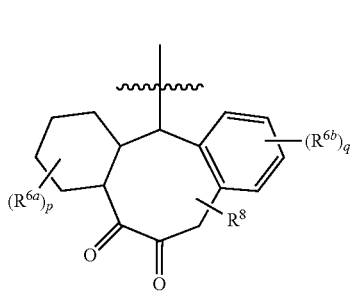
formula (4a-31)
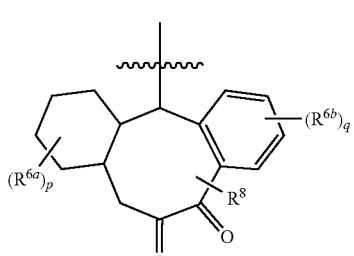

formula (4a-32)

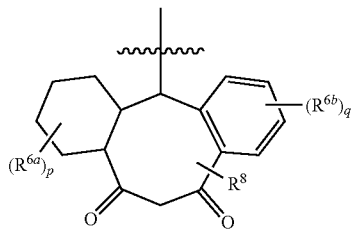

formula (4b-26)

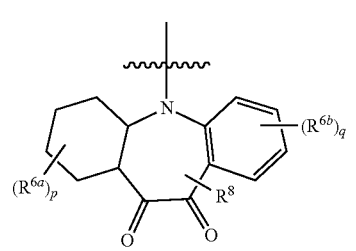

formula (4b-27)

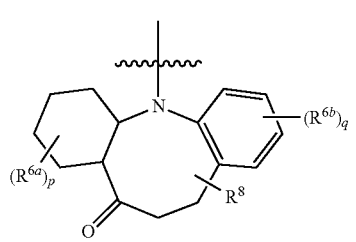

formula (4b-28)

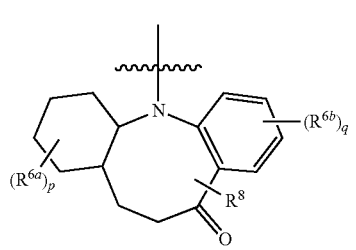

formula (4b-29)

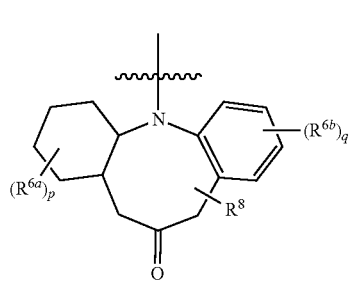

formula (4b-30)

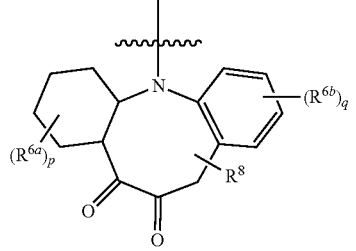

formula (4b-31)

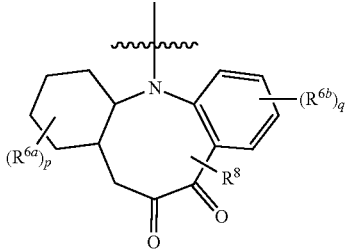

formula (4b-32)

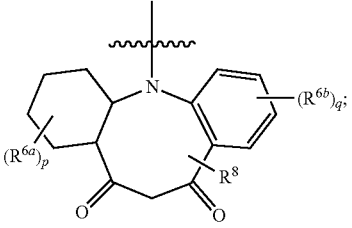

wherein $R^{5a}$, $R^{5b}$, $R^{6a}$, $R^{6b}$, $R^7$, $R^8$, m, n, p and q, at each occurrence, are each independently as defined in any of the embodiments described above;

preferably, the group of formula (1) and the group of formula (3) each have a structure selected from

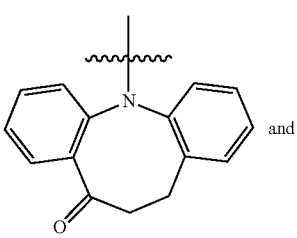

and

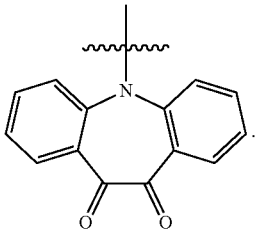

.

In other preferred embodiments, the fused ring system $Q^1$ with the structure of formula (a) is a group having a structure of formula (5):

formula (5)

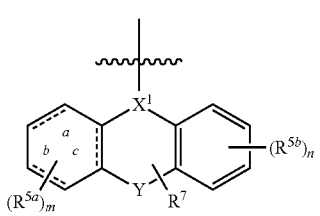

wherein, one or two of the bonds "-----" identified by a, b, and c represent a double bond, and the rest represent a single bond.

In other preferred embodiments, the fused ring system $Q^2$ with the structure of formula (b) is a group having a structure of formula (6):

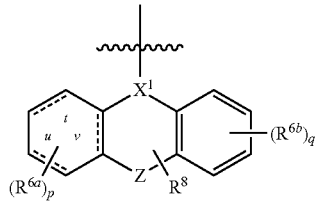

formula (6)

wherein, one or two of the bonds "-----" identified by t, u and v represent a double bond, and the rest represent a single bond.

In some further preferred embodiments, the group with the structure of formula (5) is a group having a structure of formula (7):

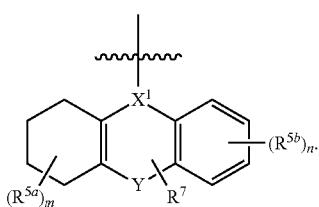

formula (7)

In some further preferred embodiments, the group with the structure of formula (6) is a group having a structure of formula (8):

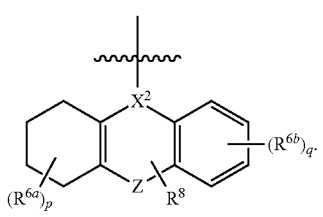

formula (8)

In some of the above-described embodiments for formula (5), formula (6), formula (7), and formula (8), Y and Z, at each occurrence, are each independently selected from the group consisting of a single bond; $NR^{10}$; O; S; and methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo, particularly from the group consisting of F, Cl, $C_{1-4}$ alkyl-O— (such as $CH_3$—O—), epoxy and oxo.

In some more preferred embodiments, the group of formula (7) has a structure selected from

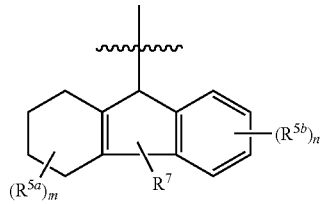

formula (7a-1)

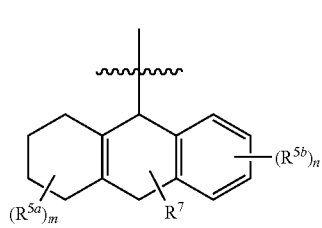

formula (7a-2)

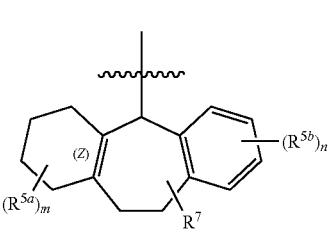

formula (7a-3)

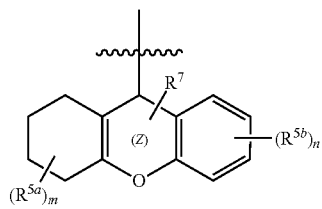

formula (7a-4)

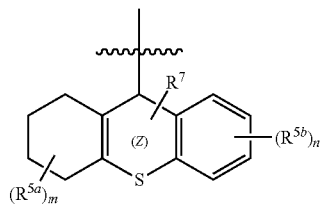

formula (7a-5)

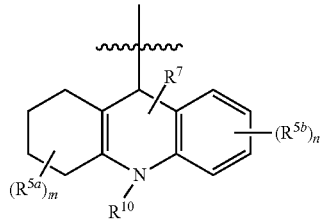

formula (7a-6)

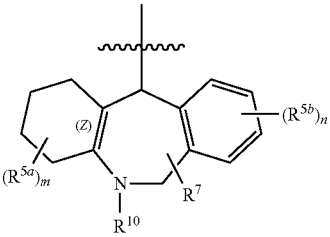

formula (7a-7)

formula (7a-8)
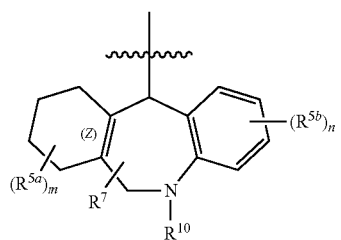
formula (7a-9)
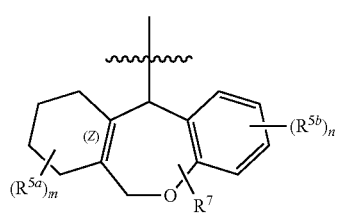
formula (7a-10)
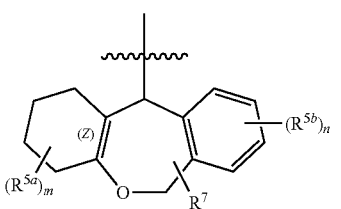
formula (7a-11)
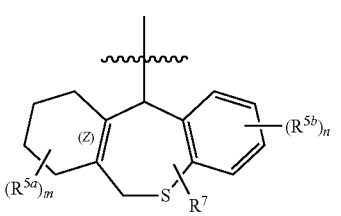
formula (7a-12)
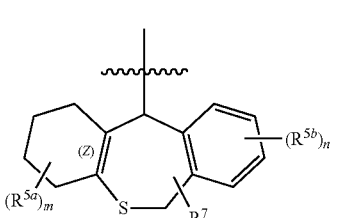
formula (7a-13)
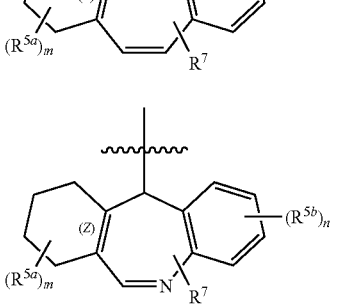
formula (7a-14)
formula (7a-15)
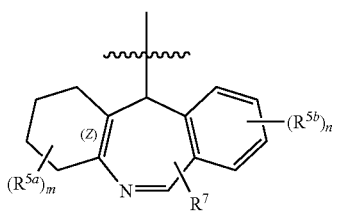
formula (7a-16)
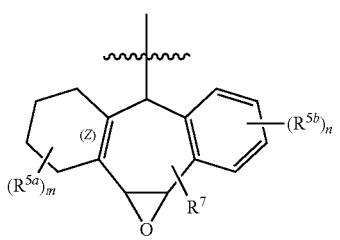
formula (7a-17)
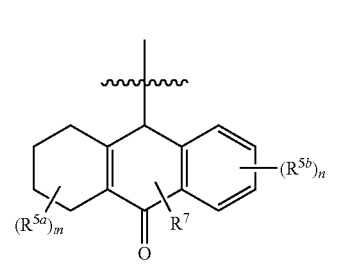
formula (7a-18)
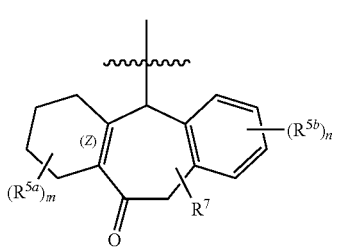
formula (7a-19)
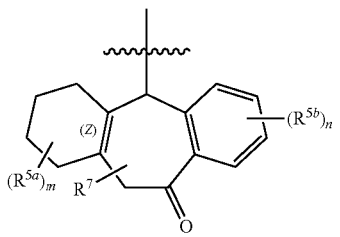
formula (7a-20)
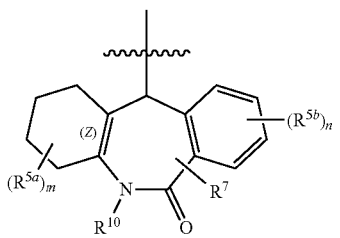

formula (7a-21)
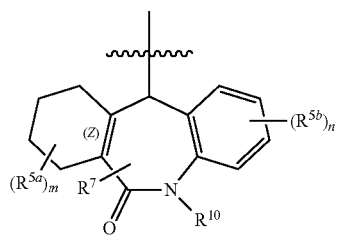
formula (7a-22)
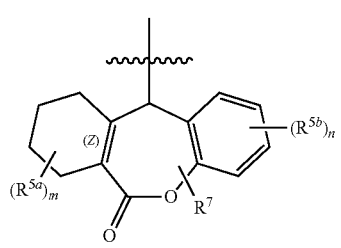
formula (7a-23)
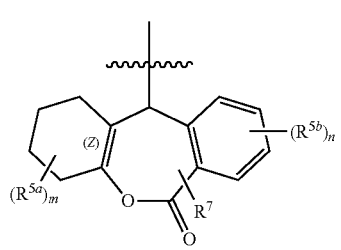
formula (7a-24)
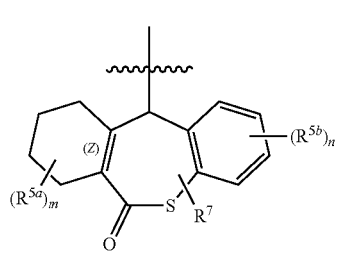
formula (7a-25)
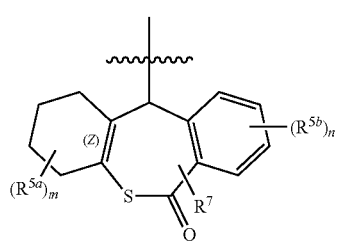
formula (7a-26)
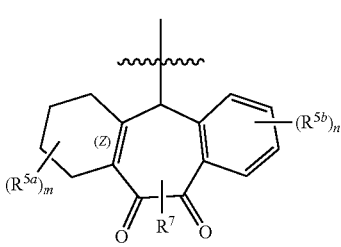
formula (7a-27)
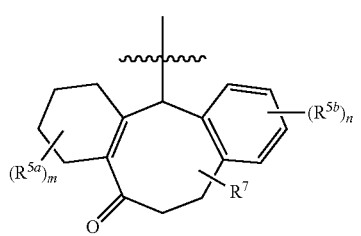
formula (7a-28)
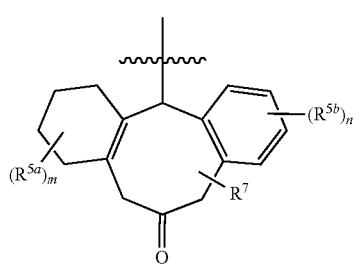
formula (7a-29)
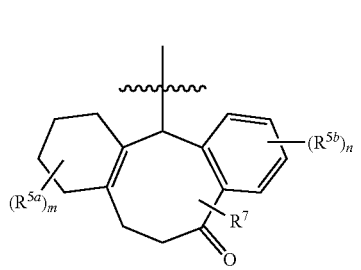
formula (7a-30)
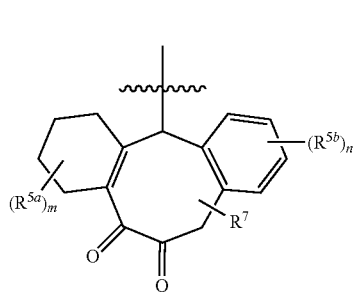
formula (7a-31)
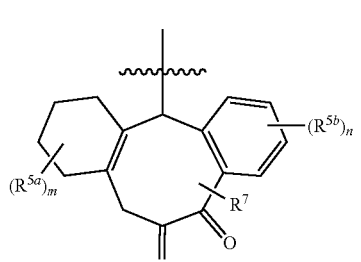
formula (7a-32)
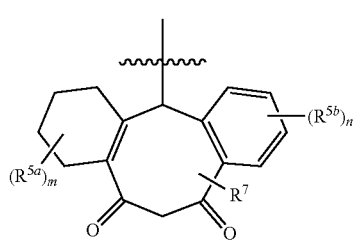

-continued
formula (7b-1)
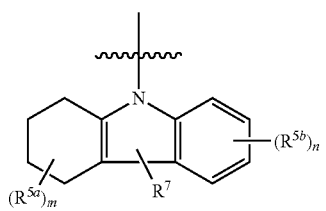
formula (7b-2)
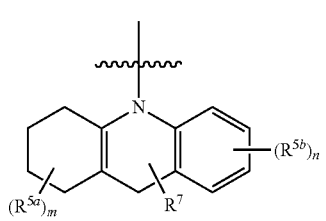
formula (7b-3)
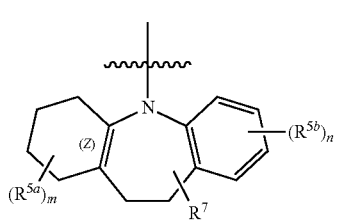
formula (7b-4)
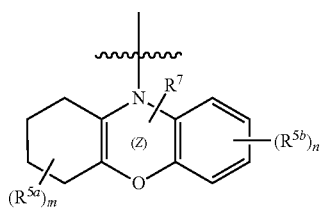
formula (7b-5)
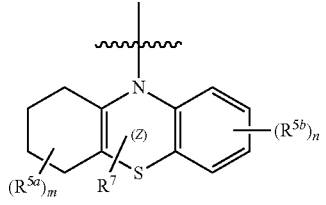
formula (7b-6)
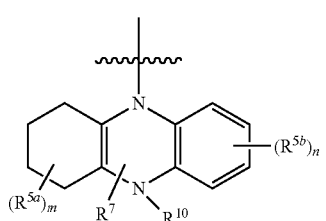
formula (7b-7)
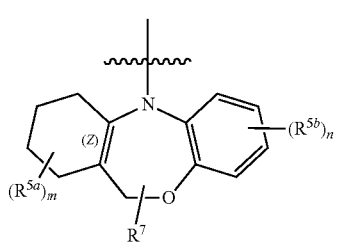
-continued
formula (7b-8)
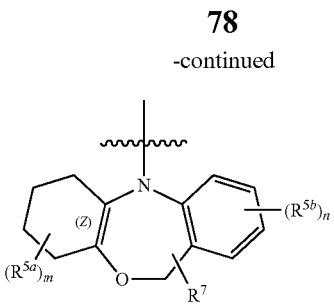
formula (7b-9)
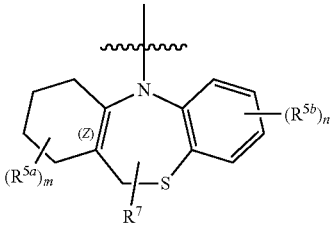
formula (7b-10)
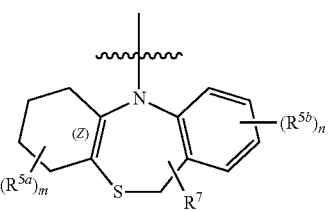
formula (7b-11)
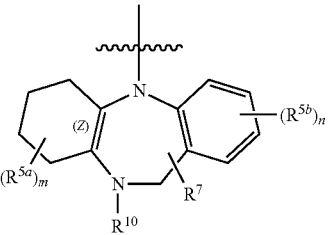
formula (7b-12)
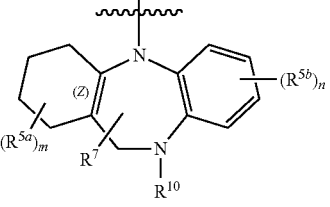
formula (7b-13)
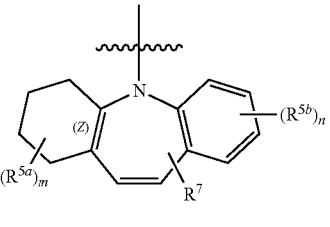
formula (7b-14)
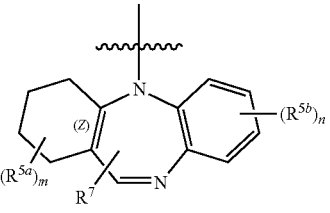

-continued
formula (7b-15)
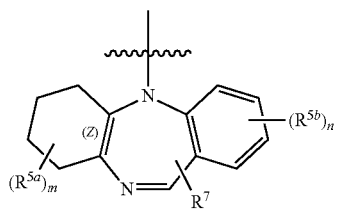
formula (7b-16)
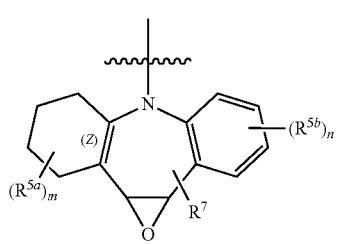
formula (7b-17)
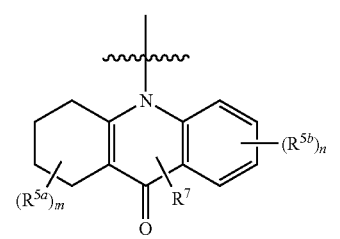
formula (7b-18)
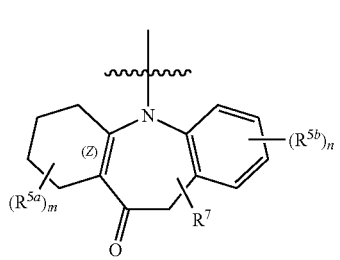
formula (7b-19)
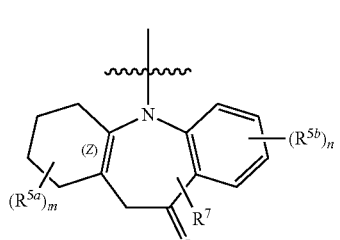
formula (7b-20)
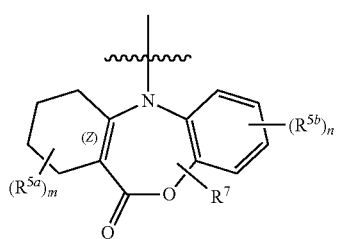
formula (7b-21)
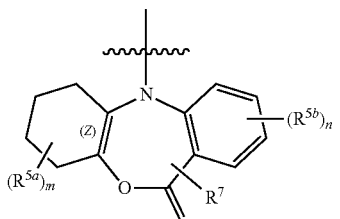
formula (7b-22)
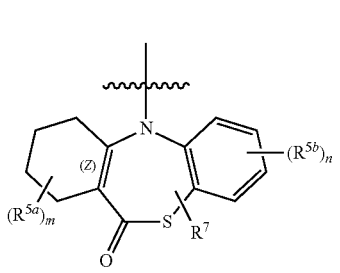
formula (7b-23)
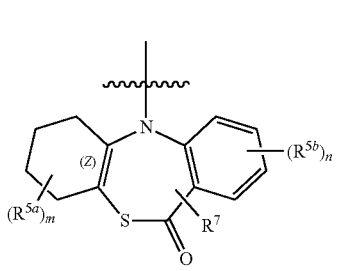
formula (7b-24)
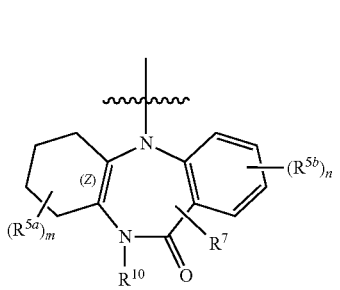
formula (7b-25)
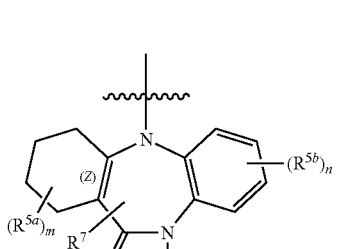
formula (7b-26)
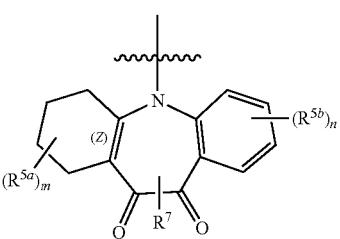

formula (7b-27)
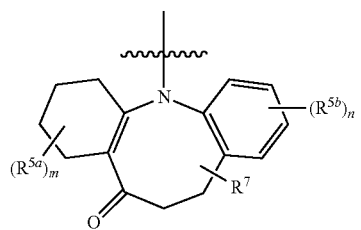
formula (7b-28)
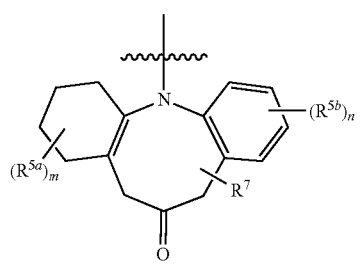
formula (7b-29)
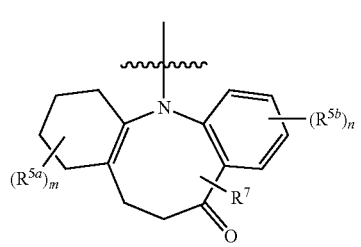
formula (7b-30)
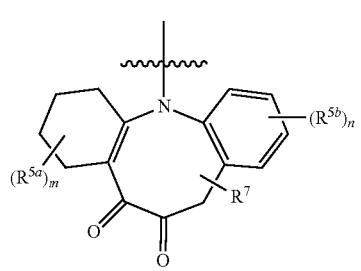
formula (7b-31)
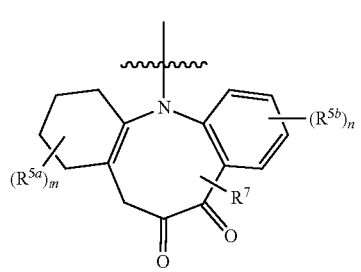
formula (7b-32)
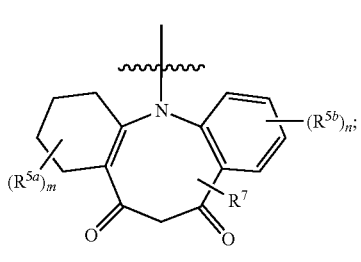
in some more preferred embodiments, the group of formula (8) has a structure selected from:
formula (8a-1)
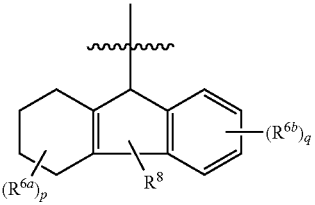
formula (8a-2)
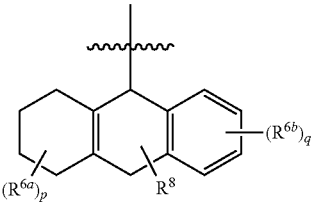
formula (8a-3)
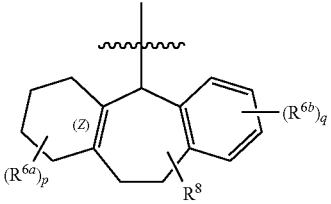
formula (8a-4)
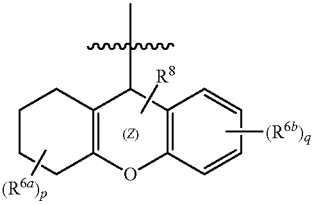
formula (8a-5)
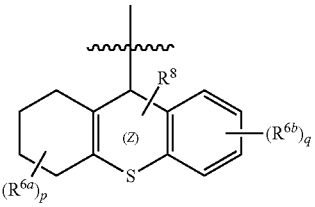
formula (8a-6)
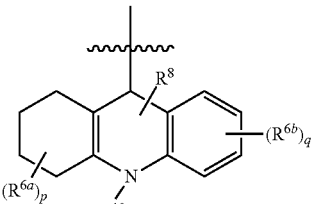
formula (8a-7)
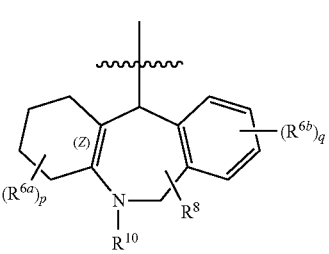

formula (8a-8)
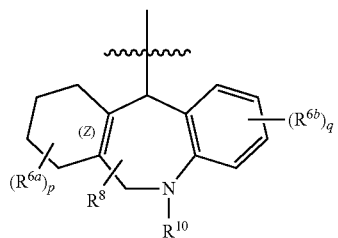
formula (8a-9)
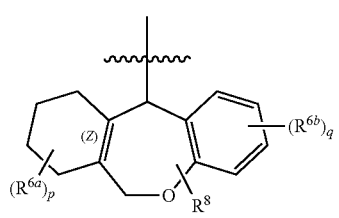
formula (8a-10)
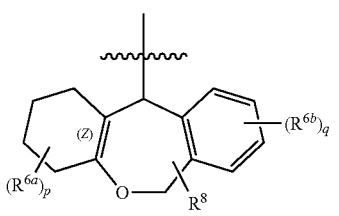
formula (8a-11)
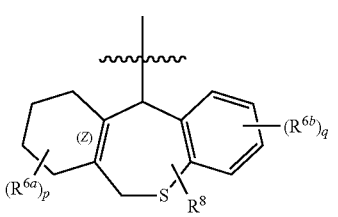
formula (8a-12)
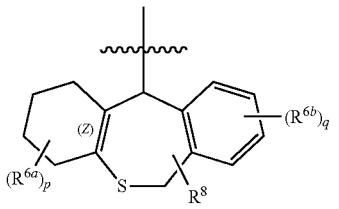
formula (8a-13)

formula (8a-14)
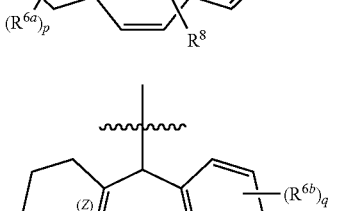
formula (8a-15)
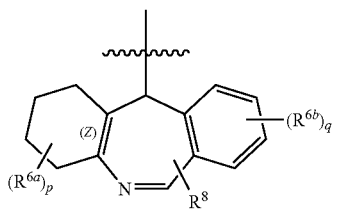
formula (8a-16)
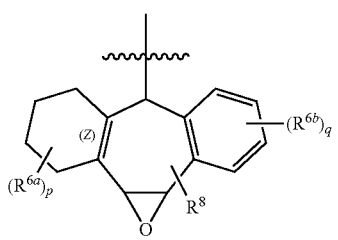
formula (8a-17)
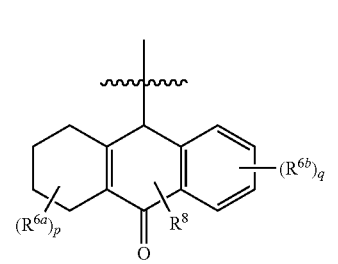
formula (8a-18)
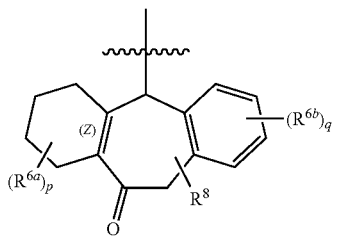
formula (8a-19)
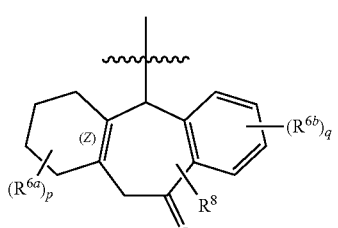
formula (8a-20)
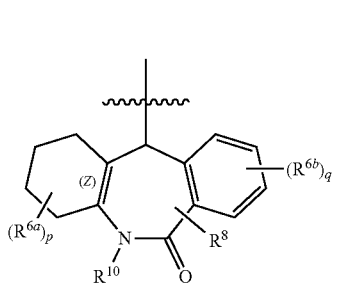

formula (8a-21)
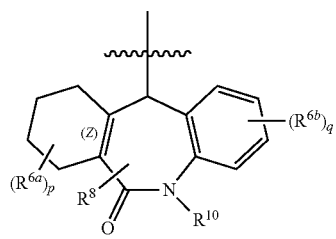
formula (8a-22)
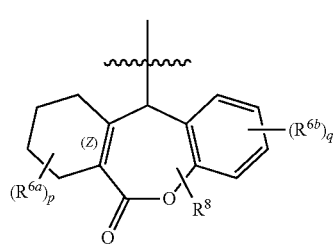
formula (8a-23)
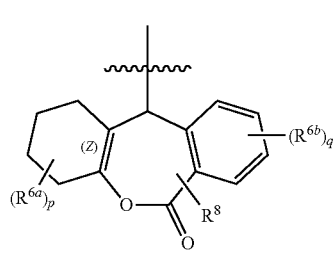
formula (8a-24)
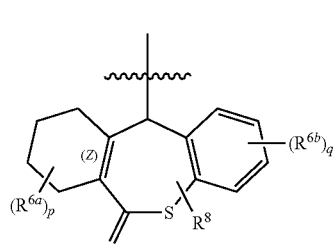
formula (8a-25)
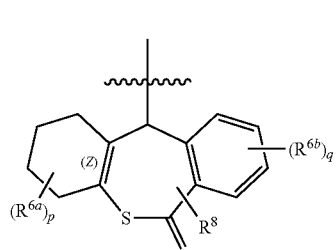
formula (8a-26)
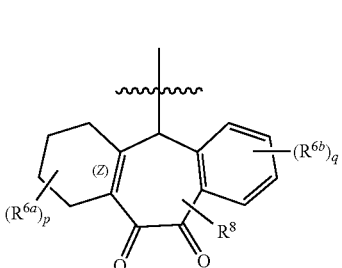
formula (8a-27)
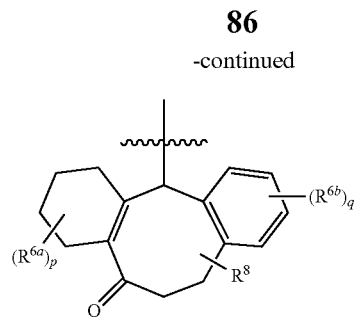
formula (8a-28)
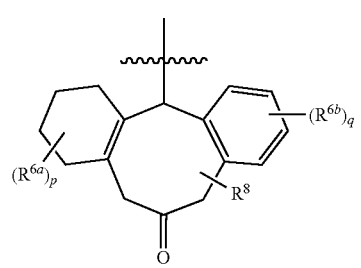
formula (8a-29)
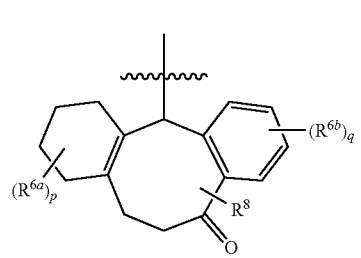
formula (8a-30)
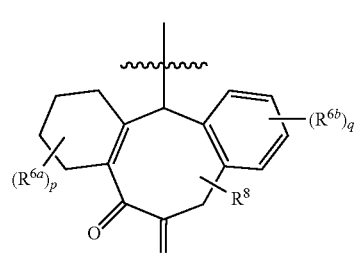
formula (8a-31)
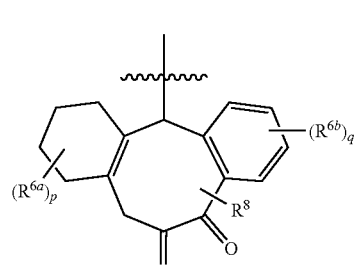
formula (8a-32)
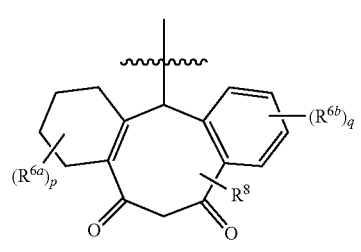

formula (8b-1)

formula (8b-2)

formula (8b-3)

formula (8b-4)

formula (8b-5)

formula (8b-6)

formula (8b-7)

formula (8b-8)

formula (8b-9)

formula (8b-10)

formula (8b-11)

formula (8b-12)

formula (8b-13)

formula (8b-14)

-continued
formula (8b-15)
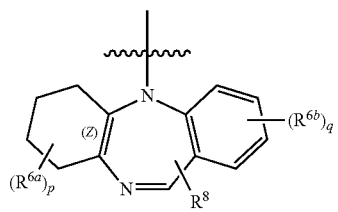
formula (8b-16)
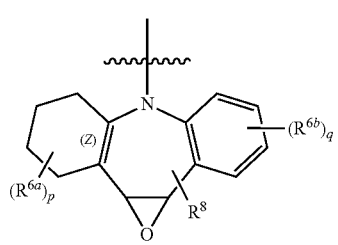
formula (8b-17)
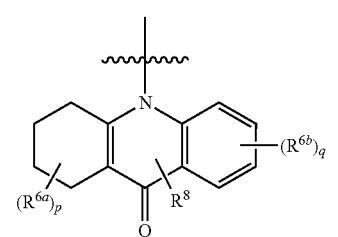
formula (8b-18)
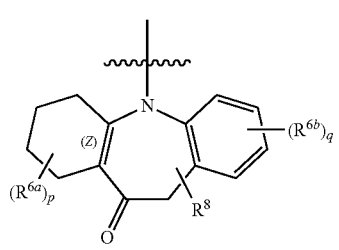
formula (8b-19)
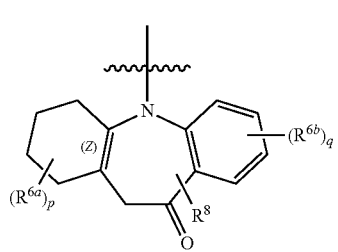
formula (8b-20)
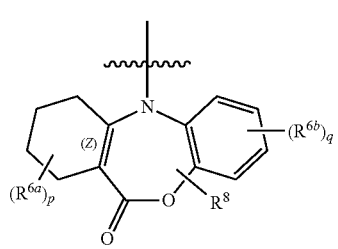
-continued
formula (8b-21)
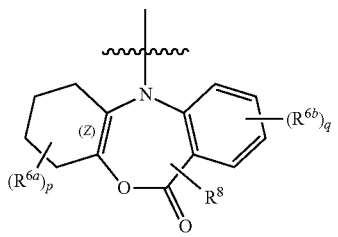
formula (8b-22)
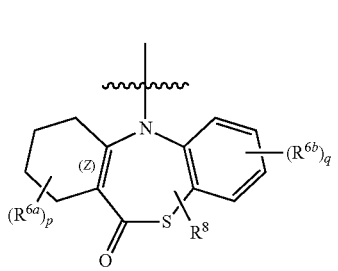
formula (8b-23)
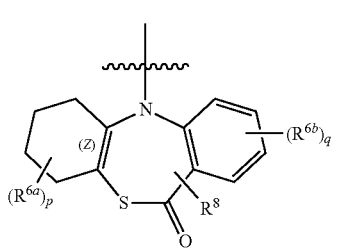
formula (8b-24)
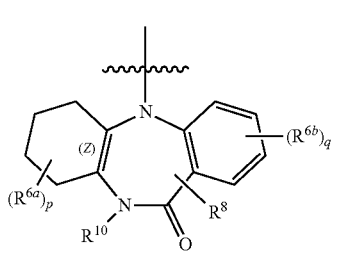
formula (8b-25)
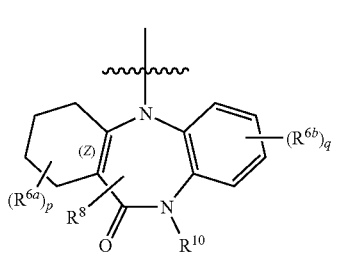
formula (8b-26)
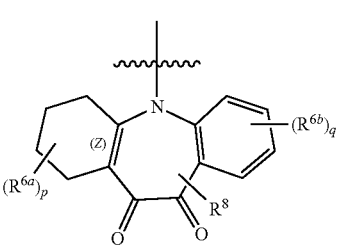

-continued formula (8b-27)
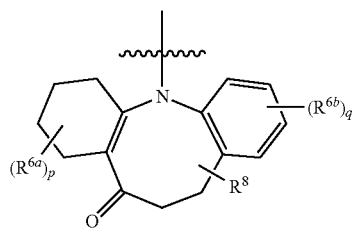

formula (8b-28)
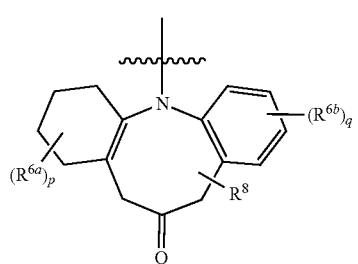

formula (8b-29)
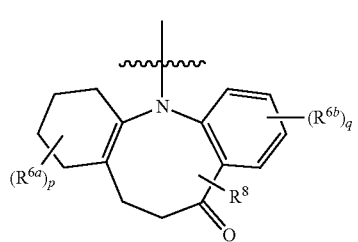

formula (8b-30)
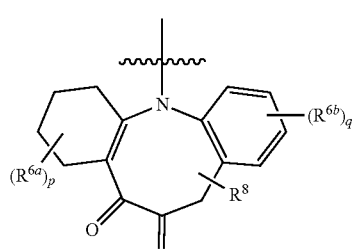

formula (8b-31)
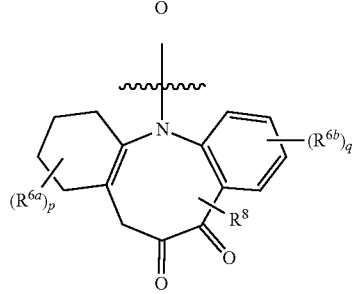

formula (8b-32)
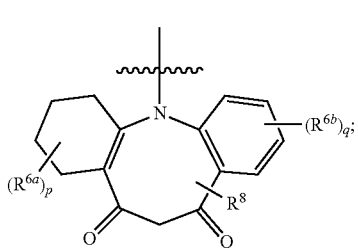

wherein $R^{5a}$, $R^{5b}$, $R^{6a}$, $R^{6b}$, $R^7$, $R^8$, $R^{10}$, m, n, p and q, at each occurrence, are each independently as defined in any of the embodiments described above.

Preferably, the group of formula (7) and the group of formula (8) are each

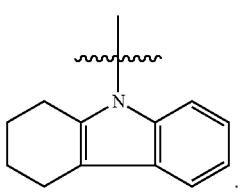 [SMILES: *n1c2c(c3ccccc31)CCCC2]

In some embodiments, the present invention provides the compound of formula (I) or a pharmaceutically acceptable salt, ester, stereoisomer, polymorph, solvate, N-oxide, isotopically labeled compound, metabolite or prodrug thereof, wherein the compound of formula (I) has a structure of formula (IIa)
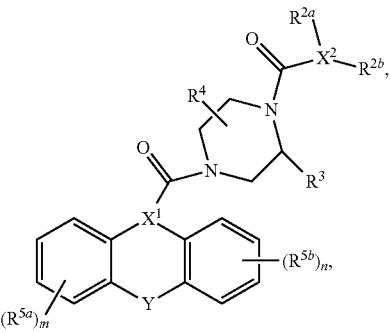

formula (IIb)
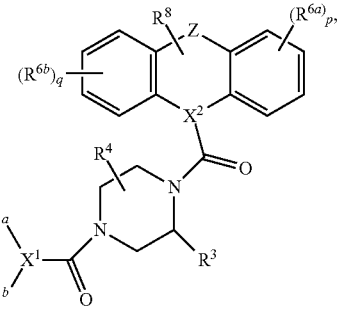

formula (IIc)
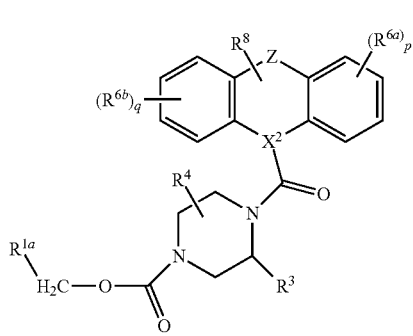

or

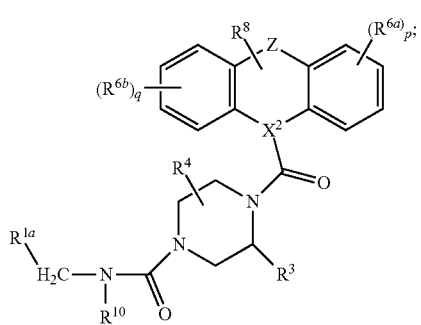
formula (IId)
preferably,
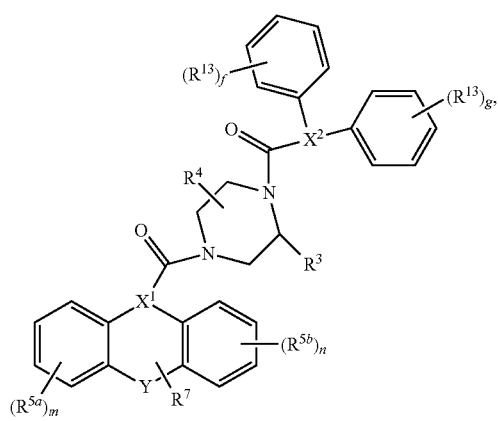
formula (IIa-1)
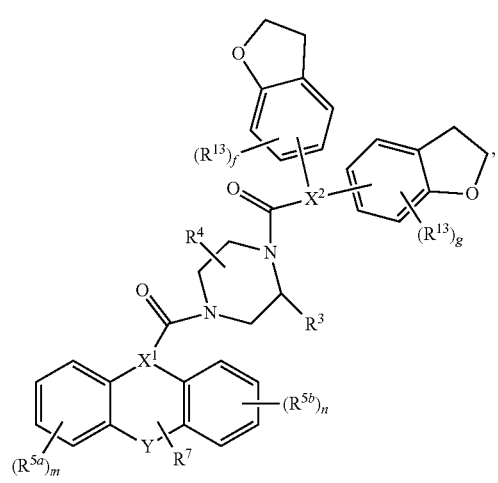
formula (IIa-2)
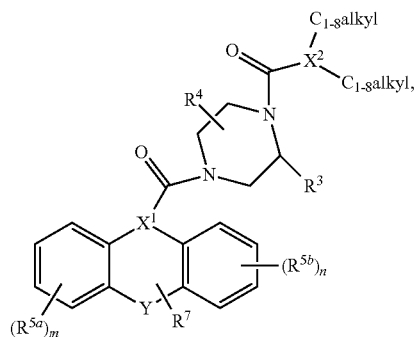
formula (IIa-3)
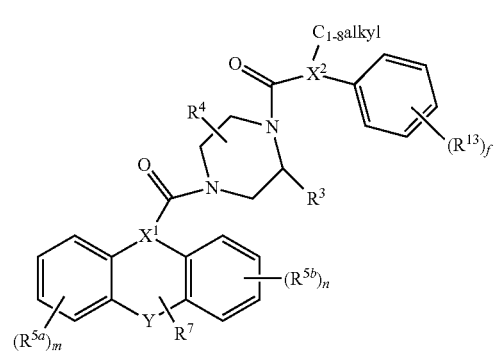
formula (IIa-4)
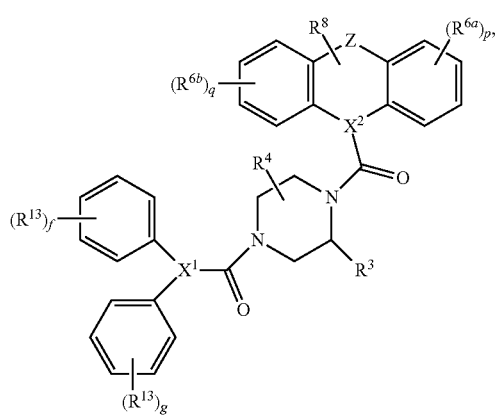
formula (IIb-1)
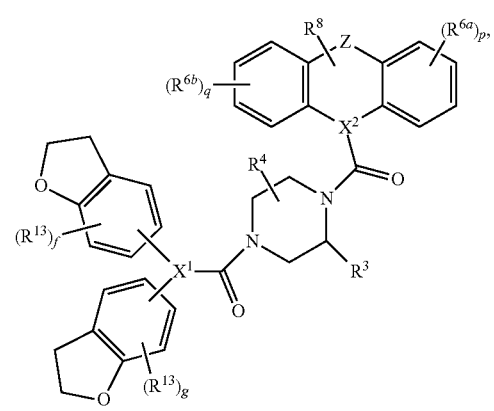
formula (IIb-2)

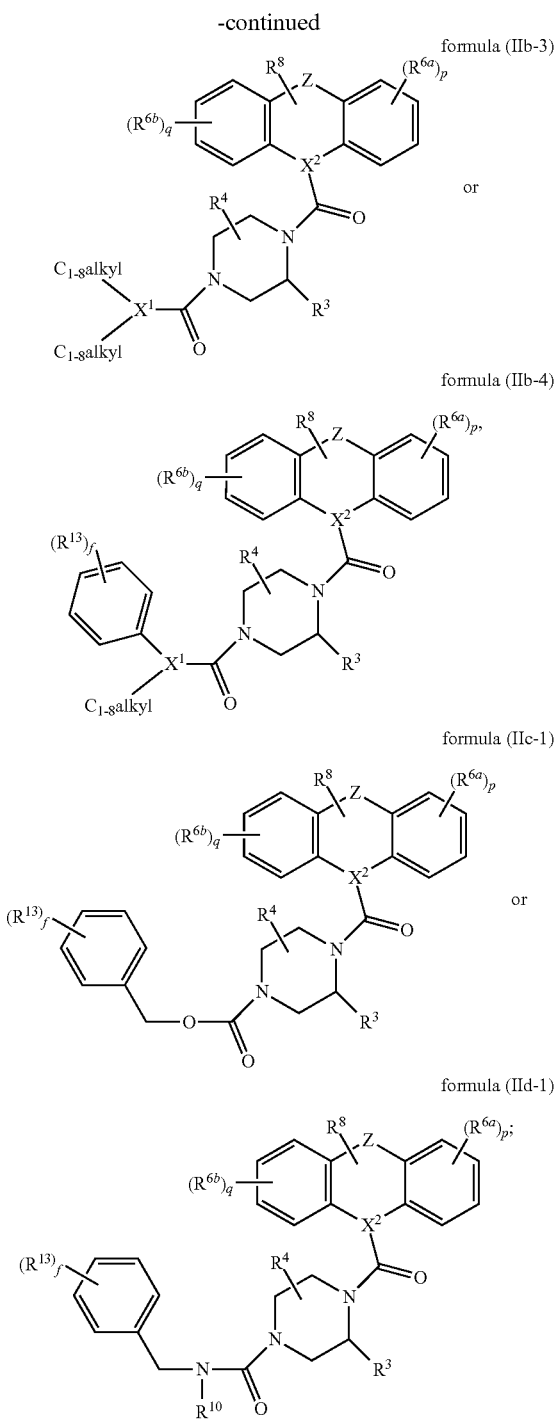

wherein f and g, at each occurrence, are each independently 0, 1, 2 or 3;

the $C_{1-8}$ alkyl, at each occurrence, is optionally substituted by 1, 2 or 3 $R^{13}$; and the above $R^{1a}$, $R^{1b}$, $R^{2a}$, $R^{2b}$, $X^1$, $X^2$, $R^3$, $R^4$, $R^{10}$, $R^{13}$, Y and Z, at each occurrence, are each independently as defined in any of the embodiments described above;

the above $R^{5a}$, $R^{5b}$, $R^{6a}$, $R^{6b}$, $R^7$, $R^8$, m, n, p and q, at each occurrence, are each independently as defined in any of the embodiments described above;

preferably, wherein Y and Z, at each occurrence, are each independently selected from the group consisting of a single bond; $NR^{10}$; O; S; and methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo, particularly from the group consisting of F, Cl, $C_{1-4}$ alkyl-O— (such as $CH_3$—O—), epoxy and oxo.

Preferably, in any of the embodiments described above, $R^3$ is F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —OC(=O)$R^{11}$, —C(=O)$OR^{11}$, —C(=O)$NR^{11}R^{12}$, —C(=O)$NR^{11}S(=O)_yNR^{11}R^{12}$, —C(=O)$NR^{11}S(=O)_yR^{12}$, —S(=O)$_yOR^{11}$, —S(=O)$_yNR^{11}R^{12}$, —S(=O)$_yNR^{11}C(=O)R^{12}$, —S(=O)$_yNR^{11}C(=O)OR^{12}$, —$C_{1-4}$ alkylene-$OR^{11}$, —$C_{1-4}$ alkylene-OC(=O)$R^{11}$, —$C_{1-4}$ alkylene-C(=O)$OR^{11}$, —$C_{1-4}$ alkylene-S(=O)$_yOR^{11}$, —$C_{1-4}$ alkylene-OC(=O)$NR^{11}R^{12}$, —$C_{1-4}$ alkylene-C(=O)$NR^{11}R^{12}$, —$C_{1-4}$ alkylene-OS(=O)$_yR^{11}$ or —$C_{1-4}$ alkylene-S(=O)$_yNR^{11}R^{12}$; preferably, 5- to 6-membered heteroaryl, —C(=O)$OR^{11}$, —C(=O)$NR^{11}R^{12}$, —C(=O)$NR^{11}S(=O)_yNR^{11}R^{12}$, —C(=O)$NR^{11}S(=O)_yR^{12}$, —S(=O)$_yOR^{11}$, —S(=O)$_yNR^{11}R^{12}$, —S(=O)$_yNR^{11}C(=O)R^{12}$, —S(=O)$_yNR^{11}C(=O)OR^{12}$, —$C_{1-3}$ alkylene-OC(=O)$R^{11}$, —$C_{1-3}$ alkylene-C(=O)$OR^{11}$, —$C_{1-3}$ alkylene-S(=O)$_yOR^{11}$, —$C_{1-3}$ alkylene-C(=O)$NR^{11}R^{12}$ or —$C_{1-3}$ alkylene-S(=O)$_yNR^{11}R^{12}$; more preferably, 5- to 6-membered heteroaryl (such as thienyl, furyl, pyrrolyl, oxazolyl, thiazolyl, imidazolyl, pyrazolyl, isoxazolyl, isothiazolyl, oxadiazolyl, triazolyl, tetrazolyl such as 1-tetrazolyl or 5-tetrazolyl, thiadiazolyl, pyridyl, pyridazinyl, pyrimidinyl, pyrazinyl or triazinyl), —C(=O)$OR^{11}$ (such as COOH), —C(=O)$NR^{11}S(=O)_yNR^{11}R^{12}$ (such as

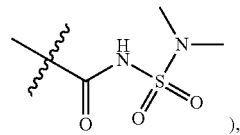 [SMILES: *C(=O)NS(=O)(=O)N(C)C]

),

—C(=O)$NR^{11}S(=O)_yR^{12}$ (such as

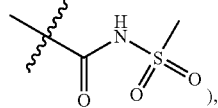 [SMILES: *C(=O)NS(C)(=O)=O]

),

—C(=O)$NR^{11}R^{12}$, —S(=O)$_yOR^{11}$ or —S(=O)$_yNR^{11}R^{12}$, —S(=O)$_yNR^{11}C(=O)R^{12}$, —S(=O)$_yNR^{11}C(=O)OR^{12}$ (such as

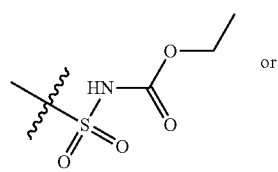

or

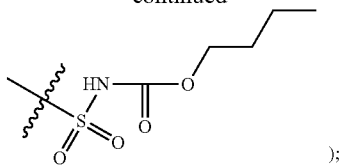

and
wherein $R^{11}$, $R^{12}$ and y are as defined in any of the embodiments described above.

In other preferred embodiments, $R^3$ is —C(=O)NR$^{11}$—OH.

Preferably, in any of the embodiments described above, $R^4$ is H, F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —OR$^{11}$, —SR$^{11}$, —OC(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$OR$^{11}$, —S(=O)$_y$NR$^{11}$R$^{12}$, —S(=O)$_y$NR$^{11}$C(=O)R$^{12}$, —S(=O)$_y$NR$^{11}$C(=O)OR$^{12}$, —C$_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; preferably, H; and wherein $R^{11}$, $R^{12}$ and y are as defined in the embodiments described above.

In other preferred embodiments, $R^4$ is —C(=O)NR$^{11}$—OH.

Preferably, in any of the embodiments described above, $R^{10}$ is H, F, Cl, Br, I, amino, cyano, nitro, $C_{1-4}$ alkyl, $C_{3-7}$ cyclic hydrocarbyl group (such as $C_{5-7}$ cyclic hydrocarbyl group), 5- to 7-membered monocyclic heterocyclic group, phenyl, 5- to 6-membered heteroaryl, —OR$^{11}$, —SR$^{11}$, —OC(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$OR$^{11}$, —S(=O)$_y$NR$^{11}$R$^{12}$, —S(=O)$_y$NR$^{11}$C(=O)R$^{12}$, —S(=O)$_y$NR$^{11}$C(=O)OR$^{12}$, —C$_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; wherein $R^{11}$, $R^{12}$ and y are as defined in the embodiments described above.

In some preferred embodiments, $R^{10}$ is H, F, Cl, Br, I, OH, —OC$_{1-6}$ alkyl (such as methoxy, ethoxy, or isopropoxy), amino, cyano, nitro, $C_{1-4}$alkyl (such as methyl, ethyl or isopropyl) or cyclopropyl.

In some preferred embodiments, $R^{10}$ is H, F, Cl, Br, I, OH, amino, cyano, nitro, or $C_{1-4}$ alkyl (such as methyl, ethyl or isopropyl).

In some preferred embodiments, $R^{10}$ is H, OH, amino, methyl or ethyl.

In some preferred embodiments, $R^{10}$ is H, F, Cl, Br, I, OH, —OC$_{1-6}$ alkyl (such as methoxy, ethoxy, or isopropoxy), amino, CM alkyl (such as methyl, ethyl or isopropyl) or $C_{3-7}$ cyclic hydrocarbyl group (such as cyclopropyl); more preferably, F, Cl, OH, methoxy, ethoxy, amino, methyl, ethyl, isopropyl or cyclopropyl.

Preferably, in any of the embodiments described above, $R^{11}$ and $R^{12}$, at each occurrence, are each independently selected from the group consisting of H, $C_{1-4}$ alkyl, $C_{5-7}$ cyclic hydrocarbyl group, 5- to 7-membered monocyclic heterocyclic group, phenyl, 5- to 6-membered heteroaryl; preferably selected from the group consisting of H and CM alkyl.

Preferably, in any of the embodiments described above, $R^{13}$, at each occurrence, is independently selected from the group consisting of F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —OR$^{11}$, —SR$^{11}$, —OC(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$OR$^{11}$, —S(=O)$_y$NR$^{11}$R$^{12}$, —S(=O)$_y$NR$^{11}$C(=O)R$^{12}$, —S(=O)$_y$NR$^{11}$C(=O)OR$^{12}$, —C$_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; preferably is F, Cl, Br, I, amino, cyano, nitro, CM alkyl, —OR$^{11}$ and —SR$^{11}$; and preferably, wherein the alkyl, alkylene, cyclic hydrocarbyl group, heterocyclic group, phenyl and heteroaryl as defined for the substituent $R^{13}$ are optionally further substituted by 1, 2, 3 or more substitutes independently selected from the group consisting of F, Cl, Br, I, OH, oxo, amino, cyano, nitro, CM alkyl, halogenated CM alkyl, $C_{5-6}$ cyclic hydrocarbyl group, 5- to 7-membered monocyclic heterocyclic group, phenyl, 5- to 6-membered heteroaryl; preferably from the group consisting of F, Cl, OH, amino, cyano, nitro, CM alkyl and halogenated CM alkyl;

wherein $R^{11}$, $R^{12}$ and y are as defined in any of the embodiments described above, and, in some further preferred embodiments, the $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl as defined for $R^{11}$ and $R^{12}$ are not further substituted.

Further preferably, in any of the embodiments described above, $R^{5a}$, $R^{5b}$, $R^{6a}$ and $R^{6b}$ as well as $R^7$ and $R^8$ are each independently selected from the group consisting of H, halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, —OR$^{11}$ and —NR$^{11}$R$^{12}$;

preferably, H, F, Cl, Br, I, OH, —OC$_{1-6}$ alkyl (such as methoxy, ethoxy, or isopropoxy), amino, $C_{1-4}$ alkyl (such as methyl, ethyl or isopropyl) or $C_{3-7}$ cyclic hydrocarbyl group (such as cyclopropyl), 5- to 7-membered monocyclic heterocyclic group, phenyl and 5- to 6-membered heteroaryl;

preferably, H, F, Cl, Br, I, OH, methoxy, ethoxy, isopropoxy, amino, methyl, ethyl, isopropyl or cyclopropyl;

more preferably, F, Cl, OH, methoxy, ethoxy, amino, methyl, ethyl, isopropyl or cyclopropyl.

A second aspect of the embodiments of the compound according to the present invention relates to the compound with the structure of formula (I), or the pharmaceutically acceptable salt, ester, stereoisomer, polymorph, solvate, N-oxide, isotopically labeled compound, metabolite, or prodrug thereof as described above, wherein $R^{1a}$, $R^{1b}$, $X^1$, $R^{2a}$, $R^{2b}$ and $X^2$ have the definitions described in the Meaning (1) described above.

As such, the second aspect of the embodiments of the compound according to the present invention relates to the compound with the structure of formula (I), or a pharmaceutically acceptable salt, ester, stereoisomer, polymorph, solvate, N-oxide, isotopically labeled compound, metabolite or prodrug thereof, wherein:

$R^{1a}$, $R^{1b}$ and $X^1$ together represent:

(i)

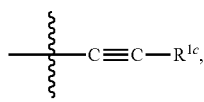

(ii)

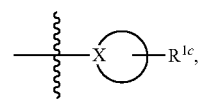

wherein:
the ring

is a saturated or partially unsaturated $C_{3-10}$ cyclic hydrocarbyl group or a saturated or partially unsaturated 3- to 10-membered heterocyclic group;

X is C, $CR^{10}$ or N;

$R^{1c}$ is selected from the group consisting of saturated or partially unsaturated $C_{3-10}$ cyclic hydrocarbyl group, saturated or partially unsaturated 3- to 10-membered heterocyclic group, $C_{6-10}$ aryl and 5- to 14-membered heteroaryl, —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group, —$C_{1-6}$ alkylene-$C_{6-10}$ aryl and —$C_{1-6}$ alkylene-(5- to 14-membered heteroaryl);

$X^2$ is $CR^{10}$ or N;

$R^{2a}$ is selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group; —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$R^{2b}$ is selected from the group consisting of H, $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

wherein, optionally, when $R^{2a}$ and $R^{2b}$ are each independently the $C_{3-10}$ cyclic hydrocarbyl group; 3- to 10-membered heterocyclic group, $C_{6-10}$ aryl, or 5- to 14-membered heteroaryl, an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

Z is selected from the group consisting of a single bond; $NR^{10}$; $C_{1-3}$ alkylene, in which 1 or 2 $CH_2$ are optionally replaced with a group independently selected from the group consisting of O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene are each optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo;

$X^3$ and $X^4$ are each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^1$ or $X^2$; preferably, $X^3$ and $X^4$ are each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}R^{12}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—$C(=O)R^{12}$, —$NR^{11}$—$C(=O)OR^{12}$, —$NR^{11}$—$S(=O)_y$—$R^{12}$, —$NR^{11}$—$C(=O)$—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—$S(=O)_yR^{12}$, —$C_{1-6}$ alkylene-$NR^{11}$—$C(=O)NR^{11}R^{12}$, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—$S(=O)_yNR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC (=O)R$^{11}$, —C(=O)R$^{11}$, —C(=O)OR$^{11}$, —C(=O)NR$^{11}$R$^{12}$, —C(=O)NR$^{11}$S(=O)$_y$NR$^{11}$R$^{12}$, —C(=O)NR$^{11}$S(=O)$_y$R$^{12}$, —S(=O)$_y$R$^{11}$, —S(=O)$_y$OR$^{11}$, —S(=O)$_y$NR$^{11}$R$^{12}$, —S(=O)$_y$NR$^{11}$S(=O)$_z$OR$^{12}$, —S(=O)$_y$NR$^{11}$C(=O)R$^{12}$, —S(=O)$_y$NR$^{11}$C(=O)OR$^{12}$, —NR$^{11}$R$^{12}$, —NR$^{11}$—C(=O)R$^{12}$, —NR$^{11}$—C(=O)OR$^{12}$, —NR$^{11}$—S(=O)$_y$—R$^{12}$, —NR$^{11}$—C(=O)—NR$^{11}$R$^{12}$, —C$_{1-6}$ alkylene-OR$^{11}$, —C$_{1-6}$ alkylene-OC(=O)R$^{11}$, —C$_{1-6}$ alkylene-C(=O)OR$^{11}$, —C$_{1-6}$ alkylene-S(=O)$_x$R$^{11}$, —C$_{1-6}$ alkylene-S(=O)$_y$OR$^{11}$, —C$_{1-6}$ alkylene-OC(=O)NR$^{11}$R$^{12}$, —C$_{1-6}$ alkylene-C(=O)NR$^{11}$R$^{12}$, —C$_{1-6}$ alkylene-C(=O)NR$^{11}$—S(=O)$_y$R$^{12}$, —C$_{1-6}$ alkylene-NR$^{11}$—C(=O)NR$^{11}$R$^{12}$, —C$_{1-6}$ alkylene-OS(=O)$_y$R$^{11}$, —C$_{1-6}$ alkylene-OS(=O)$_y$NR$^{11}$R$^{12}$, —C$_{1-6}$ alkylene-S(=O)$_y$NR$^{11}$R$^{12}$, —C$_{1-6}$ alkylene-NR$^{11}$—S(=O)$_y$NR$^{11}$R$^{12}$, —C$_{1-6}$ alkylene-NR$^{11}$R$^{12}$ and —O—C$_{1-6}$ alkylene-NR$^{11}$R$^{12}$; and wherein the alkyl, alkylene, cyclic hydrocarbyl group, heterocyclic group, aryl, heteroaryl and aralkyl as defined for the substituent R$^{13}$ are optionally further substituted by 1, 2, 3 or more substituents independently selected from the group consisting of halogen, OH, oxo, amino, cyano, nitro, C$_{1-6}$ alkyl, halogenated C$_{1-6}$ alkyl, C$_{3-6}$ cyclic hydrocarbyl group, 3- to 10-membered heterocyclic group, C$_{6-10}$ aryl, 5- to 14-membered heteroaryl and C$_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2; and y and z, at each occurrence, are each independently 1 or 2.

The embodiments of the compound according to the second aspect are further described below.

In some embodiments, the compound of formula (I) has a structure of formula (IV) or formula (V):

Formula (IV)

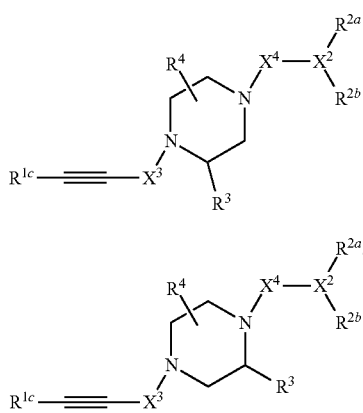

Formula (V)

In some further embodiments, X is C or N.

In some even further embodiments, the compound of formula (I) has a structure of formula (VI) or formula (VII):

Formula (VI)

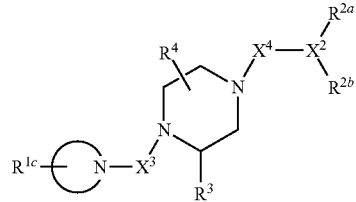

Formula (VII)

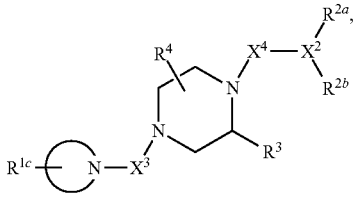

wherein the ring

is a saturated or partially unsaturated 3- to 10-membered heterocyclic group, preferably 3- to 7-membered heterocyclic group, more preferably 3- to 6-membered heterocyclic group;

preferably, wherein said heterocyclic groups optionally further contain 1, 2 or 3 heteroatoms independently selected from N, O and S; more preferably, said heterocyclic groups are selected from the group consisting of

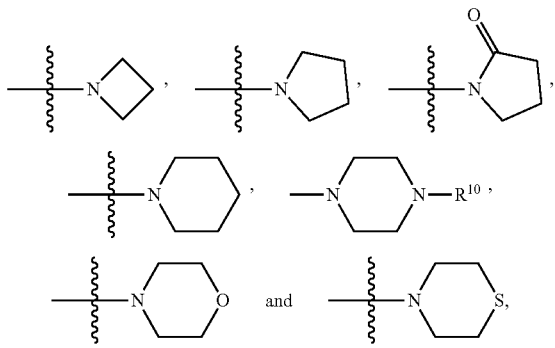

more preferably, selected from the group consisting of

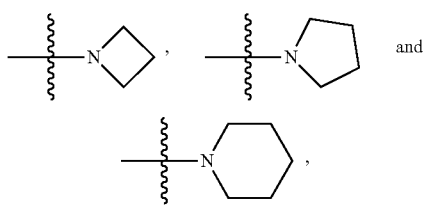

more preferably is

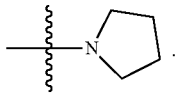

In other even further embodiments, the compound of formula (I) has a structure of formula (VIII) or formula (IX):

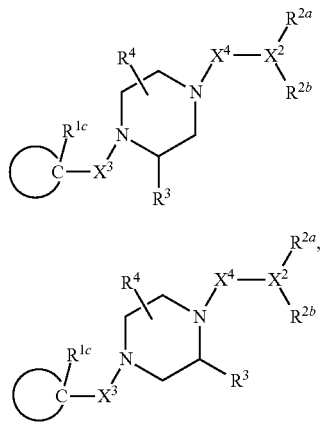

wherein the ring

is:

saturated or partially unsaturated $C_{3-10}$ cyclic hydrocarbyl group, preferably $C_{3-7}$ cyclic hydrocarbyl group, more preferably $C_{3-6}$ cyclic hydrocarbyl group; preferably, wherein said cyclic hydrocarbyl groups are selected from the group consisting of cyclopropyl, cyclobutyl, cyclopentyl and cyclohexyl, preferably selected from the group consisting of cyclopentyl and cyclohexyl;

or saturated or partially unsaturated 3- to 10-membered heterocyclic group, preferably 3- to 7-membered heterocyclic group, more preferably 3- to 6-membered heterocyclic group, wherein said heterocyclic groups contain 1, 2, 3 or 4 heteroatoms independently selected from N, O, and S; preferably, said heterocyclic groups are selected from the group consisting of

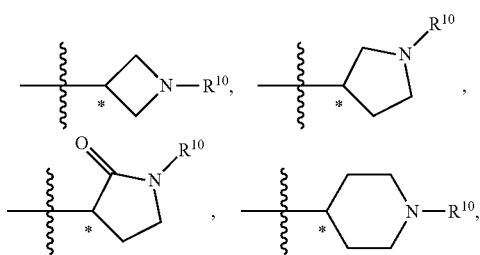

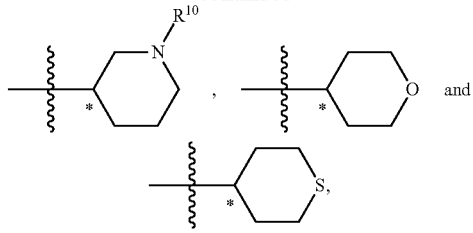

more preferably selected from the group consisting of

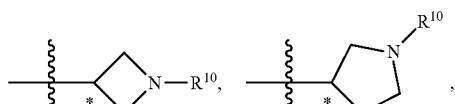

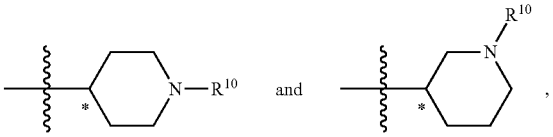

and more preferably is

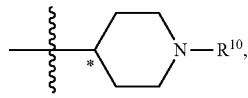

wherein the C atom identified with * is connected to $R^{1c}$ and $X^3$.

Preferably, in any of the embodiments described above, $R^{1c}$ is selected from the group consisting of $C_{3-7}$ cyclic hydrocarbyl group, 3- to 7-membered heterocyclic group, $C_{6-10}$ aryl, 5- to 6-membered heteroaryl, —$C_{1-4}$ alkylene-$C_{3-7}$ cyclic hydrocarbyl group, —$C_{1-4}$ alkylene-(3- to 7-membered heterocyclic group), —$C_{1-4}$ alkylene-$C_{6-10}$ aryl and —$C_{1-4}$ alkylene-(5- to 6-membered heteroaryl);

preferably, is selected from the group consisting of $C_{3-6}$ cyclic hydrocarbyl group, 4- to 6-membered heterocyclic group, phenyl, 5- to 6-membered heteroaryl, —$C_{1-4}$ alkylene-$C_{3-6}$ cyclic hydrocarbyl group, —$C_{1-4}$ alkylene-(4- to 6-membered heterocyclic group), —$C_{1-4}$ alkylene-phenyl and —$C_{1-4}$ alkylene-(5- to 6-membered heteroaryl);

preferably, is selected from the group consisting of $C_{3-6}$ cyclic hydrocarbyl group, phenyl, —$C_{1-4}$ alkylene-$C_{3-6}$ cyclic hydrocarbyl group and —$C_{1-4}$ alkylene-phenyl;

preferably, selected from the group consisting of cyclopentyl, cyclohexyl, phenyl, cyclopentylmethylene, cyclopentylethylene, cyclohexylmethylene, cyclohexylethylene, phenylmethylene- and phenylethylene-;

more preferably, is phenyl.

Preferably, in any of the embodiments described above, $R^{10}$ is H, F, Cl, Br, I, amino, cyano, nitro, $C_{1-4}$ alkyl, $C_{3-7}$ cyclic hydrocarbyl group (such as $C_{5-7}$ cyclic hydrocarbyl group), 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_y$ $R^{12}$, —$S(=O)_yOR^{11}$, —$S(=O)_yNR^{11}R^{12}$, —$S(=O)_y$ $NR^{11}C(=O)R^{12}$, —$S(=O)_yNR^{11}C(=O)OR^{12}$, —$C_{1-4}$ alkylene-OR$^{11}$, —C$_{1-4}$ alkylene-OC(=O)R$^{11}$, —C$_{1-4}$ alkylene-C(=O)OR$^{11}$, —C$_{1-4}$ alkylene-S(=O)$_y$OR$^{11}$, —C$_{1-4}$ alkylene-OC(=O)NR$^{11}$R$^{12}$, —C$_{1-4}$ alkylene-C(=O)NR$^{11}$R$^{12}$, —C$_{1-4}$ alkylene-OS(=O)$_y$R$^{11}$ or —C$_{1-4}$ alkylene-S(=O)$_y$NR$^{11}$R$^{12}$; wherein R$^{11}$, R$^{12}$ and y are as defined in the embodiments of the first aspect described above.

In some preferred embodiments, R$^{10}$ is H, F, Cl, Br, I, OH, —OC$_{1-6}$ alkyl (such as methoxy, ethoxy, or isopropoxy), amino, cyano, nitro, C$_{1-4}$ alkyl (such as methyl, ethyl or isopropyl) or cyclopropyl.

In some preferred embodiments, R$^{10}$ is H, F, Cl, Br, I, OH, amino, cyano, nitro, or C$_{1-4}$ alkyl (such as methyl, ethyl or isopropyl).

In some preferred embodiments, R$^{10}$ is H, OH, amino, methyl or ethyl.

In some preferred embodiments, R$^{10}$ is H, F, Cl, Br, I, OH, —OC$_{1-6}$ alkyl (such as methoxy, ethoxy, or isopropoxy), amino, C$_{1-4}$ alkyl (such as methyl, ethyl or isopropyl) or C$_{3-7}$ cyclic hydrocarbyl group (such as cyclopropyl); more preferably, F, Cl, OH, methoxy, ethoxy, amino, methyl, ethyl, isopropyl or cyclopropyl.

In some preferred embodiments, R$^{10}$ is H, methyl or ethyl.

Preferably, in any of the embodiments described above,

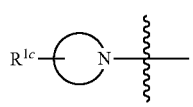

has a structure of

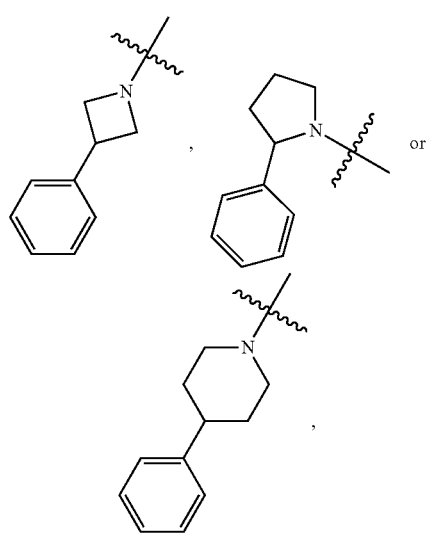

preferably

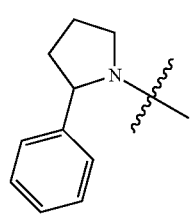 [SMILES: *N1CCCC1c1ccccc1]

(including

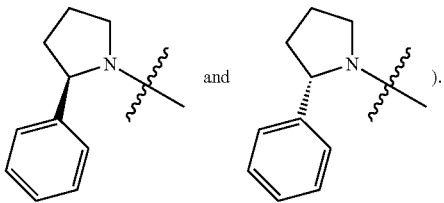 [SMILES: *N1CCC[C@@H]1c1ccccc1 ; *N1CCC[C@H]1c1ccccc1]

).

Preferably, in any of the embodiments described above,

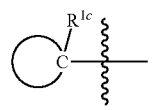

has a structure of

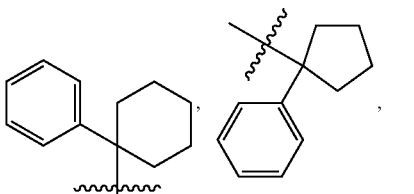

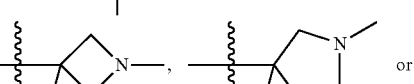

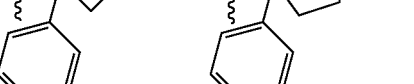 or

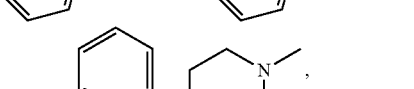

preferably

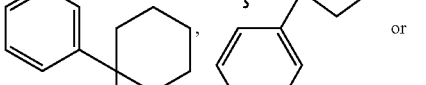 or

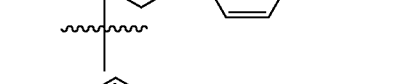

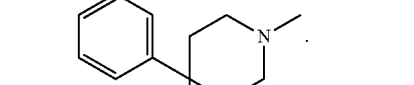

Preferably, in any of the embodiments described above, $X^2$ is CH or N.

Preferably, in any of the embodiments described above, $R^{2a}$ and $R^{2b}$ are each independently selected from the group consisting of

- $C_{1-6}$ alkyl, such as methyl, ethyl, n-propyl, isopropyl, n-butyl, isobutyl, sec-butyl, tert-butyl, n-pentyl, isopentyl, neopentyl, 1-hexyl, 1-heptyl, 1-octyl;
- $C_{2-6}$ alkenyl, such as vinyl, 1-propenyl, 2-propenyl, 2-butenyl, 3-butenyl, 2-pentenyl, 3-pentenyl, 4-pentenyl, 2-hexenyl;
- $C_{2-6}$ alkynyl, such as ethynyl, 1-propynyl, 2-propynyl, 2-butynyl, 3-butynyl, 2-pentynyl, 3-pentynyl, 4-pentynyl, 2-hexynyl, 3-hexynyl;
- $C_{3-7}$ cyclic hydrocarbyl group, such as $C_{5-7}$ cyclic hydrocarbyl group, e.g., cyclopropyl, cyclopentyl, cyclohexyl;
- 5- to 7-membered monocyclic heterocyclic group;
- 8- to 10-membered benzo-fused heterocyclic group, such as

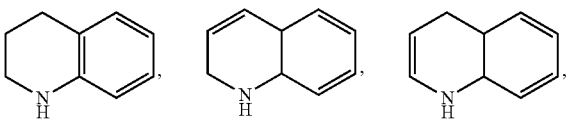
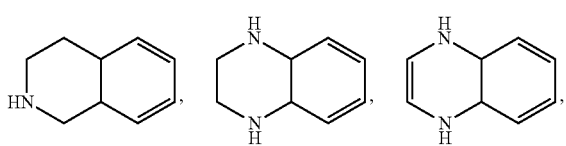
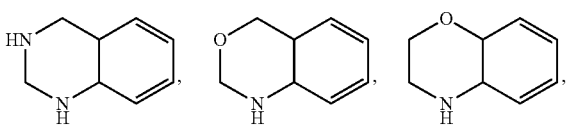
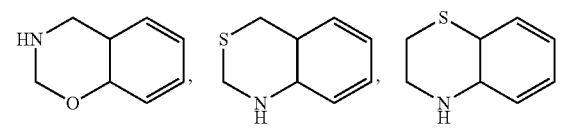
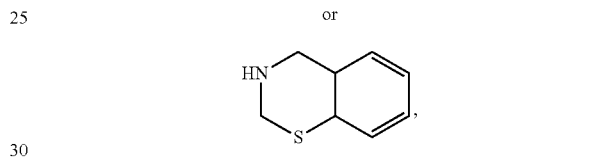

or

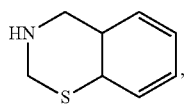

preferably

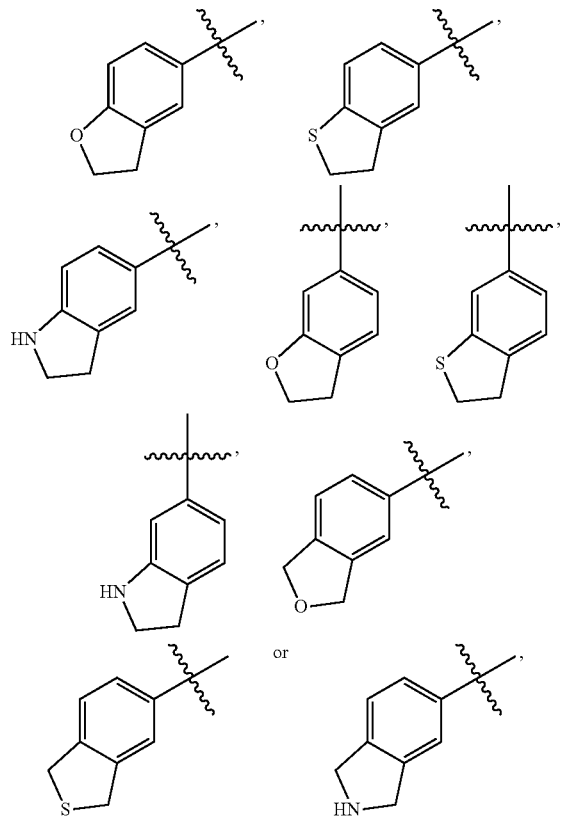

more preferably

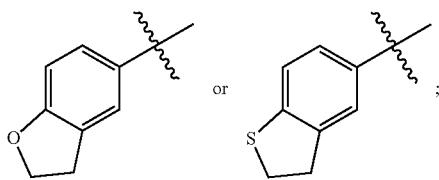 [SMILES: *c1ccc2c(c1)CCO2 ; *c1ccc2c(c1)CCS2]

phenyl; and 5- to 6-membered heteroaryl, such as thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl, more preferably thienyl or furyl, more preferably thienyl;

—$C_{1-6}$ alkylene-$C_{6-10}$ aryl, preferably-$C_{1-4}$ alkylene-$C_{6-10}$ aryl, more preferably phenylmethylene- or phenylethylene-; and —$C_{1-6}$ alkylene-(5- to 14-membered heteroaryl), preferably —$C_{1-4}$ alkylene-(5- to 10-membered heteroaryl), more preferably -methylene-(5- to 10-membered heteroaryl) and -ethylene-(5- to 10-membered heteroaryl), wherein said heteroaryl groups are preferably selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl and its benzo derivatives, more preferably selected from the group consisting of thienyl and furanyl and its benzo derivatives, more preferably selected from the group consisting of thienyl and its benzo derivatives; and the above alkyl, alkylene, alkenyl, alkynyl, cyclic hydrocarbyl group, heterocyclic group, aryl and heteroaryl, at each occurrence, are each optionally substituted by 1, 2 or 3 $R^{13}$.

In some more preferred embodiments, $R^{2a}$ is selected from the group consisting of $C_{1-6}$ alkyl, phenyl and —$C_{1-6}$ alkylene-phenyl, preferably selected from the group consisting of $C_{1-4}$ alkyl, phenyl and $C_{1-4}$ alkylene-phenyl, preferably selected from the group consisting of methyl, ethyl, isopropyl, phenyl, phenylmethylene- and phenylethylene-, more preferably selected from the group consisting of methyl, phenyl and phenylmethylene-.

In other embodiments, $R^{2b}$ may also be H.

In some more preferred embodiments, $R^{2b}$ is selected from the group consisting of H, $C_{1-6}$ alkyl, phenyl and —$C_{1-6}$ alkylene-phenyl, preferably selected from the group consisting of H, $C_{1-4}$ alkyl, phenyl and —$C_{1-4}$ alkylene-phenyl, preferably selected from the group consisting of H, methyl, ethyl, isopropyl, phenyl, phenylmethylene- and phenylethylene-, more preferably selected from the group consisting of H, methyl, phenyl and phenylmethylene-.

Alternatively, in any of the embodiments described above, $R^{2a}$ and $R^{2b}$ are preferably each independently selected from the group consisting of $C_{3-10}$ cyclic hydrocarbyl group, 3- to 10-membered heterocyclic group, $C_{6-10}$ aryl, or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings.

Preferably, the fused ring system $Q^2$ is a group having a structure shown by any one selected from formula (b), formula (3), formula (4), formula (6), formula (8), formula (3a-1) to formula (3a-22), formula (3b-1) to formula (3b-22), formula (4a-1) to formula (4a-32) and formula (4b-1) to formula (4b-32), wherein the formula (b), formula (3), formula (4), formula (6), formula (8), formula (3a-1) to formula (3a-22), formula (3b-1) to formula (3b-22), formula (4a-1) to formula (4a-32) and formula (4b-1) to formula (4b-32) are as defined in the first aspect above.

Therefore, the fused ring system $Q^2$ is a group having a structure of formula (b) in some preferred embodiments; a group with the structure of formula (3) in some more preferred embodiments; a group with the structure of formula (4) in other more preferred embodiments; a group with the structure of formula (6), preferably formula (8) in other more preferred embodiments.

In some of the embodiments with respect to any one of formula (b), formula (3), formula (4), formula (6) and formula (8), Z, at each occurrence, is independently selected from the group consisting of a single bond; $NR^{10}$; O; S; and methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo, particularly from the group consisting of F, Cl, $C_{1-4}$ alkyl-O— (such as $CH_3$—O—), epoxy and oxo.

Preferably, $R^{10}$, $R^{11}$ and $R^{12}$ are each as defined in the first aspect above.

In some further preferred embodiments, the group with the structure of formula (3) has a structure shown by formula (3a-1) to formula (3a-22) and formula (3b-1) to formula (3b-22).

In some further preferred embodiments, the group with the structure of formula (4) has a structure shown by formula (4a-1) to formula (4a-32) and formula (4b-1) to formula (4b-32).

In some further preferred embodiments, the group with the structure of formula (8) has a structure shown by formula (8a-1) to formula (8a-32) and formula (8b-1) to formula (8b-32).

Preferably, the group of formula (3) has a structure selected from:

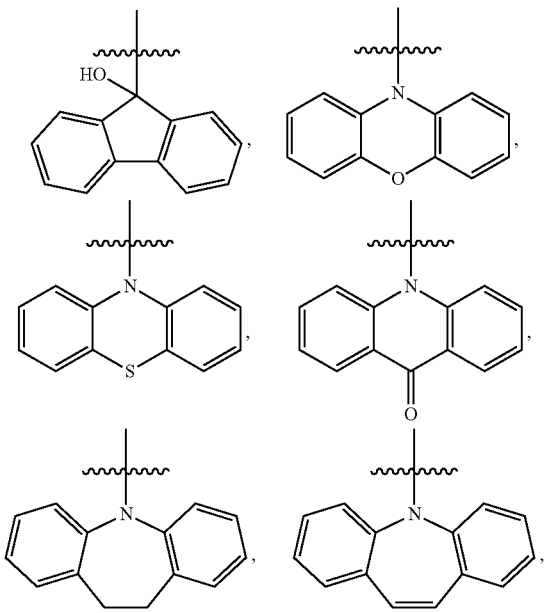

-continued

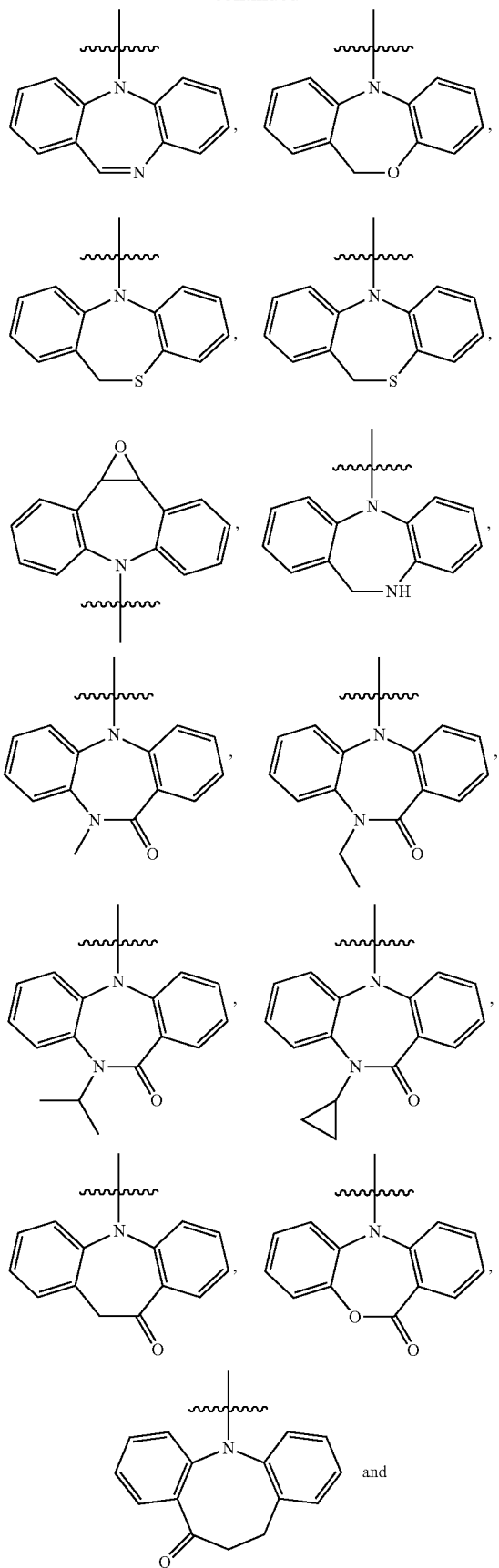

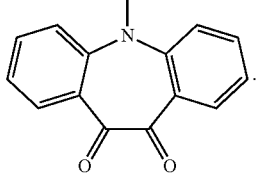

Preferably, the group of formula (4) has a structure selected from:

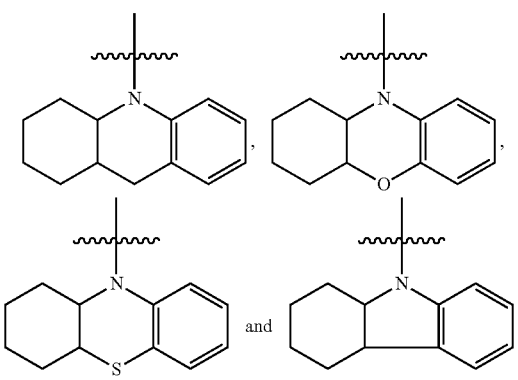

Preferably, the group of formula (8)

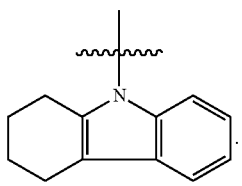 [SMILES: *n1c2c(c3ccccc31)CCCC2]

More preferably, the fused ring system $Q^2$ is

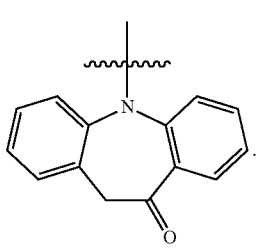 [SMILES: *N1c2ccccc2CC(=O)c2ccccc21]

Preferably, in any of the embodiments described above, $R^3$ is F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-4}$ alkylene-$OR^{11}$, —$C_{1-4}$ alkylene-OC(=O)$R^{11}$, —$C_{1-4}$ alkylene-C(=O)$OR^{11}$, —$C_{1-4}$ alkylene-S(=O)$_yOR^{11}$, —$C_{1-4}$ alkylene-OC(=O)$NR^{11}R^{12}$, —$C_{1-4}$ alkylene-C(=O)$NR^{11}R^{12}$, —$C_{1-4}$ alkylene-OS(=O)$_yR^{11}$ or —$C_{1-4}$ alkylene-$S(=O)_yNR^{11}R^{12}$; preferably, 5- to 6-membered heteroaryl, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-3}$ alkylene-$OC(=O)R^{11}$, —$C_{1-3}$ alkylene-$C(=O)OR^{11}$, —$C_{1-3}$ alkylene-$S(=O)_yOR^{11}$, —$C_{1-3}$ alkylene-$C(=O)NR^{11}R^{12}$ or —$C_{1-3}$ alkylene-$S(=O)_yNR^{11}R^{12}$; more preferably, 5- to 6-membered heteroaryl (such as thienyl, furyl, pyrrolyl, oxazolyl, thiazolyl, imidazolyl, pyrazolyl, isoxazolyl, isothiazolyl, oxadiazolyl, triazolyl, tetrazolyl such as 1-tetrazolyl or 5-tetrazolyl, thiadiazolyl, pyridyl, pyridazinyl, pyrimidinyl, pyrazinyl or triazinyl), —$C(=O)OR^{11}$ (such as COOH), —$C(=O)NR^{11}S(=O)_yNR^{11}R^{12}$ (such as

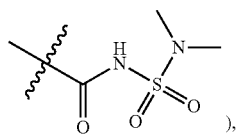 [SMILES: *C(=O)NS(=O)(=O)N(C)C]

), —$C(O)NR^{11}S(=O)_yR^{12}$ (such as

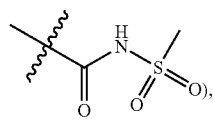

), —$C(=O)NR^{11}R^{12}$, —$S(=O)_yOR^{11}$ or —$S(=O)_yNR^{11}R^{12}$, —$S(=O)_yNR^{11}C(=O)R^{12}$, —$S(=O)_yNR^{11}C(=O)OR^{12}$ (such as

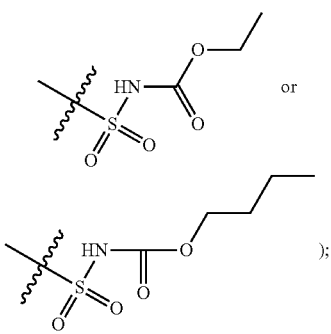

and wherein $R^{11}$, $R^{12}$ and y are as defined in any of the embodiments according to the first aspect described above.

More preferably, $R^3$ is COOH.

Preferably, in any of the embodiments described above, $R^4$ is H, F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-4}$ alkylene-$OR^{11}$, —$C_{1-4}$ alkylene-$OC(=O)R^{11}$, —$C_{1-4}$ alkylene-$C(=O)OR^{11}$, —$C_{1-4}$ alkylene-$S(=O)_yOR^{11}$, —$C_{1-4}$ alkylene-$OC(=O)NR^{11}R^{12}$, —$C_{1-4}$ alkylene-$C(=O)NR^{11}R^{12}$, —$C_{1-4}$ alkylene-$OS(=O)_yR^{11}$ or —$C_{1-4}$ alkylene-$S(=O)_yNR^{11}R^{12}$; and wherein $R^{11}$, $R^{12}$ and y are as defined in any of the embodiments according to the first aspect described above.

More preferably, $R^4$ is H.

Preferably, in any of the embodiments described above, $R^{11}$ and $R^{12}$, at each occurrence, are each independently selected from the group consisting of H, $C_{1-4}$ alkyl, $C_{5-7}$ cyclic hydrocarbyl group, 5- to 7-membered monocyclic heterocyclic group, phenyl and 5- to 6-membered heteroaryl; preferably selected from H and $C_{1-4}$ alkyl.

Preferably, in any of the embodiments described above, $R^{13}$, at each occurrence, is independently selected from the group consisting of F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-4}$ alkylene-$OR^{11}$, —$C_{1-4}$ alkylene-$OC(=O)R^{11}$, —$C_{1-4}$ alkylene-$C(=O)OR^{11}$, —$C_{1-4}$ alkylene-$S(=O)_yOR^{11}$, —$C_{1-4}$ alkylene-$OC(=O)NR^{11}R^{12}$, —$C_{1-4}$ alkylene-$C(=O)NR^{11}R^{12}$, —$C_{1-4}$ alkylene-$OS(=O)_yR^{11}$ and —$C_{1-4}$ alkylene-$S(=O)_yNR^{11}R^{12}$; preferably F, Cl, Br, I, amino, cyano, nitro, $C_{1-4}$ alkyl, —$OR^{11}$ and —$SR^{11}$; and preferably, wherein the alkyl, alkylene, cyclic hydrocarbyl group, heterocyclic group, phenyl and heteroaryl as defined for the substituent $R^{13}$ are optionally further substituted by 1, 2, 3 or more substitutes independently selected from the group consisting of F, Cl, Br, I, OH, oxo, amino, cyano, nitro, $C_{1-4}$ alkyl, halogenated $C_{1-4}$ alkyl, $C_{5-6}$ cyclic hydrocarbyl group, 5- to 7-membered monocyclic heterocyclic group, phenyl, 5- to 6-membered heteroaryl; preferably F, Cl, OH, amino, cyano, nitro, $C_{1-4}$ alkyl and halogenated $C_{1-4}$ alkyl;

wherein $R^{11}$, $R^{12}$ and y are as defined in any of the embodiments according to the first aspect described above, and, in some further preferred embodiments, the $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl as defined for $R^{11}$ and $R^{12}$ are not further substituted.

Preferably, in any of the embodiments described above, $X^3$ is $C(=O)$.

Preferably, in any of the embodiments described above, $X^4$ is $C(=O)$ or —O—$C(=O)$—.

A third aspect of the embodiments of the compound according to the present invention relates to the compound with the structure of formula (I) or the pharmaceutically acceptable salt, ester, stereoisomer, polymorph, solvate, N-oxide, isotopically labeled compound, metabolite, or prodrug thereof as described above, wherein $R^{1a}$, $R^{1b}$, $X^1$, $R^{2a}$, $R^{2b}$ and $X^2$ have the definitions described in the Meaning (2) described above.

As such, the third aspect of the embodiments of the compound according to the present invention relates to the compound with the structure of formula (I) or a pharmaceutically acceptable salt, ester, stereoisomer, polymorph, solvate, N-oxide, isotopically labeled compound, metabolite or prodrug thereof, wherein:

$R^{1a}$, $R^{2a}$, $R^{1b}$ and $R^{2b}$ are each independently selected from the group consisting of $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$ or N;

$X^2$ is $CR^{15}$;

$R^{15}$ is selected from the group consisting of halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—C(=O)R^{12}, —$NR^{11}$—C(=O)OR^{12}, —$NR^{11}$—S(=O)_y—R^{12}, —$NR^{11}$—C(=O)—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—S(=O)_yR^{12}, —$C_{1-6}$ alkylene-$NR^{11}$—C(=O)NR^{11}R^{12}, —$C_{1-6}$ alkylene-$OS(=O)_yR^{11}$, —$_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—S(=O)_yNR^{11}R^{12}, —$C_{1-6}$ alkylene-$NR^{11}R^{12}$ and —$O$—$C_{1-6}$ alkylene-$NR^{11}R^{12}$;

$X^3$ and $X^4$ are each independently selected from the group consisting of $C(=O)$; $S(=O)_y$; and —$O$—$C(=O)$—, —$S$—$C(=O)$—, —$O$—$S(=O)_y$—, —$NR^{10}$—$C(=O)$— and —$NR^{10}$—$S(=O)_y$—, wherein O, S, $NR^{10}$ are connected to $X^1$ or $X^2$; preferably, $X^3$ and $X^4$ are each independently selected from the group consisting of $C(=O)$, the —$OC(=O)$— or —$NR^{10}$—$C(=O)$—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—C(=O)R^{12}, —$NR^{11}$—C(=O)OR^{12}, —$NR^{11}$—S(=O)_y—R^{12}, —$NR^{11}$—C(=O)—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—S(=O)_yR^{12}, —$C_{1-6}$ alkylene-$NR^{11}$—C(=O)NR^{11}R^{12}, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—S(=O)_yNR^{11}R^{12}, —$C_{1-6}$ alkylene-$NR^{11}R^{12}$ and —$O$—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—C(=O)R^{12}, —$NR^{11}$—C(=O)OR^{12}, —$NR^{11}$—S(=O)_y—R^{12}, —$NR^{11}$—C(=O)—$NR^{11}R^{12}$, —$C_{1-6}$ alkylene-$OR^{11}$, —$C_{1-6}$ alkylene-$OC(=O)R^{11}$, —$C_{1-6}$ alkylene-$C(=O)OR^{11}$, —$C_{1-6}$ alkylene-$S(=O)_xR^{11}$, —$C_{1-6}$ alkylene-$S(=O)_yOR^{11}$, —$C_{1-6}$ alkylene-$OC(=O)NR^{11}R^{12}$, —$C_{1-6}$ alkylene-$C(=O)NR^{11}R^{12}$, —$C_{1-6}$ alkylene-$C(=O)NR^{11}$—S(=O)_yR^{12}, —$C_{1-6}$ alkylene-$NR^{11}$—C(=O)NR^{11}R^{12}, —$C_{1-6}$ alkylene-$OS(=O)_yR^{11}$, —$C_{1-6}$ alkylene-$OS(=O)_yNR^{11}R^{12}$, —$C_{1-6}$ alkylene-$S(=O)_yNR^{11}R^{12}$, —$C_{1-6}$ alkylene-$NR^{11}$—S(=O)_yNR^{11}R^{12}, —$C_{1-6}$ alkylene-$NR^{11}R^{12}$ and —$O$—$C_{1-6}$ alkylene-$NR^{11}R^{12}$; and wherein the alkyl, alkylene, cyclic hydrocarbyl group, heterocyclic group, aryl, heteroaryl and aralkyl as defined for the substituent $R^{13}$ are optionally further substituted by 1, 2, 3 or more substituents selected independently from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2; and y and z, at each occurrence, are each independently 1 or 2.

The embodiments of the compound according to the third aspect are further described below.

In some embodiments, the present invention provides the compound having the structure of formula (I) or a pharmaceutically acceptable salt, ester, stereoisomer, polymorph, solvate, N-oxide, isotopically labeled compound, metabolite or prodrug thereof as described above, wherein:

$R^{1a}$ and $R^{1b}$ are each independently selected from the group consisting of $C_{1-6}$ alkyl, $C_{2-6}$ alkenyl and $C_{2-6}$ alkynyl, wherein any one of the $CH_2$ moieties in the $C_{1-6}$ alkyl, $C_{2-6}$ alkenyl and $C_{2-6}$ alkynyl is optionally replaced with O or S; saturated or partially unsaturated $C_{3-7}$ cyclic hydrocarbyl group; saturated or partially unsaturated 5- to 7-membered monocyclic heterocyclic group; $C_{6-10}$ aryl; 5- to 6-membered heteroaryl; —$C_{1-4}$ alkylene-saturated or partially unsaturated $C_{3-7}$ cyclic hydrocarbyl group, —$C_{1-4}$ alkylene-saturated or partially unsaturated 5- to 7-membered heterocyclic group; —$C_{1-4}$ alkylene-$C_{6-10}$ aryl; and —$C_{1-4}$ alkylene-(5- to 6-membered heteroaryl);

preferably, selected from the group consisting of $C_{1-4}$ alkyl, $C_{2-4}$ alkenyl, CM alkynyl, $C_{6-10}$ aryl, 5- to 6-membered heteroaryl, —$C_{1-4}$ alkylene-$C_{6-10}$ aryl and —$C_{1-4}$ alkylene-(5- to 6-membered heteroaryl).

More preferably, $R^{1a}$ is selected from the group consisting of phenyl, 5- to 6-membered heteroaryl, —$C_{1-4}$ alkylene-phenyl, and —$C_{1-4}$ alkylene-(5- to 6-membered heteroaryl).

Preferably, in the above embodiments, the 5- to 6-membered heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl, more preferably is thienyl or furyl, more preferably thienyl.

More preferably, $R^{1a}$ is selected from the group consisting of phenyl and —$CH_2$-phenyl.

More preferably, $R^{1b}$ is selected from the group consisting of $C_{1-4}$ alkyl and phenyl; more preferably, selected from the group consisting of methyl, ethyl, isopropyl and phenyl.

Preferably, in any of the embodiments described above, $R^{2a}$ and $R^{2b}$ are each independently selected from the group consisting of $C_{1-6}$ alkyl, $C_{2-6}$ alkenyl and $C_{2-6}$ alkynyl, wherein any one of the $CH_2$ moieties in the $C_{1-6}$ alkyl, $C_{2-6}$ alkenyl and $C_{2-6}$ alkynyl is optionally replaced with O or S; saturated or partially unsaturated $C_{3-7}$ cyclic hydrocarbyl group; saturated or partially unsaturated 5- to 7-membered monocyclic heterocyclic group; $C_{6-10}$ aryl; 5- to 6-membered heteroaryl; —$C_{1-4}$ alkylene-saturated or partially unsaturated $C_{3-7}$ cyclic hydrocarbyl group, —$C_{1-4}$ alkylene-saturated or partially unsaturated 5- to 7-membered monocyclic heterocyclic group; —$C_{1-4}$ alkylene-$C_{6-10}$ aryl; and —$C_{1-4}$ alkylene-(5- to 6-membered heteroaryl);
preferably, selected from the group consisting of $C_{1-4}$ alkyl, $C_{2-4}$ alkenyl, CM alkynyl, $C_{6-10}$ aryl, 5- to 6-membered heteroaryl, —$C_{1-4}$ alkylene-$C_{6-10}$ aryl and —$C_{1-4}$ alkylene-(5- to 6-membered heteroaryl).

More preferably, $R^{2a}$ is selected from the group consisting of phenyl, 5- to 6-membered heteroaryl, —$C_{1-4}$ alkylene-phenyl, and —$C_{1-4}$ alkylene-(5- to 6-membered heteroaryl).

Preferably, in the above embodiments, the 5- to 6-membered heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl, more preferably is thienyl or furyl, more preferably thienyl.

More preferably, $R^{2a}$ is phenyl.

More preferably, $R^{2b}$ is selected from the group consisting of $C_{1-4}$ alkyl and phenyl; more preferably, selected from the group consisting of methyl, ethyl, isopropyl and phenyl.

Preferably, in any of the embodiments described above, $X^1$ is $CR^{10}$.

Preferably, in other embodiments described above, $X^1$ is N.

Preferably, in any of the embodiments described above, $R^{15}$ is selected from the group consisting of halogen, cyano, nitro, CM alkyl, $C_{3-7}$ cyclic hydrocarbyl group, 5- to 7-membered heterocyclic group, phenyl, 5- to 6-membered heteroaryl, $C_{6-12}$ aralkyl, —$OR^{11}$, —$SR^{11}$, —$NR^{11}R^{12}$, —$C_{1-4}$ alkylene-$OR^{11}$, —$C_{1-4}$ alkylene-$NR^{11}R^{12}$ and —O—$C_{1-6}$ alkylene-$NR^{11}R^{12}$; preferably is $C_{1-4}$ alkyl, such as methyl, ethyl and isopropyl, more preferably methyl.

Preferably, in any of the embodiments described above, $X^3$ and $X^4$ are each independently selected from the group consisting of C(=O) and S(=O)$_y$; preferably, are each C(=O).

Preferably, in any of the embodiments described above, $R^{10}$ is H, F, Cl, Br, I, amino, cyano, nitro, $C_{1-4}$ alkyl, $C_{3-7}$ cyclic hydrocarbyl group (such as $C_{5-7}$ cyclic hydrocarbyl group), 5- to 7-membered monocyclic heterocyclic group, phenyl, 5- to 6-membered heteroaryl, —$OR^{11}$, —$SR^{11}$, —OC(=O)$R^{11}$, —C(=O)$OR^{11}$, —C(=O)$NR^{11}R^{12}$, —C(=O)$NR^{11}S$(=O)$_y NR^{11}R^{12}$, —C(=O)$NR^{11}S$(=O)$_y R^{12}$, —S(=O)$_y OR^{11}$, —S(=O)$_y NR^{11}R^{12}$, —S(=O)$_y NR^{11}C$(=O)$R^{12}$, —S(=O)$_y NR^{11}C$(=O)$OR^{12}$, —$C_{1-4}$ alkylene-$OR^{11}$, —$C_{1-4}$ alkylene-OC(=O)$R^{11}$, —$C_{1-4}$ alkylene-C(=O)$OR^{11}$, —$C_{1-4}$ alkylene-S(=O)$_y OR^{11}$, —$C_{1-4}$ alkylene-OC(=O)$NR^{11}R^{12}$, —$C_{1-4}$ alkylene-C(=O)$NR^{11}R^{12}$, —$C_{1-4}$ alkylene-OS(=O)$_y R^{11}$ or —$C_{1-4}$ alkylene-S(=O)$_y NR^{11}R^{12}$; wherein $R^{11}$, $R^{12}$ and y are as defined in any of the embodiments according to the first aspect described above.

In some of such embodiments, $R^{10}$ is H, F, Cl, Br, I, OH, —$OC_{1-6}$ alkyl (such as methoxy, ethoxy, or isopropoxy), amino, cyano, nitro, $C_{1-4}$alkyl (such as methyl, ethyl or isopropyl) or cyclopropyl.

In some of such embodiments, $R^{10}$ is H, F, Cl, Br, I, OH, amino, cyano, nitro, or CM alkyl (such as methyl, ethyl or isopropyl).

In some of such embodiments, $R^{10}$ is H, OH, amino, methyl or ethyl.

In some of such embodiments, $R^{10}$ is H, F, Cl, Br, I, OH, —$OC_{1-6}$ alkyl (such as methoxy, ethoxy, or isopropoxy), amino, CM alkyl (such as methyl, ethyl or isopropyl) or $C_{3-7}$ cyclic hydrocarbyl group (such as cyclopropyl); more preferably, F, Cl, OH, methoxy, ethoxy, amino, methyl, ethyl, isopropyl or cyclopropyl.

In some of such embodiments, $R^{10}$ is H, methyl or ethyl.

Preferably, in any of the embodiments described above, $R^{11}$ and $R^{12}$, at each occurrence, are each independently selected from the group consisting of H, CM alkyl, $C_{5-7}$ cyclic hydrocarbyl group, 5- to 7-membered monocyclic heterocyclic group, phenyl and 5- to 6-membered heteroaryl; preferably selected from FI and CM alkyl.

Preferably, in any of the embodiments described above, $R^{13}$, at each occurrence, may be independently selected from the group consisting of F, Cl, Br, I, amino, cyano, nitro, CM alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —OC(=O)$R^{11}$, —C(=O)$OR^{11}$, —C(=O)$NR^{11}R^{12}$, —C(=O)$NR^{11}S$(=O)$_y NR^{11}R^{12}$, —C(=O)$NR^{11}S$(=O)$_y R^{12}$, —S(=O)$_y OR^{11}$, —S(=O)$_y NR^{11}R^{12}$, —S(=O)$_y NR^{11}C$(=O)$R^{12}$, —S(=O)$_y NR^{11}C$(=O)$OR^{12}$, —$C_{1-4}$ alkylene-$OR^{11}$, —$C_{1-4}$ alkylene-OC(=O)$R^{11}$, —$C_{1-4}$ alkylene-C(=O)$OR^{11}$, —$C_{1-4}$ alkylene-S(=O)$_y OR^{11}$, —$C_{1-4}$ alkylene-OC(=O)$NR^{11}R^{12}$, —$C_{1-4}$ alkylene-C(=O)$NR^{11}R^{12}$, —$C_{1-4}$ alkylene-OS(=O)$_y R^{11}$ and —$C_{1-4}$ alkylene-S(=O)$_y NR^{11}R^{12}$; preferably F, Cl, Br, I, amino, cyano, nitro, CM alkyl, —$OR^{11}$ and —$SR^{11}$; and
wherein the alkyl, alkylene, cyclic hydrocarbyl group, heterocyclic group, phenyl and heteroaryl as defined for the substituent $R^{13}$ are optionally further substituted by 1, 2, 3 or more substitutes independently selected from the group consisting of F, Cl, Br, I, OH, oxo, amino, cyano, nitro, CM alkyl, halogenated CM alkyl, $C_{5-6}$ cyclic hydrocarbyl group, 5- to 7-membered monocyclic heterocyclic group, phenyl, 5- to 6-membered heteroaryl; preferably F, Cl, OH, amino, cyano, nitro, CM alkyl and halogenated CM alkyl;
wherein $R^{11}$, $R^{12}$ and y are as defined in any of the embodiments according to the first aspect described above, and, in some further preferred embodiments, the $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl as defined for $R^{11}$ and $R^{12}$ are not further substituted.

A fourth aspect of the embodiments of the compound according to the present invention relates to the compound having the structure of formula (I) or the pharmaceutically acceptable salt, ester, stereoisomer, polymorph, solvate, N-oxide, isotopically labeled compound, metabolite, or prodrug thereof as described above, wherein $R^{1a}$, $R^{1b}$, $X^1$, $R^{2a}$, $R^{2b}$ and $X^2$ have the definitions described in the Meaning (3) described above.

As such, the fourth aspect of the embodiments of the compound according to the present invention relates to the compound having the structure of formula (I) or a pharmaceutically acceptable salt, ester, stereoisomer, polymorph, solvate, N-oxide, isotopically labeled compound, metabolite or prodrug thereof, wherein:

$R^{1a}$ is selected from the group consisting of —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group and —$C_{1-6}$ alkylene-(5- to 14-membered heteroaryl);

$R^{1b}$, $R^{2a}$ an $R^{2b}$ are each independently selected from the group consisting of OH; $C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl);

$X^1$ is $CR^{10}$, N, O or S; provided that: when $X^1$ is O or S, $R^{1b}$ does not exist;

$X^2$ is $CR^{10}$ or N;

$X^3$ and $X^4$ are each independently selected from the group consisting of C(=O); S(=O)$_y$; and —O—C(=O)—, —S—C(=O)—, —O—S(=O)$_y$—, —$NR^{10}$—C(=O)— and —$NR^{10}$—S(=O)$_y$—, wherein O, S, $NR^{10}$ are connected to $X^1$ or $X^2$; preferably, $X^3$ and $X^4$ are each independently selected from the group consisting of C(=O), the —OC(=O)— or —$NR^{10}$—C(=O)—;

$R^3$, $R^4$ and $R^{10}$ are each independently selected from the group consisting of H, halogen, cyano, nitro, $C_{1-6}$ alkyl, $C_{2-6}$ alkenyl, $C_{2-6}$ alkynyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —$OC(=O)R^{11}$, —$C(=O)R^{11}$, —$C(=O)OR^{11}$, —$C(=O)NR^{11}$—OH, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yR^{11}$, —$S(=O)_yOR^{11}$, —$S(=O)_yNR^{11}R^{12}$, —$S(=O)_yNR^{11}S(=O)_zOR^{12}$, —$S(=O)_yNR^{11}C(=O)R^{12}$, —$S(=O)_yNR^{11}C(=O)OR^{12}$, —$NR^{11}R^{12}$, —$NR^{11}$—$C(=O)R^{12}$, —$NR^{11}$—C(=O)OR^{12}, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_xR^{11}$, —$C_{1-6}$ alkylene-S(=O)$_y$$OR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_yR^{12}$, —$C_{1-6}$ alkylene-$NR^{11}$—C(=O)$NR^{11}R^{12}$, —$C_{1-6}$ alkylene-OS(=O)$_yR^{11}$, —$C_{1-6}$ alkylene-OS(=O)$_yNR^{11}R^{12}$, —$C_{1-6}$ alkylene-$NR^{11}$—S(=O)$_yNR^{11}R^{12}$, —$C_{1-6}$ alkylene-$NR^{11}R^{12}$ and —O—$C_{1-6}$ alkylene-$NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;

the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, —$OR^{11}$, —$SR^{11}$, —OC(=O)$R^{11}$, —C(=O)$R^{11}$, —C(=O)$OR^{11}$, —C(=O)$NR^{11}R^{12}$, —C(=O)$NR^{11}S(=O)_yNR^{11}R^{12}$, —C(=O)$NR^{11}S(=O)_yR^{12}$, —S(=O)$_yR^{11}$, —S(=O)$_yOR^{11}$, —S(=O)$_yNR^{11}R^{12}$, —S(=O)$_yNR^{11}S(=O)_zOR^{12}$, —S(=O)$_yNR^{11}C(=O)R^{12}$, —S(=O)$_yNR^{11}C(=O)OR^{12}$, —$NR^{11}R^{12}$, —$NR^{11}$—C(=O)$R^{12}$, —$NR^{11}$—C(=O)$OR^{12}$, —$NR^{11}$—S(=O)$_y$—$R^{12}$, —$NR^{11}$—C(=O)—$NR^{11}R^{12}$, —$C_{1-6}$ alkylene-$OR^{11}$, —$C_{1-6}$ alkylene-OC(=O)$R^{11}$, —$C_{1-6}$ alkylene-C(=O)$OR^{11}$, —$C_{1-6}$ alkylene-S(=O)$_xR^{11}$, —$C_{1-6}$ alkylene-S(=O)$_yOR^{11}$, —$C_{1-6}$ alkylene-OC(=O)$NR^{11}R^{12}$, —$C_{1-6}$ alkylene-C(=O)$NR^{11}R^{12}$, —$C_{1-6}$ alkylene-C(=O)$NR^{11}$—S(=O)$_yR^{12}$, —$C_{1-6}$ alkylene-$NR^{11}$—C(=O)$NR^{11}R^{12}$, —$C_{1-6}$ alkylene-OS(=O)$_yR^{11}$, —$C_{1-6}$ alkylene-OS(=O)$_yNR^{11}R^{12}$, —$C_{1-6}$ alkylene-S(=O)$_yNR^{11}R^{12}$, —$C_{1-6}$ alkylene-$NR^{11}$—S(=O)$_yNR^{11}R^{12}$, —$C_{1-6}$ alkylene-$NR^{11}R^{12}$ and —O—$C_{1-6}$ alkylene-$NR^{11}R^{12}$; and wherein the alkyl, alkylene, cyclic hydrocarbyl group, heterocyclic group, aryl, heteroaryl and aralkyl as defined for the substituent $R^{13}$ are optionally further substituted by 1, 2, 3 or more substituents selected independently from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;

x, at each occurrence, is independently 0, 1 or 2; and y and z, at each occurrence, are each independently 1 or 2.

The embodiments of the compound according to the fourth aspect are further described below.

In some embodiments, the present invention provides the compound with the structure of formula (I) or a pharmaceutically acceptable salt, ester, stereoisomer, polymorph, solvate, N-oxide, isotopically labeled compound, metabolite or prodrug thereof as described above, wherein $R^{1a}$ is selected from the group consisting of —$C_{1-4}$ alkylene-saturated or partially unsaturated $C_{3-7}$ cyclic hydrocarbyl group, —$C_{1-4}$ alkylene-saturated or partially unsaturated 5- to 7-membered heterocyclic group and —$C_{1-4}$ alkylene-(5- to 10-membered heteroaryl).

Preferably, in such embodiments, said heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl and its benzo derivatives, more preferably, selected from the group consisting of thienyl and furyl and its benzo derivatives (such as benzothienyl and benzofuryl), more preferably, selected from the group consisting of thienyl and its benzo derivatives (such as benzothienyl).

Preferably, in such embodiments, said heteroaryl is optionally substituted by 1 or 2 $R^{13}$.

Preferably, in such embodiments, $R^{13}$, at each occurrence, is independently selected from the group consisting of F, Cl, Br, I, amino, cyano, nitro, $C_{1-4}$ alkyl, —$OR^{11}$ and —$SR^{11}$; preferably, selected from the group consisting of Cl, methyl and ethyl.

More preferably, in such embodiments, $R^{1a}$ is selected from:

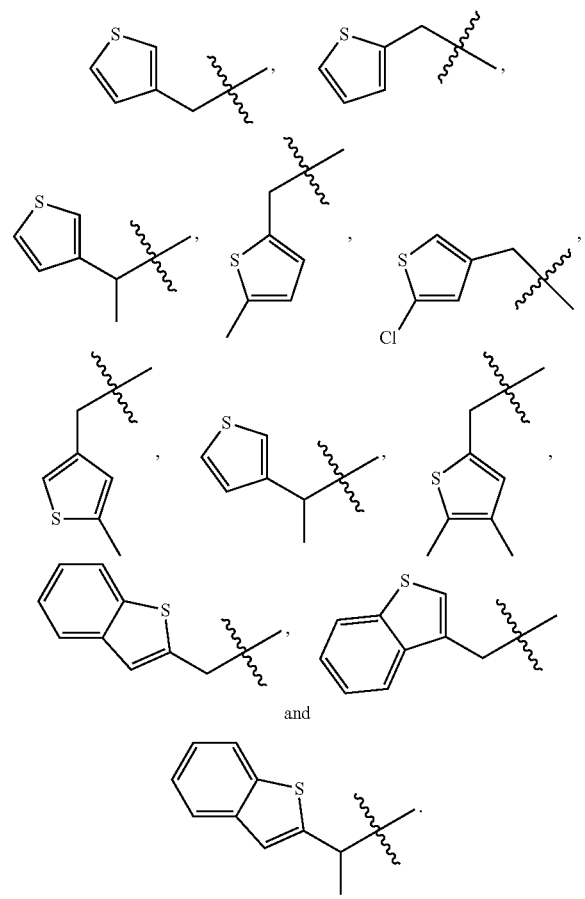

Preferably, in any of the embodiments described above, $R^{1b}$, $R^{2a}$ and $R^{2b}$ are each independently selected from the group consisting of OH; $C_{1-6}$ alkyl, $C_{2-6}$ alkenyl and $C_{2-6}$ alkynyl, wherein any one of the $CH_2$ moieties in the $C_{1-6}$ alkyl, $C_{2-6}$ alkenyl and $C_{2-6}$ alkynyl is optionally replaced with O or S; saturated or partially unsaturated $C_{3-7}$ cyclic hydrocarbyl group; saturated or partially unsaturated 5- to 7-membered heterocyclic group; $C_{6-10}$ aryl; 5- to 7-membered heteroaryl; —$C_{1-4}$ alkylene-saturated or partially unsaturated $C_{3-7}$ cyclic hydrocarbyl group, —$C_{1-4}$ alkylene-saturated or partially unsaturated 5- to 7-membered heterocyclic group; —$C_{1-4}$ alkylene-$C_{6-10}$ aryl; and —$C_{1-4}$ alkylene-(5- to 10-membered heteroaryl);

preferably selected from the group consisting of OH, $C_{1-4}$ alkyl, saturated or partially unsaturated $C_{3-7}$ cyclic hydrocarbyl group and $C_{6-10}$ aryl.

More preferably, $R^{1b}$ is selected from the group consisting of OH, $C_{1-4}$ alkyl, saturated or partially unsaturated $C_{3-5}$ cyclic hydrocarbyl group and $C_{6-10}$ aryl; more preferably, selected from the group consisting of OH, methyl, ethyl, isopropyl, cyclopropyl and phenyl.

More preferably, $R^{2a}$ is phenyl.

More preferably, $R^{2b}$ is selected from the group consisting of $C_{1-4}$ alkyl and phenyl; more preferably, selected from the group consisting of methyl, ethyl, isopropyl, cyclopropyl and phenyl.

Preferably, in any of the embodiments described above, $X^1$ is N, O or S; preferably N or O.

Preferably, in any of the embodiments described above, $X^2$ is CH or N.

Preferably, in any of the embodiments described above, $X^3$ and $X^4$ are each independently selected from C(=O) and S(=O)$_y$; preferably, are each C(=O).

Preferably, in any of the embodiments described above, $R^{10}$ is H, F, Cl, Br, I, amino, cyano, nitro, $C_{1-4}$ alkyl, $C_{3-7}$ cyclic hydrocarbyl group (such as $C_{5-7}$ cyclic hydrocarbyl group), 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-4}$ alkylene-$OR^{11}$, —$C_{1-4}$ alkylene-$OC(=O)R^{11}$, —$C_{1-4}$ alkylene-$C(=O)OR^{11}$, —$C_{1-4}$ alkylene-$S(=O)_yOR^{11}$, —$C_{1-4}$ alkylene-$OC(=O)NR^{11}R^{12}$, —$C_{1-4}$ alkylene-$C(=O)NR^{11}R^{12}$, —$C_{1-4}$ alkylene-$OS(=O)_yR^{11}$ or —$C_{1-4}$ alkylene-$S(=O)_yNR^{11}R^{12}$; wherein $R^{11}$, $R^{12}$ and y are as defined in any of the embodiments according to the first aspect described above.

In some embodiments, $R^{10}$ is H, F, Cl, Br, I, OH, —$OC_{1-6}$ alkyl (such as methoxy, ethoxy, or isopropoxy), amino, cyano, nitro, $C_{1-4}$ alkyl (such as methyl, ethyl or isopropyl) or cyclopropyl.

In some embodiments, $R^{10}$ is H, F, Cl, Br, I, OH, amino, cyano, nitro, or $C_{1-4}$ alkyl (such as methyl, ethyl or isopropyl).

In some embodiments, $R^{10}$ is H, OH, amino, methyl or ethyl.

In some embodiments, $R^{10}$ is H, F, Cl, Br, I, OH, —$OC_{1-6}$ alkyl (such as methoxy, ethoxy, or isopropoxy), amino, CM alkyl (such as methyl, ethyl or isopropyl) or $C_{3-7}$ cyclic hydrocarbyl group (such as cyclopropyl); more preferably, F, Cl, OH, methoxy, ethoxy, amino, methyl, ethyl, isopropyl or cyclopropyl.

In some embodiments, $R^{10}$ is H, methyl or ethyl.

Preferably, in any of the embodiments described above, $R^{11}$ and $R^{12}$, at each occurrence, are each independently selected from the group consisting of H, $C_{1-4}$ alkyl, $C_{5-7}$ cyclic hydrocarbyl group, 5- to 7-membered monocyclic heterocyclic group, phenyl and 5- to 6-membered heteroaryl; preferably selected from H and $C_{1-4}$ alkyl.

Preferably, in any of the embodiments described above, $R^{13}$, at each occurrence, may be independently selected from the group consisting of F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}R^{12}$, —$C(=O)NR^{11}S(=O)_yNR^{11}R^{12}$, —$C(=O)NR^{11}S(=O)_yR^{12}$, —$S(=O)_yOR^{11}$, —$S(=O)_yNR^{11}R^{12}$, —$S(=O)_yNR^{11}C(=O)R^{12}$, —$S(=O)_yNR^{11}C(=O)OR^{12}$, —$C_{1-4}$ alkylene-$OR^{11}$, —$C_{1-4}$ alkylene-$OC(=O)R^{11}$, —$C_{1-4}$ alkylene-$C(=O)OR^{11}$, —$C_{1-4}$ alkylene-$S(=O)_yOR^{11}$, —$C_{1-4}$ alkylene-$OC(=O)NR^{11}R^{12}$, —$C_{1-4}$ alkylene-$C(=O)NR^{11}R^{12}$, —$C_{1-4}$ alkylene-$OS(=O)_yR^{11}$ and —C$_{1-4}$ alkylene-S(=O)$_y$NR$^{11}$R$^{12}$; preferably F, Cl, Br, I, amino, cyano, nitro, C$_{1-4}$ alkyl, —OR$^{11}$ and —SR$^{11}$; and preferably, wherein the alkyl, alkylene, cyclic hydrocarbyl group, heterocyclic group, phenyl and heteroaryl as defined for the substituent R$^{13}$ are optionally further substituted by 1, 2, 3 or more substitutes independently selected from the group consisting of F, Cl, Br, I, OH, oxo, amino, cyano, nitro, C$_{1-4}$ alkyl, halogenated C$_{1-4}$ alkyl, C$_{5-6}$ cyclic hydrocarbyl group, 5- to 7-membered monocyclic heterocyclic group, phenyl, 5- to 6-membered heteroaryl; preferably F, Cl, OH, amino, cyano, nitro, C$_{1-4}$ alkyl and halogenated C$_{1-4}$ alkyl;

wherein R$^{11}$, R$^{12}$ and y are as defined in any of the embodiments according to the first aspect described above, and, in some further preferred embodiments, the C$_{1-6}$ alkyl, C$_{3-10}$ cyclic hydrocarbyl group, 3- to 10-membered heterocyclic group, C$_{6-10}$ aryl, 5- to 14-membered heteroaryl and C$_{6-12}$ aralkyl as defined for R$^{11}$ and R$^{12}$ are not further substituted.

The compounds obtained by any combinations of the various embodiments described above are encompassed by the invention.

In some embodiments, the present invention provides the compound of formulary (I) or a pharmaceutically acceptable salt, ester, stereoisomer, polymorph, solvate, N-oxide, isotopically labeled compound, metabolite or prodrug thereof, wherein the compound has the following structure and characterization data:

| No. | Structure | MS m/z (ESI): [M + H]$^+$ |
|---|---|---|
| C1 | | 545.0 |
| C2 | | 544.9 |
| C3 | 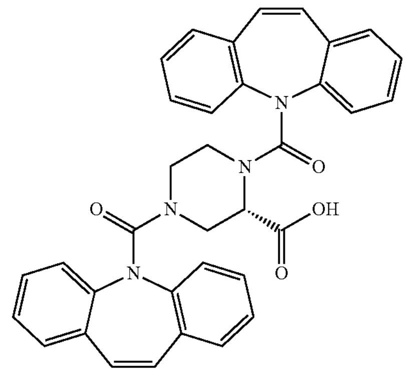 [SMILES: O=C(O)[C@@H]1CN(C(=O)N2c3ccccc3C=Cc3ccccc32)CCN1C(=O)N1c2ccccc2C=Cc2ccccc21] | 568.9 |
| C4 | 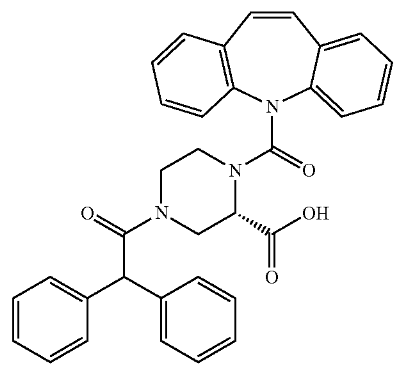 | 544.0 |
| C5 | 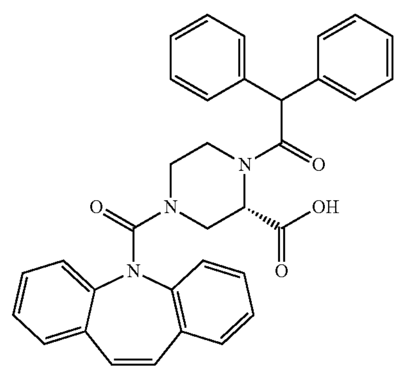 [SMILES: O=C(O)[C@@H]1CN(C(=O)N2c3ccccc3C=Cc3ccccc32)CCN1C(=O)C(c1ccccc1)c1ccccc1] | 544.0 |
| C6 | 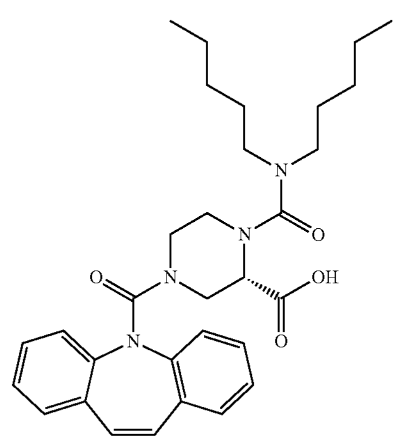 [SMILES: CCCCCN(CCCCC)C(=O)N1CCN(C(=O)N2c3ccccc3C=Cc3ccccc32)C[C@H]1C(=O)O] | 533.1 |

-continued
| No. | Structure | MS m/z (ESI): [M + H]+ |
|---|---|---|
| C7 | 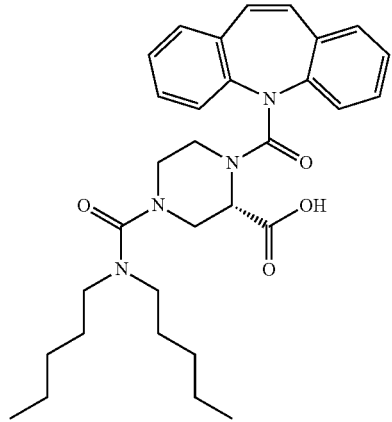 [SMILES: CCCCCN(CCCCC)C(=O)N1CCN(C(=O)N2c3ccccc3C=Cc3ccccc32)[C@H](C(=O)O)C1] | 532.8 |
| C8 | 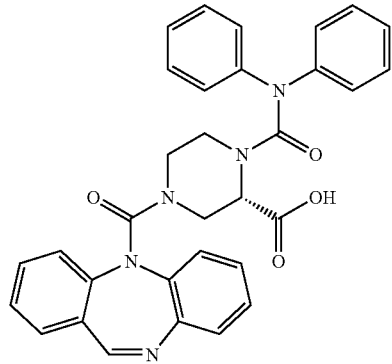 | 546.0 |
| C9 | 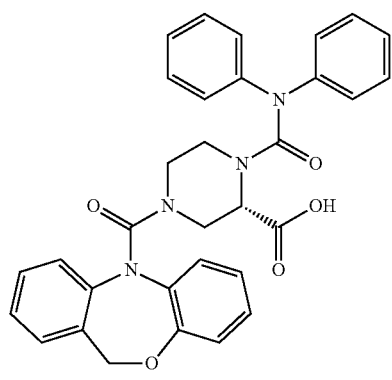 | 549.0 |
-continued
| No. | Structure | MS m/z (ESI): [M + H]+ |
|---|---|---|
| C10 | 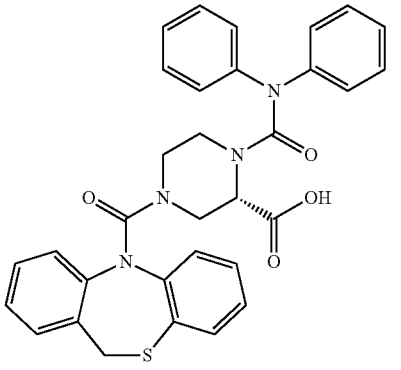 [SMILES: O=C(O)[C@@H]1CN(C(=O)N2c3ccccc3COc3ccccc32)CCN1C(=O)N(c1ccccc1)c1ccccc1] | 564.9 |
| C11 | 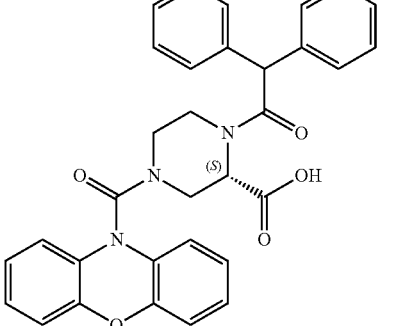 | 533.5 |
| C12 | 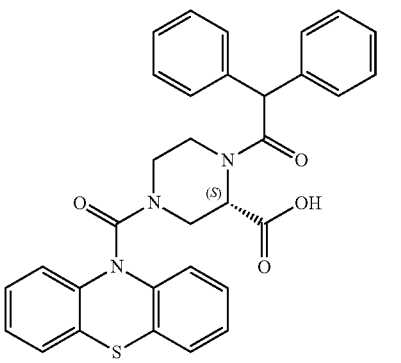 | 550.0 |
| C13 | 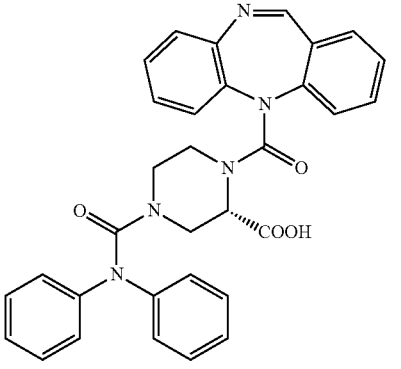 | 546.0 |

-continued

| No. | Structure | MS m/z (ESI): [M + H]⁺ |
|---|---|---|
| C14 | 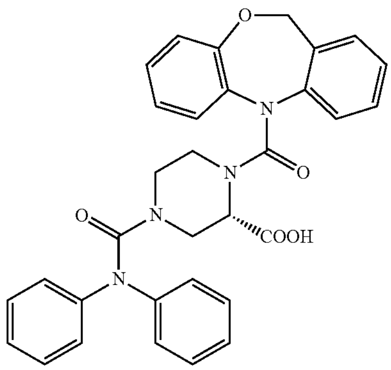 [SMILES: O=C(O)[C@@H]1CN(C(=O)N(c2ccccc2)c2ccccc2)CCN1C(=O)N1c2ccccc2COc2ccccc21] | 549.0 |
| C15 | 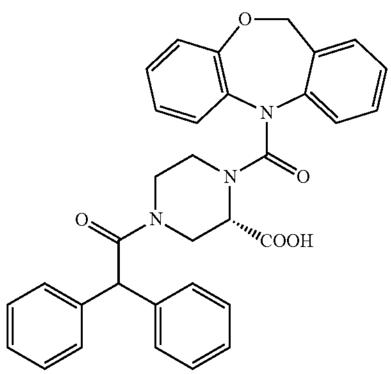 | 548.0 |
| C16 | 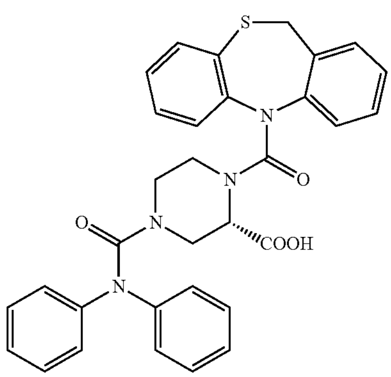 [SMILES: O=C(O)[C@@H]1CN(C(=O)N(c2ccccc2)c2ccccc2)CCN1C(=O)N1c2ccccc2CSc2ccccc21] | 564.9 |
| C17 | 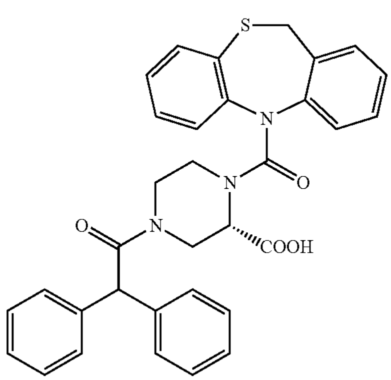 | 563.9 |

-continued

| No. | Structure | MS m/z (ESI): [M + H]⁺ |
|---|---|---|
| C18 | 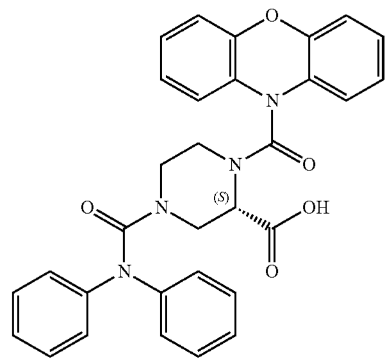 | 534.8 |
| C19 | 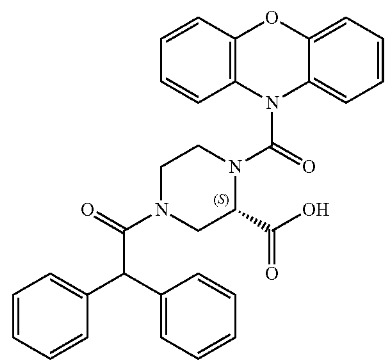 | 534.0 |
| C20 | 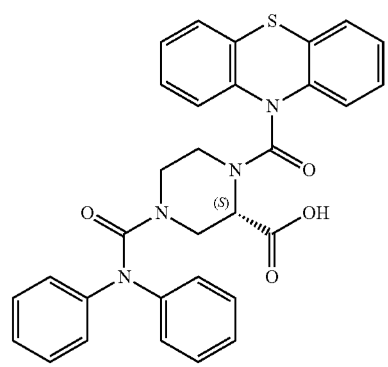 | 550.9 |
| C21 | 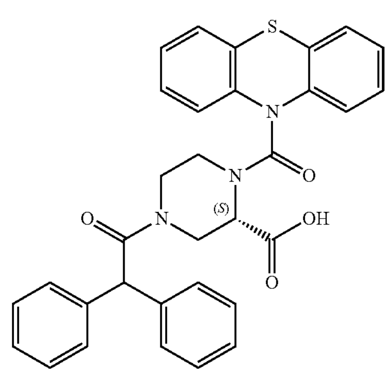 | 549.9 |

| No. | Structure | MS m/z (ESI): [M + H]+ |
|---|---|---|
| C22 | 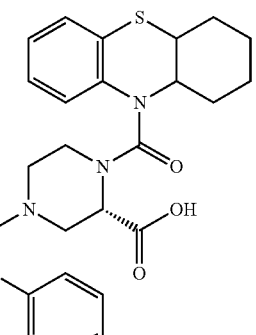 | 539.1 |
| C23 | | 538.1 |
| C24 | | 541.1 |
| C25 | | 540.0 |
| No. | Structure | MS m/z (ESI): [M + H]+ |
|---|---|---|
| C26 | 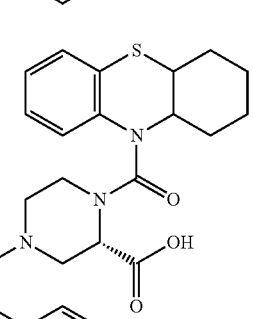 | 557.0 |
| C27 | | 556.0 |
| C28 | | 525.0 |
| C29 | | 523.1 |

| No. | Structure | MS m/z (ESI): [M + H]+ |
|---|---|---|
| C30 | 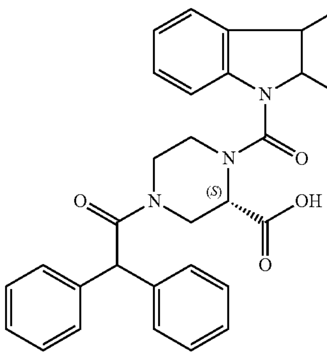 | 524.1 |
| C31 | 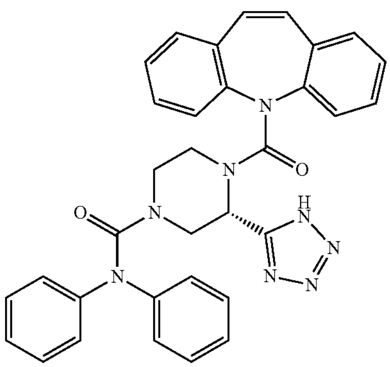 | 568.8 |
| C32 | 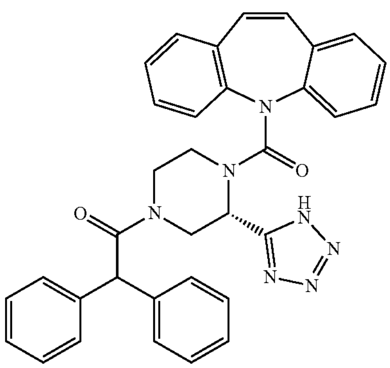 [SMILES: O=C(C(c1ccccc1)c1ccccc1)N1CCN(C(=O)N2c3ccccc3C=Cc3ccccc32)[C@H](c2nnn[nH]2)C1] | 568.0 |
| C33 | 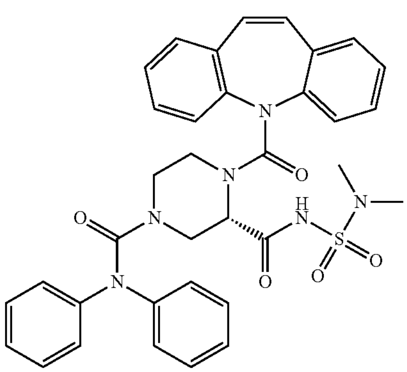 [SMILES: CN(C)S(=O)(=O)NC(=O)[C@@H]1CN(C(=O)N(c2ccccc2)c2ccccc2)CCN1C(=O)N1c2ccccc2C=Cc2ccccc21] | 651.1 |
| C34 | | 650.0 |
| C35 | | 622.0 |
| C36 | | 621.0 |
| C37 | | 680.1 |

-continued

| No. | Structure | MS m/z (ESI): [M + H]⁺ |
|---|---|---|
| C38 | 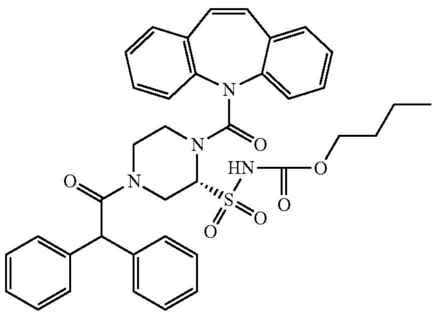 [SMILES: CCCCOC(=O)NS(=O)(=O)[C@@H]1CN(C(=O)C(c2ccccc2)c2ccccc2)CCN1C(=O)N1c2ccccc2C=Cc2ccccc21] | 679.1 |
| C39 | 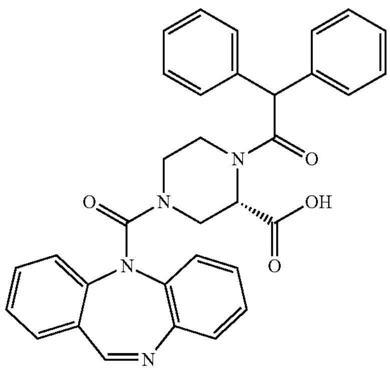 [SMILES: O=C(O)[C@@H]1CN(C(=O)N2c3ccccc3C=Nc3ccccc32)CCN1C(=O)C(c1ccccc1)c1ccccc1] | 545.0 |
| C40 | 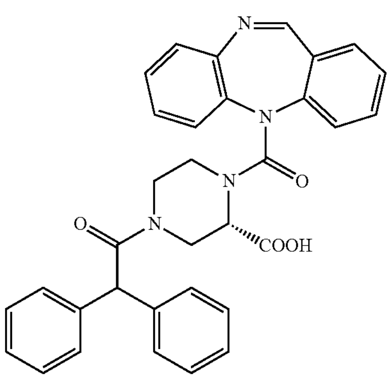 [SMILES: O=C(O)[C@@H]1CN(C(=O)C(c2ccccc2)c2ccccc2)CCN1C(=O)N1c2ccccc2C=Nc2ccccc21] | 545.0 |
| C41 | 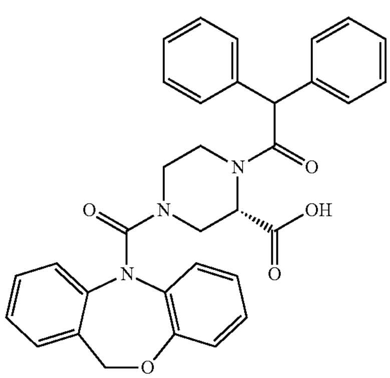 [SMILES: O=C(O)[C@@H]1CN(C(=O)N2c3ccccc3CSc3ccccc32)CCN1C(=O)C(c1ccccc1)c1ccccc1] | 548.0 |
| C42 | | 563.9 |
| C43 | | 534.7 |
| C44 | | 550.9 |
| C45 | | 544.8 |

-continued

| No. | Structure | MS m/z (ESI): [M + H]⁺ |
|---|---|---|
| C46 | 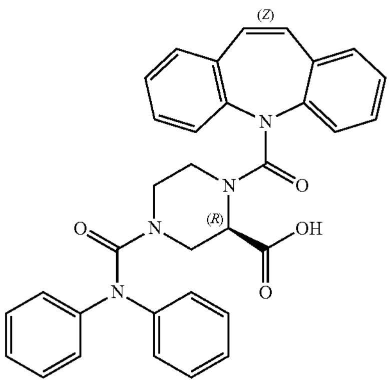 | 544.7 |
| C47 | 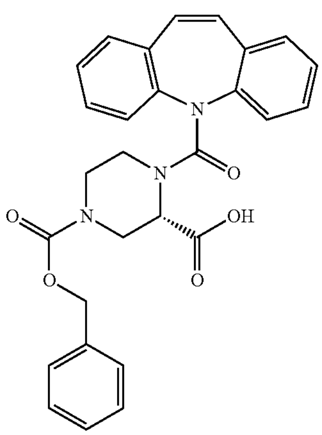 [SMILES: O=C(O)[C@@H]1CN(C(=O)OCc2ccccc2)CCN1C(=O)N1c2ccccc2C=Cc2ccccc21] | 484.0 |
| C48 | 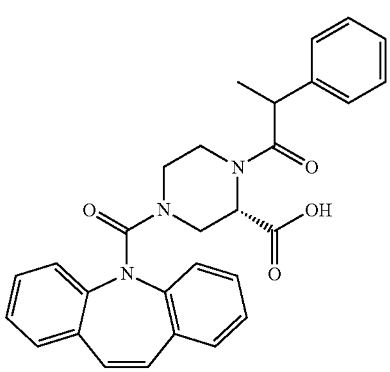 [SMILES: CC(C(=O)N1CCN(C(=O)N2c3ccccc3C=Cc3ccccc32)C[C@H]1C(=O)O)c1ccccc1] | 481.8 |
| C49 | 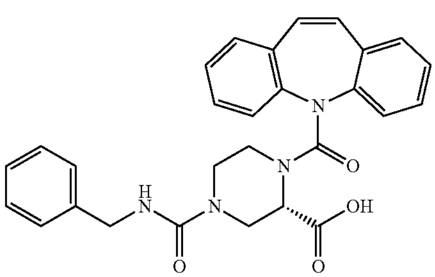 [SMILES: O=C(O)[C@@H]1CN(C(=O)NCc2ccccc2)CCN1C(=O)N1c2ccccc2C=Cc2ccccc21] | 482.8 |
| C50 | 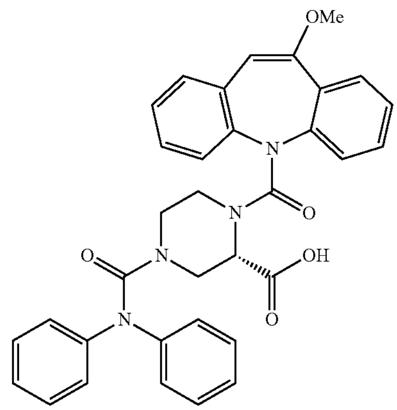 [SMILES: COC1=Cc2ccccc2N(C(=O)N2CCN(C(=O)N(c3ccccc3)c3ccccc3)C[C@H]2C(=O)O)c2ccccc21] | 574.9 |
| C51 | 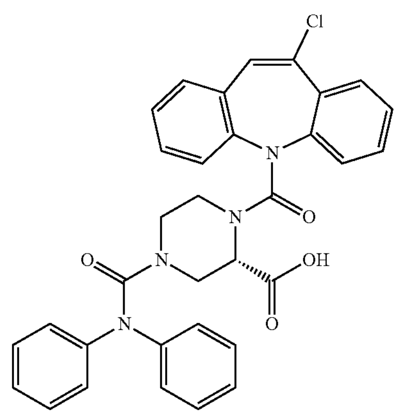 [SMILES: O=C(O)[C@@H]1CN(C(=O)N(c2ccccc2)c2ccccc2)CCN1C(=O)N1c2ccccc2C=C(Cl)c2ccccc21] | 578.7 |
| C52 | 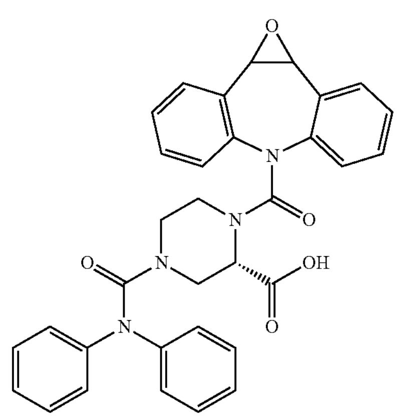 [SMILES: O=C(O)[C@@H]1CN(C(=O)N(c2ccccc2)c2ccccc2)CCN1C(=O)N1c2ccccc2C2OC2c2ccccc21] | 561.0 |

| No. | Structure | MS m/z (ESI): [M + H]+ |
|---|---|---|
| C53 | 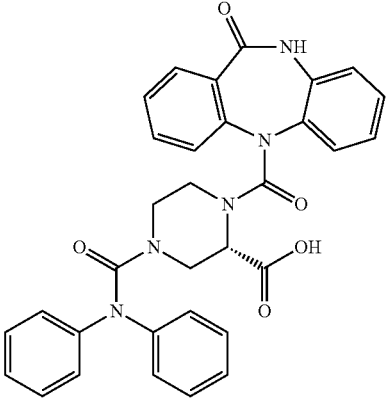 [SMILES: O=C1Nc2ccccc2N(C(=O)N2CCN(C(=O)N(c3ccccc3)c3ccccc3)C[C@H]2C(=O)O)c2ccccc21] | 561.8 |
| C54 | 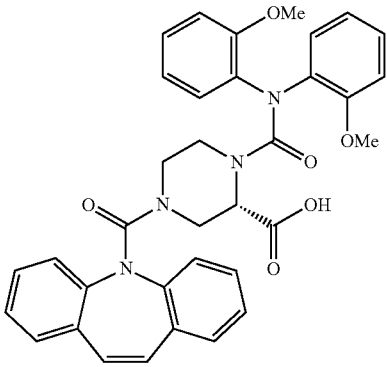 [SMILES: COc1ccccc1N(C(=O)N1CCN(C(=O)N2c3ccccc3C=Cc3ccccc32)C[C@H]1C(=O)O)c1ccccc1OC] | 604.0 |
| C55 | 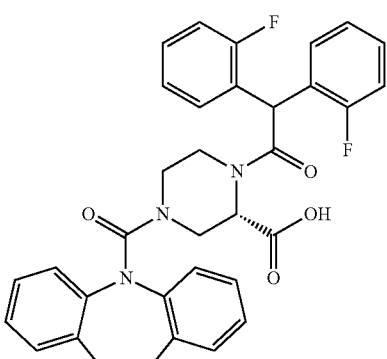 | 580.0 |
| C56 | 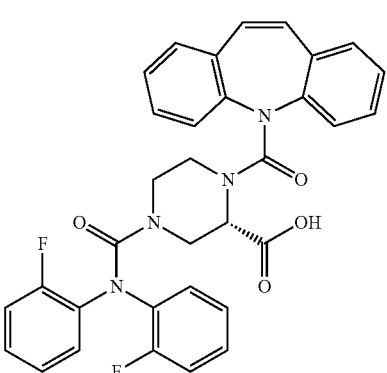 [SMILES: Cc1ccccc1N(C(=O)N1CCN(C(=O)N2c3ccccc3C=Cc3ccccc32)[C@H](C(=O)O)C1)c1ccccc1] | 580.9 |
| C57 | 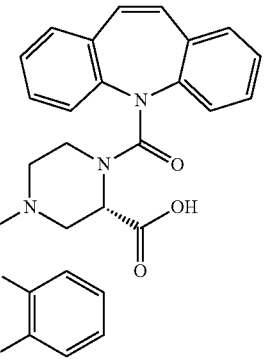 | 604.7 |
| C58 | 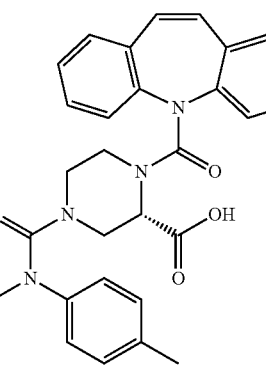 | 573.0 |
| C59 | 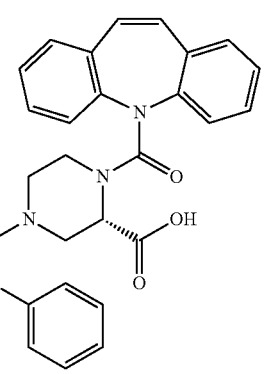 | 559.0 |
| C60 | 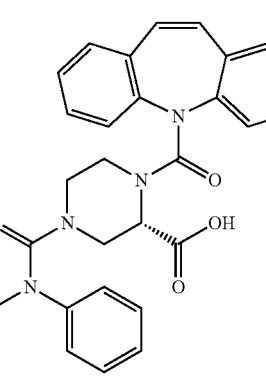 | 559.0 |

-continued
| No. | Structure | MS m/z (ESI): [M + H]+ |
|---|---|---|
| C61 | 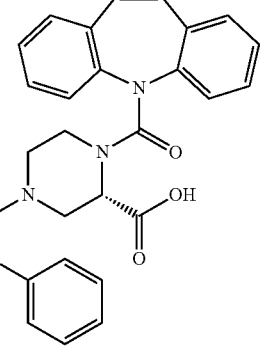 | 559.0 |
| C62 | 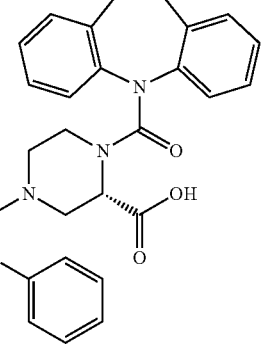 | 563.0 |
| C63 | 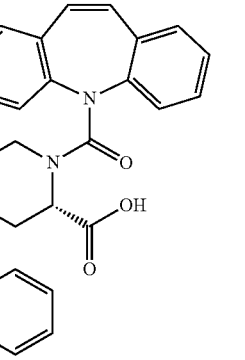 | 578.9 |
| C64 | 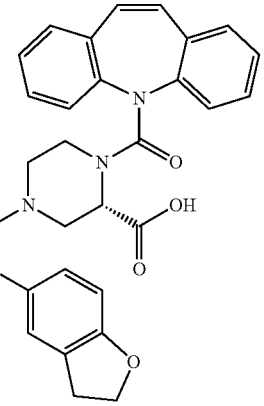 | 628.0 |
-continued
| No. | Structure | MS m/z (ESI): [M + H]+ |
|---|---|---|
| C65 | 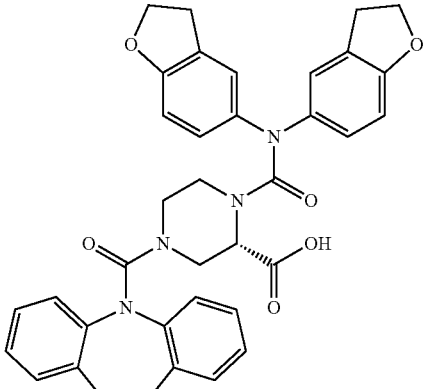 | 628.0 |
| C66 | 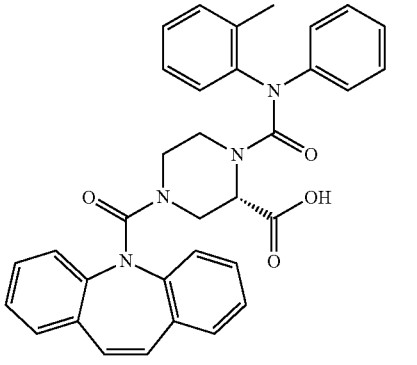 [SMILES: Cc1ccccc1N(C(=O)N1CCN(C(=O)N2c3ccccc3C=Cc3ccccc32)C[C@H]1C(=O)O)c1ccccc1] | 559.0 |
| C67 | 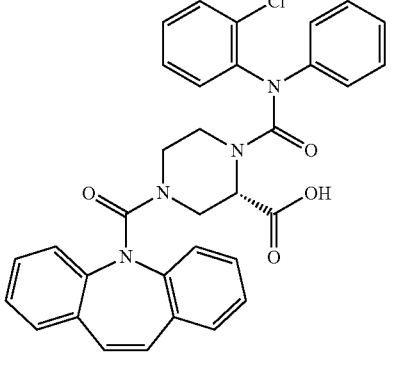 | 578.9 |
| C68 | 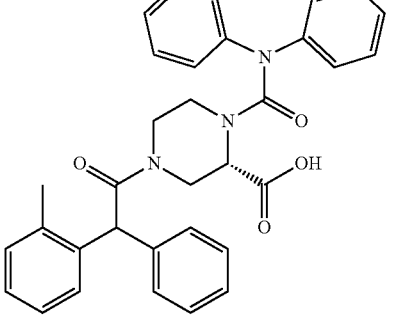 | 558.0 |

-continued

| No. | Structure | MS m/z (ESI): [M + H]⁺ |
|---|---|---|
| C69 | 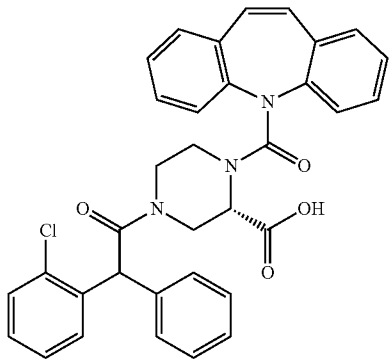 [SMILES: O=C(O)[C@@H]1CN(C(=O)C(c2ccccc2)c2ccccc2Cl)CCN1C(=O)N1c2ccccc2C=Cc2ccccc21] | 577.9 |
| C70 | 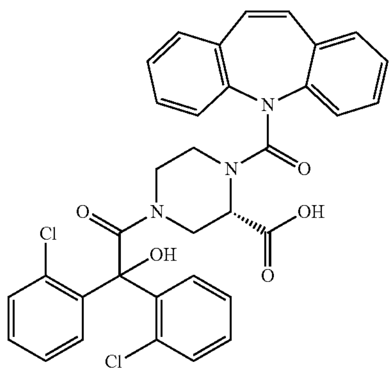 [SMILES: O=C(O)[C@@H]1CN(C(=O)C(O)(c2ccccc2Cl)c2ccccc2Cl)CCN1C(=O)N1c2ccccc2C=Cc2ccccc21] | 627.8 |
| C71 | 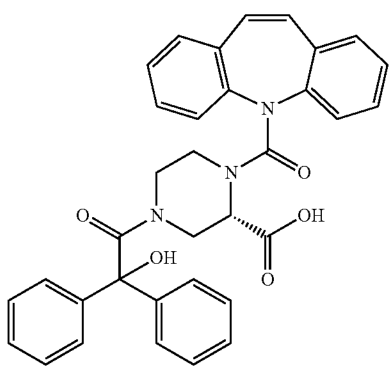 [SMILES: O=C(O)[C@@H]1CN(C(=O)C(O)(c2ccccc2)c2ccccc2)CCN1C(=O)N1c2ccccc2C=Cc2ccccc21] | 560.0 |
| C72 | 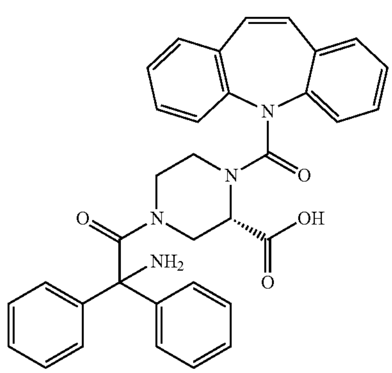 [SMILES: NC(C(=O)N1CCN(C(=O)N2c3ccccc3C=Cc3ccccc32)[C@H](C(=O)O)C1)(c1ccccc1)c1ccccc1] | 559.0 |

-continued

| No. | Structure | MS m/z (ESI): [M + H]⁺ |
|---|---|---|
| C73 | 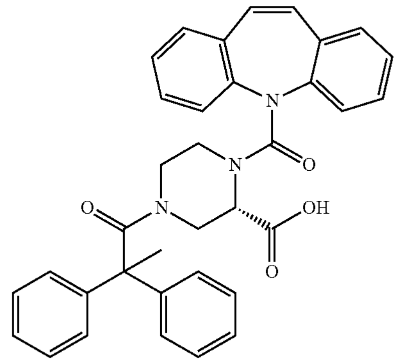 | 558.0 |
| C74 | 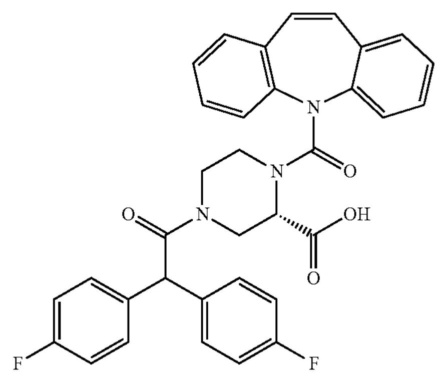 [SMILES: O=C(O)[C@@H]1CN(C(=O)C(c2ccc(F)cc2)c2ccc(F)cc2)CCN1C(=O)N1c2ccccc2C=Cc2ccccc21] | 580.0 |
| C75 | 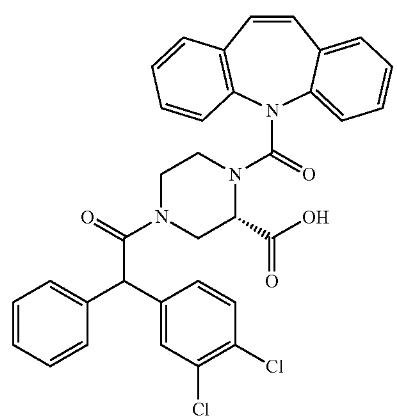 [SMILES: O=C(O)[C@@H]1CN(C(=O)C(c2ccccc2)c2ccc(Cl)c(Cl)c2)CCN1C(=O)N1c2ccccc2C=Cc2ccccc21] | 611.8 |
| C76 | 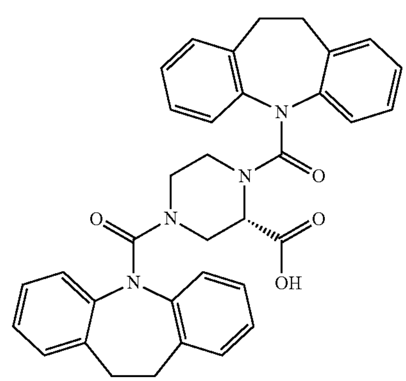 [SMILES: O=C(O)[C@@H]1CN(C(=O)N2c3ccccc3CCc3ccccc32)CCN1C(=O)N1c2ccccc2CCc2ccccc21] | 573.0 |

-continued
| No. | Structure | MS m/z (ESI): [M+H]+ |
|---|---|---|
| C77 | 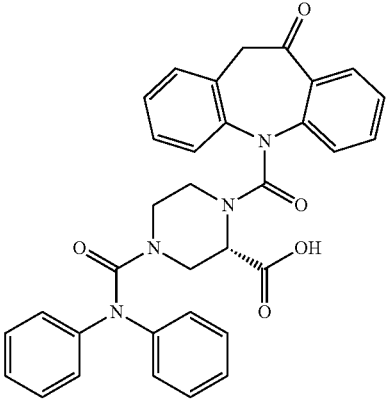 | 560.7 |
| C78 | 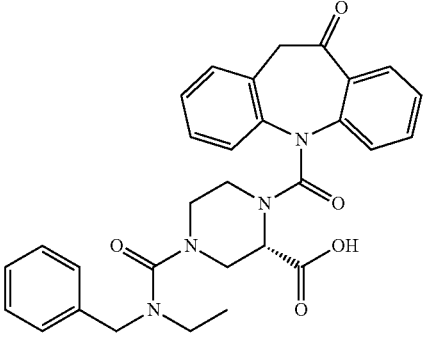 [SMILES: CCN(Cc1ccccc1)C(=O)N1CCN(C(=O)N2c3ccccc3CC(=O)c3ccccc32)[C@H](C(=O)O)C1] | 526.8 |
| C79 | 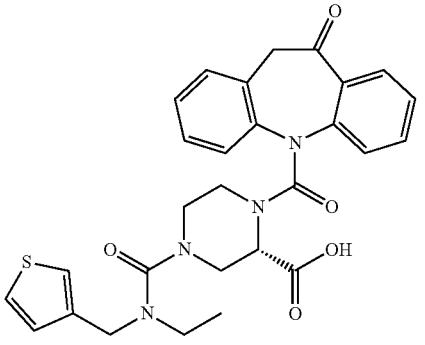 [SMILES: CCN(Cc1ccsc1)C(=O)N1CCN(C(=O)N2c3ccccc3CC(=O)c3ccccc32)[C@H](C(=O)O)C1] | 533.0 |
| C80 | 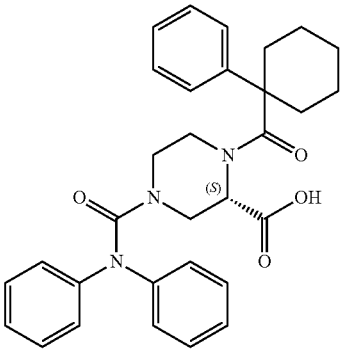 | 512.2 |
-continued
| No. | Structure | MS m/z (ESI): [M+H]+ |
|---|---|---|
| C81 | 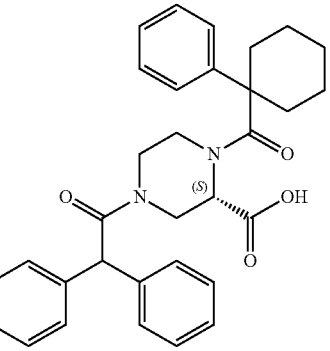 | 511.2 |
| C82 | 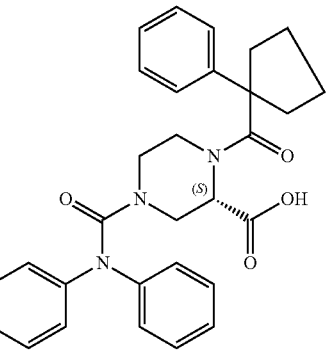 | 498.2 |
| C83 | 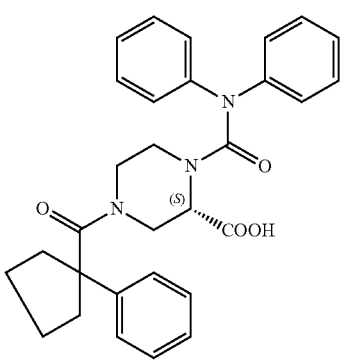 | 498.2 |
| C84 | 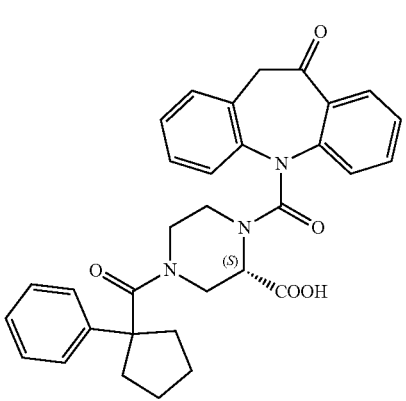 | 537.9 |

| No. | Structure | MS m/z (ESI): [M + H]+ |
|---|---|---|
| C85 | 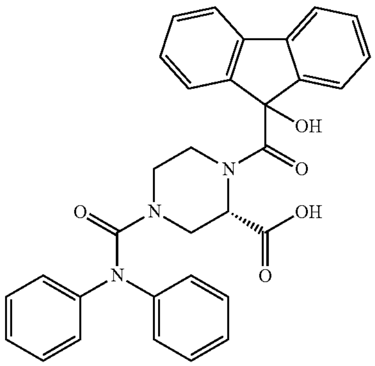 [SMILES: O=C(O)[C@@H]1CN(C(=O)N(c2ccccc2)c2ccccc2)CCN1C(=O)C1(O)c2ccccc2-c2ccccc21] | 534.1 |
| C86 | 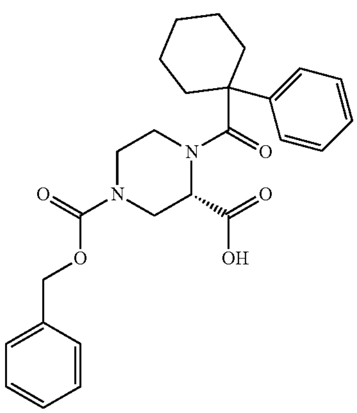 [SMILES: O=C(O)[C@@H]1CN(C(=O)OCc2ccccc2)CCN1C(=O)C1(c2ccccc2)CCCCC1] | 451.2 |
| C87 | 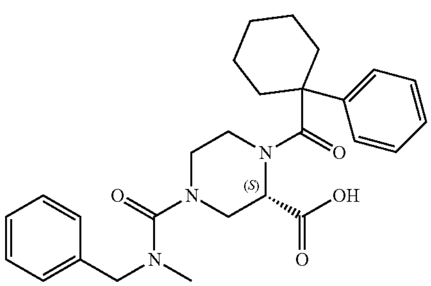 | 464.1 |
| C88 | 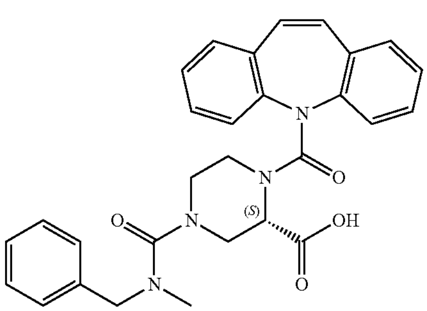 | 497.1 |

| No. | Structure | MS m/z (ESI): [M + H]+ |
|---|---|---|
| C89 | 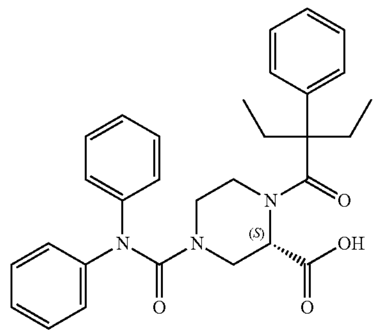 | 499.8 |
| C90 | 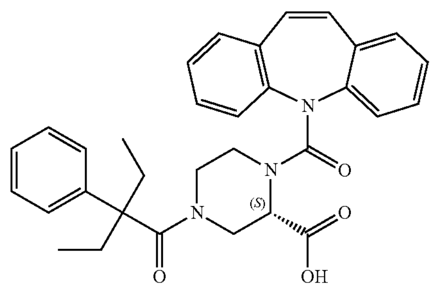 | 524.2 |
| C91 | 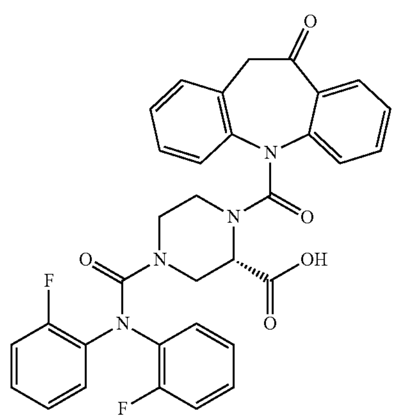 [SMILES: O=C1Cc2ccccc2N(C(=O)N2CCN(C(=O)N(c3ccccc3F)c3ccccc3F)C[C@H]2C(=O)O)c2ccccc21] | 597.0 |
| C92 | 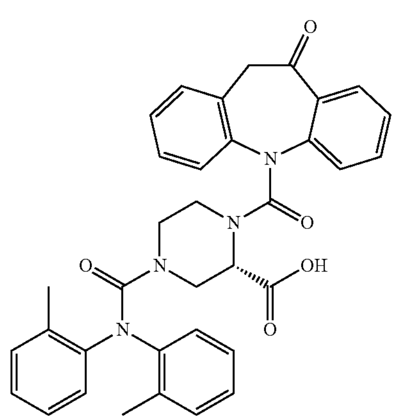 [SMILES: Cc1ccccc1N(C(=O)N1CCN(C(=O)N2c3ccccc3CC(=O)c3ccccc32)[C@H](C(=O)O)C1)c1ccccc1C] | 589.0 |

| No. | Structure | MS m/z (ESI): [M + H]+ |
|---|---|---|
| C93 | 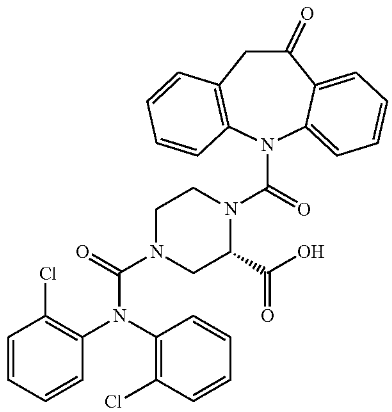 [SMILES: O=C1Cc2ccccc2N(C(=O)N2CCN(C(=O)N(c3ccccc3Cl)c3ccccc3Cl)C[C@H]2C(=O)O)c2ccccc21] | 628.9 |
| C94 | 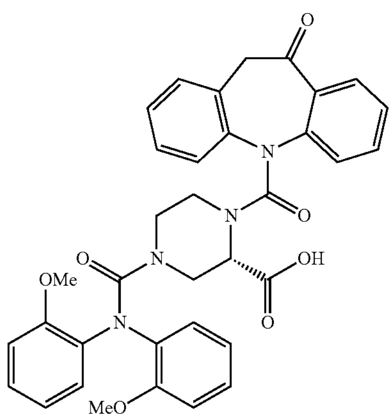 [SMILES: COc1ccccc1N(C(=O)N1CCN(C(=O)N2c3ccccc3CC(=O)c3ccccc32)[C@H](C(=O)O)C1)c1ccccc1OC] | 621.0 |
| C95 | 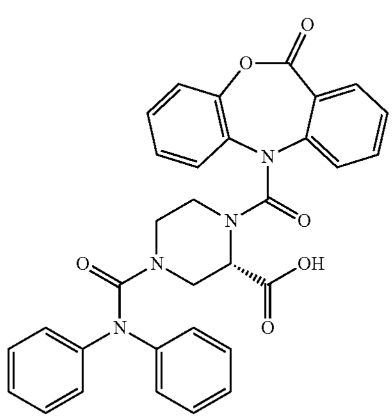 [SMILES: O=C1Oc2ccccc2N(C(=O)N2CCN(C(=O)N(c3ccccc3)c3ccccc3)C[C@H]2C(=O)O)c2ccccc21] | 562.9 |
| C96 | | 576.0 |
| C97 | | 636.0 |
| C98 | | 590.0 |

| No. | Structure | MS m/z (ESI): [M + H]+ |
|---|---|---|
| C99 | | 604.0 |
| C100 | 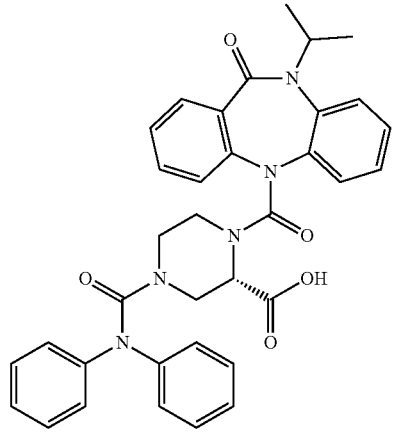 [SMILES: CC(C)N1C(=O)c2ccccc2N(C(=O)N2CCN(C(=O)N(c3ccccc3)c3ccccc3)C[C@H]2C(=O)O)c2ccccc21] | 602.0 |
| C101 | | 588.7 |
| No. | Structure | MS m/z (ESI): [M + H]+ |
|---|---|---|
| C102 | | 574.7 |
| C103 | 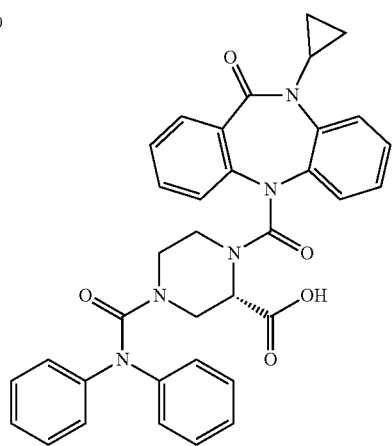 | 667.0 |
| C104 | | 585.2 |

| No. | Structure | MS m/z (ESI): [M+H]+ |
|---|---|---|
| C105 | 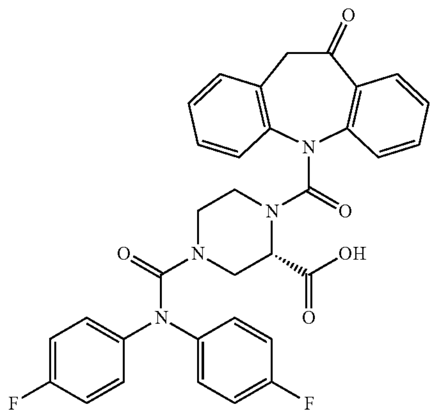 [SMILES: O=C1Cc2ccccc2N(C(=O)N2CCN(C(=O)N(c3ccc(F)cc3)c3ccc(F)cc3)C[C@H]2C(=O)O)c2ccccc21] | 597.0 |
| C106 | 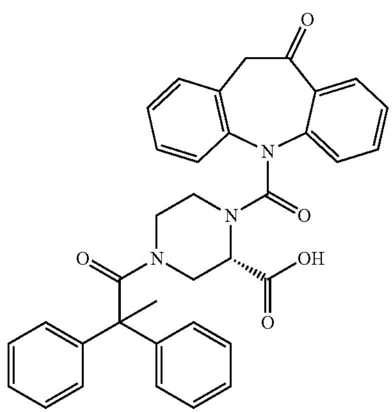 [SMILES: CC(C(=O)N1CCN(C(=O)N2c3ccccc3CC(=O)c3ccccc32)[C@H](C(=O)O)C1)(c1ccccc1)c1ccccc1] | 573.8 |
| C107 | 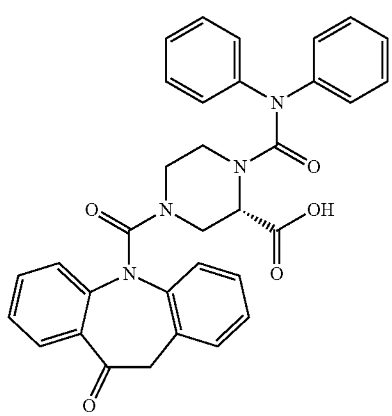 [SMILES: O=C1Cc2ccccc2N(C(=O)N2CCN(C(=O)N(c3ccccc3)c3ccccc3)[C@H](C(=O)O)C2)c2ccccc21] | 560.6 |
| C108 | | 620.7 |
| C109 | | 621.0 |
| C110 | | 629.0 |

153
-continued
| No. | Structure | MS m/z (ESI): [M + H]+ |
|---|---|---|
| C111 | 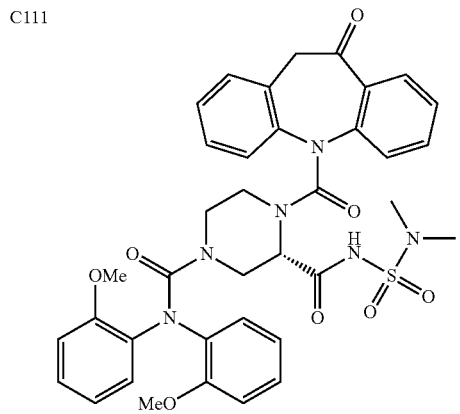 | 727.6 |
| C112 | 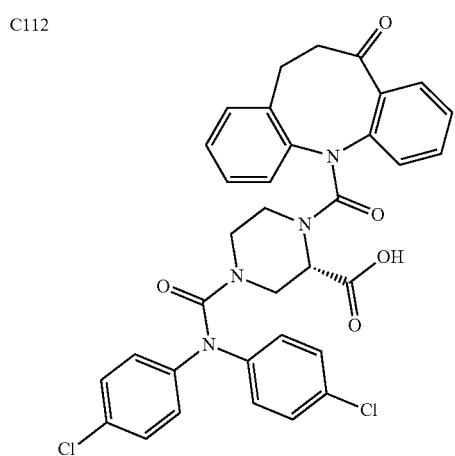 | 643.0 |
| C113 | 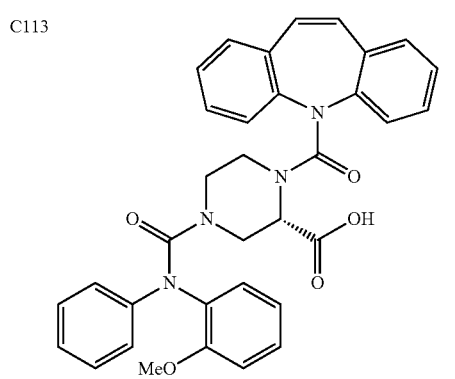 | 575.1 |
154
-continued
| No. | Structure | MS m/z (ESI): [M + H]+ |
|---|---|---|
| C114 | 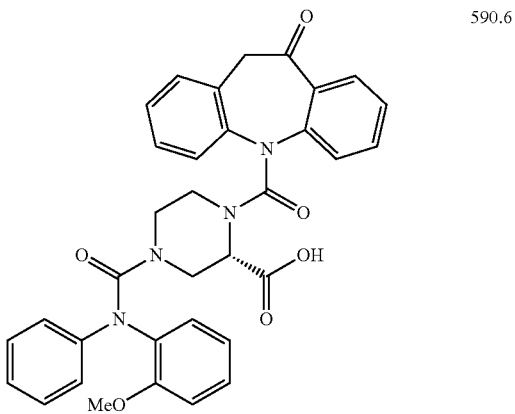 | 590.6 |
| C115 | 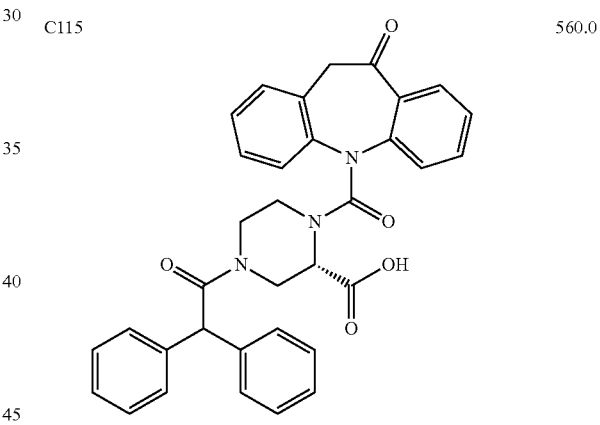 | 560.0 |
| C116 | 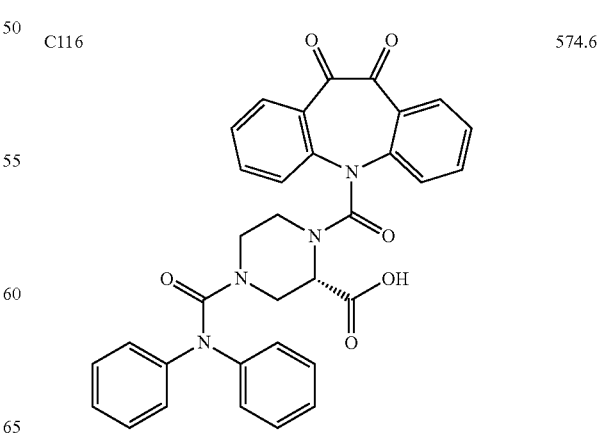 | 574.6 |

-continued
| No. | Structure | MS m/z (ESI): [M + H]+ |
|---|---|---|
| C117 | 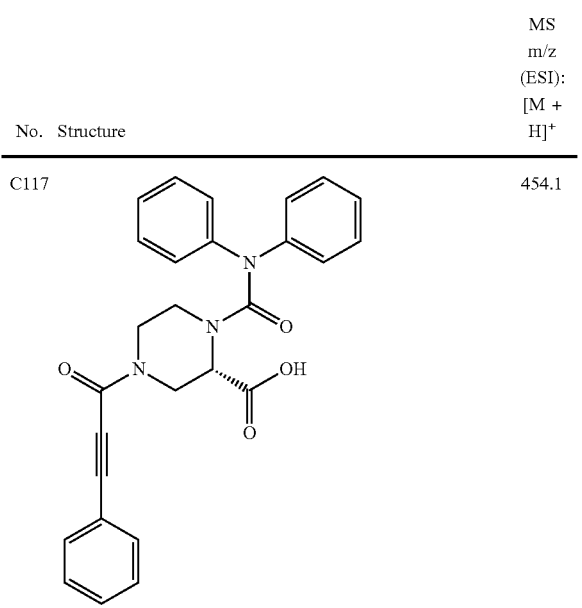 | 454.1 |
| C118 | 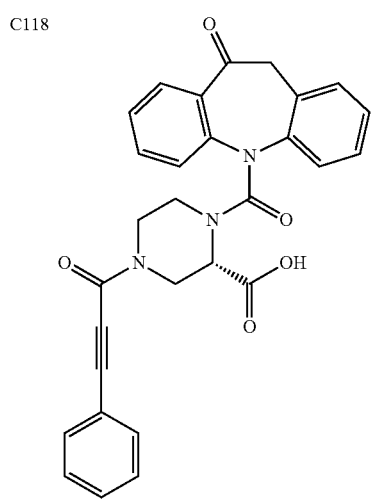 | 493.7 |
| C119 | 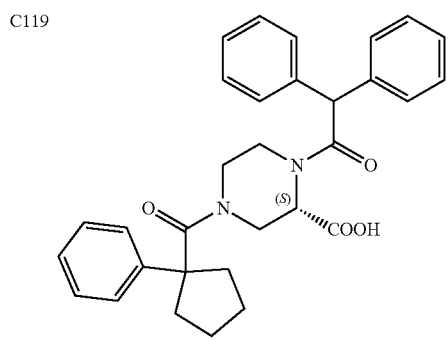 | 497.0 |
-continued
| No. | Structure | MS m/z (ESI): [M + H]+ |
|---|---|---|
| C120 | 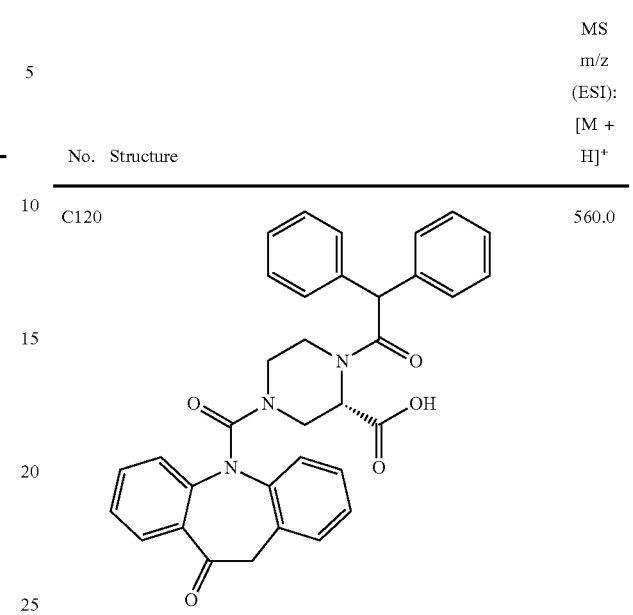 | 560.0 |
| C121 | 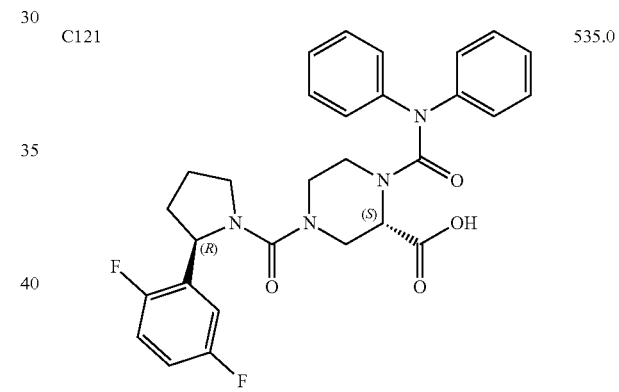 | 535.0 |
| C122 | 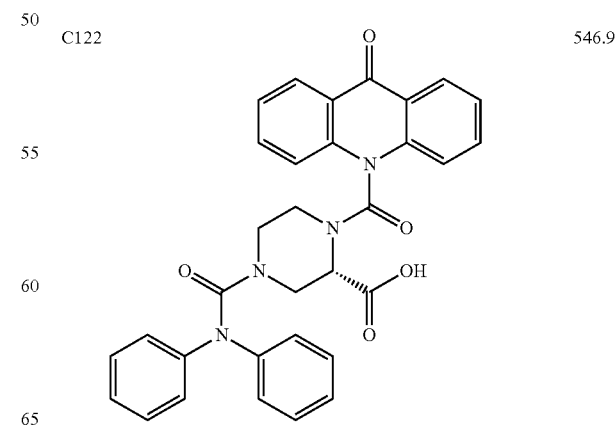 | 546.9 |

| No. | Structure | MS m/z (ESI): [M + H]+ |
|---|---|---|
| C123 | 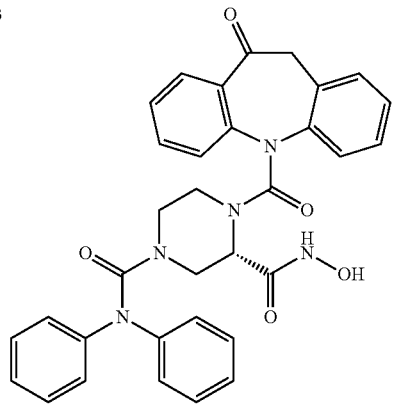 | 575.7 |
| C124 | 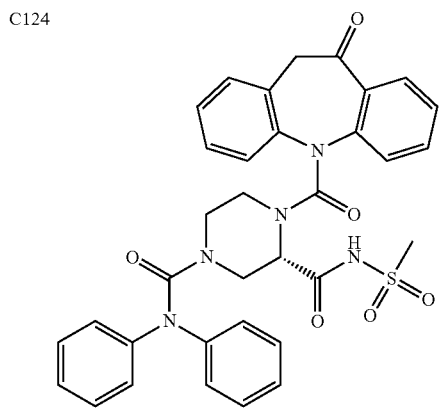 | 637.5 |
| C125 | 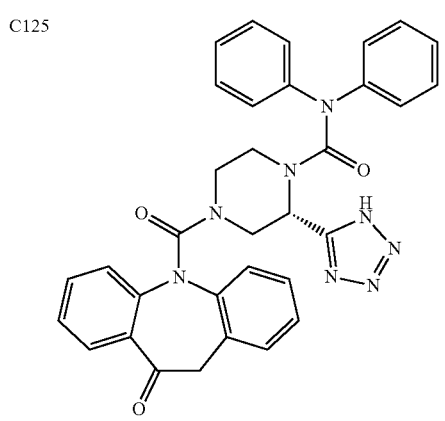 | 585.0 |
| No. | Structure | MS m/z (ESI): [M + H]+ |
|---|---|---|
| C126 | 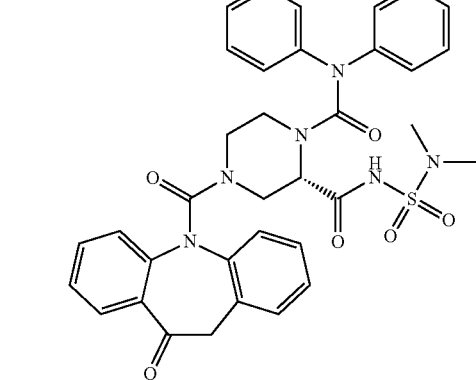 | 667.0 |
| C127 | 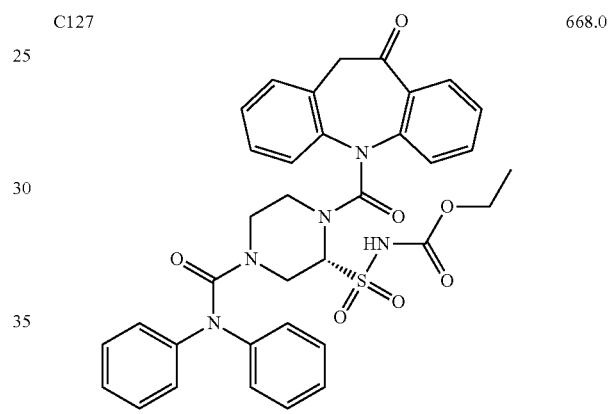 | 668.0 |
| C128 | 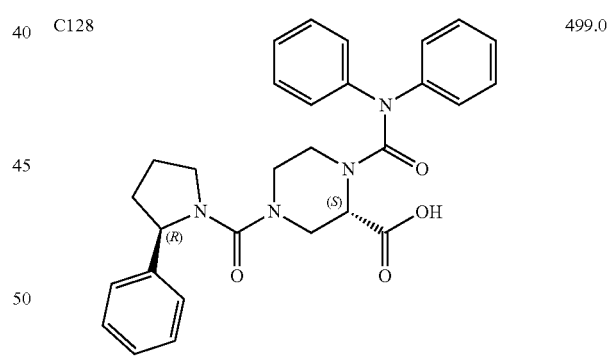 | 499.0 |
| C129 | 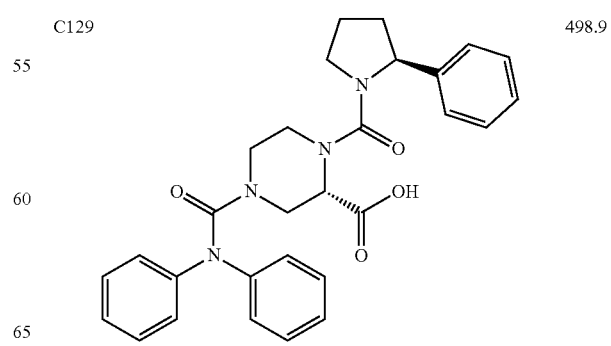 | 498.9 |

| No. | Structure | MS m/z (ESI): [M+H]⁺ |
|---|---|---|
| C130 | 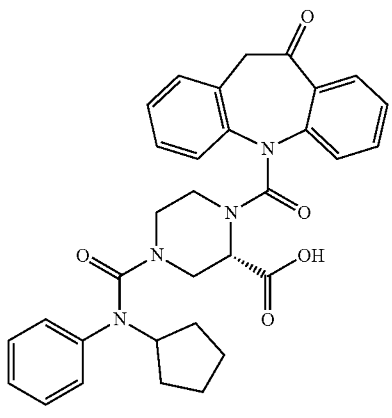 [SMILES: O=C1Cc2ccccc2N(C(=O)N2CCN(C(=O)N(c3ccccc3)C3CCCC3)C[C@H]2C(=O)O)c2ccccc21] | 553.0 |
| C131 | 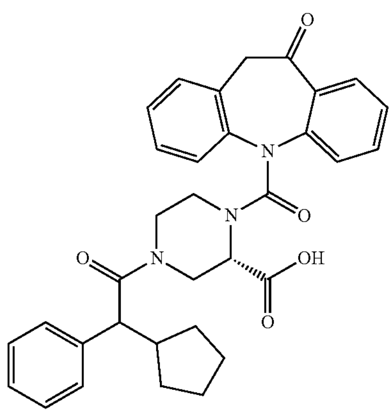 [SMILES: O=C1Cc2ccccc2N(C(=O)N2CCN(C(=O)C(c3ccccc3)C3CCCC3)C[C@H]2C(=O)O)c2ccccc21] | 552.0 |
| C132 | 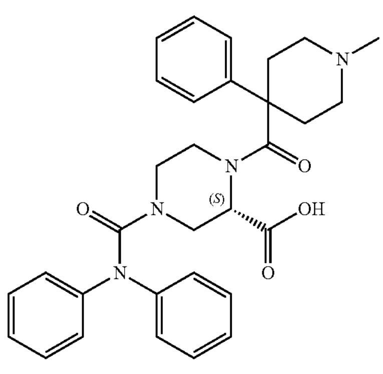 | 527.1 |
| C133 | 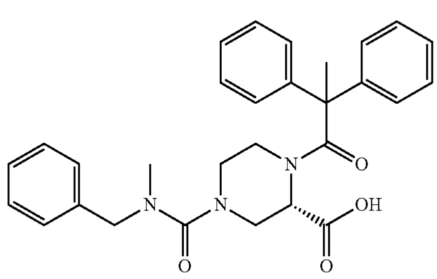 [SMILES: CN(Cc1ccccc1)C(=O)N1CCN(C(=O)C(C)(c2ccccc2)c2ccccc2)[C@H](C(=O)O)C1] | 485.8 |
| C134 | | 506.8 |
| C135 | | 492.8 |
| C136 | | 492.6 |

| No. | Structure | MS m/z (ESI): [M + H]+ |
|---|---|---|
| C137 | 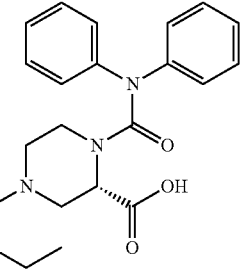 | 506.8 |
| C138 | 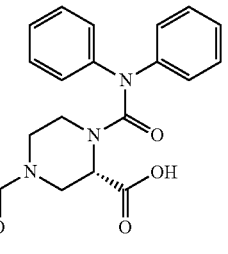 | 528.7 |
| C139 | 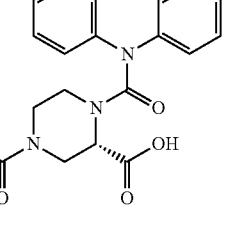 | 544.9 |
| C140 | 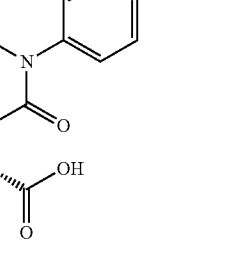 | 466.1 |
| C141 | 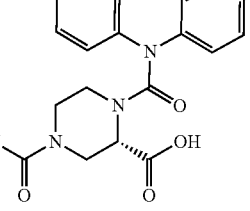 | 528.9 |
| C142 | 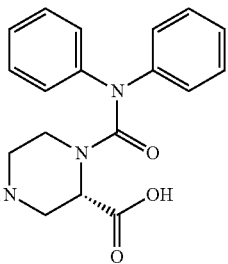 | 492.9 |
| C144 | 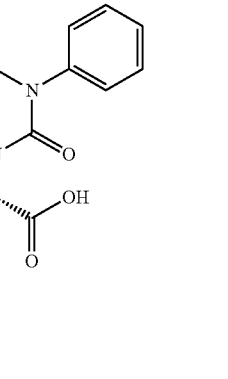 | 529.2 [M + Na]+ |
| C145 | 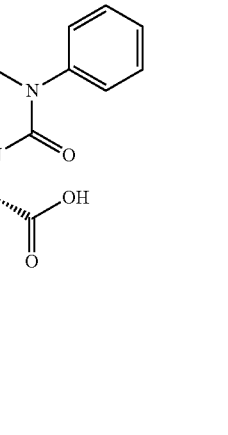 | 519.1 |

| No. | Structure | MS m/z (ESI): [M + H]+ |
|---|---|---|
| C146 | 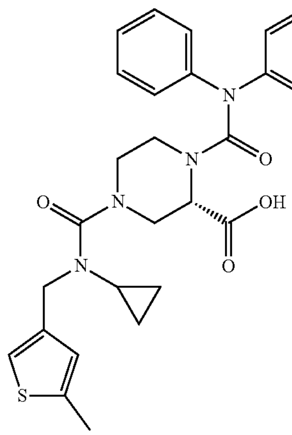 | 518.9 |
| C147 | 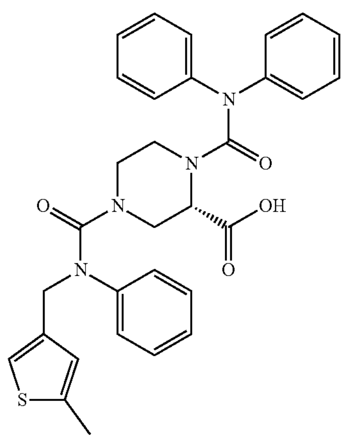 [SMILES: Cc1cc(CN(C(=O)N2CCN(C(=O)N(c3ccccc3)c3ccccc3)[C@H](C(=O)O)C2)c2ccccc2)cs1] | 555.0 |
| C148 | 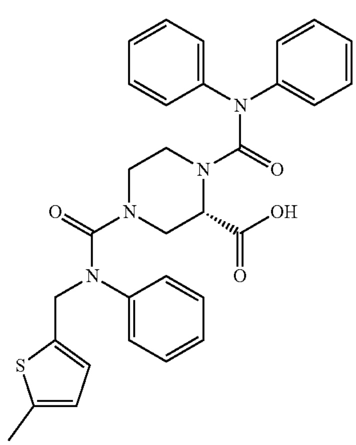 [SMILES: Cc1ccc(CN(C(=O)N2CCN(C(=O)N(c3ccccc3)c3ccccc3)[C@H](C(=O)O)C2)c2ccccc2)s1] | 555.1 |

| No. | Structure | MS m/z (ESI): [M + H]+ |
|---|---|---|
| C149 | 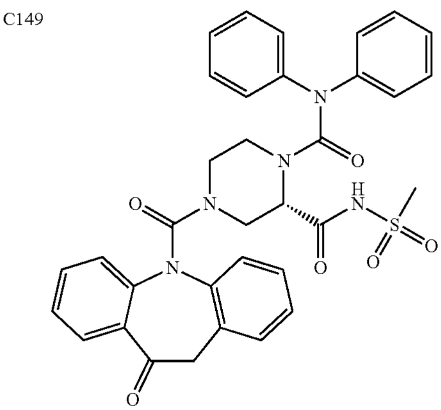 | 638.1 |
| C150 | 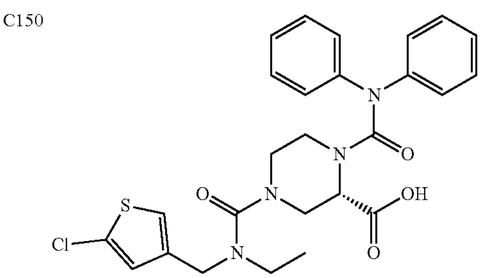 | 527.0 |
| C151 | 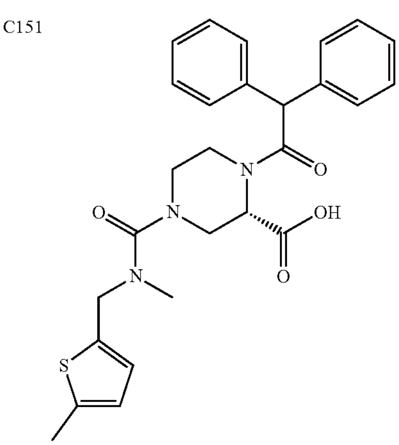 | 492.0 |

| No. | Structure | MS m/z (ESI): [M + H]+ |
|---|---|---|
| C152 | 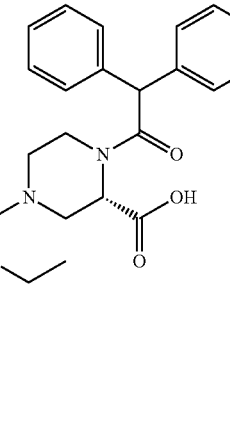 | 506.0 |
| C153 | 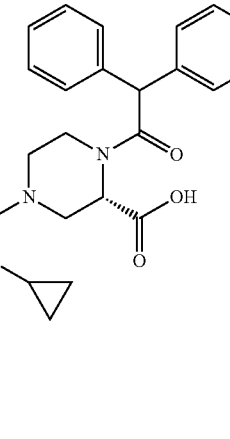 | 519.2 |
| C154 | 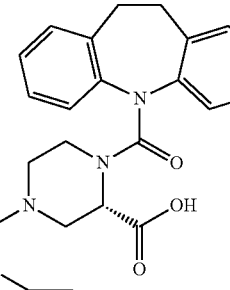 | 545.1 |

In some embodiments, the compound of the present invention has selective inhibitory activity on $AT_2$ receptors, compared to $AT_1$ receptors.

In some embodiments, the present invention provides a method for preparing the compound of formula (I), comprising the following steps:

[Reaction Scheme 1]

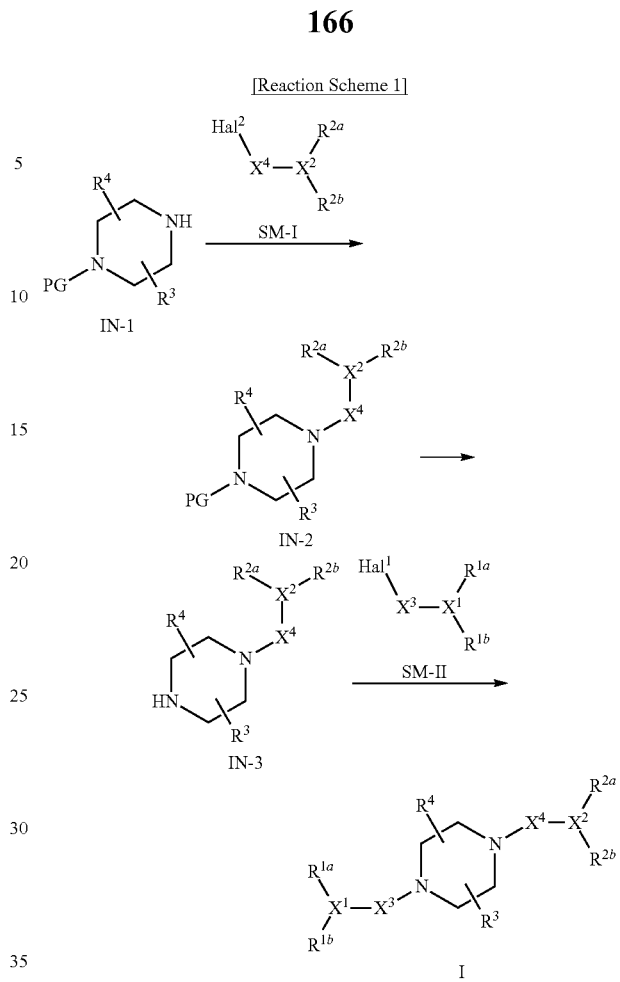

wherein
PG is an amino protecting group, preferably tert-butoxycarbonyl (Boc);
$Hal^1$ and $Hal^2$ are the same or different and are halogens, such as F, Cl, Br or I;
the remaining groups are as defined in any of the embodiments described above;

Step 1: reacting Compound IN-1 with Compound SM-1 to obtain Compound IN-2

The reaction is preferably carried out in a suitable organic solvent, which is preferably a halogenated hydrocarbon, such as halogenated methane, including methyl chloride, dichloromethane, chloroform. The reaction is preferably carried out in the presence of a suitable base which is preferably an organic base, such as organic amines, including diethylamine, triethylamine, N,N-diisopropylethylamine, N-methylmorpholine and pyridine. The reaction is preferably carried out at a suitable temperature which is preferably 0-10° C., for example 0-8° C. 1-6° C. or 2-5° C.

Step 2: deprotecting Compound IN-2 under conditions suitable for PG (preferably in an organic solvent such as 1,4-dioxane and in the presence of an acid such as HCl) to obtain Compound IN-3;

Step 3: reacting Compound IN-3 with Compound SM-II under conditions similar to those in Step 1 to obtain the compound of formula (I).

In other embodiments, the present invention provides a method for preparing a compound of formula (I'), comprising the following steps:

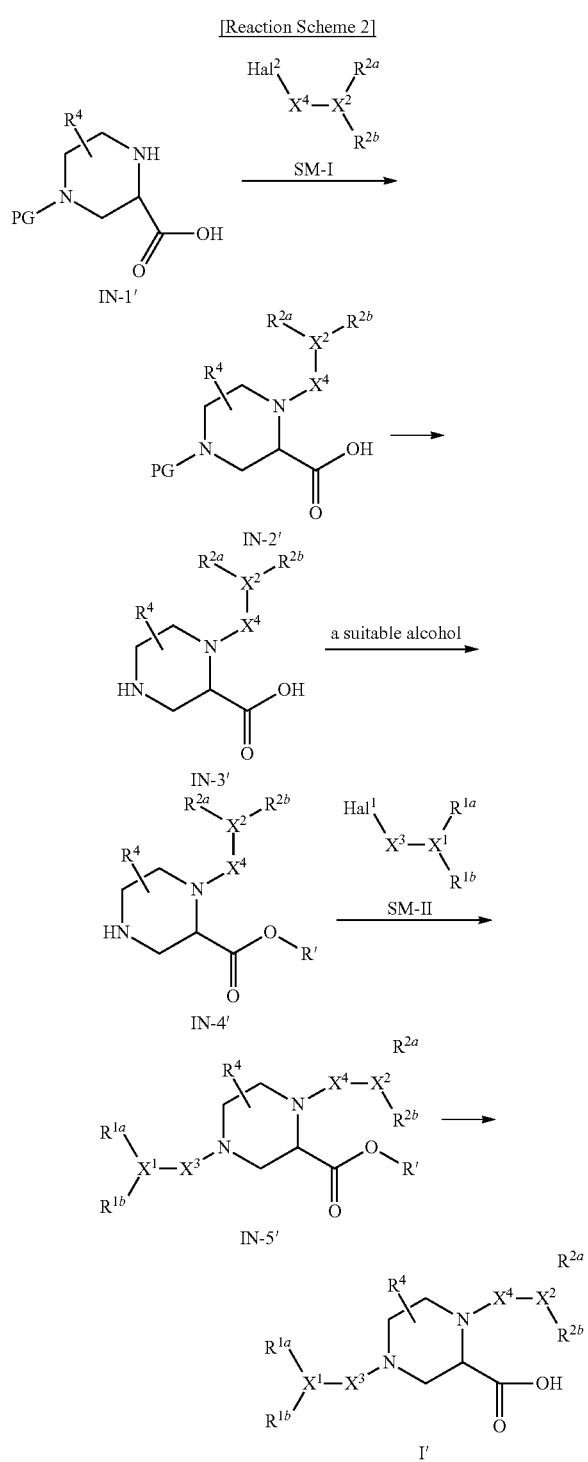

[Reaction Scheme 2]

wherein

R' is $C_{1-6}$ alkyl, such as $C_{1-4}$ alkyl, preferably methyl or ethyl;

the remaining groups are as defined in the above Reaction Scheme 1;

Step 1: reacting Compound IN-1' with Compound SM-1 as described in Step 1 of the above Reaction Scheme 1 to obtain Compound IN-2;

Step 2: deprotecting Compound IN-2' under conditions suitable for PG (preferably in an organic solvent such as 1,4-dioxane and in the presence of an acid such as HCl) as described in Step 2 of the above Reaction Scheme 1 to obtain Compound IN-3';

Step 3: esterifying Compound IN-3' with a suitable alcohol to obtain Compound IN-4';

The reaction is preferably carried out in the presence of a suitable catalyst, for example, in the presence of $SOCl_2$. The suitable alcohol may be a $C_{1-6}$ alkanol, for example, a $C_{1-4}$ alkanol, preferably methanol or ethanol.

Step 4: reacting Compound IN-4' with Compound SM-II under conditions similar to those in Step 1 to obtain Compound IN-5'; and Step 5: hydrolyzing the ester IN-5' under suitable conditions to obtain the compound of formula I'.

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for use as an angiotensin II type 2 ($AT_2$) receptor inhibitor.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as an angiotensin II type 2 ($AT_2$) receptor inhibitor.

In some embodiments, the present invention provides a method for the prophylaxis or the treatment of an $AT_2$ receptor-mediated disorder or a symptom associated therewith, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention.

In some embodiments, the AT2 receptor-mediated disorder is selected from: cerebrovascular disorders (including cerebrovascular spasm and cerebral ischemia); cognitive disorders (including amnesia, senile dementia, AIDS related dementia and Down's syndrome); central nervous system diseases or disorders (including addiction such as alcoholism, anxiety, depression or dysthymic disorders, epilepsy, hyperactivity, pain, Parkinson's disease, psychosis, sleep disorders, irregular autonomic function, and tardive dyskinesia, schizophrenia, demyelinating diseases such as multiple sclerosis and amyotrophic lateral sclerosis); respiratory diseases (including bronchospasm, asthma, chronic obstructive airways disease), neural tumors; inflammatory diseases (including inflammatory bowel disease and osteoarthritis); gastrointestinal (GI) diseases or disorders (including ulcerative colitis, Crohn's disease and incontinence); disorders of blood flow caused by vasodilation; hypersensitivity disorders (including allergies such as eczema, rhinitis and contact dermatitis); vasospastic diseases (including angina, migraine and Reynaud's disease); fibrosing and collagen diseases (including scleroderma and eosinophilic fasciolia-sis); reflex sympathetic dystrophy (including shoulder/hand syndrome); stress related somatic disorders; peripheral neuropathy; neuralgia; autoimmune disease (including systemic lupus erythematosus, rheumatoid arthritis, psoriasis and graft versus host disease); and rheumatic diseases (including fibrositis).

In some embodiments, the AT2 receptor-mediated disorder is selected from:

neuropathic conditions (including primary neuropathy and secondary neuropathy, such as peripheral neuropathy) or symptoms associated with the same (including hyperesthesia, hyperalgesia, allodynia, spontaneous burning pain, numbness, weakness, burning pain, shooting pain, and loss of reflexes), preferably neuropathic pain; wherein the secondary neuropathy includes diabetic neuropathy; Herpes Zoster-related neuropathy; uremia-associated neuropathy; amyloidosis neuropathy; HIV sensory neuropathies; hereditary motor and sensory neuropathies; hereditary sensory neuropathies; hereditary sensory and autonomic neuropathies; hereditary neuropathies with ulcero-mutilation; nitrofurantoin neuropathy; tomaculous neuropathy; neuropathy caused by nutritional deficiency; neuropathy caused by kidney failure and complex regional pain syndrome; neuropathes caused by repetitive activities (such as typing or working on an assembly line); peripheral neuropathies caused by antiretroviral drags (such as zalcitabine and didanosine), antibiotics (such metronidazole and isoniazid), gold compounds, chemotherapy drags (such as vincristine), alcohol, lead, arsenic, mercury and organophosphate pesticides; peripheral neuropathies associated with infectious processes (such as Guillian-Barre syndrome);

a condition characterized by neuronal hypersensitivity, including a hyperalgesic condition such as fibromyalgia and irritable bowel syndrome;

a disorder associated with aberrant nerve regeneration, including neuronal hypersensitivity, breast pain, interstitial cystitis, vulvodynia, a cancer chemotherapy-induced neuropathy;

inflammatory pain that can be due to conditions that are characterized by inflammation (including burns such as chemical, frictional or thermal burns; autoimmune diseases such as rheumatoid arthritis; inflammatory bowel disease such as Crohn's disease and colitis; osteoarthritis, carditis, dermatitis, myositis, neuritis and collagen vascular diseases);

impaired nerve conduction velocity which may be associated with a neuropathic condition as described above (such as a peripheral neuropathy) as well as Carpel Tunnel Syndrome, ulnar neuropathy, Guillian-Barre Syndrome, fascioscapulohumeral muscular dystrophy and spinal disc herniation;

a cell proliferative disorder, including a cancer (including leukaemia, melanoma, prostate cancer, breast cancer, ovarian cancer, basal cell carcinoma, squamous cell carcinoma, sarcoma, fibrosarcoma, colon cancer, lung cancer); and a non-cancerous proliferative disorder (including dermatological disorders such as warts, keloids, psoriasis, proud flesh disorder and also the reduction in scar tissue and cosmetic remodelling);

a disorder associated with an imbalance between bone resorption and bone formation, including osteoporosis.

In some embodiments, the present invention provides a method for regulating a reproductive function associated with $AT_2$ receptors in a female patient, comprising administering to a subject in need thereof an effective amount of the compound of the present invention or a pharmaceutically acceptable salt, ester, stereoisomer, polymorph, solvate, N-oxide, isotopically labeled compound, metabolite or prodrug thereof, or the pharmaceutical composition of the present invention. In some embodiments, the reproductive function is selected from the menstrual cycle, fertility, and hormonal balances of the estrus cycle.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (δ) are expressed in parts per million (ppm). $^1$H NMR was recorded on a Bruker 400 spectrometer, the test solvent was deuterated methanol (CD$_3$OD), deuterated chloroform (CDCl$_3$) or hexadeuterated dimethyl sulfoxide (DMSO-d$_6$), and the internal standard was tetramethylsilane (TMS).

The LC-MS assay was conducted on Agilent LC-MS-1110 liquid chromatography-mass spectrometer, Agilent LC-MS-6110 liquid chromatography-mass spectrometer, Agilent LC-MS-6120 liquid chromatography-mass spectrometer (Manufacturer: Agilent) or Shimadzu LC-MS-2020.

Preparative high-performance liquid chromatography was conducted on MS induced AutoPurification system (Waters), Gilson GX-281 (Gilson), or semi-preparative liquid chromatograph (Tong Heng Innovation Technology Co., Ltd., LC3000 (Ddlsogel, C18, 30 mm×250 mm 10 μm).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, n-hexane and ethyl acetate system, as well as petroleum ether and ethyl acetate system, and was adjusted (by adjusting the volume ratio of the solvents, or by adding triethylamine, etc.) according to the polarity of the compound to be separated.

The microwave reaction was conducted by CEM Discovery Sp (400 W, RT~300° C.) microwave reactor.

Silica gel (200~300 mesh) produced by Yucheng Chemical Co., Ltd was normally employed as a stationary phase in column chromatography. The eluent system included dichloromethane and methanol system, as well as n-hexane and ethyl acetate system, and was adjusted (by adjusting the volume ratio of the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Aldrich Chemical Company, Shanghai Bide Pharmatech Co. Ltd., Beijing Greenchem Co. Ltd., Shanghai Shaoyuan Co. Ltd. or Abies Technology Co. Ltd. etc.

The abbreviations as used in the present invention have the following meanings:

| Abbreviation | Meaning |
| --- | --- |
| CH$_3$CN | acetonitrile |
| (Boc)$_2$O | di-tert-butyl dicarbonate |
| BTC | triphosgene |
| CH$_3$OH | methanol |
| DCC | dicyclohexylcarbodiimide |
| DCE | 1,2-dichloroethane |
| DCM | dichloromethane |
| DMAP | 4-dimethylaminopyridine |
| DMSO | dimethyl sulfoxide |
| Et$_3$N | triethylamine |
| HCl | hydrochloric acid |
| H$_2$O | water |
| MeOH | methanol |
| Na$_2$CO$_3$ | sodium carbonate |
| NaOH | sodium hydroxide |
| SOCl$_2$ | thionyl chloride |
| TFA | trifluoroacetic acid |

Example 1: Preparation of (S)-4-(5H-dibenzo[b,f]azepine-5-carbonyl)-1-(diphenylcarbamoyl) piperazine-2-carboxylic acid (C1)

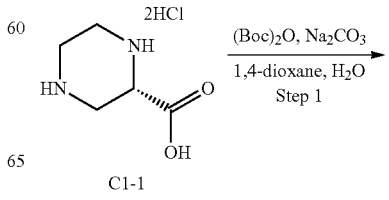

C1-1

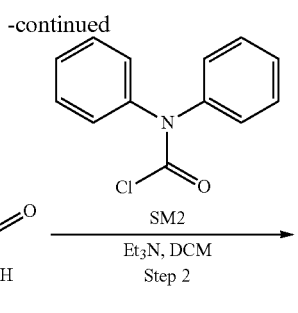

C1-2

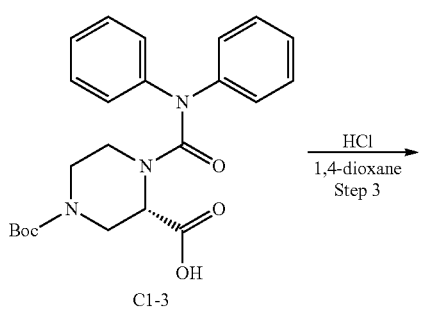

C1-3

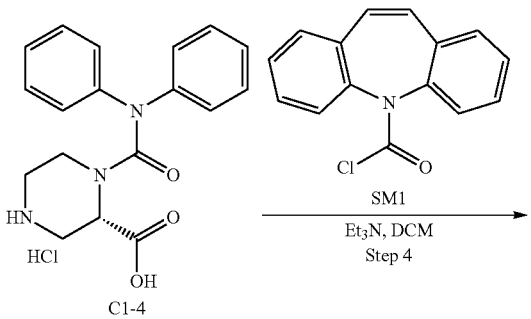

C1-4

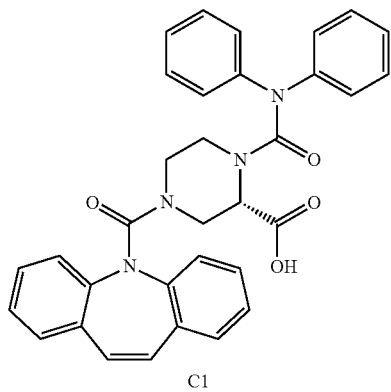

C1

Step 1:

Compound C1-1 (1015 mg, 5 mmol) was dissolved in 1,4-dioxane (20 mL) and water (20 mL), and Na$_2$CO$_3$ (795 mg, 1.08 mol) and (Boc)$_2$O (136 mg, 0.81 mol) were added sequentially. The reaction solution was reacted at room temperature for 16 hours. LC-MS indicated that the reaction of the starting materials was substantially complete. The reaction solution was concentrated under reduced pressure to evaporate off 1,4-dioxane, followed by addition of purified water (20 mL), and extraction with ethyl acetate (40 mL). The aqueous phase was adjusted to pH=4~5 by dropwise addition of 2N HCl solution, and then extracted with n-butanol (40 mL×2). n-butanol was combined, followed by addition of anhydrous sodium sulfate (10 g) to dry for 30 min, filtration and concentration under reduced pressure to obtain Compound C1-2 (1.07 g, a white solid, yield: 95%).

MS m/z (ESI): 231.0 [M+H]$^+$.

Step 2:

Compound C1-2 (460 mg, 2 mmol) was dissolved in dry dichloromethane (20 mL). After the temperature was reduced to 0° C.-5° C., triethylamine (808 mg, 8 mmol) and SM2 (462 mg, 2 mmol) were sequentially added. The reaction solution was reacted at room temperature for 3 hours. LC-MS indicated that the reaction of the starting materials was complete. The reaction was quenched by adding water (50 mL), and extracted with dichloromethane (30 mL×2). The organic phases were combined, washed once with saturated brine (50 mL), then dried over anhydrous sodium sulfate (20 g) for 30 min, filtered, and concentrated. The crude product was separated by column chromatography [dichloromethane:methanol=15:1-10:1 (0.1% formic acid)] to obtain Compound C1-3 (700 mg, a white solid, yield: 83%).

MS m/z (ESI): 448.0 [M+Na]$^+$.

Step 3:

Compound C1-3 (700 mg, 1.65 mmol) was dissolved in 1,4-dioxane (10 mL), and a solution of HCl in 1,4-dioxane (5 mL, in 1,4-dioxane, 4.0 M) was added. The reaction solution was reacted at room temperature for 3 hours. LC-MS indicated that the reaction of starting materials was complete. The reaction solution was concentrated under reduced pressure to obtain Compound C1-4 (535 mg, a white solid, yield: 100%).

MS m/z (ESI): 326.0 [M+H]$^+$.

Step 4:

Compound C1-4 (535 mg, 1.65 mmol) was dissolved in dry dichloromethane (20 mL). After the temperature was reduced to 0° C.-5° C., triethylamine (667 mg, 6.6 mmol) and SM1 (420 mg, 1.65 mmol) were sequentially added. The reaction solution was reacted at room temperature for 3 hours. LC-MS indicated that the reaction of the starting materials was complete. The reaction was quenched by adding water (50 mL), and extracted with dichloromethane (30 mL×2). The organic phases were combined, washed once with saturated brine (50 mL), then dried over anhydrous sodium sulfate (20 g) for 30 min, filtered, and concentrated, and was then separated by preparative high performance liquid chromatogram [CH$_3$CN/H$_2$O, 5%-40%, (0.1% CF$_3$COOH)] to obtain Compound C1 (350 mg, a white solid, yield: 39%).

$^1$H NMR (400 MHz, DMSO-d6) δ 13.05 (s, 1H), 7.56 (d, J=7.9 Hz, 2H), 7.40 (dd, J=16.9, 7.9 Hz, 4H), 7.33-7.25 (m, 6H), 7.13 (t, J=7.3 Hz, 2H), 7.04 (s, 2H), 6.89 (d, J=7.9 Hz, 4H), 4.19 (s, 1H), 3.93 (d, J=13.1 Hz, 1H), 3.31 (d, J=12.4 Hz, 1H), 2.92 (d, J=12.8 Hz, 1H), 2.76-2.63 (m, 2H), 2.39 (t, J=10.8 Hz, 1H).

MS m/z (ESI): 545.0 [M+H]$^+$.

The compounds in Table 1 were prepared by methods similar to that described in Example 1.

TABLE 1

| Compound No. | Compound Structure | Compound Name | Starting material or reagent different from that in Example 1 | Characterization Data |
|---|---|---|---|---|
| C4 | 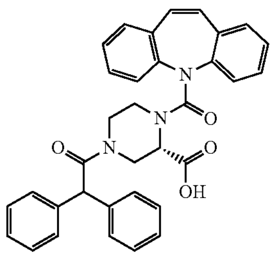 [SMILES: O=C(O)[C@@H]1CN(C(=O)C(c2ccccc2)c2ccccc2)CCN1C(=O)N1c2ccccc2C=Cc2ccccc21] | (S)-1-(5H-dibenzo[b,f]azepine-5-carbonyl)-4-(2,2-diphenylacetyl)piperazine-2-carboxylic acid | SM2 in Step 2 of Example 1 was replaced with SM1, and SM1 in Step 4 was replaced with 2,2-diphenylacetyl chloride. | $^1$H NMR (400 MHz, DMSO-d6) δ 12.82 (s, 1H), 7.56 (d, J = 7.0 Hz, 2H), 7.43-7.02 (m, 18H), 5.40 (d, J = 11.9 Hz, 1H), 4.55 (d, J = 12.8 Hz, 1H), 4.25 (s, 1H), 3.52 (d, J = 11.9 Hz, 1H), 3.15 (d, J = 13.5 Hz, 1H), 2.91-2.80 (m, 2H), 2.75-2.65 (m, 1H). MS m/z (ESI): 544.0 [M + H]$^+$. |
| C5 | 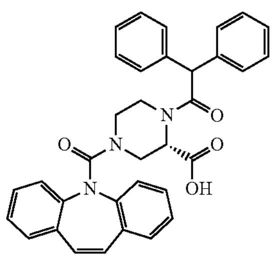 [SMILES: O=C(O)[C@@H]1CN(C(=O)N2c3ccccc3C=Cc3ccccc32)CCN1C(=O)C(c1ccccc1)c1ccccc1] | (S)-4-(5H-dibenzo[b,f]azepine-5-carbonyl)-1-(2,2-diphenylacetyl)piperazine-2-carboxylic acid | SM2 in Step 2 of Example 1 was replaced with 2,2-diphenylacetyl chloride. | $^1$H NMR (400 MHz, DMSO-d6) δ 12.93 (s, 1H), 7.62 (s, 1H), 7.48-6.91 (m, 19H), 5.45 (s, 1H), 4.85 (d, J = 11.0 Hz, 1H), 4.06 (d, J = 13.0 Hz, 1H), 3.77 (d, J = 11.6 Hz, 1H), 3.51 (d, J = 13.3 Hz, 2H), 2.91 (t, J = 11.3 Hz, 1H), 2.70-2.59 (m, 1H). MS m/z (ESI): 544.0 [M + H]$^+$. |
| C20 | 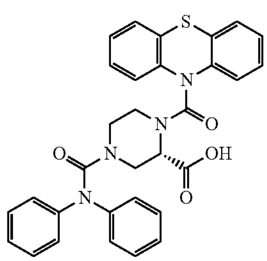 [SMILES: O=C(O)[C@@H]1CN(C(=O)N(c2ccccc2)c2ccccc2)CCN1C(=O)N1c2ccccc2Sc2ccccc21] | (S)-4-(diphenylcarbamoyl)-1-(10H-phenothiazine-10-carbonyl)piperazine-2-carboxylic acid | SM2 in Step 2 of Example 1 was replaced with 10H-phenothiazine-10-carbonyl chloride, and SM1 in Step 4 was replaced with SM2. | $^1$H NMR (400 MHz, DMSO-d6) δ 7.69 (d, J = 8.0 Hz, 2H), 7.39 (d, J = 7.5 Hz, 2H), 7.29 (dd, J = 14.2, 7.0 Hz, 6H), 7.21-7.09 (m, 4H), 6.92 (d, J = 7.7 Hz, 4H), 4.54 (s, 1H), 4.09 (d, J = 13.3 Hz, 1H), 3.46 (d, J = 12.1 Hz, 1H), 3.26 (s, 1H), 2.95-2.81 (m, 2H), 2.59 (s, 1H). MS m/z (ESI): 550.9 [M + H]$^+$. |
| C21 | 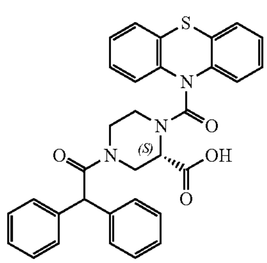 | (S)-4-(2,2-diphenylacetyl)-1-(10H-phenothiazine-10-carbonyl)piperazine-2-carboxylic acid | SM2 in Step 2 of Example 1 was replaced with 10H-phenothiazine-10-carbonyl chloride, and SM1 in Step 4 was replaced with 2,2-diphenylacetyl chloride. | $^1$H NMR (400 MHz, DMSO-d6) δ 7.70 (d, J = 7.7 Hz, 2H), 7.41 (d, J = 7.3 Hz, 2H), 7.34 (d, J = 7.3 Hz, 1H), 7.21 (ddd, J = 19.0, 13.7, 6.0 Hz, 14H), 5.42 (s, 1H), 4.73 (d, J = 13.4 Hz, 1H), 4.30 (d, J = 13.7 Hz, 1H), 3.71 (d, J = 12.1 Hz, 1H), 2.96 (d, J = 9.6 Hz, 1H), 2.84 (d, J = 11.5 Hz, 1H), 2.77 (d, J = 11.9 Hz, 1H). MS m/z (ESI): 549.9 [M + H]$^+$. |
| C46 | 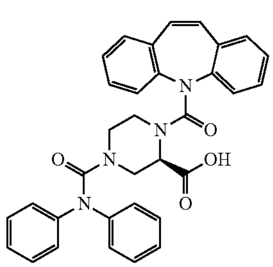 [SMILES: O=C(O)[C@H]1CN(C(=O)N(c2ccccc2)c2ccccc2)CCN1C(=O)N1c2ccccc2C=Cc2ccccc21] | (R)-1-(5H-dibenzo[b,f]azepine-5-carbonyl)-4-(diphenylcarbamoyl)piperazine-2-carboxylic acid | C1-1 in Step 1 of Example 1 was replaced with (R)-piperazine-2-formic acid dihydrochloride; SM2 in Step 2 was replaced with SM1; and SM1 in Step 4 was replaced with SM2. | $^1$H NMR (400 MHz, DMSO-d6) δ 13.04 (s, 1H), 7.54 (d, J = 7.6 Hz, 2H), 7.42-7.36 (m, 4H), 7.31-7.26 (m, 6H), 7.14-7.11 (m, 2H), 7.03 (s, 2H), 6.88 (d, J = 7.6 Hz, 2H), 4.18 (s, 1H), 3.92 (d, J = 12.8 Hz, 1H), 3.28 (s, 1H), 2.93-2.89 (m, 1H), 2.73-2.64 (m, 2H), 2.40-2.35 (m, 1H). MS m/z (ESI): 544.7 [M + H]$^+$. |

TABLE 1-continued

| No. | Compound Structure | Compound Name | Starting material or reagent different from that in Example 1 | Characterization Data |
|---|---|---|---|---|
| C3 | 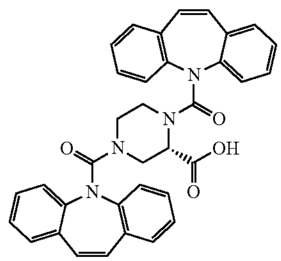 [SMILES: O=C(O)[C@@H]1CN(C(=O)N2c3ccccc3C=Cc3ccccc32)CCN1C(=O)N1c2ccccc2C=Cc2ccccc21] | (S)-1,4-bis(5H-dibenzo[b,f]azepine-5-carbonyl)piperazine-2-carboxylic acid | SM2 in Step 2 of Example 1 was replaced with SM1. | $^1$H NMR (400 MHz, DMSO-d6) δ 7.50 (d, J = 8 Hz, 2H), 7.41-7.26 (m, 12H), 7.01 (d, J = 5.2 Hz, 4H), 4.08 (s, 1H), 3.77 (d, J = 11.6 Hz, 1H), 2.76-2.61 (m, 3H), 2.27-2.22 (m, 2H). MS m/z (ESI): 568.9 [M + H]$^+$. |

Example 2: Preparation of (S)-1-(5H-dibenzo[b,f]azepine-5-carbonyl)-4-(diphenylcarbamoyl) piperazine-2-carboxylic acid (C2)

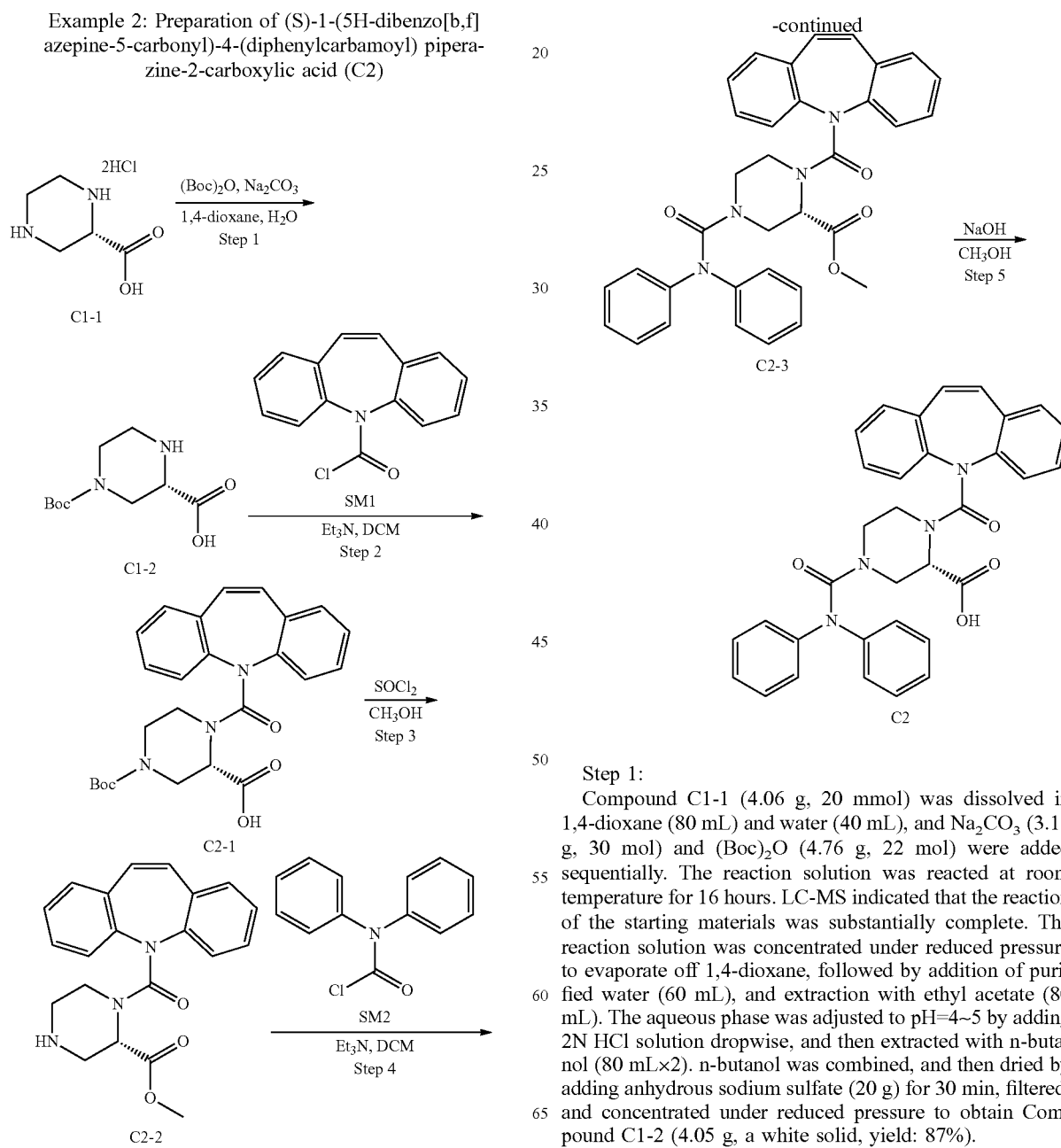

Step 1:

Compound C1-1 (4.06 g, 20 mmol) was dissolved in 1,4-dioxane (80 mL) and water (40 mL), and Na$_2$CO$_3$ (3.18 g, 30 mol) and (Boc)$_2$O (4.76 g, 22 mol) were added sequentially. The reaction solution was reacted at room temperature for 16 hours. LC-MS indicated that the reaction of the starting materials was substantially complete. The reaction solution was concentrated under reduced pressure to evaporate off 1,4-dioxane, followed by addition of purified water (60 mL), and extraction with ethyl acetate (80 mL). The aqueous phase was adjusted to pH=4~5 by adding 2N HCl solution dropwise, and then extracted with n-butanol (80 mL×2). n-butanol was combined, and then dried by adding anhydrous sodium sulfate (20 g) for 30 min, filtered, and concentrated under reduced pressure to obtain Compound C1-2 (4.05 g, a white solid, yield: 87%).

MS m/z (ESI): 231.0 [M+H]$^+$.

Step 2:

Compound C1-2 (3.24 g, 13.9 mmol) was dissolved in dry dichloromethane (50 mL). After the temperature was reduced to 0° C.-5° C., triethylamine (5.62 g, 55.6 mmol) and SM1 (3.55 g, 13.9 mmol) were sequentially added. The reaction solution was reacted at room temperature for 16 horns. LC-MS indicated that the reaction of the starting materials was complete. The reaction was quenched by adding water (50 mL), and extracted with dichloromethane (60 mL×2). The organic phases were combined, washed once with saturated brine (60 mL), then dried over anhydrous sodium sulfate (20 g) for half an horn, filtered, and concentrated to obtain Compound C2-1 (3.62 g, a white solid, yield: 60%).

MS m/z (ESI): 394.0 [M+H-56]$^+$.

Step 3:

Compound C2-1 (3.62 g, 8.24 mmol) was dissolved in dry methanol (40 mL). After the temperature was reduced to 0° C.-5° C., SOCl$_2$ (1.47 g, 12.4 mmol) was added dropwise. The reaction solution was reacted at room temperature for 3 hours. LC-MS indicated that the reaction of the starting materials was complete. The reaction solution was concentrated under reduced pressure, and methanol was removed by rotary vaporization. The residue was then dissolved with dichloromethane (80 mL), washed once with saturated brine (50 mL), and then dried over anhydrous sodium sulfate (20 g) for half an hour, followed by filtration and concentration. The crude product was separated by column chromatography (dichloromethane:methanol=15:1-10:1) to obtain compound C2-2 (2.90 g, a white solid, yield: 95%). MS m/z (ESI): 364.0 [M+H]$^+$.

Step 4:

Compound C2-2 (2.90 g, 8.0 mmol) was dissolved in dry dichloromethane (60 mL). After the temperature was reduced to 0° C.-5° C., triethylamine (3.23 g, 32 mmol) and SM2 (1.84 g, 8.0 mmol) were added sequentially. The reaction solution was reacted at room temperature for 3 horns. LC-MS indicated that the reaction of the starting materials was complete. The reaction was quenched by adding water (50 mL) and extracted with dichloromethane (60 mL×2). The organic phases were combined, washed once with saturated brine (60 mL), and then dried over anhydrous sodium sulfate (20 g) for half an hour, followed by filtration and concentration. The crude product was separated by column chromatography (dichloromethane:methanol=15:1-10:1) to obtain Compound C2-3 (2.80 g, a white solid, yield: 64%).

MS m/z (ESI): 559.0 [M+H]$^+$.

Step 5:

Compound C2-3 (2.80 g, 5.0 mmol) was dissolved in dry methanol (30 mL) and water (10 mL), and sodium hydroxide (1.6 g, 40 mmol) was added. The reaction solution was reacted at 40° C. for 16 hours. LC-MS indicated that the reaction of the starting materials was complete. The reaction solution was concentrated under reduced pressure, and methanol was removed by rotary vaporization. The residue was dissolved by adding water (60 mL), and adjusted to pH=4-5 by adding dropwise 2N HCl solution, resulting in a white precipitate. The mixture was filtered with the white solid being rinsed with water (50 mL), and was then concentrated under reduced pressure. The white solid was dried by rotary vaporization to remove the water therein, to obtain Compound C2 (2.5 g, a white solid, yield: 93%).

$^1$HNMR (400 MHz, DMSO-d6) δ 13.31-12.74 (s, 1H), 7.39-7.27 (m, 12H), 7.14 (t, J=7.0 Hz, 2H), 7.03-6.93 (m, 6H), 4.39 (s, 1H), 3.92 (d, J=12.8 Hz, 1H), 3.12 (d, J=8.8 Hz, 1H), 2.93 (d, J=9.2 Hz, 1H), 2.67 (s, 1H), 2.42 (t, J=10.2 Hz, 2H).

MS m/z (ESI): 544.9 [M+H]$^+$.

The compounds in Table 2 were prepared by methods similar to that described in Example 2.

TABLE 2

| No. | Compound Structure | Compound Name | Starting material or reagent different from that in Example 2 | Charaterization data |
|---|---|---|---|---|
| C12 | 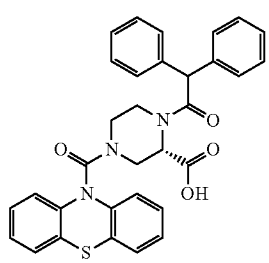 [SMILES: O=C(O)[C@@H]1CN(C(=O)N2c3ccccc3Sc3ccccc32)CCN1C(=O)C(c1ccccc1)c1ccccc1] | (S)-1-(2,2-diphenylacetyl)-4-(10H-phenothiazine-10-carbonyl)piperazine-2-carboxylic acid | SM1 in Step 2 of Example 2 was replaced with 2,2-diphenylacetyl chloride, and SM2 in Step 4 was replaced with 10H-phenothiazine-10-carbonyl chloride. | $^1$H NMR (400 MHz, DMSO-d6) δ 13.34-13.01 (s, 1H), 7.53 (d, J = 7.8 Hz, 2H), 7.39 (d, J = 6.8 Hz, 2H), 7.31-7.11 (m, 14H), 5.50 (s, 1H), 4.98 (d, J = 11.2 Hz, 1H), 4.32 (t, J = 12.6 Hz, 1H), 4.06-3.93 (m, 1H), 3.69 (d, J = 12.9 Hz, 1H), 3.07 (dd, J = 13.2, 3.5 Hz, 1H), 2.84 (dt, J = 21.2, 10.6 Hz, 1H), 2.75-2.65 (m, 1H). MS m/z (ESI): 550.0 [M + H]$^+$. |
| C47 | 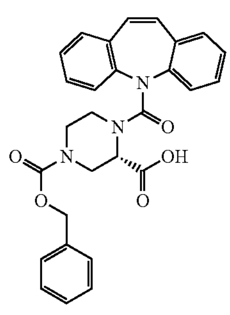 [SMILES: O=C(O)[C@@H]1CN(C(=O)OCc2ccccc2)CCN1C(=O)N1c2ccccc2C=Cc2ccccc21] | (S)-4-((benzyloxy)carbonyl)-1-(5H-dibenzo[b,f]azepine-5-carbonyl)piperazine-2-formic acid | SM2 in Step 4 of Example 2 was replaced with benzyl chloroformate. | $^1$H NMR (400 MHz, DMSO-d6) δ 12.43 (s, 1H), 7.58 (d, J = 6.7 Hz, 2H), 7.37 (ddd, J = 18.4, 13.5, 6.3 Hz, 11H), 7.07 (s, 2H), 5.00 (s, 2H), 4.27 (s, 1H), 4.14 (d, J = 11.2 Hz, 1H), 3.48 (d, J = 12.3 Hz, 1H), 3.34 (s, 1H), 3.10 (s, 1H), 2.95 (d, J = 12.6 Hz, 2H). MS m/z (ESI): 484.0 [M + H]$^+$. |

TABLE 2-continued

| Compound No. | Compound Structure | Compound Name | Starting material or reagent different from that in Example 2 | Charaterization data |
|---|---|---|---|---|
| C45 | 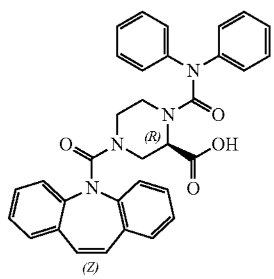 | (R)-4-(5H-dibenzo[b,f]azepine-5-carbonyl)-1-(diphenylcarbamoyl)piperazine-2-carboxylic acid | C1-1 in Step 1 of Example 2 was replaced with (R)-piperazine-2-formic acid dihydrochloride; SM1 in Step 2 was replaced with SM2; and SM2 in Step 4 was replaced with SM1. | ¹H NMR (400 MHz, DMSO-d6) δ 13.09 (s, 1H), 7.35-6.92 (m, 20H), 4.37 (s, 1H), 3.92-3.87 (m, 1H), 3.12-3.08 (m, 1H), 2.67-2.63 (m, 2H), 2.43-2.37 (m, 1H). MS m/z (ESI): 544.8 [M + H]⁺. |
| C18 | 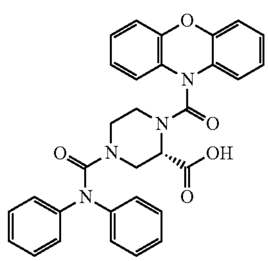 [SMILES: O=C(O)[C@@H]1CN(C(=O)N(c2ccccc2)c2ccccc2)CCN1C(=O)N1c2ccccc2Oc2ccccc21] | (S)-4-(diphenylcarbamoyl)-1-(10H-phenoxazine-10-carbonyl)piperazine-2-carboxylic acid | SM1 in Step 2 of Example 2 was replaced with 10H-phenoxazine-10-carbonyl chloride. | ¹H NMR (400 MHz, DMSO-d6) δ 13.74 (brs, 1H), 7.32 (t, J = 7.6 Hz, 4H), 7.14 (t, J = 7.2 Hz, 2H), 6.97 (d, J = 8 Hz, 5H), 6.87-6.85 (m, 7H), 4.78 (s, 1H), 4.27 (d, J = 13.2 Hz, 1H), 3.71 (s, 2H), 3.10 (s, 2H), 2.92-2.85 (m, 1H). MS m/z (ESI): 534.8 [M + H]⁺. |
| C11 | 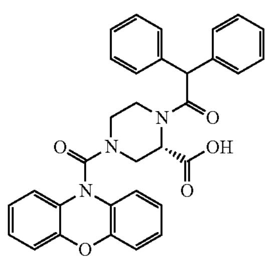 [SMILES: O=C(O)[C@@H]1CN(C(=O)N2c3ccccc3Oc3ccccc32)CCN1C(=O)C(c1ccccc1)c1ccccc1] | (S)-1-(2,2-diphenylacetyl)-4-(10H-phenoxazine-10-carbonyl)piperazine-2-carboxylic acid | SM1 in Step 2 of Example 2 was replaced with 2,2-diphenylacetyl chloride, and SM2 in Step 4 was replaced with 10H-phenoxazine-10-carbonyl chloride. | ¹H NMR (400 MHz, DMSO-d6) δ 13.23 (s, 1H), 7.34-7.14 (m, 10H), 6.88 (s, 6H), 6.77-6.55 (m, 2H), 5.56 (s, 1H), 5.05 (s, 1H), 4.45 (t, J = 14 Hz, 1H), 3.89 (d, J = 13.2 Hz, 1H), 3.75 (d, J = 12.8 Hz, 1H), 3.18 (t, J = 12.8 Hz, 1H), 3.09-2.91 (m, 2H). MS m/z (ESI): 533.5 [M + H]⁺. |
| C76 | 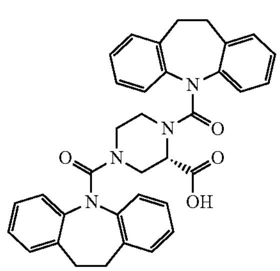 [SMILES: O=C(O)[C@@H]1CN(C(=O)N2c3ccccc3CCc3ccccc32)CCN1C(=O)N1c2ccccc2CCc2ccccc21] | (S)-1,4-bis(10,11-dihydro-5H-dibenzo[b,f]azepine-5-carbonyl)piperazine-2-carboxylic acid | Both SM1 in Step 2 of Example 2 and SM2 in Step 4 were replaced with 10,11-dihydro-5H-dibenzo[bf]azepine-5-carbonyl chloride. | ¹H NMR (400 MHz, DMSO-d6) δ 13.04 (s, 1H), 7.38 (m, 2H), 7.25-7.14 (m, 14H), 4.31 (s, 1H), 3.96-3.92 (m, 1H), 3.45-3.42 (m, 1H), 3.27-3.24 (m, 1H), 3.16-3.00 (m, 8H), 2.77-2.62 (m, 3H). MS m/z (ESI): 573.0 [M + H]⁺. |
| C43 | 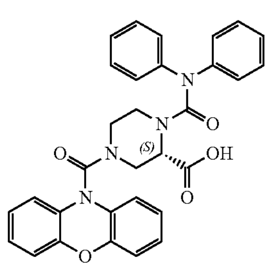 | (S)-1-(diphenylcarbamoyl)-4-(10H-phenoxazine-10-carbonyl)piperazine-2-carboxylic acid | SM1 in Step 2 of Example 2 was replaced with diphenylcarbamyl chloride; and SM2 in Step 4 was replaced with | ¹H NMR (400 MHz, DMSO-d6) δ 13.33 (s, 1H), 7.33 (t, J = 7.6 Hz, 4H), 7.16 (t, J = 7.2 Hz, 2H), 7.04 (d, J = 7.6 Hz, 4H), 6.88 (brs, 5H), 6.77-6.75 (m, 2H), 4.64 (s, 1H), 4.34 (d, J = 13.6 Hz, 1H), 3.75 (d, J = 11.6 Hz, 1H), 3.57 (d, J = 11.6 Hz, 1H), 3.18 (d, J = 11.2 Hz, 1H), 3.07-2.95 (m, 2H). MS m/z (ESI): 534.7 [M + H]⁺. |

TABLE 2-continued

| No. | Compound Structure | Compound Name | Starting material or reagent different from that in Example 2 | Charaterization data |
|---|---|---|---|---|
| C44 | 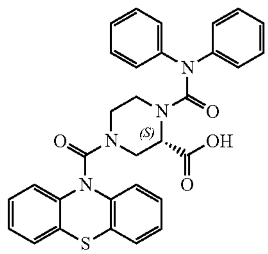 | (S)-1-(diphenylcarbamoyl)-4-(10H-phenothiazine-10-carbonyl)piperazine-2-carboxylic acid | SM1 in Step 2 of Example 2 was replaced with diphenylcarbamyl chloride, and SM2 in Step 4 was replaced with [phenothiazine carbonyl chloride] | $^1$H NMR (400 MHz, DMSO-d6) δ 7.52 (d, J = 8 Hz, 2H), 7.38 (dd, J = 7.6, 1.2 Hz, 2H), 7.31-7.24 (m, 6H), 7.18-7.11 (m, 4H), 6.99 (d, J = 7.2 Hz, 4H), 4.51 (s, 1H), 4.18 (d, J = 13.2 Hz, 1H), 3.32-3.26 (m, 2H), 2.84 (d, J = 11.2 Hz, 1H), 2.74-2.64 (m, 2H). MS m/z (ESI): 550.9 [M + H]$^+$. |
| C48 | 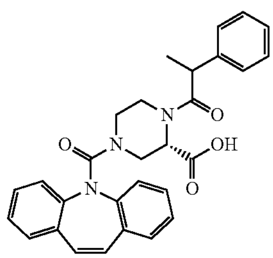 [SMILES: CC(C(=O)N1CCN(C(=O)N2c3ccccc3C=Cc3ccccc32)C[C@H]1C(=O)O)c1ccccc1] | (2S)-4-(5H-dibenzo[b,f]azepine-5-carbonyl)-1-(2-phenylpropionyl)piperazine-2-carboxylic acid | SM1 in Step 2 of Example 2 was replaced with 2-phenylpropionyl chloride; and SM2 in Step 4 was replaced with SM1. | $^1$H NMR (400 MHz, DMSO-d6) δ 12.71 (s, 1H), 7.35-7.00 (m, 15H), 4.88-4.84 (m, 1H), 4.64-4.56 (m, 1H), 4.07-3.98 (m, 2H), 3.74-3.68 (m, 1H), 3.45-3.29 (m, 1H), 3.14-3.04 (m, 1H), 3.91-2.82 (m, 1H), 1.21 (s, 3H). MS m/z (ESI): 481.8 [M + H]$^+$. |
| C49 | 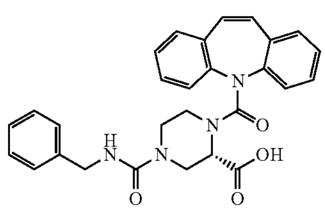 [SMILES: O=C(O)[C@@H]1CN(C(=O)NCc2ccccc2)CCN1C(=O)N1c2ccccc2C=Cc2ccccc21] | (S)-4-(benzylcarbamoyl)-1-(5H-dibenzo[b,f]azepine-5-carbonyl)piperazine-2-carboxylic acid | SM2 in Step 4 of Example 2 was replaced with benzyl isocyanate. | $^1$H NMR (400 MHz, DMSO-d6) δ 12.78 (s, 1H), 8.68 (s, 1H), 7.58 (d, J = 7.2 Hz, 2H), 7.45-7.39 (m, 4H), 7.32-7.24 (m, 4H), 7.21-7.16 (m, 3H), 7.07 (s, 2H), 7.02-6.99 (m, 1H), 4.22-4.09 (m, 4H), 3.06 (d, J = 12.8 Hz, 1H), 2.95-2.89 (m, 1H), 2.84-2.78 (m, 1H), 2.42-2.33 (m, 2H). MS m/z (ESI): 482.8 [M + H]$^+$. |
| C50 | 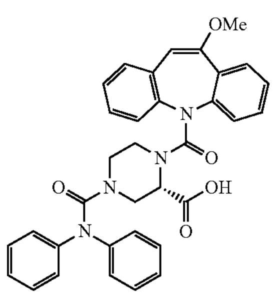 [SMILES: COC1=Cc2ccccc2N(C(=O)N2CCN(C(=O)N(c3ccccc3)c3ccccc3)C[C@H]2C(=O)O)c2ccccc21] | (S)-4-(diphenylcarbamoyl)-1-(10-methoxy-5H-dibenzo[b,f]azepine-5-carbonyl)piperazine-2-carboxylic acid | SM1 in Step 2 of Example 2 was replaced with [10-methoxy dibenzazepine carbonyl chloride] | $^1$H NMR (400 MHz, DMSO-d6) δ 7.94 (d, J = 7.6 Hz, 1H), 7.78 (d, J = 8 Hz, 1H), 7.60 (s, 2H), 7.47-7.27 (m, 8H), 7.14-7.10 (m, 3H), 6.91 (d, J = 8 Hz, 4H), 4.53 (s, 1H), 4.01 (d, J = 13.6 Hz, 1H), 3.52-3.39 (m, 5H), 2.93-2.82 (m, 2H). MS m/z (ESI): 574.9 [M + H]$^+$. |
| C89 | 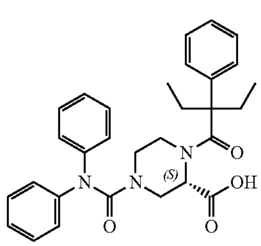 | (S)-4-(diphenylcarbamoyl)-1-(2-ethyl-2-phenylbutyryl)piperazine-2-carboxylic acid | SM1 in Step 2 of Example 2 was replaced with 2-ethyl-2-phenylbutyryl chloride. | $^1$H NMR (400 MHz, DMSO-d6) δ 13.08 (s, 1H), 7.33-7.27 (m, 6H), 7.24-7.20 (m, 1H), 7.18-7.10 (m, 4H), 6.89 (d, J = 7.6 Hz, 1H), 4.97 (s, 1H), 4.08 (d, J = 13.6 Hz, 1H), 3.13 (d, J = 12.8 Hz, 1H), 3.04-2.94 (m, 2H), 2.67-2.61 (m, 1H), 2.26-2.21 (s, 1H), 1.93-1.80 (m, 4H), 0.67 (brs, 3H), 0.57 (t, J = 6.4 Hz, 3H). MS m/z (ESI): 499.8 [M + H]$^+$. |

TABLE 2-continued

| No. | Compound Structure | Compound Name | Starting material or reagent different from that in Example 2 | Charaterization data |
|---|---|---|---|---|
| C82 | 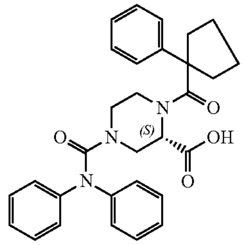 | (S)-4-(diphenylcarbamoyl)-1-(1-phenylcyclopentanecarbonyl)piperazine-2-carboxylic acid | SM1 in Step 2 of Example 2 was replaced with 1-phenylcyclopentane-1-carbonyl chloride. | $^1$H NMR (400 MHz, DMSO-d6) δ 13.10 (s, 1H), 7.35-7.25 (m, 6H), 7.23-7.17 (m, 3H), 7.15-7.09 (m, 2H), 6.89 (d, J = 7.2 Hz, 4H), 4.95 (s, 1H), 4.12 (d, J = 13.6 Hz, 1H), 3.75-3.68 (m, 1H), 3.24 (d, J = 13.2 Hz, 1H), 3.09 (d, J = 13.2 Hz, 1H), 2.97-2.93 (m, 1H), 2.62-2.52 (m, 1H), 2.40-2.32 (m, 1H), 2.25-2.21 (m, 1H), 1.95 (brs, 1H), 1.80 (brs, 1H), 1.72-1.55 (m, 4H). MS m/z (ESI): 498.2 [M + H]$^+$. |
| C85 | 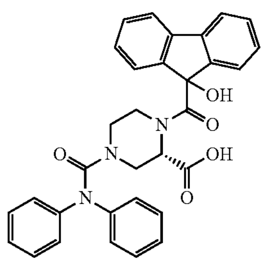 [SMILES: O=C(O)[C@@H]1CN(C(=O)N(c2ccccc2)c2ccccc2)CCN1C(=O)C1(O)c2ccccc2-c2ccccc21] | (S)-4-(diphenylcarbamoyl)-1-(9-hydroxy-9H-fluorene-9-carbonyl)piperazine-2-carboxylic acid | SM1 in Step 2 of Example 2 was replaced with <br><br> the reaction condition in Step 4 was changed to stirring at room temperature for 16 hours. | $^1$H NMR (400 MHz, DMSO-d6) δ 13.12 (s, 1H), 7.81 (d, J = 7.2 Hz, 2H), 7.45-7.40 (m, 2H), 7.35-7.25 (m, 8H), 7.15-7.08 (m, 2H), 6.86 (d, J = 7.6 Hz, 4H), 4.92 (s, 1H), 4.02 (d, J = 14 Hz, 1H), 3.76 (s, 1H), 3.07-2.98 (m, 1H), 2.75-2.68 (m, 1H), 2.21 (brs, 1H). MS m/z (ESI): 534.1 [M + H]$^+$. |
| C80 | 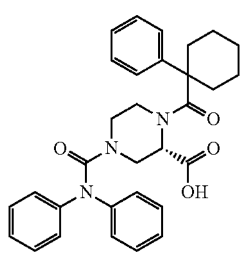 [SMILES: O=C(O)[C@@H]1CN(C(=O)N(c2ccccc2)c2ccccc2)CCN1C(=O)C1(c2ccccc2)CCCCC1] | (S)-4-(diphenylcarbamoyl)-1-(1-phenylcyclohexanecarbonyl)piperazine-2-carboxylic acid | SM1 in Step 2 of Example 2 was replaced with 1-phenylcyclohexane-1-carbonyl chloride. | $^1$H NMR (400 MHz, DMSO-d6) δ 12.76 (s, 1H), 7.33-7.24 (m, 9H), 7.13 (m, 2H), 6.89 (m, 4H), 4.96 (s, 1H), 4.07 (m, 1H), 3.14 (m, 2H), 2.95 (m, 1H), 2.66 (m, 1H), 2.24 (s, 1H), 2.13 (s, 2H), 1.59 (m, 6H), 1.24 (s, 2H). MS m/z (ESI): 512.2 [M + H]$^+$. |
| C81 | 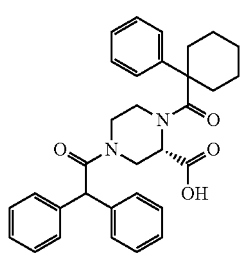 [SMILES: O=C(O)[C@@H]1CN(C(=O)C(c2ccccc2)c2ccccc2)CCN1C(=O)C1(c2ccccc2)CCCCC1] | (S)-4-(2,2-diphenylacetyl)-1-(1-phenylcyclohexanecarbonyl)piperazine-2-carboxylic acid | SM1 in Step 2 of Example 2 was replaced with 1-phenylcyclohexane-1-carbonyl chloride, and SM2 in Step 4 was replaced with 2,2-diphenylacetyl chloride. | $^1$H NMR (400 MHz, DMSO-d6) δ 12.87 (s, 1H), 7.35-7.07 (m, 15H), 5.32 (s, 1H), 5.01 (m, 1H), 4.70 (m, 1H), 3.60 (m, 1H), 3.24-2.95 (m, 2H), 2.70 (m, 1H), 2.15 (m, 2H), 1.58 (m, 7H), 1.24 (m, 2H). MS m/z (ESI): 511.2 [M + H]$^+$. |
| C86 | 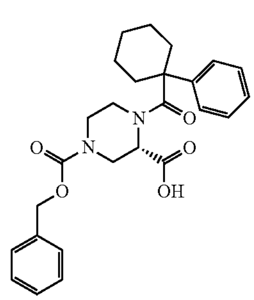 [SMILES: O=C(O)[C@@H]1CN(C(=O)OCc2ccccc2)CCN1C(=O)C1(c2ccccc2)CCCCC1] | (S)-4-((benzyloxy)carbonyl)-1-(1-phenylcyclohexanecarbonyl)piperazine-2-carboxylic acid | SM1 in Step 2 of Example 2 was replaced with 1-phenylcyclohexane-1-carbonyl chloride; and SM2 in Step 4 was replaced with benzyl chloroformate. | $^1$H NMR (400 MHz, DMSO-d6) δ 12.90 (s, 1H), 7.31 (m, 10H), 5.01 (s, 3H), 4.30 (m, 1H), 3.17 (m, 2H), 2.85 (m, 1H), 2.61 (m, 1H), 2.14 (m, 3H), 1.60 (m, 7H), 1.24 (m, 1H). MS m/z (ESI): 451.2 [M + H]$^+$. |

TABLE 2-continued

| No. | Compound Structure | Compound Name | Starting material or reagent different from that in Example 2 | Charaterization data |
|---|---|---|---|---|
| C87 | 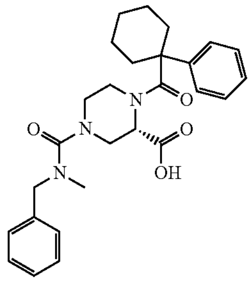 [SMILES: CN(Cc1ccccc1)C(=O)N1CCN(C(=O)C2(c3ccccc3)CCCCC2)[C@H](C(=O)O)C1] | (S)-4-(benzyl(methyl)carbamoyl)-1-(1-phenylcyclohexanecarbonyl)piperazine-2-carboxylic acid | SM1 in Step 2 of Example 2 was replaced with 1-phenylcyclohexyl-1-carbonyl chloride. SM2 in Step 4 was replaced with <br><br> *N-methylbenzylamine structure*, and the reaction conditions were changed to: firstly adding 3 equivalents of triethylamine and 1 equivalent of triphosgene, and reacting at 0° C. for 0.5 h; and then adding *N-methylbenzylamine*, and reacting at room temperature for 16 h. | $^1$H NMR (400 MHz, DMSO-d6) δ 12.93 (s, 1H), 7.39-7.16 (m, 10H), 5.11 (s, 1H), 4.33-4.20 (m, 2H), 3.87 (d, J = 12.4 Hz, 1H), 3.32-3.25 (m, 2H), 3.08-2.92 (m, 3H), 2.58 (s, 3H), 2.29-2.08 (m, 4H), 1.70-1.56 (m, 6H).<br>MS m/z (ESI): 464.1 [M + H]$^+$. |
| C88 | 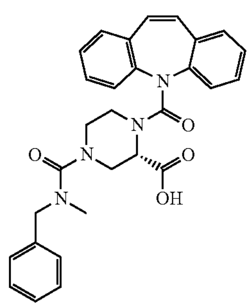 [SMILES: CN(Cc1ccccc1)C(=O)N1CCN(C(=O)N2c3ccccc3C=Cc3ccccc32)[C@H](C(=O)O)C1] | (S)-4-(benzyl(methyl)carbamoyl)-1-(5H-dibenzo[b,f]azepine-5-carbonyl)piperazine-2-carboxylic acid | SM2 in Step 4 in Example 2 was replaced with <br><br> *N-methylbenzylamine structure*, and the reaction conditions were changed to: firstly adding 3 equivalents of triethylamine and 1 equivalent of triphosgene, and reacting at 0° C. for 0.5 h; and then adding *N-methylbenzylamine*, and reacting at room temperature for 16 h. | $^1$H NMR (400 MHz, DMSO-d6) δ 12.61 (s, 1H), 7.67-6.96 (m, 16H), 4.37-4.15 (m, 3H), 3.66 (m, 1H), 3.19-2.95 (m, 3H), 2.80-2.70 (m, 1H), 2.58 (m, 3H).<br>MS m/z (ESI): 497.1 [M + H]$^+$. |

TABLE 2-continued

| Compound No. | Compound Structure | Compound Name | Starting material or reagent different from that in Example 2 | Characterization data |
|---|---|---|---|---|
| C90 | 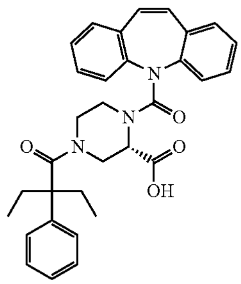 [SMILES: CCC(CC)(C(=O)N1CCN(C(=O)N2c3ccccc3C=Cc3ccccc32)[C@H](C(=O)O)C1)c1ccccc1] | (S)-1-(5H-dibenzo[b,f]azepine-5-carbonyl)-4-(2-ethyl-2-phenylbutyryl)piperazine-2-carboxylic acid | SM2 in Step 4 of Example 2 was replaced with 2-ethyl-2-phenylbutyryl chloride. | $^1$HNMR (400 MHz, DMSO-d6) δ 12.38 (s, 1H), 7.72-6.87 (m, 16H), 4.66 (s, 1H), 4.12 (s, 2H), 2.98-2.58 (m, 3H), 1.88-1.72 (m, 4H), 0.62-0.46 (m, 6H). MS m/(ESI): 524.2 [M + H]$^+$. |
| C29 | 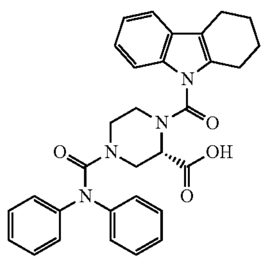 [SMILES: O=C(O)[C@@H]1CN(C(=O)N(c2ccccc2)c2ccccc2)CCN1C(=O)n1c2c(c3ccccc31)CCCC2] | (S)-4-(diphenylcarbamoyl)-1-(2,3,4,9-tetrahydro-1H-carbazole-9-carbonyl)piperazine-2-carboxylic acid | SM1 in Step 2 of Example 2 was replaced with | $^1$H NMR (400 MHz, DMSO-d6) δ 13.60 (s, 1H), 7.43-6.98 (m, 14H), 4.37-4.22 (m, 1H), 3.87-3.62 (m, 1H), 3.26-2.96 (m, 3H), 2.97-2.57 (m, 5H), 1.78 (s, 5H). MS m/z (ESI): 523.1 [M + H]$^+$. |
| C57 | 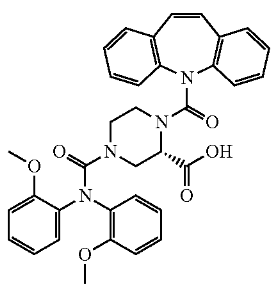 [SMILES: COc1ccccc1N(C(=O)N1CCN(C(=O)N2c3ccccc3C=Cc3ccccc32)[C@H](C(=O)O)C1)c1ccccc1OC] | (S)-4-(bis(2-methoxylphenyl)carbamoyl)-1-(5H-dibenzo[b,f]azepine-5-carbonyl)piperazine-2-carboxylic acid | SM2 in Step 4 of Example 2 was replaced with | $^1$H NMR (400 MHz, DMSO-d6) δ 12.71 (s, 1H), 7.53 (s, 2H), 7.45-7.35 (m, 4H), 7.32-7.25 (m, 2H), 7.16-7.09 (m, 2H), 7.05-6.96 (m, 4H), 6.85-6.77 (m, 2H), 6.74-6.66 (m, 2H), 4.08 (s, 1H), 3.87-3.80 (m, 1H), 3.64 (s, 6H), 3.13-3.04 (m, 1H), 2.84-2.73 (m, 2H), 2.61-2.54 (m, 1H), 2.37-2.28 (m, 1H). MS m/z (ESI): 604.7 [M + H]$^+$. |
| C113 | 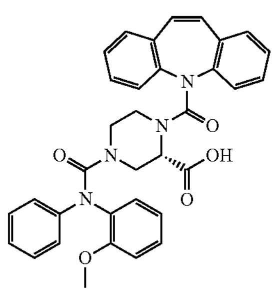 [SMILES: COc1ccccc1N(C(=O)N1CCN(C(=O)N2c3ccccc3C=Cc3ccccc32)[C@H](C(=O)O)C1)c1ccccc1] | (S)-1-(5H-dibenzo[b,f]azepine-5-carbonyl)-4-((2-methoxylphenyl)(phenyl)carbamoyl)piperazine-2-carboxylic acid | SM2 in Step 4 of Example 2 was replaced with | $^1$H NMR (400 MHz, DMSO-d6) δ 12.89 (s, 1H), 7.54 (d, J = 7.2 Hz, 2H), 7.42-7.35 (m, 4H), 7.28 (t, J = 7.2 Hz, 4H), 7.21 (t, J = 7.6 Hz, 3H), 7.09-6.98 (m, 4H), 6.92-6.83 (m, 2H), 6.77 (d, J = 8 Hz, 2H), 4.15 (s, 1H), 3.91 (d, J = 12.8 Hz, 1H), 3.64 (s, 3H), 3.14 (d, J = 12.8 Hz, 1H), 2.84 (d, J = 12.8 Hz, 1H), 2.75 (dd, J = 13.2, 4Hz, 1H), 2.64-2.57 (m, 1H), 2.37-2.32 (m, 1H). MS m/z (ESI): 575.1 [M + H]$^+$. |
| C59 | 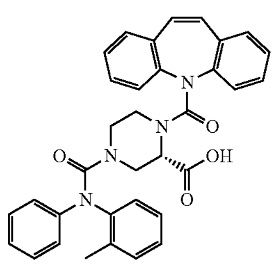 [SMILES: Cc1ccccc1N(C(=O)N1CCN(C(=O)N2c3ccccc3C=Cc3ccccc32)[C@H](C(=O)O)C1)c1ccccc1] | (S)-1-(5H-dibenzo[b,f]azepine-5-carbonyl)-4-(phenyl(orthomethylphenyl)carbamoyl)piperazine-2-carboxylic acid | SM2 in Step 4 of Example 2 was replaced with | $^1$H NMR (400 MHz, CD$_3$OD) δ 7.65-7.56 (m, 3H), 7.43-7.27 (m, 8H), 7.18-7.12 (m, 2H), 7.02-6.93 (m, 4H), 6.78 (s, 1H), 6.73 (d, J = 7.6 Hz, 1H), 4.35-4.24 (m, 1H), 4.14-4.07 (m, 1H), 3.87-3.78 (m, 1H), 3.10-3.06 (m, 1H), 2.82-2.67 (m, 1H), 2.58-2.51 (m, 1H), 2.27 (s, 3H). MS m/z (ESI): 559.1 [M + H]$^+$. |

TABLE 2-continued

| No. | Compound Structure | Compound Name | Starting material or reagent different from that in Example 2 | Charaterization data |
|---|---|---|---|---|
| C83 | 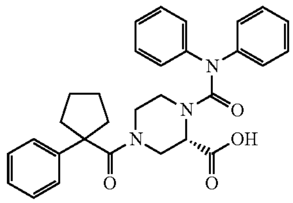 [SMILES: O=C(O)[C@@H]1CN(C(=O)C2(c3ccccc3)CCCC2)CCN1C(=O)N(c1ccccc1)c1ccccc1] | (S)-1-(diphenylcarbamoyl)-4-(1-phenylcyclopentanecarbonyl)piperazine-2-carboxylic acid | SM1 in Step 2 of Example 2 was replaced with diphenylcarbamyl chloride; and SM2 in Step 4 was replaced with | 1H NMR (400 MHz DMSO-d6) δ 13.00 (s, 1H), 7.36-7.24 (m, 6H), 7.23-7.16 (m, 1H), 7.16-7.06 (m, 4H), 6.96 (d, J = 7.6 Hz, 4H), 4.76 (s, 1H), 4.45 (s, 1H), 3.45 (s, 2H), 3.17 (s, 2H), 2.68 (s, 1H), 2.33 (s, 2H), 2.03-1.88 (m, 1H), 1.62 (s, 2H), 1.56 (d, J = 5.7 Hz, 3H). MS m/z (ESI): 498.2 [M + H]+. |
| C117 | 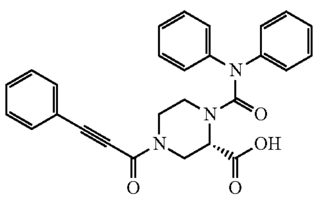 [SMILES: O=C(O)[C@@H]1CN(C(=O)C#Cc2ccccc2)CCN1C(=O)N(c1ccccc1)c1ccccc1] | (S)-1-(diphenylcarbamoyl)-4-(3-phenylpropioloyl)piperazine-2-carboxylic acid | SM1 in Step 2 of Example 2 was replaced with diphenylcarbamyl chloride; and SM2 in Step 4 was replaced with | 1H NMR (400 MHz, DMSO-d6) δ 13.29 (s, 1H), 7.65-7.57 (m, 2H), 7.56-7.43 (m, 3H), 7.36 (t, J = 7.6 Hz, 4H), 7.18 (t, J = 7.2 Hz, 2H), 7.07 (d, J = 7.6 Hz, 4H), 4.7-4.5 (m, 2H), 4.15-4.0 (m, 1H), 3.68 (d, J = 10.4 Hz, 1H), 3.21-3.10 (m, 1H), 3.05-2.97 (m, 1H), 2.75-2.60 (m, 1H). MS m/z (ESI): 454.1 [M + H]+. |
| C140 | 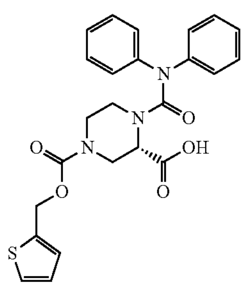 [SMILES: O=C(O)[C@@H]1CN(C(=O)OCc2cccs2)CCN1C(=O)N(c1ccccc1)c1ccccc1] | (S)-1-(diphenylcarbamoyl)-4-((thiophene-2-ylmethoxy)carbonyl)piperazine-2-carboxylic acid | SM1 in Step 2 of Example 2 was replaced with diphenylcarbamyl chloride; and SM2 in Step 4 was replaced with | 1H NMR (400 MHz, DMSO-d6) δ 7.53 (dd, J = 4.8, 1.2 Hz, 1H), 7.35 (t, J = 8.0 Hz, 4H), 7.19-7.11 (m, 3H), 7.07-6.98 (m, 5H), 5.21 (s, 2H), 4.54 (s, 1H), 4.21 (d, J = 12.8 Hz, 1H), 3.65-3.55 (m, 1H), 3.13-2.98 (m, 3H), 2.75-2.65 (m, 1H). MS m/z (ESI): 466.1 [M + H]+. |
| C136 | 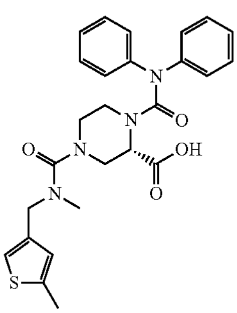 [SMILES: Cc1cc(CN(C)C(=O)N2CCN(C(=O)N(c3ccccc3)c3ccccc3)[C@H](C(=O)O)C2)cs1] | (S)-1-(diphenylcarbamoyl)-4-(methyl((5-methylthiophen-3-yl)methyl)carbamoyl)piperazine-2-carboxylic acid | SM1 in Step 2 in Example 2 was replaced with diphenylcarbamyl chloride. SM2 in Step 4 was replaced with 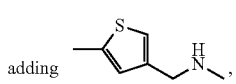 and the reaction conditions were changed to: firstly adding 3 equivalents of triethylamine and 1 equivalent of triphosgene, and reacting at 0° C. for 0.5 h; and then adding 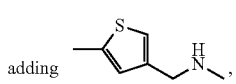, and reacting at room temperature for 16 h. | 1H NMR (400 MHz, DMSO-d6) δ 7.40-7.30 (m, 4H), 7.17 (t, J = 7.2 Hz, 2H), 7.06-7.00 (m, 5H), 6.66 (s, 1H), 4.56 (s, 1H), 4.16 (dd, J = 31.6, 15.2 Hz, 2H), 3.78 (d, J = 13.2 Hz, 1H), 3.59 (d, J = 13.2 Hz, 1H), 3.32-3.25 (m, 1H), 3.21-3.13 (m, 1H), 2.85-2.75 (m, 1H), 2.63 (s, 3H), 2.59-2.52 (m, 1H), 2.40 (d, J = 0.8 Hz, 3H). MS m/z (ESI): 492.6 [M + H]+. |

TABLE 2-continued

| No. | Compound Structure | Compound Name | Starting material or reagent different from that in Example 2 | Characterization data |
|---|---|---|---|---|
| C137 | 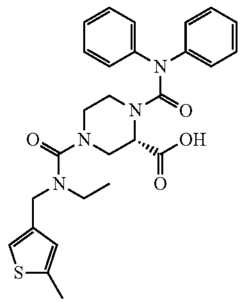 [SMILES: CCN(Cc1csc(C)c1)C(=O)N1CCN(C(=O)N(c2ccccc2)c2ccccc2)[C@H](C(=O)O)C1] | (S)-1-(diphenylcarbamoyl)-4-(ethyl((5-methylthiophen-3-yl)methyl)carbamoyl)piperazine-2-carboxylic acid | SM1 in Step 2 in Example 2 was replaced with diphenylcarbamyl chloride. SM2 in Step 4 was replaced with [structure], the reaction conditions were changed to: firstly adding 3 equivalents of triethylamine and 1 equivalent of triphosgene, and reacting at 0° C. for 0.5 h; and then adding [structure], and reacting at room temperature for 16 h. | $^1$H NMR (400 MHz, DMSO-d6) δ 7.40-7.31 (m, 4H), 7.16 (t, J = 7.2 Hz, 2H), 7.06-7.04 (m, 5H), 6.65 (s, 1H), 4.55 (s, 1H), 4.18 (dd, J = 35.6, 15.6 Hz, 2H), 3.77 (d, J = 13.2 Hz, 1H), 3.59 (d, J = 12.8 Hz, 1H), 3.29 (d, J = 12.4 Hz, 1H), 3.22-3.12 (m, 1H), 3.10-3.00 (m, 1H), 2.96-2.75 (m, 2H, 2.63-2.53 (m, 1H), 2.40 (d, J = 0.8 Hz, 3H), 0.97 (t, J = 7.0 Hz, 3H). MS m/z (ESI): 506.8 [M + H]$^+$. |
| C138 | 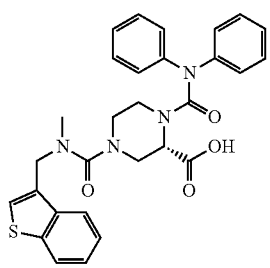 [SMILES: CN(Cc1csc2ccccc12)C(=O)N1CCN(C(=O)N(c2ccccc2)c2ccccc2)[C@H](C(=O)O)C1] | (S)-4-(benzo[b]thiophene-3-ylmethyl)(methyl)carbamoyl)-1-(diphenylcarbamoyl)piperazine-2-carboxylic acid | SM1 in Step 2 of Example 2 was replaced with diphenylcarbamyl chloride. SM2 in Step 4 was replaced with [structure], and the reaction conditions were changed to: firstly adding 3 equivalents of triethylamine and 1 equivalent of triphosgene, and reacting at 0° C. for 0.5 h; and then adding [structure], and reacting at room temperature for 16 h. | 1H NMR (400 MHz, DMSO-d6) δ 8.00-7.96 (m, 1H), 7.77-7.73 (m, 1H), 7.61 (s, 1H), 7.42-7.35 (m, 2H), 7.31 (t, J = 8.0 Hz, 4H), 7.15-7.05 (m, 6H), 4.70-4.55 (m, 3H), 3.85 (s, 1H), 3.61 (s, 1H), 3.32-3.15 (m, 4H), 2.68 (s, 3H). MS m/z (ESI): 528.7 [M + H]$^+$. |

TABLE 2-continued

| No. | Compound Structure | Compound Name | Starting material or reagent different from that in Example 2 | Charaterization data |
|---|---|---|---|---|
| C146 | (structure) | (S)-4-(cyclopropyl((5-methylthiophen-3-yl)methyl)carbamoyl)-1-(diphenylcarbamoyl)piperazine-2-carboxylic acid | SM1 in Step 2 of Example 2 was replaced with diphenylcarbamyl chloride. SM2 in Step 4 was replaced with (structure), and the reaction conditions were changed to: firstly adding 3 equivalents of triethylamine and 1 equivalent of triphosgene, and reacting at 0° C. for 0.5 h; and then adding (structure), and reacting at room temperature for 16 h. | $^1$H NMR (400 MHz, DMSO-d6) δ 13.12 (s, 1H), 7.40-7.30 (m, 4H), 7.17 (t, J = 7.2 Hz, 2H), 7.08-6.91 (m, 5H), 6.65 (s, 1H), 4.54 (s, 1H), 4.35 (d, J = 14.8 Hz, 1H), 4.00 (d, J = 15.2 Hz, 1H), 3.93 (d, J = 13.2 Hz, 1H), 3.58 (d, J = 11.2 Hz, 2H), 3.21 (t, J = 11.2 Hz, 1H), 2.90-2.77 (m, 1H), 2.67-2.57 (m, 1H), 2.43-2.32 (m, 4H), 0.69-0.58 (m, 1H), 0.58-0.39 (m, 3H).<br>MS m/z (ESI): 518.9 [M + H]$^+$. |
| C128 | (structure) | (S)-1-(diphenylcarbamoyl)-4-((R)-2-phenylpyrrolidine-1-carbonyl)piperazine-2-carboxylic acid | SM1 in Step 2 of Example 2 was replaced with diphenylcarbamyl chloride. SM2 in Step 4 was replaced with (structure), and the reaction conditions were changed to: firstly adding 3 equivalents of triethylamine and 1 equivalent of triphosgene, and reacting at 0° C. for 0.5 h; and then adding (structure), and reacting at room temperature for 16 h. | $^1$H NMR (400 MHz, DMSO-d6) δ 13.04 (s, 1H), 7.42-7.30 (m, 4H), 7.30-7.23 (m, 2H), 7.23-7.10 (m, 5H), 7.10-6.95 (m, 4H), 4.86 (t, J = 7.2 Hz, 1H), 4.53 (s, 1H), 3.83 (d, J = 12.8 Hz, 1H), 3.58 (s, 3H), 3.35-3.25 (m, 1H), 3.24-3.12 (m, 1H), 2.80 (d, J = 10 Hz, 1H), 2.71-2.54 (m, 1H), 2.27 (s, 1H), 1.84 (s, 1H), 1.74 (s, 1H), 1.56 (dd, J = 18.4, 9.2 Hz, 1H).<br>MS m/z (ESI): 499.0 [M + H]$^+$. |

TABLE 2-continued

| No. | Compound Structure | Compound Name | Starting material or reagent different from that in Example 2 | Characterization data |
|---|---|---|---|---|
| C145 | 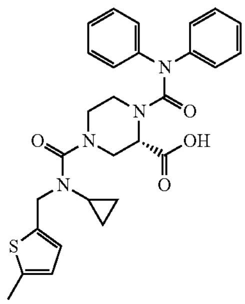 [SMILES: Cc1ccc(CN(C(=O)N2CCN(C(=O)N(c3ccccc3)c3ccccc3)[C@H](C(=O)O)C2)C2CC2)s1] | (S)-4-(cyclopropyl((5-methylthiophen-2-yl)methyl)carbamoyl)-1-(diphenylcarbamoyl)piperazine-2-carboxylic acid | SM1 in Step 2 of Example 2 was replaced with diphenylcarbamyl chloride. SM2 in Step 4 was replaced with [5-methylthiophen-2-yl-methyl-cyclopropylamine], and the reaction conditions were changed to: firstly adding 3 equivalents of triethylamine and 1 equivalent of triphosgene, and reacting at 0° C. for 0.5 h; and then adding [5-methylthiophen-2-yl-methyl-cyclopropylamine], and reacting at room temperature for 16 h. | ¹H NMR (400 MHz, CD₃OD) δ 7.40-7.34 (m, 4H), 7.22 (dd, J = 7.2, 7.6 Hz, 2H), 7.16-7.11 (m, 4H), 6.75 (d, J = 3.6 Hz, 1H), 6.61-6.57 (m, 1H), 4.70 (s, 1H), 4.62 (d, J = 15.2 Hz, 1H), 4.32 (d, J = 15.2 Hz, 1H), 4.13 (d, J = 13.6 Hz, 1H), 3.69 (d, J = 11.6 Hz, 2H), 3.39 (dd, J = 10.8, 3.3 Hz, 1H), 3.05 (d, J = 11.6 Hz, 1H), 2.78 (t, J = 10.8 Hz, 1H), 2.52-2.45 (m, 1H), 2.43 (d, J = 0.8 Hz, 3H), 0.82-0.71 (m, 1H), 0.71-0.49 (m, 3H). MS m/z (ESI): 519.1 [M + H]⁺. |
| C150 | 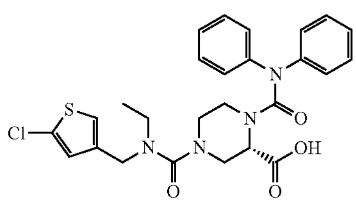 [SMILES: CCN(Cc1csc(Cl)c1)C(=O)N1CCN(C(=O)N(c2ccccc2)c2ccccc2)[C@H](C(=O)O)C1] | (S)-4-(((5-chlorothiophene-3-yl)methyl)(ethyl)carbamoyl)-1-(diphenylcarbamoyl)piperazine-2-carboxylic acid | SM1 in Step 2 of Example 2 was replaced with diphenylcarbamyl chloride. SM2 in Step 4 was replaced with [5-chlorothiophen-3-yl-methyl-ethylamine], and the reaction conditions were changed to: firstly adding 3 equivalents of triethylamine and 1 equivalent of triphosgene, and reacting at 0° C. for 0.5 h; and then adding [5-chlorothiophen-3-yl-methyl-ethylamine], and reacting at room temperature for 16 h. | ¹H NMR (400 MHz, DMSO-d6) δ 7.32 (t, J = 7.6 Hz, 4H), 7.24 (s, 1H), 7.13 (t, J = 7.2 Hz, 2H), 7.07 (d, J = 7.6 Hz, 4H), 6.98 (d, J = 1.6 Hz, 1H), 4.42-4.10 (m, 3H), 3.83 (d, J = 11.6 Hz, 1H), 3.61 (d, J = 12.8 Hz, 1H), 3.23-3.05 (m, 3H), 3.05-2.94 (m, 1H), 2.56 (d, J = 12.4 Hz, 2H), 0.98 (t, J = 7.2 Hz, 3H). MS m/z (ESI): 527.0 [M + H]⁺. |

TABLE 2-continued

| No. | Compound Structure | Compound Name | Starting material or reagent different from that in Example 2 | Charaterization data |
| --- | --- | --- | --- | --- |
| C135 | 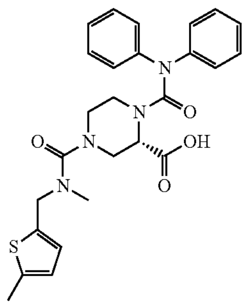 [SMILES: Cc1ccc(CN(C)C(=O)N2CCN(C(=O)N(c3ccccc3)c3ccccc3)[C@H](C(=O)O)C2)s1] | (S)-1-(diphenylcarbamoyl)-4-(methyl((5-methylthiophen-2-yl)methyl)carbamoyl)piperazine-2-carboxylic acid | SM1 in Step 2 of Example 2 was replaced with diphenylcarbamyl chloride. SM2 in Step 4 was replaced with [structure], and the reaction conditions were changed to: firstly adding 3 equivalents of triethylamine and 1 equivalent of triphosgene, and reacting at 0° C. for 0.5 h; and then adding [structure], and reacting at room temperature for 16 h. | $^1$H NMR (400 MHz, DMSO-d6) δ 13.08 (s, 1H), 7.37-7.03 (m, 10H), 6.77 (d, J = 2.0 Hz, 1H), 6.62 (s, 1H), 4.55 (s, 1H), 4.33 (s, 2H), 3.77 (d, J = 12.8 Hz, 1H), 3.60 (d, J = 12.4 Hz, 1H), 3.30-3.25 (m, 1H), 3.21-3.14 (m, 1H), 2.82 (s, 1H), 2.65 (s, 3H), 2.58-2.54 (m, 1H), 2.38 (s, 3H).<br>MS m/z (ESI): 492.8 [M + H]$^+$. |
| C133 | 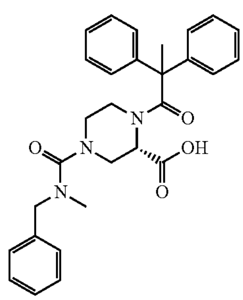 [SMILES: CN(Cc1ccccc1)C(=O)N1CCN(C(=O)C(C)(c2ccccc2)c2ccccc2)[C@H](C(=O)O)C1] | (S)-4-(benzyl(methyl)carbamoyl)-1-(2,2-diphenylpropionyl)piperazine-2-carboxylic acid | SM1 in Step 2 of Example 2 was replaced with 2,2-diphenylpropionyl chloride. SM2 in Step 4 was replaced with [structure], and the reaction conditions were changed to: firstly adding 3 equivalents of triethylamine and 1 equivalent of triphosgene, and reacting at 0° C. for 0.5 h; and then adding [structure], and reacting at room temperature for 16 h. | $^1$H NMR (400 MHz, DMSO-d6) δ 13.09 (s, 1H), 7.51-7.15 (m, 15H), 5.13 (s, 1H), 4.24 (s, 2H), 3.82 (d, J = 12.8 Hz, 1H), 3.22-3.16 (m, 1H), 2.98-2.88 (m, 3H), 2.59-2.53 (m, 4H), 1.81 (s, 3H).<br>MS m/z (ESI): 485.8 [M + H]$^+$. |

TABLE 2-continued

| No. | Compound Structure | Compound Name | Starting material or reagent different from that in Example 2 | Charaterization data |
|---|---|---|---|---|
| C134 | 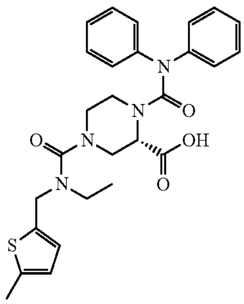 [SMILES: CCN(Cc1ccc(C)s1)C(=O)N1CCN(C(=O)N(c2ccccc2)c2ccccc2)[C@H](C(=O)O)C1] | (S)-1-(diphenylcarbamoyl)-4-(ethyl((5-methylthiophen-2-yl)methyl)carbamoyl)piperazine-2-carboxylic acid | SM1 in Step 2 of Example 2 was replaced with diphenylcarbamyl chloride. SM2 in Step 4 was replaced with [5-methylthiophen-2-yl-methyl-ethylamine], and the reaction conditions were changed to: firstly adding 3 equivalents of triethylamine and 1 equivalent of triphosgene, and reacting at 0° C. for 0.5 h; and then adding [5-methylthiophen-2-yl-methyl-ethylamine], and reacting at room temperature for 16 h. | $^1$H NMR (400 MHz, DMSO-d6) δ 13.06 (s, 1H), 7.35-7.02 (m, 10H), 6.76 (s, 1H), 6.61 (s, 1H), 4.54 (s, 1H), 4.34 (s, 2H), 3.80-3.74 (m, 1H), 3.64-3.58 (m, 1H), 3.27-3.15 (m, 2H), 3.09-2.97 (m, 2H), 2.87-2.78 (m, 1H), 2.61-2.55 (m, 1H), 2.38 (s, 3H), 1.00 (t, J = 6.8 Hz, 3H). MS m/z (ESI): 506.8 [M + H]$^+$. |
| C148 | 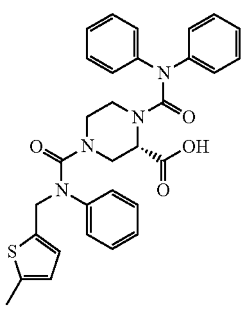 [SMILES: Cc1ccc(CN(C(=O)N2CCN(C(=O)N(c3ccccc3)c3ccccc3)[C@H](C(=O)O)C2)c2ccccc2)s1] | (S)-1-(diphenylcarbamoyl)-4-(((5-methylthiophen-2-yl)methyl)(phenyl)carbamoyl)piperazine-2-carboxylic acid | SM1 in Step 2 of Example 2 was replaced with diphenylcarbamyl chloride. SM2 in Step 4 was replaced with [N-((5-methylthiophen-2-yl)methyl)aniline], and the reaction conditions were changed to: firstly adding 3 equivalents of triethylamine and 1 equivalent of triphosgene, and reacting at 0° C. for 0.5 h; and then adding [N-((5-methylthiophen-2-yl)methyl)aniline], and reacting at room temperature for 16 h. | $^1$H NMR (400 MHz DMSO-d6) δ 13.32 (s, 1H), 7.34-7.24 (m, 7H), 7.15-7.05 (m, 3H), 7.00 (dd, J = 9.2, 7.6 Hz, 7H), 6.54 (d, J = 3.6 Hz, 1H), 6.48 (dd, J = 3.3, 1.1 Hz, 1H), 4.85-4.71 (m, 2H), 4.37 (s, 1H), 3.98 (d, J = 13.2 Hz, 1H), 3.34 (s, 1H), 3.23 (d, J = 11.6 Hz, 2H), 2.79-2.62 (m, 2H), 2.32 (s, 3H). MS m/z (ESI): 555.1 [M + H]$^+$. |

TABLE 2-continued

| No. | Compound Structure | Compound Name | Starting material or reagent different from that in Example 2 | Charaterization data |
|---|---|---|---|---|
| C153 | 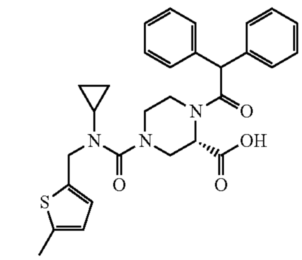 [SMILES: Cc1ccc(CN(C(=O)N2CCN(C(=O)C(c3ccccc3)c3ccccc3)[C@H](C(=O)O)C2)C2CC2)s1] | (S)-4-(cyclopropyl((5-methylthiophen-2-yl)methyl)carbamoyl)-1-(2,2-diphenylacetyl)piperazine-2-carboxylic acid | SM1 in Step 2 of Example 2 was replaced with 2,2-diphenylacetyl chloride. SM2 in Step 4 was replaced with [structure], and the reaction conditions were changed to: firstly adding 3 equivalents of triethylamine and 1 equivalent of triphosgene, and reacting at 0° C. for 0.5 h; and then adding [structure], and reacting at room temperature for 16 h. | $^1$H NMR (400 MHz, DMSO-d6) δ 13.00 (s, 1H), 7.35-7.21 (m, 10H), 6.73 (d, J = 2.8 Hz, 1H), 6.63 (d, J = 1.2 Hz, 1H), 5.61-5.52 (m, 1H), 5.02-4.90 (m, 1H), 4.60-4.49 (m, 1H), 4.25-4.15 (m, 2H), 4.08-3.96 (m, 1H), 3.90 (d, J = 13.2 Hz, 1H), 3.79-3.55 (m, 1H), 3.10-3.00 (m, 1H), 2.73-2.59 (m, 2H), 2.43-2.31 (m, 4H), 0.70-0.46 (m, 4H). MS m/z (ESI): 519.2 [M + H]$^+$. |
| C129 | 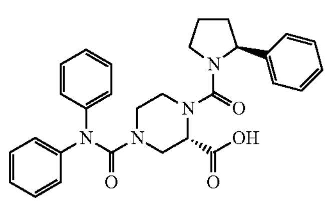 [SMILES: O=C(O)[C@@H]1CN(C(=O)N(c2ccccc2)c2ccccc2)CCN1C(=O)N1CCC[C@H]1c1ccccc1] | (S)-4-(diphenylcarbamoyl)-1-((S)-2-phenylpyrrolidinyl-1-carbonyl)piperazine-2-carboxylic acid | SM1 in Step 2 of Example 2 was replaced with [structure]. | $^1$H NMR (400 MHz, DMSO-d6) δ 13.10 (s, 1H), 7.33 (t, J = 7.6 Hz, 4H), 7.27-7.20 (m, 3H), 7.20-7.12 (m, 3H), 7.03-6.92 (m, 4H), 4.92-4.85 (m, 1H), 4.50 (s, 1H), 4.15 (d, J = 13.4 Hz, 1H), 3.72 (d, J = 10.8 Hz, 1H), 3.61-3.53 (m, 1H), 3.53-3.49 (m, 1H), 3.33 (s, 1H), 2.94-2.87 (m, 1H), 2.87-2.75 (m, 2H), 2.33-2.24 (m, 1H), 1.85 (s, 1H), 1.74 (s, 1H), 1.58-1.47 (m, 1H). MS m/z (ESI): 498.9 [M + H]$^+$. |
| C144 | 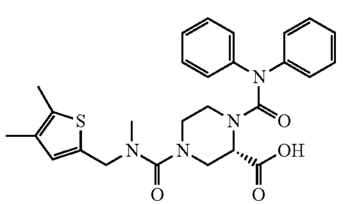 [SMILES: Cc1cc(CN(C)C(=O)N2CCN(C(=O)N(c3ccccc3)c3ccccc3)[C@H](C(=O)O)C2)sc1C] | (S)-4-(((4,5-dimethylthiophen-2-yl)methyl)(methyl)carbamoyl)-1-(diphenylcarbamoyl)piperazine-2-carboxylic acid | SM1 in Step 2 of Example 2 was replaced with 2,2-diphenylcarbamyl chloride. SM2 in Step 4 was replaced with [structure], and the reaction conditions were changed to: firstly adding 3 equivalents of triethylamine and 1 equivalent of triphosgene, and reacting at 0° C. for 0.5 h; and then | $^1$H NMR (400 MHz DMSO-d6) δ 13.18 (s, 1H), 7.35 (t, J = 7.6 Hz, 4H), 7.16 (t, J = 7.2 Hz, 2H), 7.08-7.01 (m, 4H), 6.66 (s, 1H), 4.53 (s, 1H), 4.29 (s, 2H), 3.77 (d, J = 13.3 Hz, 1H), 3.60 (d, J = 12.4 Hz, 1H), 3.42-3.21 (m, 2H), 3.21-3.11 (m, 1H), 2.79 (s, 1H), 2.67 (d, J = 14.8 Hz, 3H), 2.55 (d, J = 12.0 Hz, 1H), 2.23 (s, 3H), 2.02 (s, 3H). MS m/z (ESI): 529.2 [M + Na]$^+$. |

TABLE 2-continued

| No. | Compound Structure | Compound Name | Starting material or reagent different from that in Example 2 | Characterization data |
|---|---|---|---|---|
| C147 | (structure shown) | (S)-1-(diphenylcarbamoyl)-4-(((5-methylthiophen-3-yl)methyl)(phenyl)carbamoyl)piperazine-2-carboxylic acid | SM1 in Step 2 of Example 2 was replaced with 2,2-diphenylcarbamyl chloride. SM2 in Step 4 was replaced with (structure), and the reaction conditions were changed to: firstly adding 3 equivalents of triethylamine and 1 equivalent of triphosgene, and reacting at 0° C. for 0.5 h; and then adding (structure), and reacting at room temperature for 16 h. | $^1$H NMR (400 MHz, DMSO-d6) δ 7.33-7.23 (m, 6H), 7.12 (t, J = 7.2 Hz, 2H), 7.06 (t, J = 7.2 Hz, 1H), 7.00 (d, J = 8.4 Hz, 6H), 6.91 (s, 1H), 6.69 (s, 1H), 4.74 (d, J = 15.6 Hz, 1H), 4.51 (d, J = 15.6 Hz, 1H), 4.32 (s, 1H), 3.98 (d, J = 13.6 Hz, 1H), 3.33-3.17 (m, 3H), 2.80-2.67 (m, 2H), 2.35 (s, 3H). MS m/z (ESI): 555.0 [M + H]$^+$. |

Example 3: Preparation of (S)-1-(5H-dibenzo[b,f]azepine-5-carbonyl)-4-(dipentylcarbamoyl) piperazine-2-carboxylic acid (C7)

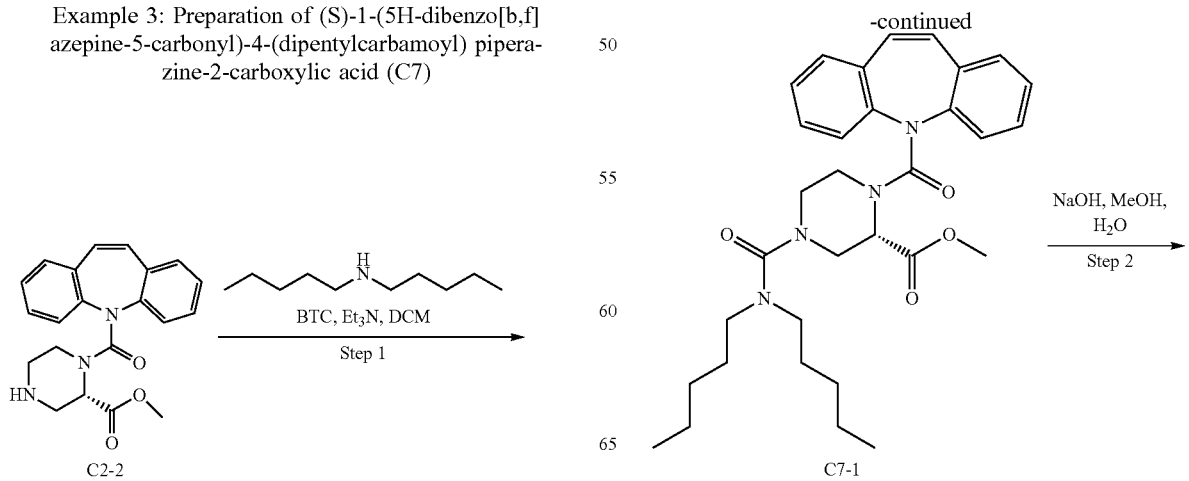

207

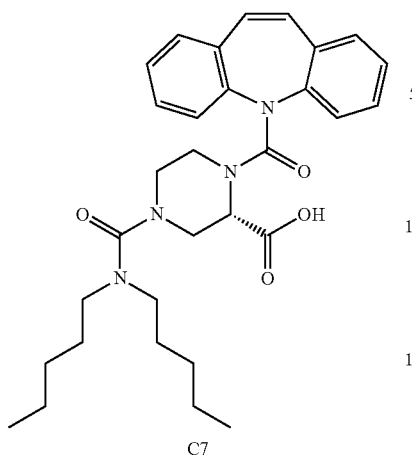

C7

Step 1:

Compound C2-2 (100 mg, 0.27 mmol) and triethylamine (82 mg, 0.81 mmol) were added to dry dichloromethane (10 mL). After cooling to 0° C., triphosgene (80 mg, 0.27 mmol) was added. After stirring for another 0.5 hour, dipentylamine (43 mg, 0.27 mmol) was slowly added. The reaction solution was reacted at room temperature for 16 hours. LC-MS indicated that the reaction of the starting materials was complete. After adding dichloromethane (30 mL), it was washed with saturated brine (20 mL×3), dried over anhydrous sodium sulfate (20 g) for half an hour, and then filtered. The filtrate was concentrated under reduced pressure to obtain a crude compound. The crude product was separated by preparative plate chromatography (petroleum ether:ethyl acetate=3:1) to obtain Compound C7-1 (80 mg, a white solid, yield: 53%).

MS m/z (ESI): 546.4 [M+H]$^+$.

Step 2:

Compound C7-1 (80 mg, 0.15 mmol) was dissolved in methanol (8 mL) and water (6 mL), and sodium hydroxide (59 mg, 1.5 mmol) was added at room temperature, then heated to 40° C. and stirred for 16 horns, and then concentrated under reduced pressure. The residue was dissolved in water (20 mL), adjusted to pH 5 with 1N dilute hydrochloric acid, and then extracted with ethyl acetate (20 mL×3). The organic phases were washed with saturated brine (30 mL×2), dried over anhydrous sodium sulfate (20 g) for half an horn, and then filtered. The filtrate was concentrated under reduced pressure to obtain a crude compound. The crude product was separated by preparative high-performance liquid chromatography (CH$_3$CN:H$_2$O (0.1% TFA)=30%-70%) to obtain Compound C7 (10 mg, a white solid, yield: 12.8%).

$^1$H NMR (400 MHz, -DMSO-d6): δ 12.81 (brs, 1H), 7.57 (d, J=7.6, 2H), 7.45-7.35 (m, 4H), 7.31-7.28 (m, 2H), 7.06 (s, 1H), 4.20 (s, 1H), 3.55-3.52 (m, 1H), 3.13-2.92 (m, 3H), 2.64-2.60 (m, 1H), 2.23-2.17 (m, 1H), 1.39-1.31 (m, 4H), 1.25-1.18 (m, 4H), 1.14-1.08 (m, 4H), 0.82 (t, 7=7.6 Hz, 6H).

MS m/z (ESI): 532.8 [M+H]$^+$.

208

Example 4: Preparation of (S)-4-(diphenylcarbamoyl)-1-(10-oxo-10,11-dihydro-5H-dibenzo[b,f]azepine-5-carbonyl)piperazine-2-carboxylic acid (C77)

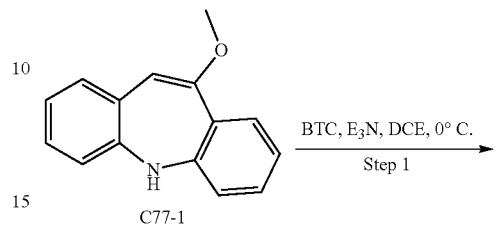

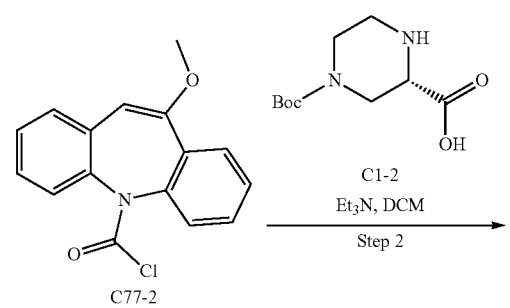

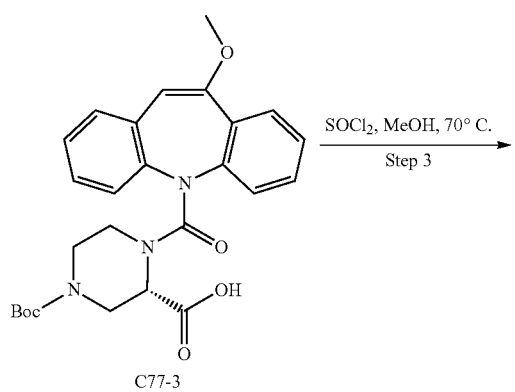

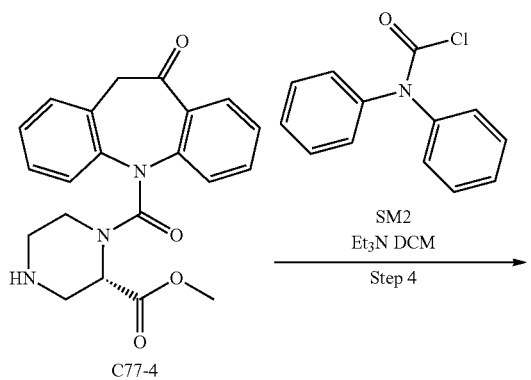

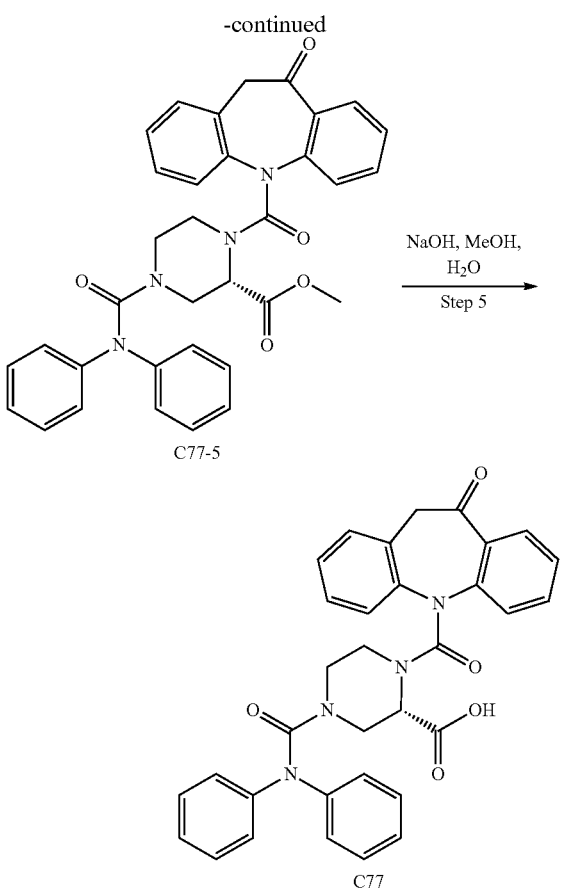

Step 1:

Compound C77-1 (10 g, 44.8 mmol) and triethylamine (13.6 g, 133.4 mmol) were dissolved in 1,2-dichloroethane (150 mL), and triphosgene (13.2 g, 44.8 mmol) was added in portions at 0° C., and the reaction solution was reacted at room temperature for 16 hours. LC-MS indicated that the reaction of the starting materials was substantially complete. After that, the reaction solution was washed with saturated brine (60 mL×3), and then dried by adding anhydrous sodium sulfate (20 g) for half an horn. After that, it was filtered, and concentrated under reduced pressure to obtain a crude product. The crude product was separated by column chromatography on silica gel (dichloromethane:petroleum ether=1:10) to obtain Compound C77-2 (7.2 g, a yellow solid, yield: 57%).

$^1$HNMR (400 MHz, CDCl$_3$) δ 7.78 (d, J=8 Hz, 1H), 7.52-7.41 (m, 4H), 7.34-7.32 (m, 3H), 7.26 (s, 1H), 6.19 (s, 1H), 3.93 (d, J=5.2 Hz, 3H).

MS m/z (ESI): 285.7 [M+H]$^+$.

Step 2:

Compound C1-2 (5.8 g, 25 mmol) was dissolved in dry dichloromethane (100 mL). After the temperature was reduced to 0° C.-5° C., triethylamine (7.6 g, 75 mmol) and C77-2 (7.2 g, 25 mmol) were sequentially added. The reaction solution was reacted at room temperature for 16 horns. LC-MS indicated that the reaction of the starting materials was complete. The reaction was quenched by adding water (100 mL), and extracted with dichloromethane (100 mL×2). The organic phases were combined, washed once with saturated brine (100 mL), then dried over anhydrous sodium sulfate (40 g) for half an hour, filtered, and concentrated to obtain Compound C77-3 (10 g, a yellow solid, yield: 83%).

MS m/z (ESI): 424.1 [M+H-56]$^+$.

Step 3:

Compound C77-3 (10 g, 20.9 mmol) was dissolved in dry methanol (100 mL). After the temperature was reduced to 0° C.-5° C., SOCl$_2$ (10 mL) was added dropwise. The reaction solution was reacted at 70° C. for 48 hours. LC-MS indicated that the reaction of the starting materials was complete. The reaction solution was concentrated under reduced pressure, dried by rotary vaporization, and then saturated sodium bicarbonate aqueous solution (100 mL) was added thereto. It was then extracted with ethyl acetate (60 mL×3), washed with saturated brine (80 mL×2), and then dried over anhydrous sodium sulfate (40 g) for half an hour. After that, it was filtered, and concentrated. The crude product was separated by column chromatography on silica gel (dichloromethane:methanol=30:1) to obtain Compound C77-4 (4 g, a light yellow solid, yield: 50.6%).

$^1$HNMR (400 MHz, CDCl$_3$) δ 8.12 (d, J=8.0 Hz, 1H), 7.85 (d, J=7.6 Hz, 1H), 7.57 (d, J=3.2 Hz, 2H), 7.31-7.22 (m, 4H), 5.30 (s, 1H), 4.81 (brs, 1H), 4.17-4.05 (m, 2H), 3.79 (s, 3H), 3.51-3.42 (m, 2H), 3.14 (s, 1H), 2.93-2.89 (m, 2H), 2.55 (t, J=10.8 Hz, 1H).

MS m/z (ESI): 379.7 [M+H]$^+$.

Step 4:

Compound C77-4 (4 g, 10.5 mmol) was dissolved in dry dichloromethane (100 mL). After the temperature was reduced to 0° C.-5° C., triethylamine (3.2 g, 31.5 mmol) and SM2 (2.43 g, 8.0 mmol) were sequentially added. The reaction solution was reacted at room temperature for 16 hours. LC-MS indicated that the reaction of the starting materials was complete. The reaction was quenched by adding water (100 mL), and extracted with dichloromethane (80 mL×2). The organic phases were combined, washed twice with saturated brine (60 mL), then dried over anhydrous sodium sulfate (30 g) for half an hour, filtered, and concentrated. The crude product was separated by column chromatography on silica gel (ethyl acetate:petroleum ether=1:1) to obtain Compound C77-5 (5.4 g, a light yellow solid, yield: 90%).

$^1$HNMR (400 MHz, CDCl$_3$) δ 8.10 (d, J=8 Hz, 1H), 7.82 (d, J=7.6 Hz, 1H), 7.56-7.53 (m, 2H), 7.29-7.21 (m, 8H), 7.12 (t, J=7.2 Hz, 2H), 6.96 (d, J=8 Hz, 2H), 4.76 (s, 1H), 4.22 (d, J=13.6 Hz, 1H), 4.08 (brs, 2H), 3.77 (s, 3H), 3.55 (d, J=12.4 Hz, 1H), 3.27 (d, J=12.8 Hz, 1H), 3.05-3.01 (m, 2H), 2.66 (t, J=11.2 Hz, 1H).

MS m/z (ESI): 574.5 [M+H]$^+$.

Step 5:

Compound C77-5 (5.3 g, 9.2 mmol) was dissolved in dry methanol (100 mL) and water (40 mL), and sodium hydroxide (2.2 g, 55.2 mmol) was added. The reaction solution was reacted at room temperature for 3 hours. LC-MS indicated that the reaction of starting materials was complete. The reaction solution was concentrated under reduced pressure, dissolved with water (150 mL), and then adjusted to pH=4~5 by adding 1N HCl solution dropwise until a white precipitate occurred, which was then filtered. The white solid was washed with water (50 mL), and then dried in vacuo to obtain Compound C77 (4.5 g, a light yellow solid, yield: 88%).

$^1$HNMR (400 MHz, DMSO-d6) δ 10.14 (s, 1H), 7.92 (d, J=8 Hz, 1H), 7.79 (d, 0.7=7.2 Hz, 1H), 7.68-7.66 (m, 2H), 7.61-7.55 (m, 1H), 7.37-7.25 (m, 8H), 7.09 (t, J=7.6 Hz, 2H), 6.94 (d, J=8 Hz, 2H), 4.31-3.89 (m, 4H), 3.58 (s, 1H), 3.34 (brs, 1H), 2.82-2.60 (m, 3H).

MS m/z (ESI): 560.7 [M+H]$^+$.

The compounds in Table 3 were prepared by methods similar to that described in Example 4.

TABLE 3

| No. | Compound Structure | Compound Name | Starting material or reagent different from that in Example 4 | Characterization data |
|---|---|---|---|---|
| C91 | 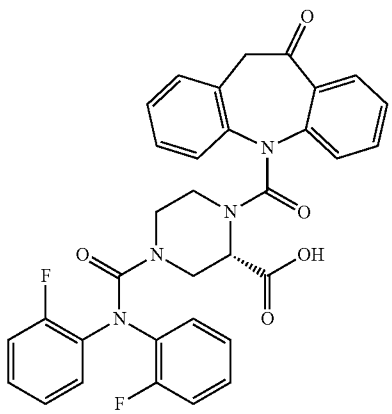 [SMILES: O=C1Cc2ccccc2N(C(=O)N2CCN(C(=O)N(c3ccccc3F)c3ccccc3F)C[C@H]2C(=O)O)c2ccccc21] | (S)-4-(bis(2-fluophenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with bis(2-fluophenyl)carbamyl chloride. | $^1$H NMR (400 MHz, DMSO-d6) δ 13.19 (s, 1H), 7.94 (d, J = 8 Hz, 1H), 7.76 (d, J = 6.8 Hz, 1H), 7.60 (s, 2H), 7.39 (d, J = 5.6 Hz, 1H), 7.33-7.20 (m, 6H), 7.14 (t, J = 7.2 Hz, 2H), 7.01 (t, J = 8 Hz, 2H), 4.52 (s, 1H), 4.16 (s, 1H), 4.01 (d, J = 12.8 Hz, 1H), 3.43-3.27 (m, 3H), 2.99 (s, 1H), 2.67 (m, 2H). MS m/z (ESI): 597.0 [M + H]$^+$. |
| C105 | 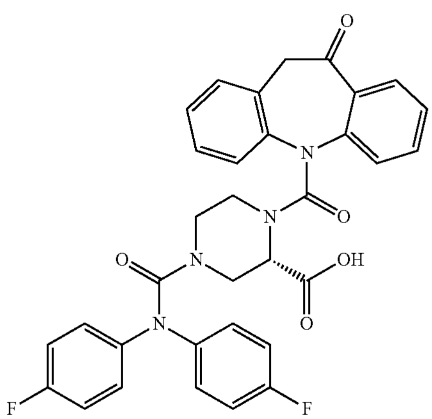 [SMILES: O=C1Cc2ccccc2N(C(=O)N2CCN(C(=O)N(c3ccc(F)cc3)c3ccc(F)cc3)C[C@H]2C(=O)O)c2ccccc21] | (S)-4-(bis(4-fluorinephenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with (4-fluophenyl)carbamyl chloride. | $^1$H NMR (400 MHz, DMSO-d6) δ 13.23 (s, 1H), 7.95 (d, J = 8 Hz, 1H), 7.78 (d, J = 6.4 Hz, 1H), 7.60 (s, 2H), 7.39 (s, 1H), 7.32-7.27 (m, 3H), 7.15-7.11 (m, 4H), 7.02-6.96 (m, 4H), 4.53 (s, 1H), 3.46-3.43 (m, 2H), 2.99-2.78 (m, 2H), 2.67 (m, 2H). MS m/z (ESI): 597.0 [M + H]$^+$. |
| C94 | 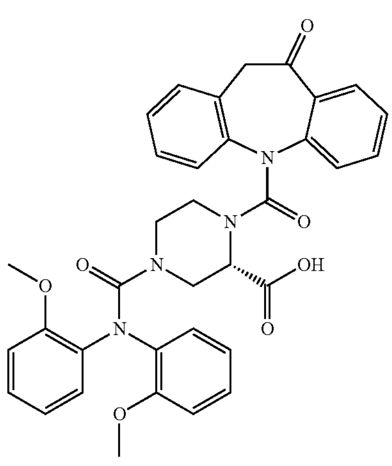 [SMILES: COc1ccccc1N(C(=O)N1CCN(C(=O)N2c3ccccc3CC(=O)c3ccccc32)[C@H](C(=O)O)C1)c1ccccc1OC] | (S)-4-(bis(2-methoxylphenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with bis(2-methoxylphenyl)carbamyl chloride. | $^1$H NMR (400 MHz, DMSO-d6) δ 12.97 (s, 1H), 7.94 (d, J = 8 Hz, 1H), 7.77 (d, J = 6.8 Hz, 1H), 7.61 (s, 2H), 7.40-7.27 (m, 4H), 7.13-7.10 (m, 2H), 7.00-6.98 (m, 2H), 6.83-6.79 (m, 2H), 6.74-6.72 (m, 2H), 4.44 (s, 1H), 4.20-4.01 (m, 2H), 3.96 (d, J = 13.2 Hz, 1H), 3.64 (s, 6H), 3.24-3.16 (m, 2H), 2.96 (d, J = 9.6 Hz, 1H), 2.58 (s, 2H). MS m/z (ESI): 621.0 [M + H]$^+$. |

TABLE 3-continued

| No. | Compound Structure | Compound Name | Starting material or reagent different from that in Example 4 | Characterization data |
|---|---|---|---|---|
| C110 | 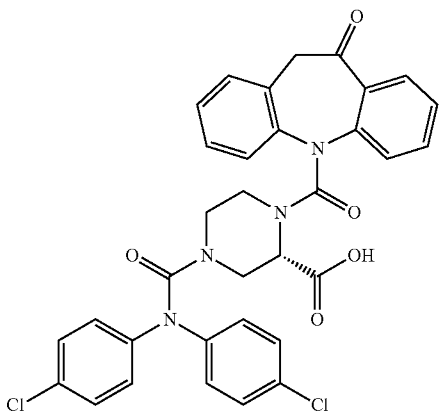 [SMILES: O=C1Cc2ccccc2N(C(=O)N2CCN(C(=O)N(c3ccc(Cl)cc3)c3ccc(Cl)cc3)C[C@H]2C(=O)O)c2ccccc21] | (S)-4-(bis(4-chlorphenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with bis(4-chlorphenyl)carbamyl chloride. | $^1$H NMR (400 MHz, DMSO-d6) δ 13.30 (s, 1H), 7.95 (d, J = 8 Hz, 1H), 7.78 (d, J = 6.8 Hz, 1H), 7.61-7.59 (m, 2H), 7.40-7.27 (m, 8H), 6.95-6.93 (d, J = 8.4 Hz, 2H), 4.56 (s, 1H), 4.28-4.05 (m, 3H), 3.96 (d, J = 13.2 Hz, 1H), 3.45 (d, J = 10 Hz, 1H), 3.32 (d, J = 11.6 Hz, 1H), 2.94 (s, 1H), 2.74 (s, 1H). MS m/z (ESI): 629.0 [M + H]$^+$. |
| C115 | 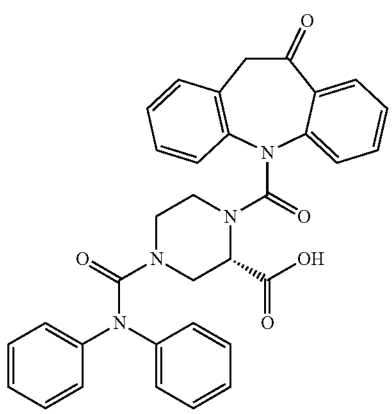 [SMILES: O=C1Cc2ccccc2N(C(=O)N2CCN(C(=O)N(c3ccccc3)c3ccccc3)C[C@H]2C(=O)O)c2ccccc21] | (S)-4-(2,2-diphenylacetyl)-1-(10-oxo-10,11-dihydro-5H-dibenzo[b,f]azepine-5-carbonyl)piperazine-2-carboxylic acid | SM2 in Step 4 of Example 4 was replaced with 2,2-diphenylacetyl chloride. | $^1$H NMR (400 MHz, DMSO-d6) 13.49 (s, 1H), 13.04 (s, 1H), 7.96 (t, J = 6.8 Hz, 1H), 7.78 (s, 1H), 7.64-7.56 (m, 2H), 7.40 (s, 17H), 7.34-7.31 (m, 2H), 7.28-7.19 (m, 7H), 7.17-7.14 (m, 2H), 7.12-7.08 (m, 2H), 5.49-5.39 (m, 1H), 4.66-4.59 (m, 2H), 4.22 (d, J = 13.2 Hz, 1H), 4.04 (s, 1H), 3.69-3.56 (m, 2H), 3.29 (d, J = 11.2 Hz, 1H), 3.00 (d, J = 12.4 Hz, 1H), 2.88 (s, 1H). MS m/z (ESI): 560.0 [M + H]$^+$. |
| C101 | 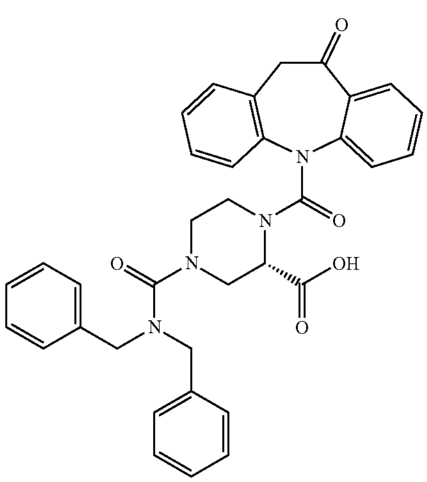 [SMILES: O=C1Cc2ccccc2N(C(=O)N2CCN(C(=O)N(Cc3ccccc3)Cc3ccccc3)C[C@H]2C(=O)O)c2ccccc21] | (S)-4-(dibenzylcarbamoyl)-1-(10-oxo-10,11-dihydro-5H-dibenzo[b,f]azepine-5-carbonyl)piperazine-2-carboxylic acid | SM2 in Step 4 of Example 4 was replaced with dibenxylcarbamyl chloride. | $^1$H NMR (400 MHz, DMSO-d6) δ 13.18 (s, 1H), 7.98 (d, J = 8 Hz, 1H), 7.82 (d, J = 6.8 Hz, 1H), 7.64 (brs, 2H), 7.42-7.25 (m, 10H), 7.11 (d, J = 6.8 Hz, 4H), 4.65 (s, 1H), 4.27 (d, J = 15.2 Hz, 2H), 4.21-4.19 (m, 1H), 4.03 (d, J = 15.2 Hz, 2H), 3.89 (d, J = 12.4 Hz, 1H), 3.51 (d, J = 12.8 Hz, 1H), 3.06-2.92 (m, 2H), 2.33 (s, 1H). MS m/z (ESI): 588.7 [M + H]$^+$. |

TABLE 3-continued

| No. | Compound Structure | Compound Name | Starting material or reagent different from that in Example 4 | Characterization data |
|---|---|---|---|---|
| C102 | 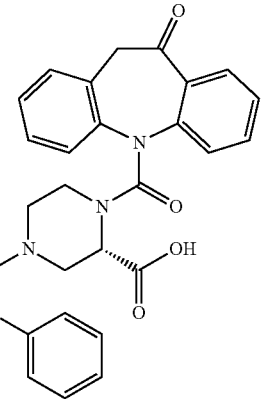 | (S)-4-(benzyl (phenyl)carbamoyl)-1-(10-oxo-10,11-dihydro-5H-dibenzo[b,f]azepine-5-carbonyl)piperazine-2-carboxylic acid | SM2 in Step 4 of Example 5 was replaced with benzyl(phenyl)carbamyl chloride. | $^1$H NMR (400 MHz, DMSO-d6) δ 13.18 (s, 1H), 7.93 (d, J = 7.6 Hz, 1H), 7.76 (d, J = 6.8 Hz, 2H), 7.58 (d, J = 2.8 Hz, 3H), 7.39-7.37 (m, 1H), 7.32-7.16 (m, 9H), 7.04-6.98 (m, 4H), 4.82 (d, J = 15.6 Hz, 1H), 4.70 (d, J = 15.6 Hz, 2H), 4.50 (s, 1H), 4.14 (s, 1H), 3.96 (d, J = 13.2 Hz, 1H), 3.24-3.16 (m, 2H), 2.89-2.86 (m, 1H), 2.57 (m, 1H). MS m/z (ESI): 574.7 [M + H]$^+$. |
| C114 | 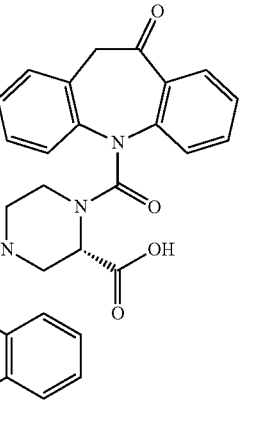 | (S)-4-((2-methoxylphenyl)(phenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with (2-methoxylphenyl)(phenyl)carbamyl chloride. | $^1$H NMR (400 MHz, DMSO-d6) δ 13.11 (s, 1H), 7.94 (d, J = 7.6 Hz, 1H), 7.77 (d, J = 6.8 Hz, 1H), 7.61 (brs, 2H), 7.39 (d, J = 7.6 Hz, 1H), 7.35-7.26 (m, 6H), 7.06-7.00 (m, 2H), 6.89 (d, J = 4.0 Hz, 2H), 6.80 (d, J = 8 Hz, 2H), 4.50 (s, 1H), 4.16 (s, 1H), 4.02 (d, J = 12.6 Hz, 1H), 3.64 (s, 3H), 3.33-3.21 (m, 2H), 3.01-2.93 (m, 1H), 2.79-2.73 (m, 1H). MS m/z (ESI): 590.6 [M + H]$^+$. |
| C108 | 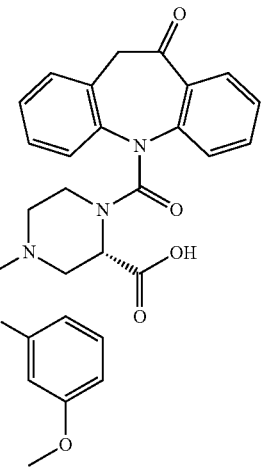 | (S)-4-(bis(3-methoxylphenyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with bis(3-methoxylphenyl)carbamyl chloride. | $^1$H NMR (400 MHz, DMSO-d6) δ 13.19 (s, 1H), 7.95 (d, J = 7.6 Hz, 1H), 7.79 (d, J = 6.8 Hz, 1H), 7.63-7.57 (m, 2H), 7.41-7.18 (m, 6H), 6.72 (d, J = 7.6 Hz, 2H), 6.53-6.43 (m, 4H), 4.55 (s, 1H), 4.18 (s, 1H), 4.05-4.01 (m, 2H), 3.69 (s, 6H), 3.53-3.49 (m, 1H), 3.36-3.33 (m, 1H), 2.98-2.78 (m, 2H), 2.71-2.68 (m, 1H). MS m/z (ESI): 620.7 [M + H]$^+$. |

TABLE 3-continued

| No. | Compound Structure | Compound Name | Starting material or reagent different from that in Example 4 | Characterization data |
| --- | --- | --- | --- | --- |
| C106 | 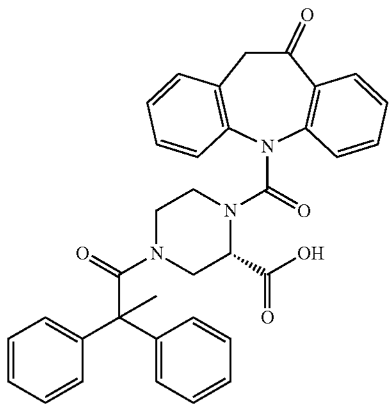 [SMILES: CC(C(=O)N1CCN(C(=O)N2c3ccccc3CC(=O)c3ccccc32)[C@H](C(=O)O)C1)(c1ccccc1)c1ccccc1] | (S)-4-(2,2-diphenylpropionyl)-1-(10-oxo-10,11-dihydro-5H-dibenzo[b,f]azepine-5-carbonyl)piperazine-2-carboxylic acid | SM2 in Step 4 of Example 4 was replaced with 2,2-diphenylpropionyl chloride. | $^1$HNMR (400 MHz, DMSO-d6) δ 13.10 (s, 1H), 7.91 (d, J = 7.6 Hz, 1H), 7.72 (d, J = 5.6 Hz, 1H), 7.60-7.51 (m, 2H), 7.35-7.12 (m, 14H), 4.80 (s, 1H), 4.59 (s, 1H), 4.32 (s, 1H), 4.18-3.86 (m, 3H), 3.09-2.84 (m, 3H), 1.73 (s, 3H). MS m/z (ESI): 573.8 [M + H]$^+$. |
| C78 | 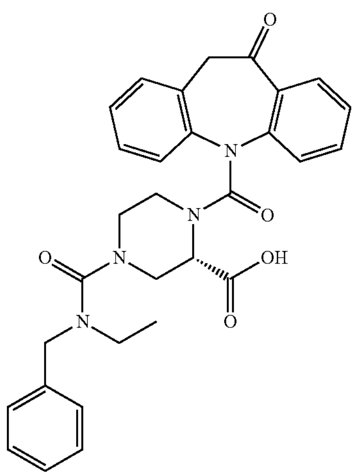 [SMILES: CCN(Cc1ccccc1)C(=O)N1CCN(C(=O)N2c3ccccc3CC(=O)c3ccccc32)[C@H](C(=O)O)C1] | (S)-4-(benzyl(ethyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with benzyl(ethyl)carbamyl chloride. | $^1$H NMR (400 MHz, CDCl$_3$) δ 8.15 (d, J = 8.0 Hz, 1H), 7.83 (d, J= 7.6 Hz, 1H), 7.58 (s, 2H), 7.40-7.28 (m, 6H), 7.21 (d, J = 6.8 Hz, 2H), 4.82 (s, 1H), 4.49 (d, J = 15.2 Hz, 1H), 4.33 (d, J = 15.6 Hz, 1H), 4.15 (brs, 1H), 4.06 (d, J = 12.8 Hz, 1H), 3.81 (brs, 2H), 3.44-3.32 (m, 2H), 3.21-3.07 (m, 4H), 2.74 (s, 1H), 1.08 (t, J = 6.8 Hz, 3H). MS m/z (ESI): 526.8 [M + H]$^+$. |
| C118 | 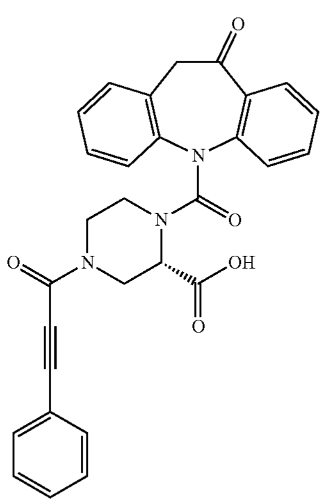 [SMILES: O=C1Cc2ccccc2N(C(=O)N2CCN(C(=O)C#Cc3ccccc3)C[C@H]2C(=O)O)c2ccccc21] | (S)-1-(10-oxo-10,11-dihydro-5H-dibenzo[b,f]azepine-5-carbonyl)-4-(3-phenylpropioloyl)piperazine-2-carboxylic acid | SM2 in Step 4 of Example 4 was replaced with 3-phenylpropioloyl chloride. | $^1$H NMR (400 MHz, CDCl$_3$) δ 8.14 (d, J = 6.8 Hz, 1H), 7.79 (s, 1H), 7.57-7.21 (m, 11H), 4.93-4.87 (m, 1H), 4.15 (brs, 4H), 3.49 (s, 1H), 3.11 (brs, 2H), 2.65 (brs, 1H). MS m/z (ESI):493.7 [M + H]$^+$. |

TABLE 3-continued

| No. | Compound Structure | Compound Name | Starting material or reagent different from that in Example 4 | Characterization data |
|---|---|---|---|---|
| C107 | 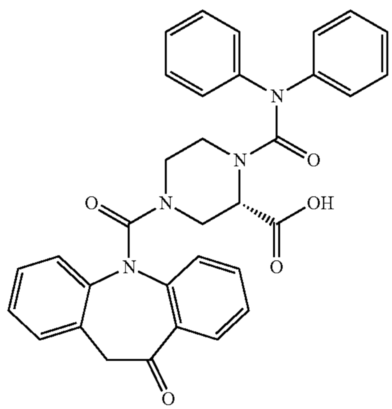 [SMILES: O=C1Cc2ccccc2N(C(=O)N2CCN(C(=O)N(c3ccccc3)c3ccccc3)[C@H](C(=O)O)C2)c2ccccc21] | (S)-1-(diphenylcarbamoyl)-4-(10-oxo-10,11-dihydro-5H-dibenzo[b,f]azepine-5-carbonyl)piperazine-2-carboxylic acid | Step 1 in Example 4 was omitted. C77-2 in Step 2 was replaced with SM2. SM2 in Step 4 was replaced with C77-2. After Step 4, Step 3 was repeated to hydrolyze methoxy, and then the reaction in Step 5 is carried out. | $^1$H NMR (400 MHz, DMSO-d6) δ 13.23 (s, 1H), 7.94 (d, J = 7.6 Hz, 1H), 7.76 (d, J = 6.8 Hz, 1H), 7.58 (t, J = 7.6 Hz, 1H), 7.39-7.37 (m, 1H), 7.35-7.23 (m, 8H), 7.13 (t, J = 7.6 Hz, 2H), 6.98 (d, J = 7.6 Hz, 4H), 4.49 (s, 1H), 4.44-4.36 (m, 1H), 3.98 (d, J = 12.8 Hz, 1H), 3.93-3.85 (m, 1H), 3.49 (s, 1H), 3.36 (d, J = 9.6 Hz, 1H), 2.83-2.70 (m, 3H). MS m/z (ESI): 560.6 [M + H]$^+$. |
| C79 | 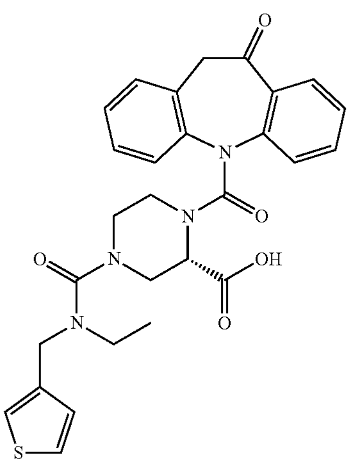 [SMILES: CCN(Cc1ccsc1)C(=O)N1CCN(C(=O)N2c3ccccc3CC(=O)c3ccccc32)[C@H](C(=O)O)C1] | (S)-4-(ethyl(thiophene-3-ylmethyl)carbamoyl)-1-(10-oxo-10,11-dihydro-5H-dibenzo[b,f]azepine-5-carbonyl)piperazine-2-carboxylic acid | SM2 in Step 4 of Example 4 was replaced with | $^1$H NMR (400 MHz, CDCl$_3$) δ 8.15 (d, J = 7.6 Hz, 1H), 7.83 (d, J = 7.0 Hz, 1H), 7.64-7.53 (m, 3H), 7.33 (d, J = 6.6 Hz, 4H), 7.11 (s, 1H), 6.97 (s, 1H), 4.81 (s, 1H), 4.45 (d, J = 15.0 Hz, 1H), 4.32 (d, J = 15.3 Hz, 1H), 4.05 (d, J = 14.4 Hz, 1H), 3.47-3.39 (m, 1H), 3.37-3.27 (m, 1H), 3.26-3.03 (m, 5H), 2.73 (s, 1H), 1.40 (s, 1H), 1.09 (t, J = 6.5 Hz, 3H). MS m/z (ESI): 533.0 [M + H]$^+$. |
| C84 | 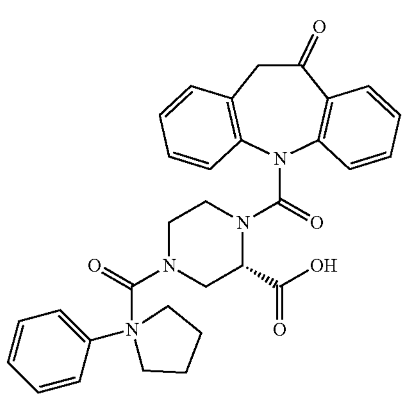 | (S)-1-(10-oxo-10,11-dihydro-5H-dibenzo[b,f]azepine-5-carbonyl)-4-(1-phenylcyclopentyl-1-carbonyl)piperazine-2-caboxylic acid | SM2 in Step 4 of Example 4 was replaced with | $^1$H NMR (400 MHz, CDCl$_3$) δ 8.16-8.07 (m, 2H), 7.82-7.72 (m, 2H), 7.61-7.45 (m, 4H), 7.27-7.21 (m, 2H), 7.20-7.04 (m, 3H), 4.00-3.77 (m, 4H), 3.10-2.80 (m, 4H), 2.39 (s, 2H), 2.11 (s, 1H), 1.87-1.57 (m, 8H). MS m/z (ESI): 5637.9 [M + H]$^+$. |

Example 5: Preparation of (S)-4-(5H-dibenzo[b,f]azepine-5-carbonyl)-N³—(N,N-dimethylsulphamoyl)-N¹,N¹-phenylpiperazine-1,3-dicarboxamide (C33)

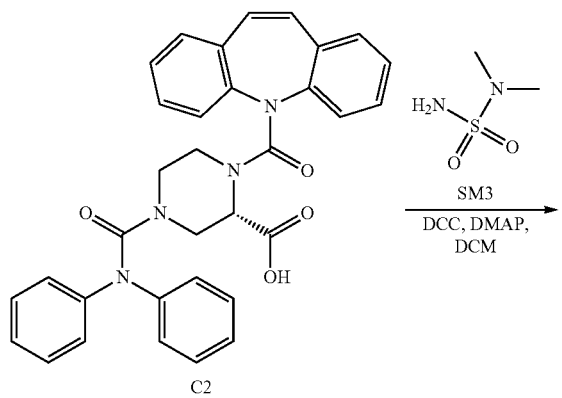

Compound C2 (55 mg, 0.1 mmol) and SM3 (25 mg, 0.2 mmol) were dissolved in dry dichloromethane (20 mL), and cicyclohexylcarbodiimide (31 mg, 0.15 mmol) and 4-dimethylaminopyridine (7 mg, 0.075 mmol) were sequentially added. The reaction solution was reacted at room temperature for 16 hours. LC-MS indicated that the reaction of the starting materials was complete. The reaction was quenched by adding water (30 mL), and extracted with dichloromethane (30 mL×2). The organic phases were combined, washed once with saturated brine (30 mL), then dried over anhydrous sodium sulfate (20 g) for half an horn, filtered, and concentrated. The crude product was separated by preparative plate chromatography (dichloromethane:methanol=30:1) to obtain Compound C33 (30 mg, a white solid, yield: 48%).

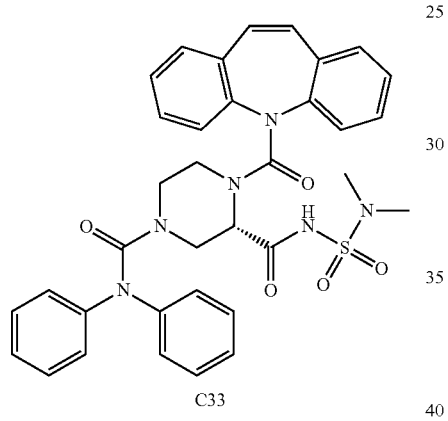

¹H NMR (400 MHz, DMSO-d6) δ 11.62 (s, 1H), 7.57 (m, 2H), 7.40 (m, 4H), 7.28 (m, 6H), 7.12 (t, J=7.1 Hz, 2H), 7.04 (m, 2H), 6.91 (m, 4H), 4.28 (s, 1H), 3.96 (m, 1H), 3.07 (m, 2H), 2.90 (m, 1H), 2.81 (s, 6H), 2.70 (m, 1H), 2.36 (m, 1H).

MS m/z (ESI): 651.1 [M+H]⁺.

The compounds in Table 4 were prepared by methods similar to that described in Example 5.

TABLE 4

| Compound No. | Compound Structure | Compound Name | Starting material or reagent different from that in Example 5 | Characterization data |
|---|---|---|---|---|
| C103 | (structure shown) | (S)-N³-(N,N-dimethylsulphamoyl)-4-(10-oxo-10,11-dihydro-5H-dibenzo[b,f]azepine-5-carbonyl))-N¹,N¹-dipbenylpiperazine-1,3-dicarboxamide | C2 in Example 5 was replaced with C77. | ¹H NMR (400 MHz, DMSO-d6) δ 11.65 (s, 1H), 7.96 (d, J = 7.5 Hz, 1H), 7.77 (s, 1H), 7.60 (s, 2H), 7.44-7.25 (m, 8H), 7.15-7.09 (m, 2H), 6.98-6.87 (m, 4H), 4.53 (s, 1H), 4.18-3.93 (m, 3H), 3.33-3.16 (m, 5H), 2.81 (s, 6H). MS m/z (ESI): 667.0 [M + H]⁺. |

TABLE 4-continued

| No. | Compound Structure | Compound Name | Starting material or reagent different from that in Example 5 | Characterization data |
|---|---|---|---|---|
| C111 | 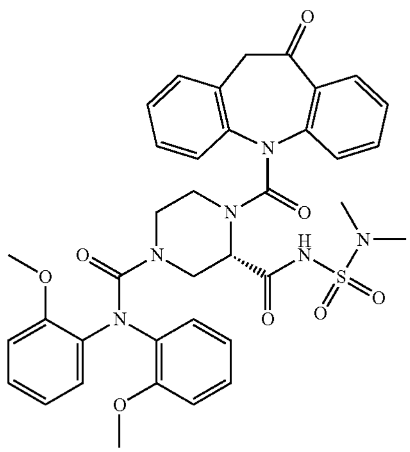 [SMILES: COc1ccccc1N(C(=O)N1CCN(C(=O)N2c3ccccc3CC(=O)c3ccccc32)[C@H](C(=O)NS(=O)(=O)N(C)C)C1)c1ccccc1OC] | (S)-N³-(N,N-dimethylsulphamoyl)-N¹,N¹-bis(2-methoxyphenyl)-4-(10-oxo-10,11-dihydro-5H-dibenzo[b,f]azepine-5-carbonyl)piperazine-1,3-dicarboxamide | C2 in Example 5 was replaced with C94. | ¹H NMR (400 MHz, DMSO-d6) δ 11.62 (s, 1H), 7.96 (d, J = 7.8 Hz, 1H), 7.76 (d, J = 6.5 Hz, 1H), 7.60 (s, 2H), 7.36 (dd, J = 38.2, 15.2 Hz, 5H), 7.13 (t, J = 7.5 Hz, 2H), 7.00 (d, J = 8.1 Hz, 2H), 6.83 (t, J = 7.4 Hz, 2H), 6.74 (d, J = 7.4 Hz, 2H), 4.48 (s, 1H), 3.98-3.77 (m, 5H), 3.63 (s, 6H), 3.14-3.09 (m, 1H), 2.80 (s, 6H), 2.55 (s, 1H). MS m/z (ESI): 727.6 [M + H]⁺. |
| C124 | 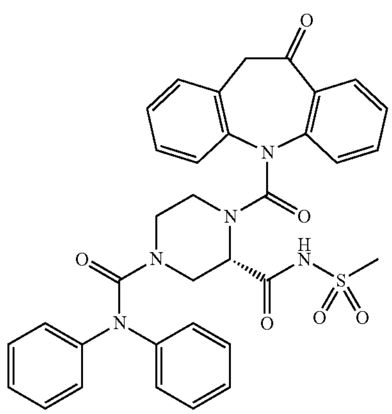 [SMILES: CS(=O)(=O)NC(=O)[C@@H]1CN(C(=O)N(c2ccccc2)c2ccccc2)CCN1C(=O)N1c2ccccc2CC(=O)c2ccccc21] | (S)-N³-(methylsulfuryl)-4-(10-oxo-10,11-dihydro-5H-dibenzo[b,f]azepine-5-carbonyl))-N¹,N¹-diphenylpiperazine-1,3-dicarboxamide | C2 in Example 5 was replaced with C77; and SM3 was replaced with methylsulfonamide. | ¹H NMR (400 MHz, d6-DMSO) δ 12.00 (s, 1H), 7.96 (d, J = 7.9 Hz, 1H), 7.81-7.75 (m, 1H), 7.60 (s, 2H), 7.43-7.38 (m, 1H), 7.37-7.24 (m, 7H), 7.12 (t, J = 7.4 Hz, 2H), 6.91 (d, J = 7.5 Hz, 4H), 4.56 (s, 1H), 4.10-3.62 (m, 8H), 3.19 (s, 3H). MS m/z (ESI): 637.5 [M + H]⁺. |
| C149 | 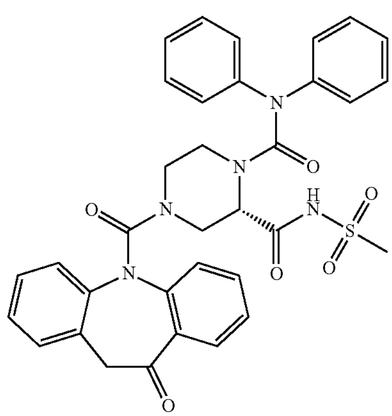 [SMILES: CS(=O)(=O)NC(=O)[C@@H]1CN(C(=O)N2c3ccccc3CC(=O)c3ccccc32)CCN1C(=O)N(c1ccccc1)c1ccccc1] | (S)-N²-(methylsulfuryl)-4-(10-oxo-10,11-dihydro-5H-dibenzo[b,f]azepine-5-carbonyl))-N¹,N¹-diphenylpiperazine-1,2-dicarboxamide | C2 in Example 5 was replaced with C107; and SM3 was replaced with methylsulfonamide. | ¹H NMR (400 MHz, DMSO-d6) δ 12.07 (s, 1H), 7.94 (dd, J = 8.0, 1.6 Hz, 1H), 7.78 (d, J = 8.8 Hz, 1H), 7.60-7.50 (m, 1H), 7.45-7.21 (m, 9H), 7.14 (t, J = 7.2 Hz, 2H), 6.99 (d, J = 7.6 Hz, 4H), 4.52 (s, 1H), 4.07 (d, J = 11.2 Hz, 2H), 3.29-3.06 (m, 7H), 2.88-2.75 (m, 1H), 2.55-2.51 (m, 1H). MS m/z (ESI): 638.1 [M + H]⁺. |

TABLE 4-continued

| No. | Compound Structure | Compound Name | Starting material or reagent different from that in Example 5 | Characterization data |
|---|---|---|---|---|
| C123 | (structure shown) | (S)-N$^3$-hydroxyl-4-(10-oxo-10,11-dihydro-5H-dibenzo[b,f]azepine-5-carbonyl))-N$^1$,N$^1$-diphenylpiperazine-1,3-dicarboxamide | C2 in Example 5 was replaced with C77. The condensation reagent was changed from DCC to HATU, and the solvent was changed to DMF. DMAP was changed to DIEA. | $^1$H NMR (400 MHz, CDCl$_3$) δ 8.12 (s, 1H), 7.77 (s, 2H), 7.57 (s, 2H), 7.31 (s, 5H), 7.16 (s, 2H), 7.03 (s, 3H), 4.67 (s, 1H), 4.51-3.89 (m, 3H), 3.46-3.16 (m, 2H), 3.05-2.70 (m, 2H), 2.51-2.20 (m, 1H). MS m/z (ESI): 575.7 [M + H]$^+$. |

Example 6: Preparation of (S)-1-(10-chloro-5H-dibenzo[b,f]azepine-5-carbonyl)-4-(diphenylcarbamoyl)piperazine-2-carboxylic acid (C51)

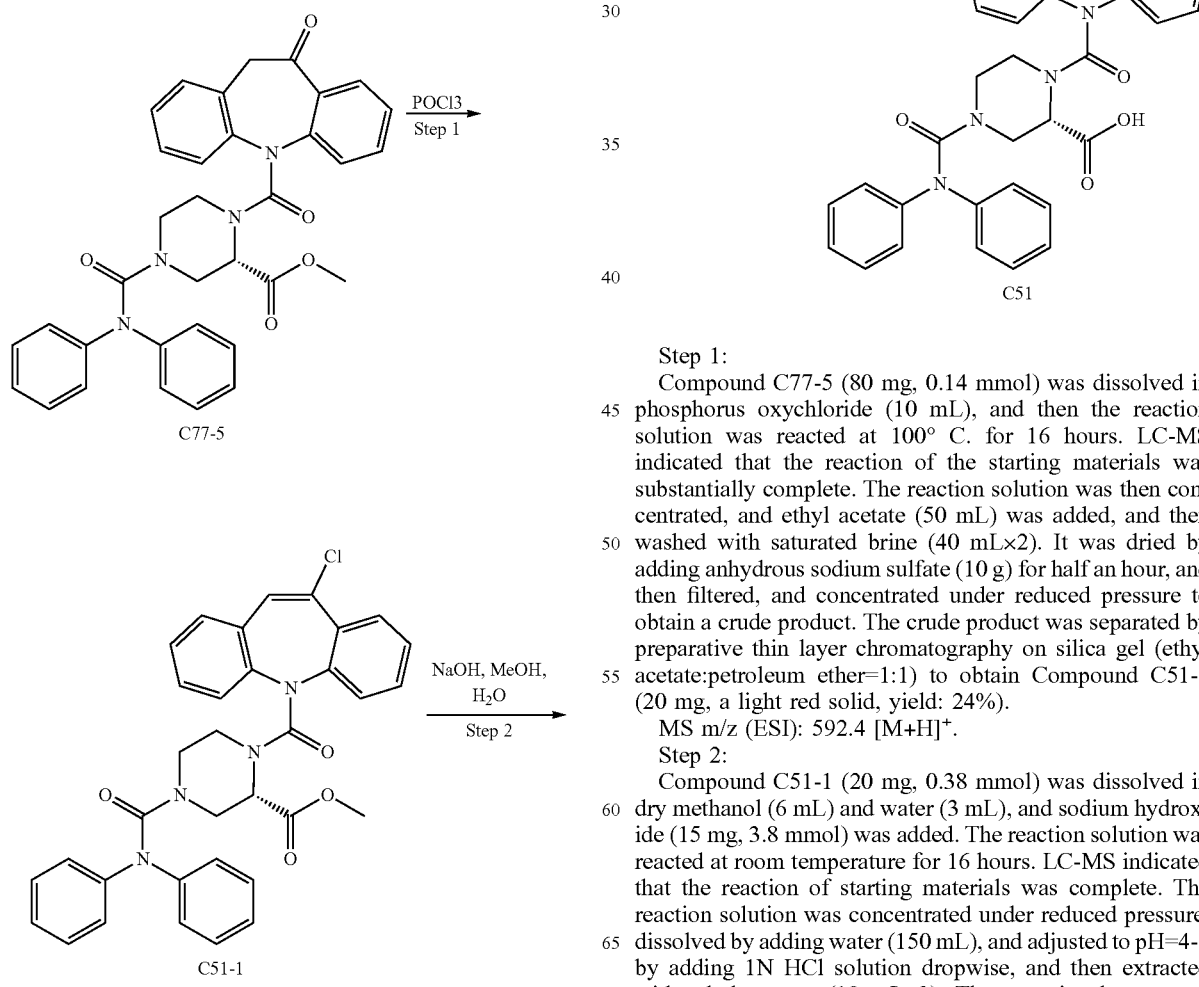

Step 1:
Compound C77-5 (80 mg, 0.14 mmol) was dissolved in phosphorus oxychloride (10 mL), and then the reaction solution was reacted at 100° C. for 16 hours. LC-MS indicated that the reaction of the starting materials was substantially complete. The reaction solution was then concentrated, and ethyl acetate (50 mL) was added, and then washed with saturated brine (40 mL×2). It was dried by adding anhydrous sodium sulfate (10 g) for half an hour, and then filtered, and concentrated under reduced pressure to obtain a crude product. The crude product was separated by preparative thin layer chromatography on silica gel (ethyl acetate:petroleum ether=1:1) to obtain Compound C51-1 (20 mg, a light red solid, yield: 24%).
MS m/z (ESI): 592.4 [M+H]$^+$.

Step 2:
Compound C51-1 (20 mg, 0.38 mmol) was dissolved in dry methanol (6 mL) and water (3 mL), and sodium hydroxide (15 mg, 3.8 mmol) was added. The reaction solution was reacted at room temperature for 16 hours. LC-MS indicated that the reaction of starting materials was complete. The reaction solution was concentrated under reduced pressure, dissolved by adding water (150 mL), and adjusted to pH=4-5 by adding 1N HCl solution dropwise, and then extracted with ethyl acetate (10 mL×3). The organic phases were combined, washed with saturated brine (30 mL×2), and then dried by adding anhydrous sodium sulfate (10 g) for half an hour, filtered, and concentrated under reduced pressure to obtain a crude product. The crude product was separated by preparative high-performance liquid chromatography (acetonitrile:water (0.1% trifluoroacetic acid), gradient: 30%-60%) to obtain Compound C51 (2.5 mg, a white solid, yield: 13%).

$^1$H NMR (400 MHz, DMSO-d6) δ 13.14 (s, 1H), 7.70-7.51 (m, 6H), 7.48-7.38 (m, 2H), 7.31-7.27 (m, 4H), 7.16-7.10 (m, 2H), 6.89 (d, J=7.2 Hz, 4H), 6.53 (s, 1H), 4.21 (d, J=22 Hz, 2H), 4.02-3.93 (m, 2H), 3.02-2.95 (m, 3H).

MS m/z (ESI): 578.7 [M+H]$^+$.

Example 7: Preparation of (S)-4-(diphenylcarbamoyl)-1-(11-oxo-10,11-dihydro-5H-dibenzo[b,e][1,4]diazepine-5-carbonyl)piperazine-2-carboxylic acid (C53)

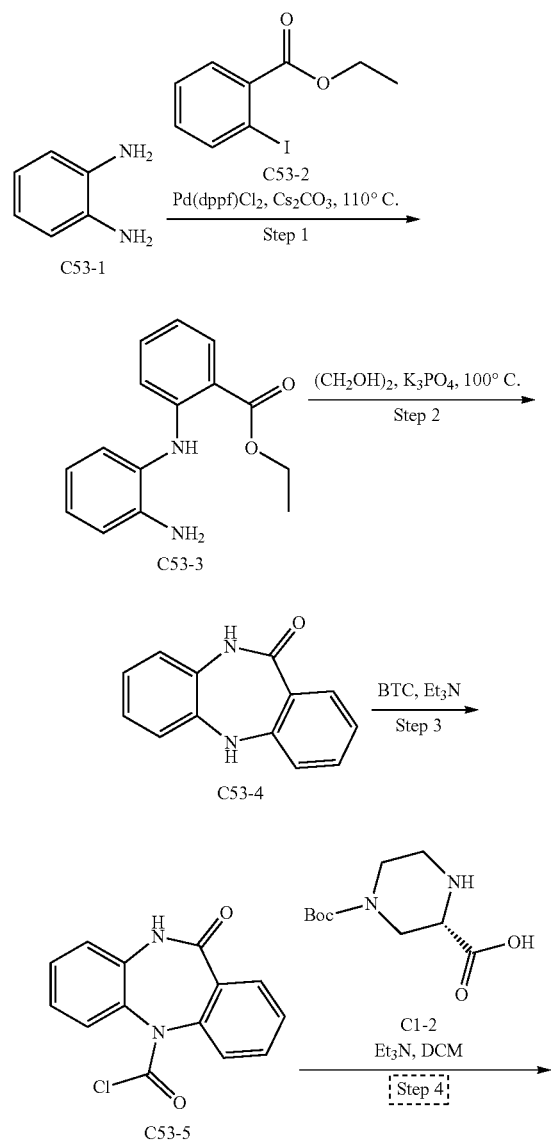

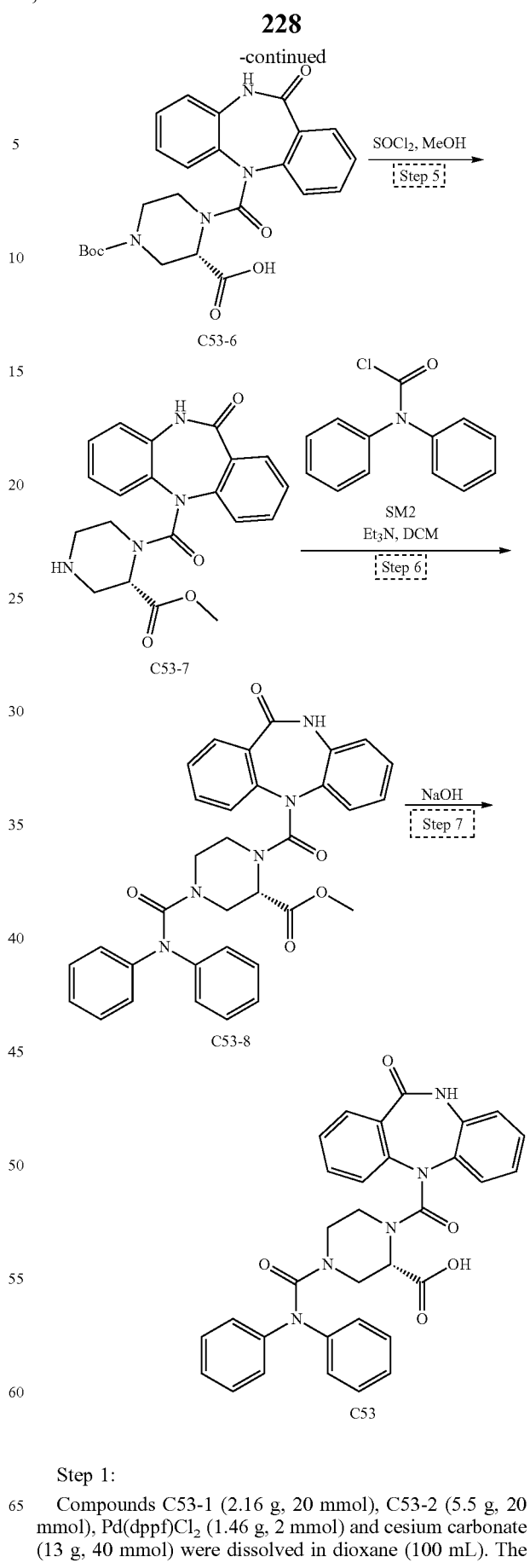

Step 1:

Compounds C53-1 (2.16 g, 20 mmol), C53-2 (5.5 g, 20 mmol), Pd(dppf)Cl$_2$ (1.46 g, 2 mmol) and cesium carbonate (13 g, 40 mmol) were dissolved in dioxane (100 mL). The reaction was heated at 100° C. for 16 hours. LC-MS indicated that the reaction of the starting materials was substantially complete. It was then cooled to room temperature, filtered, and the filtrate was concentrated under reduced pressure to obtain a crude product. The crude product was separated by column chromatography on silica gel (ethyl acetate:petroleum ether=1:8) to obtain Compound C53-3 (2.5 g, a yellow solid, yield: 49%).

$^1$HNMR (400 MHz, CDCl$_3$) δ 9.02 (s, 1H), 7.97 (d, J=8.0 Hz, 1H), 7.26 (t, J=7.2 Hz, 1H), 7.16 (d, J=8.0 Hz, 1H), 7.10 (t, J=7.6 Hz, 1H), 6.91 (d, J=7.2 Hz, 1H), 6.84 (t, J=7.6 Hz, 1H), 6.70-6.62 (m, 2H), 4.34 (q, J=7.2 Hz, 2H), 1.40 (t, J=7.2 Hz, 3H).

MS m/z (ESI): 257.0 [M+H]$^+$.

Step 2:

Compound C53-3 (2.5 g, 9.8 mmol) and potassium phosphate (3.1 g, 14.6 mmol) were dissolved in ethylene glycol (50 mL), and then reacted at 100° C. for 16 horns. After cooling and adding water (100 mL), ethyl acetate (50 mL×3) was added for extraction, followed by washing with saturated brine (80 mL×2), and drying over anhydrous sodium sulfate (20 g) for half an horn. After filtration and concentration, a crude compound C53-4 was obtained (2 g, a black solid, yield: 100%).

$^1$HNMR (400 MHz, DMSO-d6) δ 9.83 (s, 1H), 7.84 (s, 1H), 7.68 (dd, J=8.0 Hz, 1.5 Hz, 1H), 7.35-7.31 (m, 1H), 7.01-6.87 (m, 6H).

MS m/z (ESI): 211.0 [M+H]$^+$.

Step 3:

Compound C53-4 (1.9 g, 9 mmol) and triethylamine (1.8 g, 18 mmol) were dissolved in 1,2-dichloroethane (50 mL), and triphosgene (2.9 g, 10 mmol) was added in portions at 0° C. The reaction solution was reacted at room temperature for 16 hours. LC-MS indicated that the reaction of the starting materials was substantially complete. The reaction solution was then washed with saturated brine (50 mL×2), dried by adding anhydrous sodium sulfate (20 g) for half an hour, then filtered, and concentrated under reduced pressure to obtain a crude Compound C53-5 (1.5 g, a black solid, yield: 61%).

MS m/z (ESI): 272.8 [M+H]$^+$.

Step 4:

Compound C1-2 (127 mg, 0.55 mmol) was dissolved in dry dichloromethane (20 mL). After the temperature was reduced to 0° C.-5° C., triethylamine (112 mg, 1.1 mmol) and C53-5 (150 mg, 0.55 mmol) were sequentially added. The reaction solution was reacted at room temperature for 16 hours. LC-MS indicated that the reaction of the starting materials was complete. The reaction was quenched by adding water (30 mL), and extracted with dichloromethane (30 mL×2). The organic phases were combined, washed twice with saturated brine (30 mL), then dried over anhydrous sodium sulfate (10 g) for half an hour, filtered, and concentrated to obtain Compound C53-6 (150 mg, a light yellow solid, yield: 58%).

MS m/z (ESI): 489.0 [M+Na]$^+$.

Step 5:

Compound C53-6 (150 mg, 0.32 mmol) was dissolved in dry methanol (10 mL). After the temperature was reduced to 0° C.-5° C., SOCl$_2$ (0.5 mL) was added dropwise. The reaction solution was reacted at 50° C. for 16 hours. LC-MS indicated that the reaction of the starting materials was complete. The reaction solution was concentrated under reduced pressure, followed by addition of saturated sodium bicarbonate aqueous solution (10 mL). It was then extracted with ethyl acetate (20 mL×3), washed with saturated brine (30 mL×2), and then dried over anhydrous sodium sulfate (10 g) for half an hour. After that, it was filtered, and concentrated. The crude product was separated by column chromatography(dichloromethane:methanol=20:1) to obtain Compound C53-7 (50 mg, a light yellow solid, yield: 41%).

MS m/z (ESI): 381.1[M+H]$^+$.

Step 6:

Compound C53-7 (50 mg, 0.13 mmol) was dissolved in dry dichloromethane (10 mL). After the temperature was reduced to 0° C.-5° C., triethylamine (27 mg, 0.26 mmol) and SM2 (30 mg, 0.13 mmol) were sequentially added. The reaction solution was reacted at 35° C. for 16 hours. LC-MS indicated that the reaction of the starting materials was complete. The reaction was quenched by adding water (10 mL), and extracted with dichloromethane (20 mL×2). The organic phases were combined, washed twice with saturated brine (30 mL), then dried over anhydrous sodium sulfate (10 g) for half an hour, filtered, and concentrated. The crude product was separated by column chromatography(ethyl acetate:petroleum ether=1:1) to obtain a compound C53-8 (60 mg, a light yellow solid, yield: 79%).

MS m/z (ESI): 576.0 [M+H]$^+$.

Step 7:

Compound C53-8 (60 mg, 0.1 mmol) was dissolved in dry methanol (4 mL) and water (2 mL), and sodium hydroxide (40 mg, 1 mmol) was added. The reaction solution was reacted at 30° C. for 16 hours. LC-MS indicated that the reaction of starting materials was complete. The reaction solution was concentrated under reduced pressure, dissolved with water (10 mL), followed by adding 1N HCl solution dropwise to pH=4~5 until a white precipitate occurred. The white solid was filtered, washed with water (10 mL), and then dried in vacuo to obtain Compound C53 (25 mg, a white solid, yield: 42%).

$^1$HNMR (400 MHz, DMSO-d$_6$) δ 8.32 (s, 1H), 7.83 (d, J=7.6 Hz, 1H), 7.37-7.24 (m, 8H), 7.14 (t, J=7.2 Hz, 3H), 7.04-6.97 (m, 5H), 6.69 (d, J=7.2 Hz, 1H), 4.63 (s, 1H), 4.21 (d, J=13.2 Hz, 1H), 3.71-3.63 (m, 2H), 2.91-2.80 (m, 3H).

MS m/z (ESI): 561.8[M+H]$^+$.

Example 8: Preparation of (S)-4-(diphenylaminomethyl)-1-(10-methyl-11-oxo-10,11-dihydro-5H-dibenzo[b,e][1,4]diazepine-5-carbonyl)piperazine-2-carboxylic acid (C96)

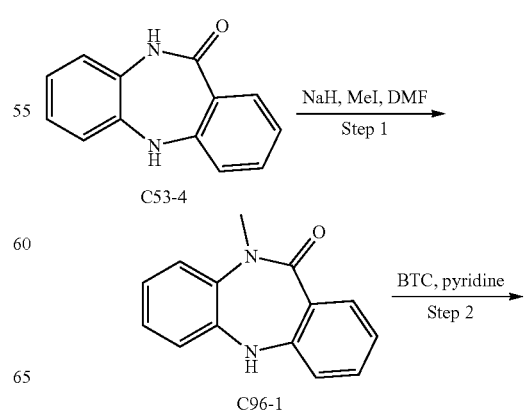

-continued

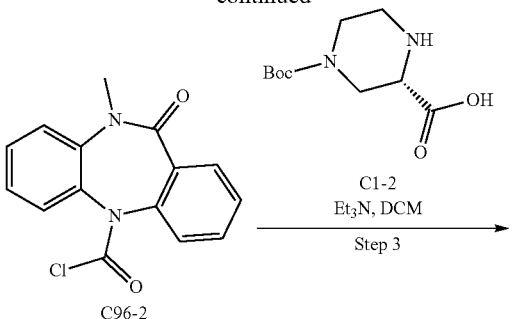

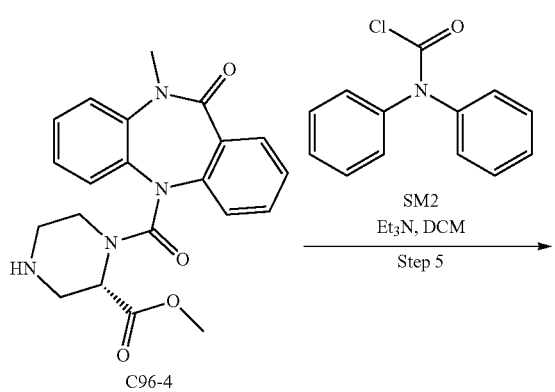

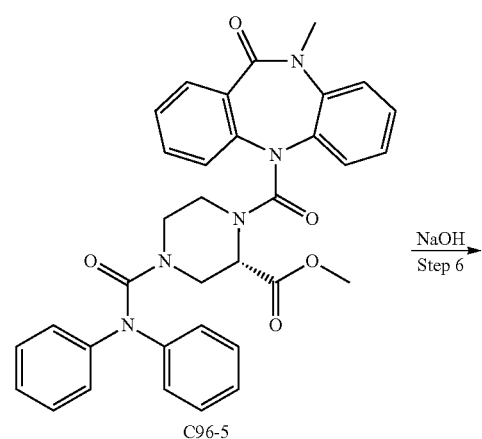

-continued

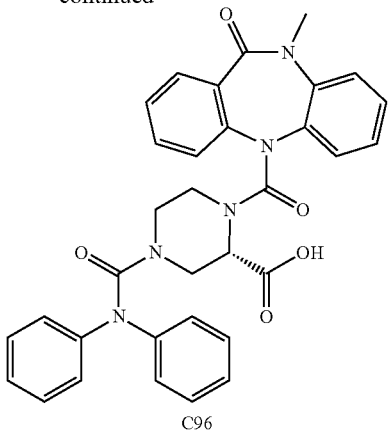

Step 1:
Compound C53-4 (100 mg, 0.48 mmol) was dissolved in dry DMF (10 mL). After the temperature was reduced to 0° C., NaH (19 mg, 0.48 mmol) was added, and then stirred for 0.5 h. Iodomethane (68 mg, 0.48 mmol) was added to the reaction solution and reacted at room temperature for 1 hour. LC-MS indicated that the reaction of the starting materials was complete. The reaction was quenched by adding ice water (10 mL), and extracted with ethyl acetate (10 mL×3). The organic phases were combined, washed twice with saturated brine (20 mL), then dried over anhydrous sodium sulfate (5 g) for half an hour, filtered, and concentrated. The resulting crude product was separated by column chromatography (ethyl acetate:petroleum ether=1:1) to obtain Compound C96-1 (80 mg, a light yellow solid, yield: 74.7%).
$^1$HNMR (400 MHz, CDCl$_3$) δ 7.90 (s, 1H), 7.64 (d, J=7.6 Hz, 1H), 7.33 (t, J=7.2 Hz, 1H), 7.29-7.27 (m, 1H), 7.14-7.05 (m, 4H), 6.94 (t, J=7.6 Hz, 1H), 3.37 (s, 3H).
MS m/z (ESI): 225.0 [M+H]$^+$.

Step 2:
Compound C96-1 (80 mg, 0.36 mmol) and pyridine (1.8 g, 18 mmol) were dissolved in 1,2-dichloroethane (10 mL), and triphosgene (106 mg, 0.36 mmol) was added in portions at 0° C. The reaction solution was reacted at room temperature for 16 hours. LC-MS indicated that the reaction of the starting materials was substantially complete. DCM (20 mL) was added. The reaction solution was then washed with saturated brine (20 mL×2), and dried by adding anhydrous sodium sulfate (10 g) for half an hour, filtered, and concentrated under reduced pressure to obtain a crude Compound C96-2 (100 mg, a light red solid, yield: 97%).
MS m/z (ESI): 287.0 [M+H]$^+$.

Step 3:
Compound C1-2 (80 mg, 0.35 mmol) was dissolved in anhydrous dichloromethane (20 mL). After the temperature was reduced to 0° C.-5° C., triethylamine (106 mg, 1.05 mmol) and C96-2 (100 mg, 0.35 mmol) were sequentially added. The reaction solution was reacted at room temperature for 16 horns. LC-MS indicated that the reaction of the starting materials was complete. The reaction was quenched by adding water (30 mL), and extracted with dichloromethane (30 mL×3). The organic phases were combined, washed with saturated brine (30 mL×3), then dried over anhydrous sodium sulfate (10 g) for half an horn, filtered, and concentrated to obtain Compound C96-3 (140 mg, a light yellow solid, yield: 83%).
MS m/z (ESI): 425.0 [M-56+H]$^+$.

Step 4:

Compound C96-3 (140 mg, 0.29 mmol) was dissolved in anhydrous methanol (5 mL). After the temperature was reduced to 0° C.-5° C., SOCl$_2$ (0.5 mL) was added dropwise. The reaction solution was reacted at 50° C. for 16 horns. LC-MS indicated that the reaction of the starting materials was complete. The reaction solution was concentrated under reduced pressure, followed by adding saturated sodium bicarbonate aqueous solution (10 mL). It was then extracted with ethyl acetate (20 mL×3), washed with saturated brine (30 mL×2), and then dried over anhydrous sodium sulfate (10 g) for half an hour. After that, it was filtered, and concentrated. The crude product was separated by preparative plate chromatography (dichloromethane:methanol=20:1) to obtain Compound C96-4 (60 mg, a light yellow solid, yield: 52%).

MS m/z (ESI): 395.0 [M+H]$^+$.

Step 5:

Compound C96-4 (60 mg, 0.15 mmol) was dissolved in dry dichloromethane (10 mL). After the temperature was reduced to 0° C.-5° C., triethylamine (46 mg, 0.26 mmol) and SM2 (35 mg, 0.15 mmol) were sequentially added. The reaction solution was reacted at 35° C. for 16 horns. LC-MS indicated that the reaction of the starting materials was complete. The reaction was quenched by adding water (10 mL), and extracted with dichloromethane (20 mL×2). The organic phases were combined, washed twice with saturated brine (30 mL), then dried over anhydrous sodium sulfate (10 g) for half an hour, filtered, and concentrated. The resulting crude product was separated by preparative thin layer chromatography on silica gel (ethyl acetate:petroleum ether=1:1) to obtain Compound C96-5 (50 mg, a light yellow solid, yield: 55%).

MS m/z (ESI): 589.0 [M+H]$^+$.

Step 6:

Compound C96-5 (50 mg, 0.085 mmol) was dissolved in dry methanol (5 mL) and water (2 mL), and sodium hydroxide (40 mg, 1 mmol) was added. The reaction solution was reacted at room temperature for 16 hours. LC-MS indicated that the reaction of starting materials was complete. The reaction solution was concentrated under reduced pressure, dissolved with water (10 mL), followed by adding 1N HCl solution dropwise to pH=4-5 until a white precipitate occurred. The white solid was then filtered, washed with water (10 mL), and then dried in vacuo to obtain Compound C96 (35 mg, a white solid, yield: 71%).

$^1$HNMR (400 MHz, DMSO-d$_6$) δ 13.26 (s, 1H), 7.67-7.62 (m, 2H), 7.58-7.46 (m, 3H), 7.33-7.28 (m, 6H), 7.24-7.20 (m, 2H), 7.13 (t, J=7.2 Hz, 2H), 6.90 (d, J=7.6 Hz, 4H), 4.29 (d, J=26.4 Hz, 1H), 4.00 (d, J=13.2 Hz, 1H), 3.47 (s, 3H), 3.43 (s, 1H), 3.12-3.05 (m, 1H), 2.87-2.77 (m, 2H), 2.63-2.60 (m, 1H).

MS m/z (ESI): 576.0 [M+H]$^+$.

The compounds in Table 5 were prepared by methods similar to that described in Example 8.

TABLE 5

| No. | Compound Structure | Compound Name | Starting material or reagent different from that in Example 8 | |
|---|---|---|---|---|
| C97 | 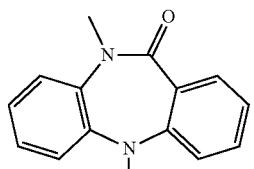 | (S)-4-(bis(2-methoxyphenyl)carbamoyl)-1-(10-methyl-11-oxo-10,11-dihydro-5H-dibenzo[b,e][1,4]diazepine-5-carbonyl)piperazine-2-carboxylic acid | SM2 in Step 5 of Example 8 was replaced with bis(2-methoxylphenyl)carbamyl chloride. | $^1$H NMR (400 MHz, DMSO-d6) δ 12.92 (s, 1H), 7.66-7.45 (m, 6H), 7.36-7.29 (m, 2H), 7.24-7.20 (m, 1H), 7.12 (t, J = 7.6 Hz, 2H), 6.99 (d, J = 8.0 Hz, 2H), 6.81 (t, J = 7.6 Hz, 2H), 6.73 (d, J = 7.6 Hz, 2H), 4.17 (d, J = 39.2 Hz, 1H), 3.93 (d, J = 11.2 Hz, 1H), 3.64 (s, 6H), 3.46 (s, 3H), 3.25-3.22 (m, 1H), 3.00-2.75 (m, 3H), 2.64-2.61 (m. 1H). MS m/z (ESI): 636.0 [M + H]$^+$. |
| C98 | 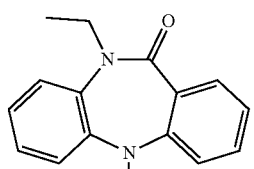 | (S)-4-(diphenylcarbamoyl)-1-(10-ethyl-11-oxo-10,11-dihydro-5H-dibenzo[b,e][1,4]diazepine-5-carbonyl)piperazine-2-carboxylic acid | Iodomethane in Step 1 of Example 8 was replaced with bromoethane. | $^1$H NMR (400 MHz, DMSO-d6) δ 13.24 (s, 1H), 7.62-7.47 (m, 4H), 7.31-7.21 (m, 5H), 7.29 (s, 1H), 7.13 (t, J = 7.2 Hz, 2H), 6.91 (d, J = 7.6 Hz, 4H), 4.38-4.26 (m, 2H), 4.02 (d, J = 11.6 Hz, 1H), 3.89-3.79 (m, 1H), 3.45-3.43 (m, 1H), 3.11 (d, J = 12.4 Hz, 1H), 2.79-2.75 (m, 2H), 2.63-2.60 (m, 1H). MS m/z (ESI): 590.0 [M + H]$^+$. |

TABLE 5-continued

| No. | Compound Structure | Compound Name | Starting material or reagent different from that in Example 8 | |
|---|---|---|---|---|
| C99 | 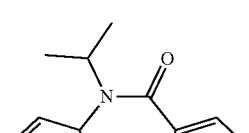 | (S)-4-(diphenylcarbamoyl)-1-(10-isopropyl-11-oxo-10,11-dihydro-5H-dibenzo[b,e][1,4]diazepine-5-carbonyl)piperazine-2-carboxylic acid | Iodomethane in Step 1 of Example 8 was replaced with iodo-isopropane. | $^1$H NMR (400 MHz, DMSO-d6) δ 13.31 (s, 1H), 7.65-7.43 (m, 5H), 7.31-7.21 (m, 6H), 7.14-7.11 (m, 2H), 6.92 (d, J = 8.0 Hz, 4H), 4.45-4.38 (m, 2H), 4.06-3.98 (m, 2H), 3.52 (d, J = 12.0 Hz, 1H), 3.21-3.09 (m, 2H), 2.59 (s, 1H), 1.49 (d, J = 6.4 Hz, 3H), 1.38-1.31 (m, 3H). MS m/z (ESI): 604.0 [M + H]$^+$. |

Example 9: Preparation of (S)-4-(5H-dibenzo[b,f]azepine-5-carbonyl)-N,N-diphenyl-3-(1H-tetrazol-5-yl)piperazine-1-carboxamide (C31)

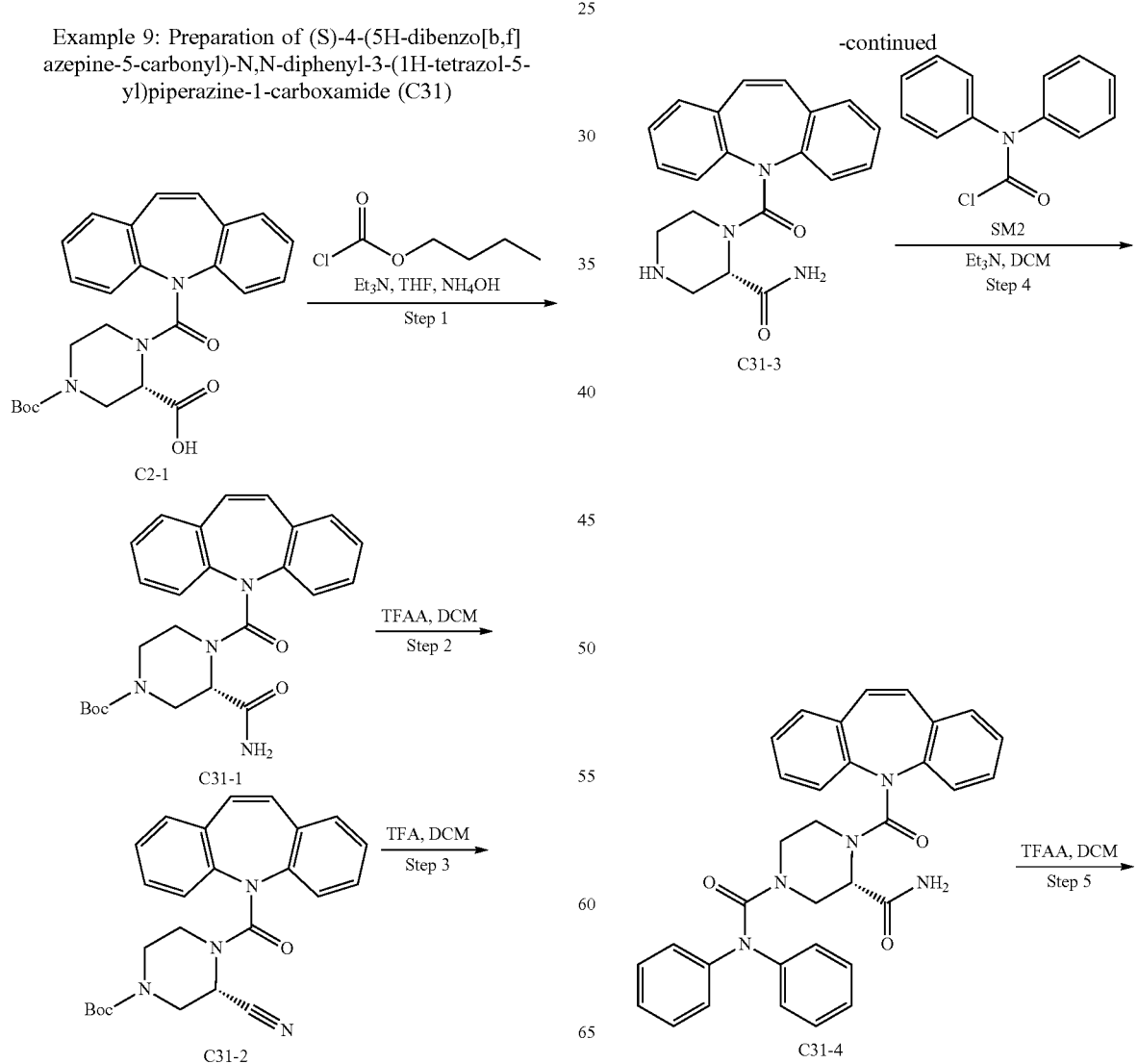

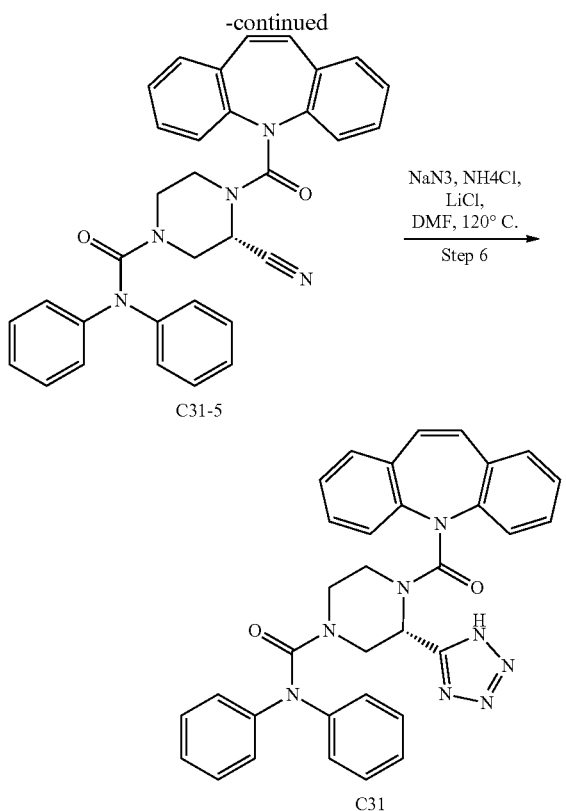

Step 1:

Compound C2-1 (550 mg, 1.22 mmol) and triethylamine (247 mg, 2.44 mmol) were dissolved in tetrahydrofuran (20 mL), and butyl chloroformate (183 mg, 1.34 mmol) was added at 0° C., and the reaction solution was reacted at 0° C. for 0.5 h. To the reaction solution, ammonia water (1 mL) was added, and stirred at room temperature for 16 horns. LC-MS indicated that the reaction of the starting materials was substantially complete. After adding ethyl acetate (30 mL), the reaction solution, was washed with saturated brine (30 mL×3), dried by adding anhydrous sodium sulfate (20 g) for half an hour, and then filtered, and concentrated under reduced pressure to obtain a crude product. The crude product was separated by column chromatography on silica gel (dichloromethane:methanol=20:1) to obtain Compound C31-1 (500 mg, a yellow oily matter, yield: 91%).

MS m/z (ESI): 448.7 [M+H]$^+$.

Step 2:

Compound C31-1 (450 mg, 1 mmol) and triethylamine (202 mg, 2 mmol) were dissolved in dry dichloromethane (20 mL). After the temperature was reduced to 0° C.-5° C., trifluoroacetic anhydride (231 mg, 1.1 mmol) was added slowly. The reaction solution was reacted at room temperature for 16 hours. LC-MS indicated that the reaction of the starting materials was complete. The reaction was quenched by adding water (20 mL), and extracted with dichloromethane (20 mL×2). The organic phases were combined, washed with saturated brine (30 mL) for three times, dried over anhydrous sodium sulfate (10 g) for half an horn, then filtered, and concentrated under reduced pressure to obtain a crude product. The crude product was separated by column chromatography (ethyl acetate:petroleum ether=1:2) to obtain Compound C31-2 (400 mg, a yellow solid, yield: 92%).

$^1$H NMR (400 MHz, CDCl$_3$) δ 7.49 (brs, 2H), 7.43 (brs, 2H), 7.36-7.26 (m, 4H), 6.98 (s, 2H), 4.89 (s, 1H), 4.21 (m, 1H), 3.86-3.78 (m, 1H), 3.15 (d, J=13.2 Hz, 1H), 2.97 (m, 1H), 2.78 (m, 1H), 2.33 (m, 1H), 1.43 (s, 9H).

MS m/z (ESI): 430.7 [M+H]$^+$.

Step 3:

Compound C31-2 (300 mg, 0.7 mmol) was dissolved in dry dichloromethane (4 mL), trifluoroacetic acid (1 mL) was added slowly at room temperature, and the reaction solution was reacted at room temperature for 16 hours. LC-MS indicated that the reaction of the starting materials was complete. The reaction solution was concentrated to dryness, followed by adding saturated sodium bicarbonate aqueous solution (10 mL) and extraction with ethyl acetate (20 mL×3). The organic phases were combined, washed with saturated brine (30 mL×2), and then dried over anhydrous sodium sulfate (10 g) for half an hour, filtered and concentrated under reduced pressure to obtain a crude product. The crude product was separated by column chromatography (dichloromethane:methanol=20:1) to obtain Compound C31-3 (240 mg, a light yellow solid, yield: 99%).

MS m/z (ESI): 348.8 [M+H]$^+$.

Step 4:

Compound C31-3 (240 mg, 0.69 mmol) and triethylamine (139 mg, 1.38 mmol) were dissolved in dichloromethane (20 mL), and SM2 (159 mg, 0.69 mmol) was added at room temperature, and the reaction solution was reacted at 30° C. for 16 h. LC-MS indicated that the reaction of the starting materials was substantially complete. To the reaction solution, dichloromethane (20 mL) was added and then washed with saturated brine (20 mL×3). The organic phases were dried by adding anhydrous sodium sulfate (10 g) for 30 minutes, and then filtered and concentrated under reduced pressure to obtain a crude product. The crude product was separated by column chromatography on silica gel (dichloromethane:ethyl acetate=2:1) to obtain Compound C31-4 (200 mg, a yellow oily matter, yield: 53%).

MS m/z (ESI): 544.0 [M+H]$^+$.

Step 5:

Compound C31-4 (180 mg, 0.33 mmol) and triethylamine (100 mg, 1 mmol) were dissolved in anhydrous dichloromethane (20 mL). After the temperature was reduced to 0° C.-5° C., trifluoroacetic anhydride (77 mg, 0.36 mmol) was added slowly. The reaction solution was reacted at room temperature for 16 horns. LC-MS indicated that the reaction of the starting materials was complete. The reaction was quenched by adding water (100 mL), and extracted with dichloromethane (20 mL×2). The organic phases were combined, washed with saturated brine (20 mL) for three times, then dried over anhydrous sodium sulfate (10 g) for half an horn, filtered, and concentrated under reduced pressure to obtain a crude product. The crude product was separated by column chromatography (ethyl acetate:dichloromethane=1:3) to obtain Compound C31-5 (160 mg, a yellow solid, yield: 91%).

MS m/z (ESI): 525.8 [M+H]$^+$.

Step 6:

Compound C31-5 (100 mg, 0.19 mmol), sodium azide (15 mg, 0.28 mmol), lithium chloride (8 mg, 0.19 mmol) and ammonium chloride (18 mg, 0.28 mmol) were dissolved in dry DMF (3 mL). The reaction solution was reacted at 120° C. for 16 hours. LC-MS indicated that the reaction of starting materials was complete. The reaction was quenched by adding water (10 mL), and extracted with ethyl acetate (20 mL×3). The organic phases were combined, washed with saturated brine (30 mL) for three times, then dried over anhydrous sodium sulfate (10 g) for half an hour, filtered, and concentrated under reduced pressure to obtain a crude product. The crude product was purified by high-performance liquid chromatography (acetonitrile-water (0.1% trifluoroacetic acid), gradient: 40%-70%) to obtain Compound C31 (45 mg, a white solid, yield: 42%).

¹H NMR (400 MHz, DMSO-$d_6$) δ 7.67 (brs, 1H), 7.49 (brs, 1H), 7.41-7.35 (m, 4H), 7.30-7.16 (m, 6H), 7.11-7.01 (m, 4H), 6.71 (d, J=7.6 Hz, 4H), 5.25 (s, 1H), 4.10 (d, J=12.8 Hz, 1H), 3.16-3.05 (m, 2H), 2.93 (d, J=12.4 Hz, 1H), 2.65-2.62 (m, 1H), 2.36 (s, 1H).

MS m/z (ESI): 568.8 [M+H]⁺.

Example 10: Preparation of (S)-4-(10-oxo-10,11-dihydro-5H-dibenzo[b,f]azepine-5-carbonyl)-N,N-diphenyl-3-(1H-tetrazol-5-yl)piperazine-1-carboxamide (C104)

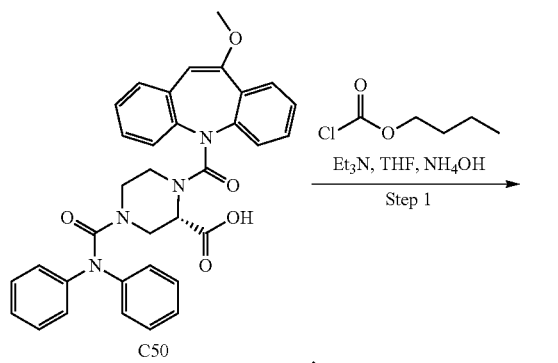

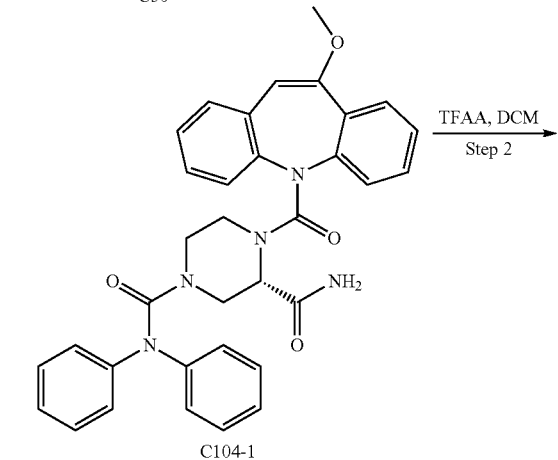

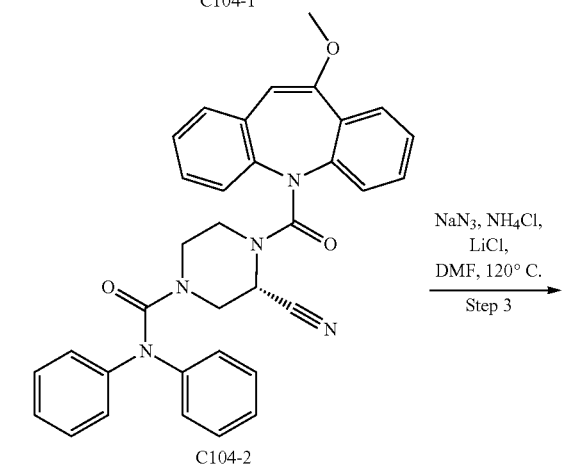

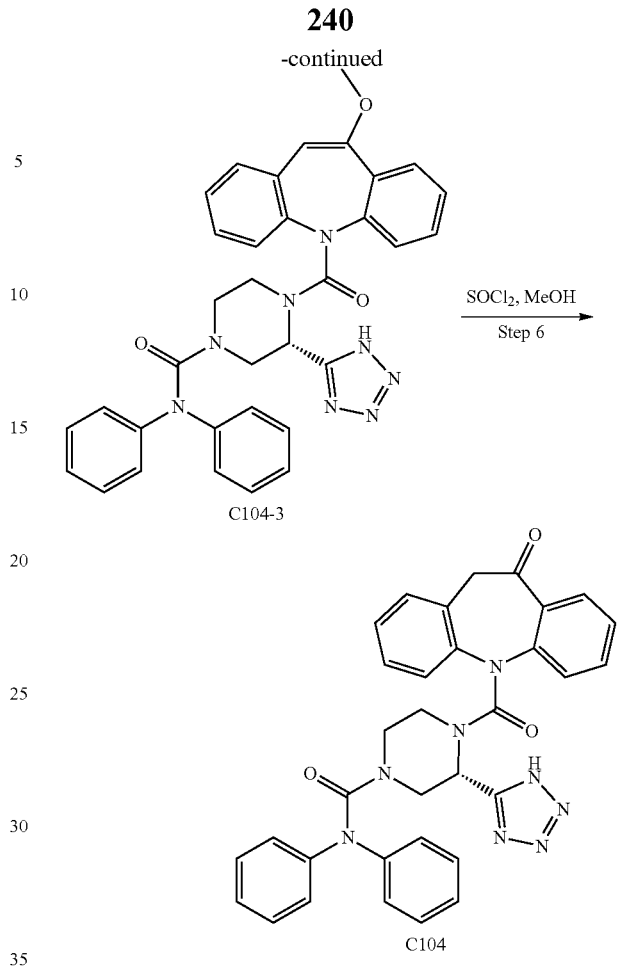

Step 1:

Compound C50 (160 mg, 0.28 mmol) and triethylamine (56 mg, 0.56 mmol) were dissolved in tetrahydrofuran (10 mL), and butyl chloroformate (45 mg, 0.33 mmol) was added at 0° C., and the reaction solution was reacted at 0° C. for half an horn. To the reaction solution, ammonia water (1 mL) was added, and stirred at room temperature for 16 horns. LC-MS indicated that the reaction of the starting materials was substantially complete. After adding ethyl acetate (40 mL), the reaction solution was washed with saturated brine (30 mL×3), and then dried by adding anhydrous sodium sulfate (20 g) for half an horn. After that, it was filtered, and concentrated under reduced pressure to obtain a crude Compound C104-1 (150 mg, a light yellow solid, yield: 94%).

MS m/z (ESI): 574.1[M+H]⁺.

Step 2:

Compound C104-1 (150 mg, 0.26 mmol) and triethylamine (79 mg, 0.78 mmol) were dissolved in anhydrous dichloromethane (20 mL). After the temperature was reduced to 0° C.-5° C., trifluoroacetic anhydride (231 mg, 1.1 mmol) was added slowly. The reaction solution was reacted at room temperature for 16 horns. LC-MS indicated that the reaction of the starting materials was complete. The reaction was quenched by adding water (20 mL), and extracted with dichloromethane (20 mL×2). The organic phases were combined, washed with saturated brine (30 mL) for three times, dried over anhydrous sodium sulfate (10 g) for half an hour, then filtered, and concentrated under reduced pressure to obtain a crude product. The crude product was separated by column chromatography (ethyl acetate:petroleum ether=1:1) to obtain Compound C104-2 (140 mg, a light yellow solid, yield: 96%).

MS m/z (ESI): 556.2 [M+H]⁺.

Step 3:

Compound C104-2 (140 mg, 0.25 mmol), sodium azide (20 mg, 0.38 mmol), lithium chloride (12 mg, 0.28 mmol) and ammonium chloride (18 mg, 0.28 mmol) were dissolved in dry DMF (5 mL). The reaction solution was reacted at 120° C. for 16 hours. LC-MS indicated that the reaction of starting materials was complete. The reaction was quenched by adding water (10 mL), and extracted with ethyl acetate (20 mL×2). The organic phases were combined, washed twice with saturated brine (30 mL), dried over anhydrous sodium sulfate (10 g) for half an hour, and then filtered, and concentrated under reduced pressure to obtain a crude product. The crude product was separated by column chromatography on silica gel (dichloromethane:methanol=20:1) to obtain Compound C104-3 (100 mg, a light yellow solid, yield: 67%).

MS m/z (ESI): 599.2 [M+H]⁺.

Step 4:

Compound C104-3 (90 mg, 0.15 mmol) was dissolved in dry methanol (20 mL). After the temperature was reduced to 0° C.-5° C., SOCl₂ (3 mL) was added dropwise. The reaction solution was reacted at 70° C. for 48 hours. LC-MS indicated that the reaction of the starting materials was complete. The reaction solution was concentrated under reduced pressure, dried by rotatory vaporization, followed by adding ethyl acetate (60 mL). It was washed with saturated brine (50 mL×2), and then dried over anhydrous sodium sulfate (10 g) for half an hour, filtered and concentrated. The crude product was separated by high performance liquid chromatography (acetonitrile-water (0.1% trifluoroacetic acid), gradient: 40%-80%) to obtain Compound C104 (20 mg, a white solid, yield: 22.7%).

¹H NMR (400 MHz, DMSO-rid) δ 10.03 (s, 1H), 8.07-8.01 (m, 1H), 7.95 (d, J=7.6 Hz, 1H), 7.77 (s, 1H), 7.67-7.58 (m, 2H), 7.45-7.18 (m, 9H), 7.15-7.07 (m, 2H), 6.78-6.68 (m, 4H), 5.53 (s, 1H), 4.22-4.19 (m, 1H), 3.63-3.49 (m, 2H), 3.03-2.86 (m, 2H), 2.59 (m, 1H).

MS m/z (ESI): 585.2 [M+H]⁺.

Example 11: Preparation of (S)-1-(10,11-dioxo-10,11-dihydro-5H-dibenzo[b,f]azepine-5-carbonyl)-4-(diphenylcarbamoyl)piperazine-2-carboxylic acid (C16)

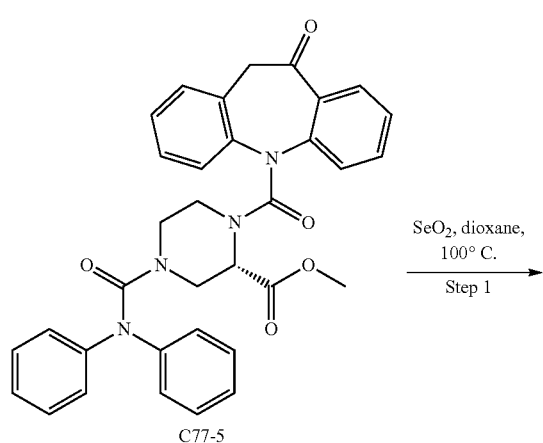

C77-5

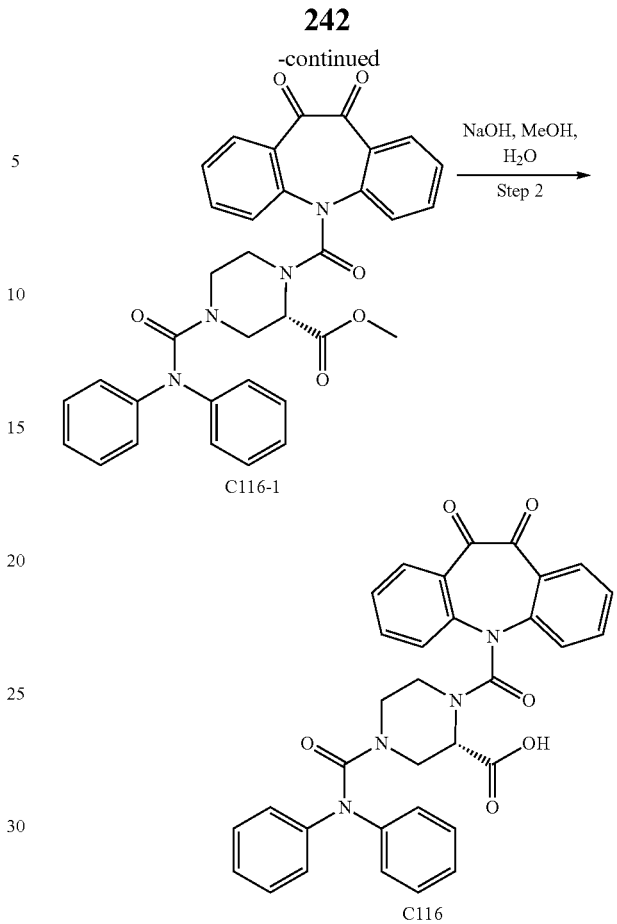

Step 1:

Compound C77-5 (90 mg, 0.15 mmol) and selenium dioxide (352 mg, 0.31 mmol) were dissolved in dioxane (20 mL), and then the reaction solution was reacted at 100° C. for 16 hours. LC-MS indicated that the reaction of the starting materials was substantially complete. To the reaction solution, ethyl acetate (30 mL) was added and then washed with saturated brine (40 mL×2). The organic phases was then dried by adding anhydrous sodium sulfate (10 g) for half an hour, and then filtered and concentrated under reduced pressure to obtain a crude product. The crude product was separated by preparative thin layer chromatography on silica gel (petroleum ether:ethyl acetate=1:1) to obtain a crude Compound C116-1 (80 mg, a yellow solid, yield: 87%).

MS m/z (ESI): 589.1 [M+H]⁺.

Step 2:

Compound C116-1 (80 mg, 0.13 mmol) was dissolved in dry methanol (10 mL) and water (2 mL), and sodium hydroxide (52 mg, 1.3 mmol) was added. The reaction solution was reacted at room temperature for 16 hours. LC-MS indicated that the reaction of starting materials was complete. The reaction solution was concentrated under reduced pressure, and dissolved by adding water (10 mL). After that, it was adjusted to pH=4-5 by adding 1N HCl solution, and then extracted with ethyl acetate (30 mL×2). The organic phases were combined, washed twice with saturated brine (30 mL), then dried over anhydrous sodium sulfate (10 g) for half an hour, filtered, and concentrated under reduced pressure to obtain a crude product. The crude product was separated by high-performance liquid chromatography (acetonitrile-water (0.1% trifluoroacetic acid), gradient: 30%-50%) to obtain a compound 016 (30 mg, a yellow solid, yield: 38%).

$^1$H NMR (400 MHz, CD$_3$OD) δ 8.45 (s, 1H), 7.92-7.83 (m, 1H), 7.55-7.46 (m, 2H), 7.42-7.32 (m, 6H), 7.19 (t, J=7.2 Hz, 2H), 7.13 (t, J=6.8 Hz, 2H), 7.08-7.03 (m, 4H), 5.23 (s, 1H), 4.52 (d, J=13.6 Hz, 1H), 3.74-3.64 (m, 2H), 3.16-3.05 (m, 1H), 2.95-2.73 (m, 2H).

MS m/z (ESI): 574.6 [M+H]$^+$.

Biological Assay

Experimental Example 1. Measurement of Inhibitory Activity on AT$_1$ Receptor (AT$_1$R)/AT$_2$ Receptor (AT$_2$R)

Through the following steps, the inhibitory activity of the compound on AT$_1$R/AT$_2$R (IC$_{50}$ value) was determined:
1) An appropriate amount of 1×TLB (Tag-lite Buffer) was prepared and well mixed for use.
2) The compound was diluted by 10 times with ddH$_2$O or DMSO. The compound was then dilute to 4 times of the working concentration with IX TLB and mixed well for use.
3) 8600 nM Tag-lite angiotensin receptor red agonist was diluted to 12 nM (4×Kd) with 1×TLB.
4) 5 ml 1×TLB was taken into a 15 ml centrifuge tube.
5) After thawing 1 tube of Tb-labeled AT$_1$R/AT$_2$R cells in a 37° C. water bath, the cells were quickly transferred to the IX TLB in step 4), mixed gently, and centrifuged at 1200 g for 5 minutes at room temperature.
6) The supernatant was aspirated gently, and the cells were resuspended and mixed in 2.7 ml 1× TLB, and then placed at room temperature until use.
7) 10 μl cells were added to all test wells, and 5 μl 4× working solution of the compound from step 2) was added to the corresponding test wells. 5 μl 4× Tag-lite angiotensin receptor red agonist well diluted in step 3) was added to all test wells.
8) After leaving the reaction plate at room temperature for 1 h, data were measured and analyzed using Envision HTRF Reader, and the half inhibitory concentration (IC$_{50}$) of the compound on AT$_1$R/AT$_2$R was calculated with the GraphPad Prism four-parameter equation.

The measured IC$_{50}$ values of the compounds are shown in Table 6 below.

TABLE 6

| Compound No. | AT$_2$R IC$_{50}$ (nM) | AT$_1$R IC$_{50}$ (nM) |
|---|---|---|
| C1 | 18.84 | >10000 |
| C2 | 20.27 | >10000 |
| C3 | 32.55 | >10000 |
| C4 | 45.06 | >10000 |
| C5 | 6.47 | >10000 |
| C7 | 37.15 | NA |
| C11 | 106.90 | NA |
| C12 | 43.71 | >10000 |
| C18 | 278.00 | NA |
| C20 | 36.68 | >10000 |
| C21 | 190.10 | NA |
| C31 | 218.8 | NA |
| C33 | 35.85 | >10000 |
| C43 | 246.90 | NA |
| C44 | 62.65 | >10000 |
| C45 | 55.46 | >10000 |
| C46 | 54.45 | >10000 |
| C50 | 38.46 | >10000 |
| C51 | 51.47 | NA |
| C53 | 1344 | NA |

TABLE 6-continued

| Compound No. | AT$_2$R IC$_{50}$ (nM) | AT$_1$R IC$_{50}$ (nM) |
|---|---|---|
| C57 | 7.09 | NA |
| C59 | 67.94 | NA |
| C76 | 156.10 | NA |
| C77 | 32.33 | >10000 |
| C78 | 88.24 | NA |
| C79 | 460.00 | NA |
| C80 | 12.68 | >10000 |
| C81 | 22.66 | >10000 |
| C82 | 13.07 | NA |
| C83 | 6.35 | NA |
| C85 | 461.10 | NA |
| C86 | 503.60 | NA |
| C87 | 389.30 | NA |
| C88 | 386.60 | NA |
| C89 | 19.77 | >10000 |
| C90 | 128.60 | NA |
| C91 | 30.71 | NA |
| C94 | 10.59 | >10000 |
| C96 | 13.14 | NA |
| C97 | 137.70 | NA |
| C98 | 8.18 | NA |
| C99 | 23.04 | NA |
| C101 | 189.3 | NA |
| C102 | 201.0 | NA |
| C103 | 334.40 | NA |
| C104 | 297.60 | NA |
| C105 | 160.90 | NA |
| C106 | 281.90 | NA |
| C107 | 59.17 | NA |
| C108 | 51.11 | NA |
| C110 | 384.3 | NA |
| C111 | 229.40 | NA |
| C113 | 7.37 | NA |
| C114 | 33.03 | NA |
| C115 | 38.11 | NA |
| C123 | 503.3 | NA |
| C124 | 65.29 | NA |
| C128 | 12.45 | NA |
| C129 | 98.63 | NA |
| C133 | 24.3 | NA |
| C134 | 18.51 | NA |
| C135 | 28.22 | NA |
| C136 | 72.55 | NA |
| C137 | 36.49 | NA |
| C138 | 60.96 | NA |
| C140 | 330.6 | NA |
| C144 | 98.13 | NA |
| C145 | 3.607 | NA |
| C146 | 14.18 | NA |
| C148 | 53.87 | NA |
| C149 | 290.0 | NA |
| C150 | 26.09 | NA |
| C153 | 5.47 | NA |

Note:
NA means Not Assayed.

Experimental Example 2. Pharmacokinetic (PK) Test in Mice

To male ICR mice, the solution of Compound C2 (1 mg/mL) of the present invention and the solution of control Compound A (1 mg/mL) were administered intravenously (IV) and intragastrically (PO), in both of which the vehicle system is DMSO, solutol and deionized water (1:2:17, v:v:v). For Compound C2 and Compound A, the IV and PO dosages were 3 mg/kg and 20 mg/kg, respectively. For IV administration, blood was collected from the ophthalmic venous plexus of the mice at (0) horn before the administration and at 0.083, 0.25, 0.5, 1, 2, 4, 6, 8, and 24 horns after the administration, while for PO administration, blood was collected from ophthalmic venous plexus of the mice at (0) hour before the administration and at 0.25, 0.5, 1, 2, 4, 6, 8, and 24 horns after the administration. For Compound C2, a 0.05 mL blood sample was taken at each time point, while for Compound A, a 0.03 mL blood sample was taken at each time point. The collected blood sample was placed in a clean sample tube containing EDTA-K$_2$ (4%), and centrifuged at 5000 rpm at 4° C. for 5 minutes. The resulting plasma was transferred to another clean sample tube, and stored at −20° C. LC-MS/MS analysis was performed on the plasma samples. The pharmacokinetic parameters were calculated using WinNonlin 6.3 software. The results are shown in Table 7.

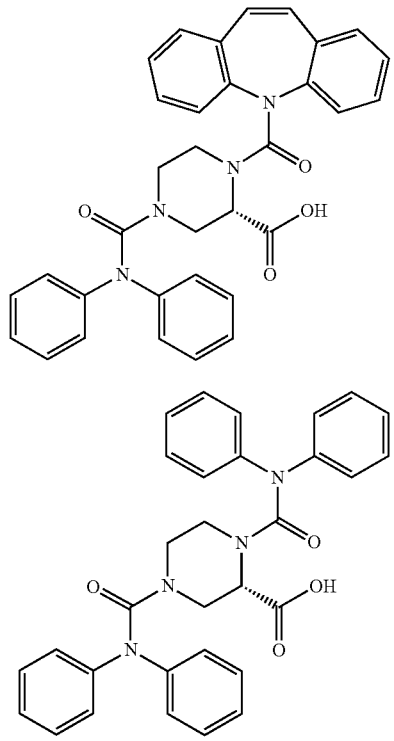

cally labeled compound, or prodrug thereof, wherein the compound has a structure of formula (I):

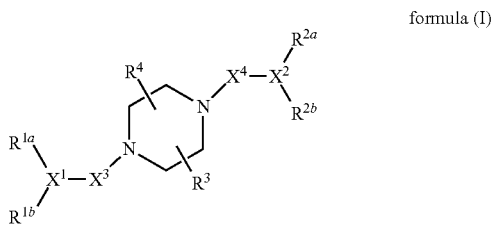

wherein:

X$^1$ and X$^2$ are each independently CR$^{10}$ or N;

R$^{1a}$ and R$^{1b}$ are each independently selected from the group consisting of C$_{1-8}$ alkyl, C$_{2-8}$ alkenyl and C$_{2-6}$ alkynyl, wherein any one of the CH$_2$ moieties in the C$_{1-8}$ alkyl, C$_{2-8}$ alkenyl and C$_{2-8}$ alkynyl is optionally replaced with O or S; saturated or partially unsaturated C$_{3-10}$ cyclic hydrocarbyl group; saturated or partially unsaturated 3- to 10-membered monocyclic heterocyclic group; C$_{6-10}$ aryl; 5- to 14-membered heteroaryl; —C$_{1-6}$ alkylene-saturated or partially unsaturated C$_{3-10}$ cyclic hydrocarbyl group, —C$_{1-6}$ alkylene-saturated or partially unsaturated 3- to 10-membered heterocyclic group; —C$_{1-6}$ alkylene-C$_{6-10}$ aryl; and —C$_{1-6}$ alkylene-(5- to 14-membered heteroaryl);

R$^{1b}$ and R$^{2b}$ are each independently selected from the group consisting of H, C$_{1-8}$ alkyl, C$_{2-8}$ alkenyl and C$_{2-8}$ alkynyl, wherein any one of the CH$_2$ moieties in the C$_{1-8}$ alkyl, C$_{2-8}$ alkenyl and C$_{2-8}$ alkynyl is optionally replaced with O or S; saturated or partially unsaturated C$_{3-10}$ cyclic hydrocarbyl group; saturated or partially unsaturated 3- to 10-membered heterocyclic group; C$_{6-10}$ aryl; 5- to 14-membered heteroaryl; —C$_{1-6}$ alkylene-saturated or partially unsaturated C$_{3-10}$ cyclic hydrocarbyl group, —C$_{1-6}$ alkylene-saturated or partially unsaturated 3- to 10-membered heterocyclic group; —C$_{1-6}$ alkylene-C$_{6-10}$ aryl; and —C$_{1-6}$ alkylene-(5- to 14-membered heteroaryl);

TABLE 7

Results of pharmacokinetic test in mice

| Cpd | Route of administration | t$_{1/2}$ (h) | C$_0$/C$_{max}$ (ng/mL) | AUC$_{last}$ (h*ng/mL) | AUC$_{INF\_obs}$ (h*ng/mL) | Cl_F_obs (mL/min/kg) | MRT$_{last}$ (h) | Bioavailability (%) |
|---|---|---|---|---|---|---|---|---|
| C2 | IV | 4.512 | 43383.399 | 48979.635 | 49522.186 | 1.010 | 1.895 | 45.73 |
|    | PO | 3.054 | 62035.274 | 150534.790 | 150991.510 | NA | 2.337 | |
| A  | IV | 0.5000 | 7172.7810 | 1192.9873 | 1195.8110 | 41.8933 | 0.2900 | 6.2633 |
|    | PO | 0.8717 | 366.0393 | 494.5963 | 499.3013 | NA | 1.0600 | |

Note:
NA means Not Assayed.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A compound or a pharmaceutically acceptable salt, ester, stereoisomer, polymorph, solvate, N-oxide, isotopiprovided that:

R$^{1a}$ and R$^{1b}$ are each independently the C$_{3-10}$ cyclic hydrocarbyl group, 3- to 10-membered heterocyclic group, C$_{6-10}$ aryl or 5- to 14-membered heteroaryl, and an available ring atom on R$^{1a}$ is connected to an available ring atom on R$^{1b}$ through Y group, such that R$^{1a}$ and R$^{1b}$ together with X$^1$ to which they are attached form an optionally substituted saturated or partially unsaturated fused ring system Q$^1$ containing 3 or more rings; and/or R$^{2a}$ and R$^{2b}$ are each independently the C$_{3-10}$ cyclic hydrocarbyl group, 3- to 10-membered heterocyclic group, $C_{6-10}$ aryl or 5- to 14-membered heteroaryl, and an available ring atom on $R^{2a}$ is connected to an available ring atom on $R^{2b}$ through Z group, such that $R^{2a}$ and $R^{2b}$ together with $X^2$ to which they are attached form an optionally substituted saturated or partially unsaturated fused ring system $Q^2$ containing 3 or more rings;

the fused ring system $Q^1$ has a structure of formula (a):

formula (a)

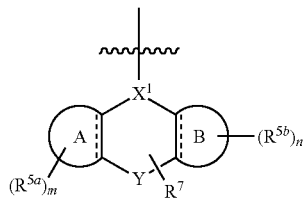

wherein
ring A and ring B are each independently $C_{3-10}$ cyclic hydrocarbyl group, 3- to 10-membered heterocyclic group, $C_{6-10}$ aryl or 5- to 14-membered heteroaryl;
"=====" means a single bond or a double bond; and
the fused ring system $Q^2$ has a structure of formula (b):

formula (b)

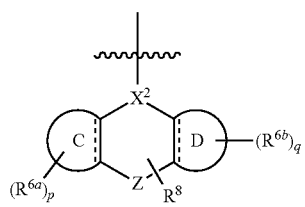

wherein
ring C and ring D are each independently $C_{3-10}$ cyclic hydrocarbyl group, 3- to 10-membered heterocyclic group, $C_{6-10}$ aryl or 5- to 14-membered heteroaryl;
"=====" means a single bond or a double bond; and
$R^{5a}$, $R^{5b}$, $R^{6a}$ and $R^{6b}$, at each occurrence, are each independently $R^{10}$;
$R^7$ and $R^8$ are each independently absent or $R^{10}$;
m, n, p and q are each independently 0, 1, 2 or 3;
Y and Z are each independently selected from the group consisting of a single bond; $NR^{10}$; $C_{1-3}$ alkylene, wherein 1 or 2 $CH_2$ moieties are optionally replaced with a group independently selected from O, S, or $NR^{10}$; and $C_{2-3}$ alkenylene, in which any one of the CH moieties forming a C=C double bond is optionally replaced with N; and wherein the $C_{1-3}$ alkylene and $C_{2-3}$ alkenylene are each optionally substituted by 1, 2, 3 or more groups selected from the group consisting of halogen, OH, $-NR^{11}R^{12}$, cyano, nitro, $C_{1-6}$ alkyl, $C_{1-6}$ alkyl-O—, epoxy and oxo;
$X^3$ and $X^4$ are each independently C(=O);
$R^3$ is selected from the group consisting of 5 to 14-membered heteroaryl, $-C(=O)OR^{11}$, $-C(=O)NR^{11}-$OH, $-C(=O)NR^{11}S(=O)_yNR^{11}R^{12}$, $-C(=O)NR^{11}S(=O)_yR^{12}$, and $-S(=O)_yNR^{11}C(=O)OR^{12}$;
$R^4$ is selected from the group consisting of H, $C_{1-6}$ alkyl, and $-C(=O)OR^{11}$;
$R^{10}$ is selected from the group consisting of H, $C_{1-6}$ alkyl, $C_{3-10}$ cyclic hydrocarbyl group, $-OR^{11}$, $-SR^{11}$, $-C(=O)OR^{11}$ and $-NR^{11}R^{12}$;

$R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl;
the above alkyl, alkylene, alkenyl, alkenylene, alkynyl, cyclic hydrocarbyl group, heterocyclic group, aryl, heteroaryl and aralkyl, at each occurrence, are each optionally substituted by 1, 2, 3 or more $R^{13}$, wherein $R^{13}$, at each occurrence, is independently selected from the group consisting of halogen, cyano, nitro, $C_{1-6}$ alkyl, $C_{3-10}$ cyclic hydrocarbyl group, 3- to 10-membered heterocyclic group, $C_{6-10}$ aryl, 5- to 14-membered heteroaryl, $C_{6-12}$ aralkyl, $-OR^{11}$, $-SR^{11}$, $-OC(=O)R^{11}$, $-C(=O)R^{11}$, $-C(=O)OR^{11}$, $-C(=O)NR^{11}R^{12}$, $-C(=O)NR^{11}S(=O)_yNR^{11}R^{12}$, $-C(=O)NR^{11}S(=O)_yR^{12}$, $-S(=O)_yR^{11}$, $-S(=O)_yOR^{11}$, $-S(=O)_yNR^{11}R^{12}$, $-S(=O)_yNR^{11}S(=O)_zOR^{12}$, $-S(=O)_yNR^{11}C(=O)R^{12}$, $-S(=O)_yNR^{11}C(=O)OR^{12}$, $-NR^{11}R^{12}$, $-NR^{11}-C(=O)R^{12}$, $-NR^{11}-C(=O)OR^{12}$, $-NR^{11}-S(=O)_y-R^{12}$, $-NR^{11}-C(=O)-NR^{11}R^{12}$, $-C_{1-6}$ alkylene-$OR^{11}$, $-C_{1-6}$ alkylene-$OC(=O)R^{11}$, $-C_{1-6}$ alkylene-$C(=O)OR^{11}$, $-C_{1-6}$ alkylene-$S(=O)_xR^{11}$, $-C_{1-6}$ alkylene-$S(=O)_yOR^{11}$, $-C_{1-6}$ alkylene-$OC(=O)NR^{11}R^{12}$, $-C_{1-6}$ alkylene-$C(=O)NR^{11}R^{12}$, $-C_{1-6}$ alkylene-$C(=O)NR^{11}S(=O)_yR^{12}$, $-C_{1-6}$ alkylene-$NR^{11}-C(=O)NR^{11}R^{12}$, $-C_{1-6}$ alkylene-$OS(=O)_yR^{11}$, $-C_{1-6}$ alkylene-$OS(=O)_yNR^{11}R^{12}$, $-C_{1-6}$ alkylene-$S(=O)_yNR^{11}R^{12}$, $-C_{1-6}$ alkylene-$NR^{11}-S(=O)_yNR^{11}R^{12}$, $-C_{1-6}$ alkylene-$NR^{11}R^{12}$ and $-O-C_{1-6}$ alkylene-$NR^{11}R^{12}$; and wherein the alkyl, alkylene, cyclic hydrocarbyl group, heterocyclic group, aryl, heteroaryl and aralkyl recited for the substituent $R^{13}$ are optionally further substituted by 1, 2, 3 or more substituents independently selected from the group consisting of halogen, OH, oxo, amino, cyano, nitro, $C_{1-6}$ alkyl, halogenated $C_{1-6}$ alkyl, $C_{3-6}$ cyclic hydrocarbyl group, 3- to 10-membered heterocyclic group, $C_{6-10}$ aryl, 5- to 14-membered heteroaryl and $C_{6-12}$ aralkyl; and wherein the heterocyclic group, aryl or heteroaryl when being a substituent is connected to the rest of the molecule through a ring C atom, or where possible, through a ring N atom;
x, at each occurrence, is independently 0, 1 or 2;
y and z, at each occurrence, are each independently 2; and provided that:
when $R^{1a}$ and $R^{1b}$ are each independently $C_{1-8}$ alkyl, Z is not $-CH_2-$, $-CH_2-CH_2-$ or $-CH_2-CH_2-CH_2-$; or when $R^{2a}$ and $R^{2b}$ are each independently $C_{1-8}$ alkyl, Y is not $-CH_2-$, $-CH_2-CH_2-$ or $-CH_2-CH_2-CH_2-$.

2. The compound according to claim 1, or a pharmaceutically acceptable salt, ester, stereoisomer, polymorph, solvate, N-oxide, isotopically labeled compound, or prodrug thereof, wherein said rings A, B, C and D are each independently $C_{5-7}$ cyclic hydrocarbyl group, 5- to 7-membered monocyclic heterocyclic group, phenyl or 5- to 6-membered heteroaryl.

3. The compound according to claim 1, or a pharmaceutically acceptable salt, ester, stereoisomer, polymorph, solvate, N-oxide, isotopically labeled compound, or prodrug thereof, wherein:
said rings A, B, C and D are each independently cyclopentyl, cyclohexyl, 5- to 7-membered monocyclic heterocyclic group, phenyl or 5- to 6-membered heteroaryl; and/or R³ is selected from the group consisting of 5 to 14-membered heteroaryl, —C(=O)OR¹¹, —C(=O)NR¹¹—OH, —C(=O)NR¹¹S(=O)ᵧNR¹¹R¹², —C(=O)NR¹¹S(=O)ᵧR¹², and —S(=O)ᵧNR¹¹C(=O)OR¹²; and/or R⁴ is H; and/or R¹⁰ is selected from the group consisting of H, $C_{1-6}$ alkyl, $C_{3-10}$ cyclic hydrocarbyl group, —OR¹¹, —SR¹¹, and —NR¹¹R¹².

4. The compound according to claim 3, or a pharmaceutically acceptable salt, ester, stereoisomer, polymorph, solvate, N-oxide, isotopically labeled compound, or prodrug thereof, wherein the compound has a structure of formula (II):

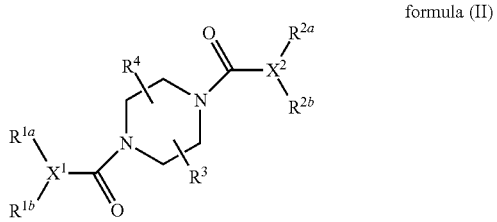

formula (II)

wherein, when the structure of formula (b) is formed, $R^{1b}$ is selected from the group consisting of, or when the structure of formula (a) is formed, $R^{2b}$ is selected from the group consisting of:

$C_{1-8}$ alkyl, $C_{2-8}$ alkenyl and $C_{2-8}$ alkynyl, wherein any one of the $CH_2$ moieties in the $C_{1-8}$ alkyl, $C_{2-8}$ alkenyl and $C_{2-8}$ alkynyl is optionally replaced with O or S; saturated or partially unsaturated $C_{3-10}$ cyclic hydrocarbyl group; saturated or partially unsaturated 3- to 10-membered heterocyclic group; $C_{6-10}$ aryl; 5- to 14-membered heteroaryl; —$C_{1-6}$ alkylene-saturated or partially unsaturated $C_{3-10}$ cyclic hydrocarbyl group, —$C_{1-6}$ alkylene-saturated or partially unsaturated 3- to 10-membered heterocyclic group; —$C_{1-6}$ alkylene-$C_{6-10}$ aryl; and —$C_{1-6}$ alkylene-(5- to 14-membered heteroaryl).

5. The compound according to claim 1, or a pharmaceutically acceptable salt, ester, stereoisomer, polymorph, solvate, N-oxide, isotopically labeled compound, or prodrug thereof, wherein, when the structure of formula (b) is formed, $R^{1a}$ and $R^{1b}$ are each independently selected from the group consisting of, or when the structure of formula (a) is formed, $R^{2a}$ and $R^{2b}$ are each independently selected from the group consisting of:

$C_{1-6}$ alkyl;

$C_{2-6}$ alkenyl;

$C_{2-6}$ alkynyl;

$C_{3-7}$ cyclic hydrocarbyl group;

5- to 7-membered monocyclic heterocyclic group;

8- to 10-membered benzo-fused heterocyclic group;

phenyl;

5- to 6-membered heteroaryl;

—$C_{1-6}$ alkylene-$C_{6-10}$ aryl; and

—$C_{1-6}$ alkylene-(5- to 14-membered heteroaryl); and the above alkyl, alkylene, alkynyl, cyclic hydrocarbyl group, heterocyclic group, aryl and heteroaryl, at each occurrence, are each optionally substituted by 1, 2 or 3 R¹³; and R¹³ is as defined in claim 1.

6. The compound according to claim 1, or a pharmaceutically acceptable salt, ester, stereoisomer, polymorph, solvate, N-oxide, isotopically labeled compound, or prodrug thereof, wherein the structure of formula (a) is a group having a structure of formula (1) or formula (2):

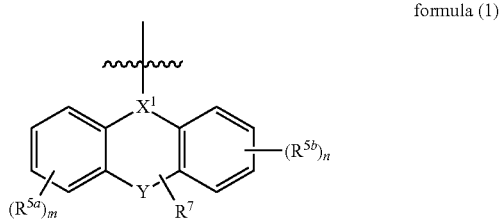

formula (1)

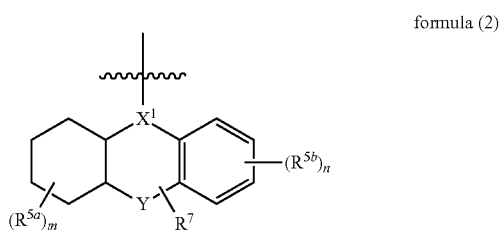

formula (2)

and/or the structure of formula (b) is a group having a structure of formula (3) or formula (4):

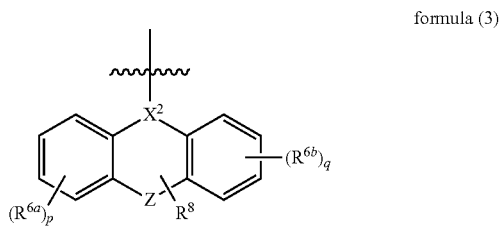

formula (3)

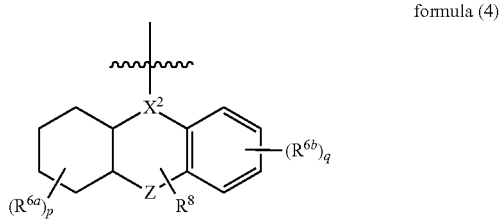

formula (4)

wherein $R^{5a}$, $R^{5b}$, $R^{6a}$, $R^{6b}$, $R^7$, $R^8$, m, n, p, q, $X^1$, $X^2$, $R^{10}$, Y and Z are as defined in claim 1.

7. The compound according to claim 6, or a pharmaceutically acceptable salt, ester, stereoisomer, polymorph, solvate, N-oxide, isotopically labeled compound, or prodrug thereof, wherein the group of formula (1) has a structure selected from
formula (1a-1)
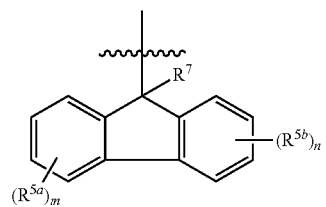
formula (1a-2)
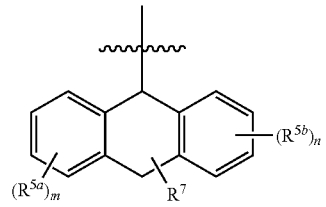
formula (1a-3)
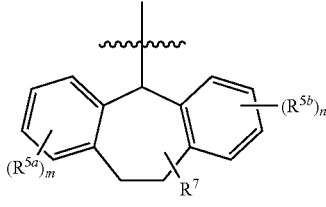
formula (1a-4)
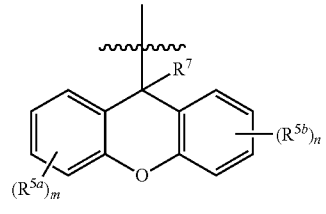
formula (1a-5)
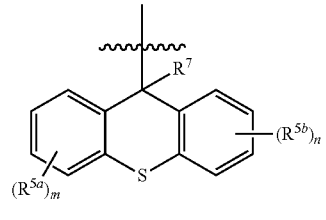
formula (1a-6)
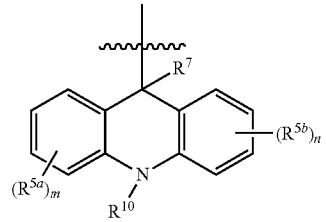
formula (1a-7)
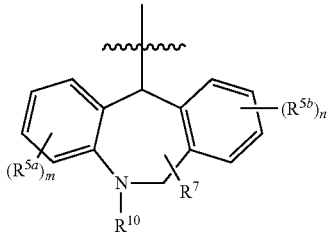
-continued
formula (1a-8)
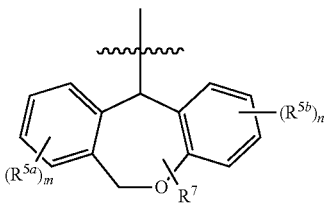
formula (1a-9)
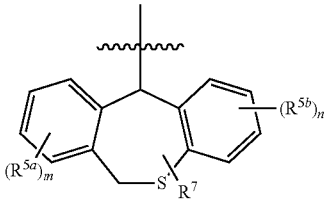
formula (1a-10)
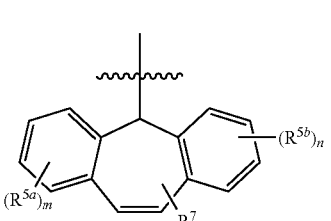
formula (1a-11)
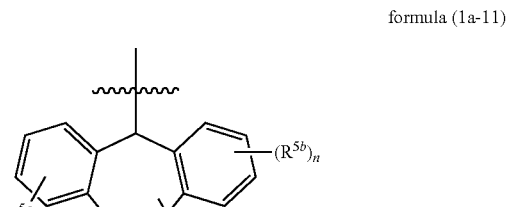
formula (1a-12)
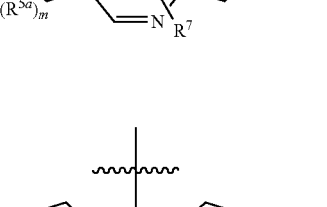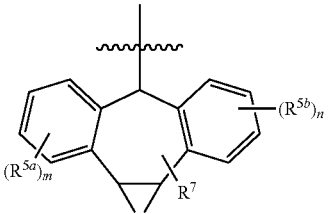
formula (1a-13)
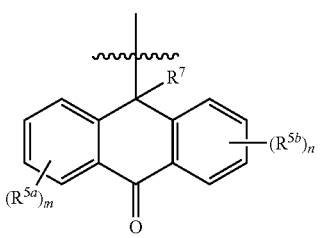

253
-continued
formula (1a-14)
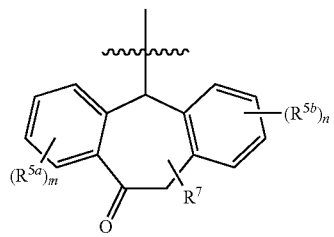
formula (1a-15)
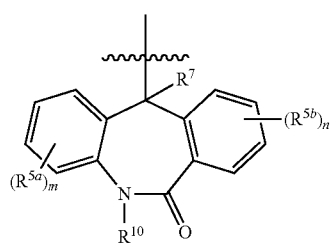
formula (1a-16)
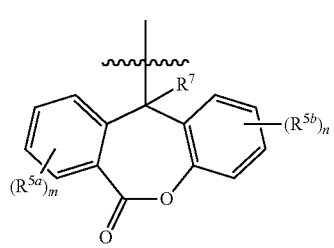
formula (1a-17)
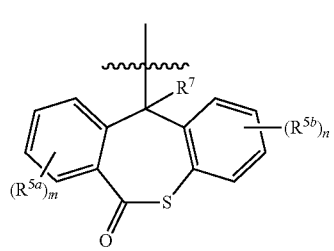
formula (1a-18)
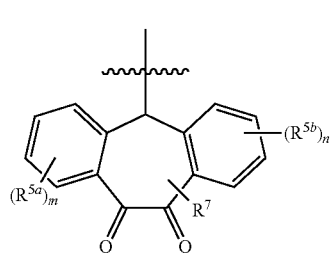
formula (1a-19)
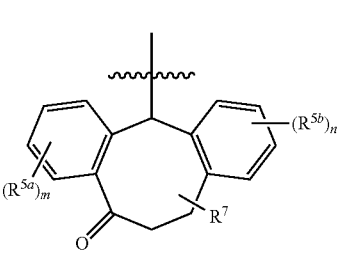
254
-continued
formula (1a-20)
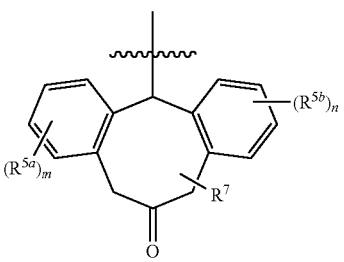
formula (1a-21)
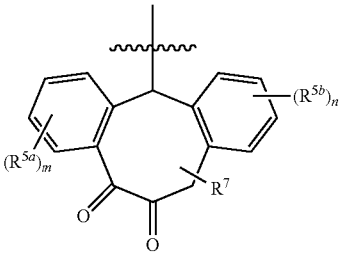
formula (1a-22)
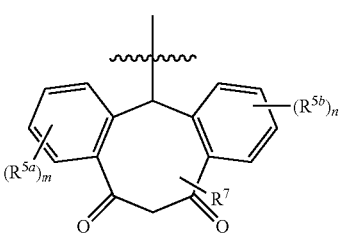
formula (1b-1)
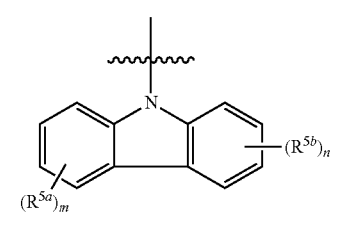
formula (1b-2)
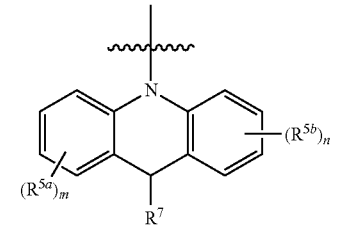
formula (1b-3)
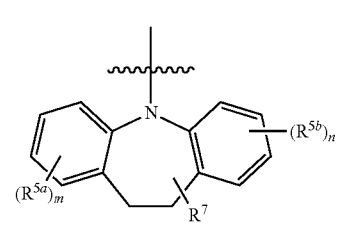
formula (1b-4)
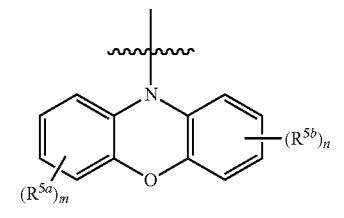

formula (1b-5)
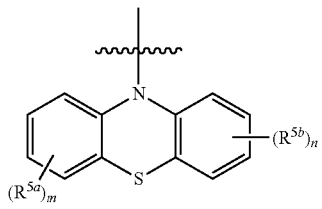
formula (1b-6)
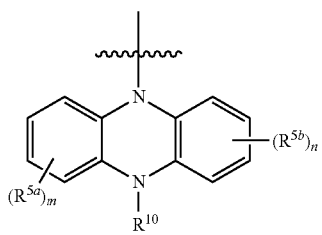
formula (1b-7)
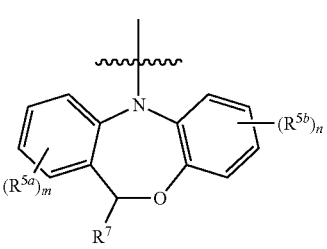
formula (1b-8)
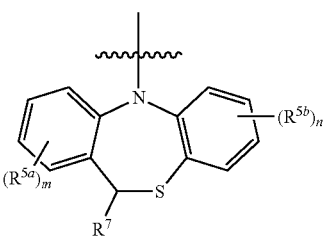
formula (1b-9)
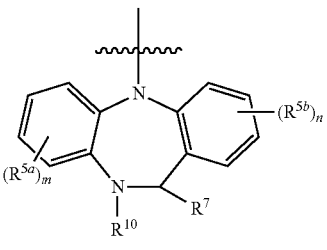
formula (1b-10)
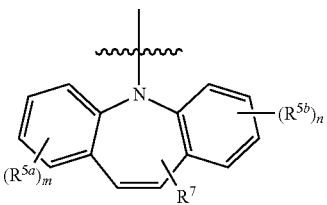
formula (1b-11)
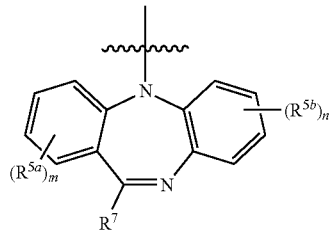
formula (1b-12)
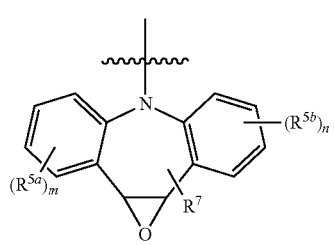
formula (1b-13)
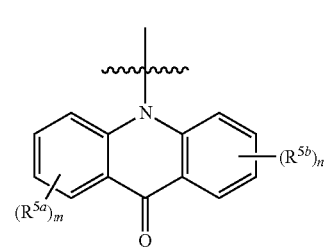
formula (1b-14)
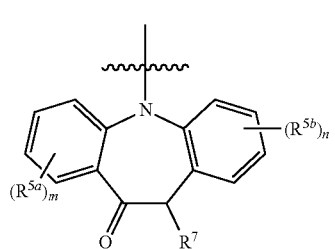
formula (1b-15)
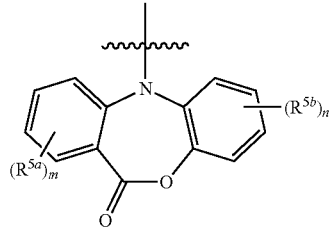
formula (1b-16)
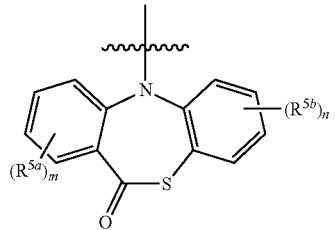

-continued
formula (1b-17)
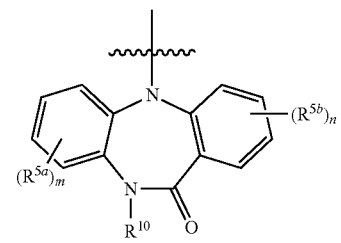
formula (1b-18)
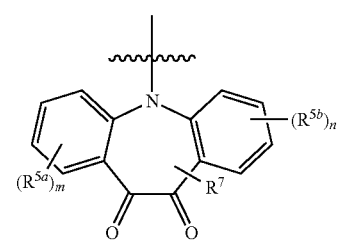
formula (1b-19)
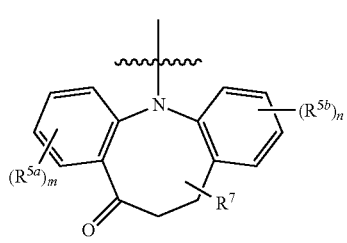
formula (1b-20)
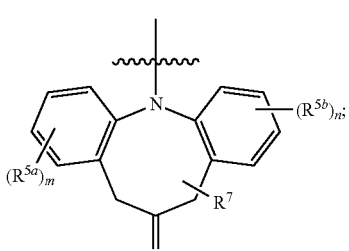
formula (1b-21)
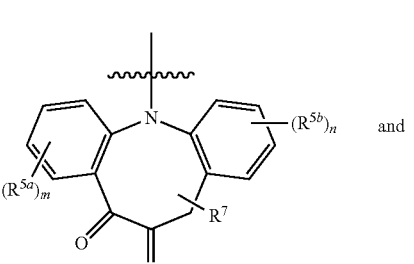
and
formula (1b-22)
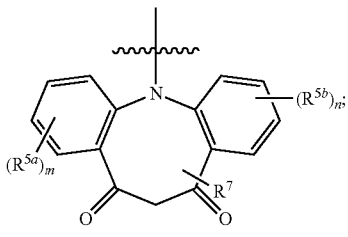
the group of formula (2) has a structure selected from
formula (2a-1)
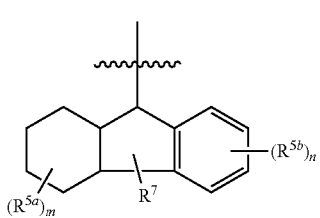
formula (2a-2)
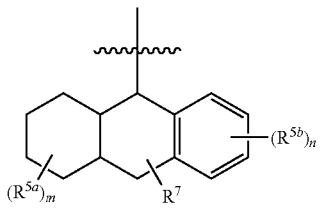
formula (2a-3)
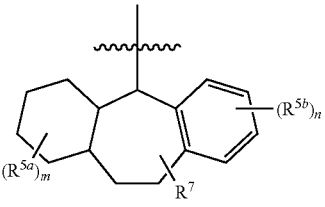
formula (2a-4)
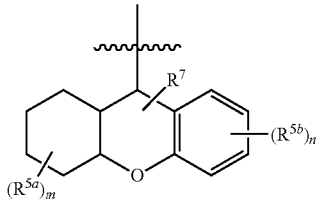
formula (2a-5)
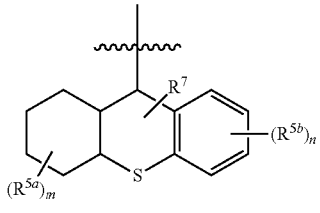
formula (2a-6)
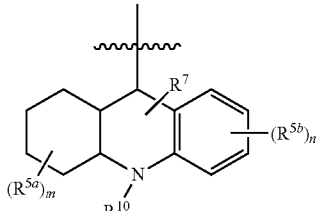
formula (2a-7)
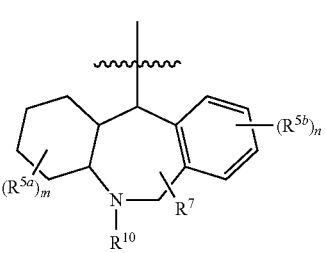

-continued
formula (2a-8)
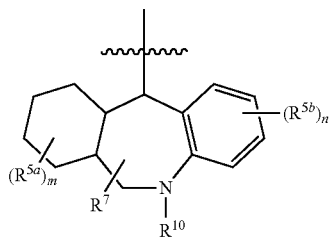
formula (2a-9)
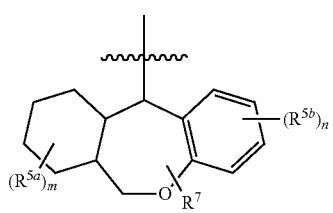
formula (2a-10)
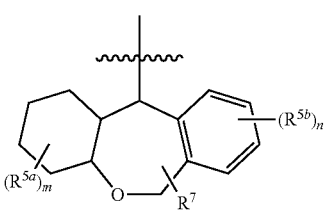
formula (2a-11)
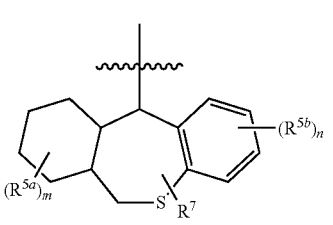
formula (2a-12)
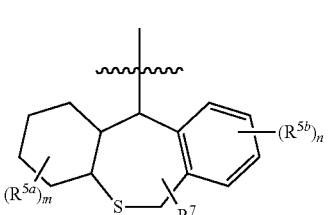
formula (2a-13)
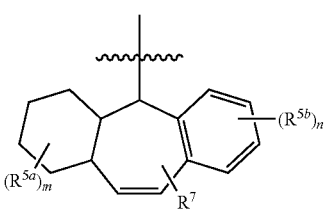
formula (2a-14)
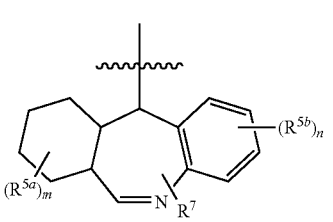
-continued
formula (2a-15)
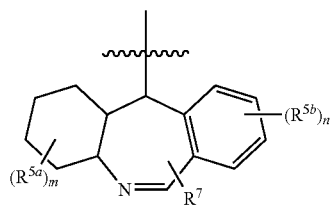
formula (2a-16)
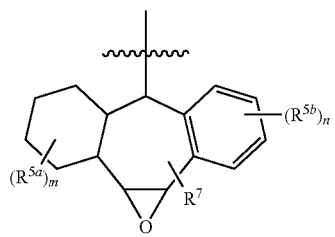
formula (2a-17)
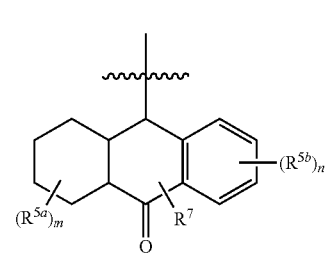
formula (2a-18)
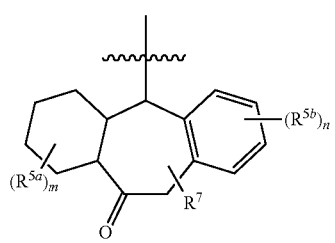
formula (2a-19)
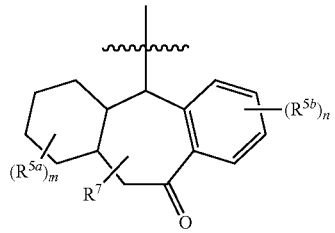
formula (2a-20)
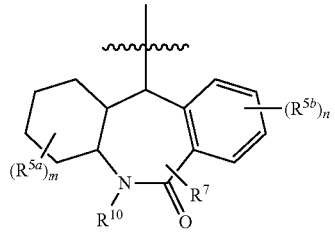

formula (2a-21)
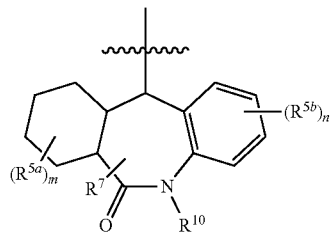
formula (2a-22)
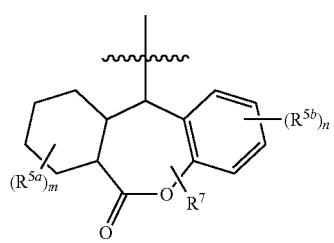
formula (2a-23)
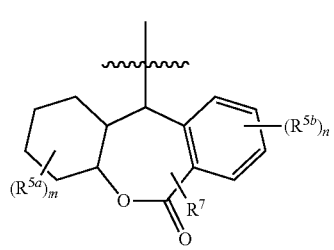
formula (2a-24)
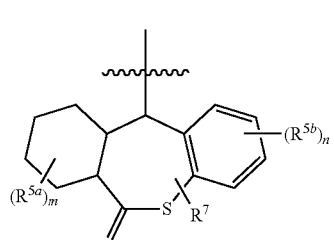
formula (2a-25)
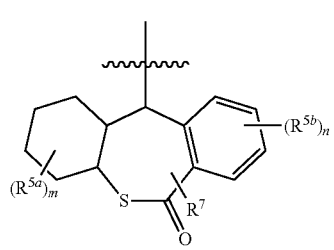
formula (2a-26)
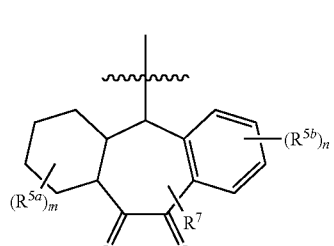
formula (2a-27)
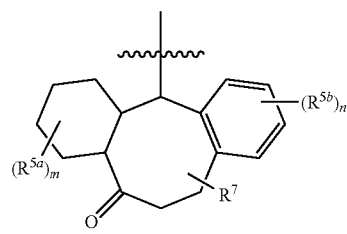
formula (2a-28)
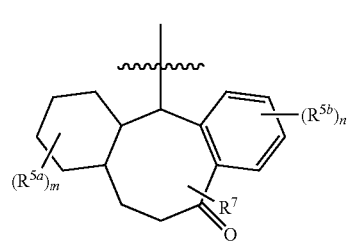
formula (2a-29)
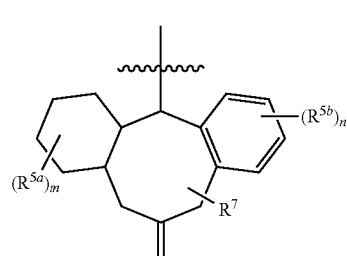
formula (2a-30)
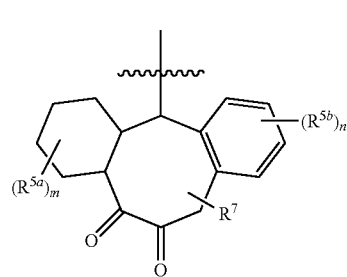
formula (2a-31)
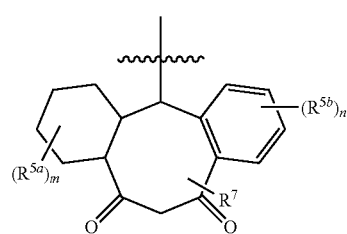
formula (2a-32)
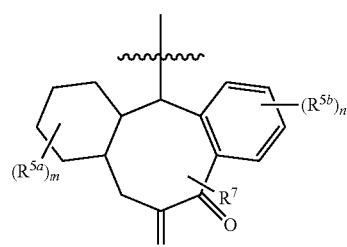

formula (2b-1)
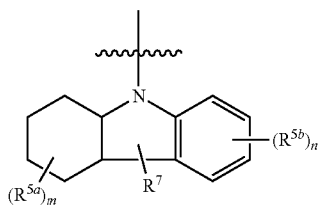
formula (2b-2)
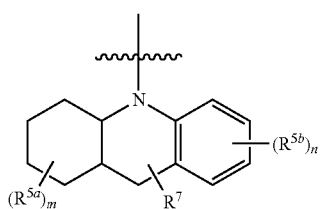
formula (2b-3)
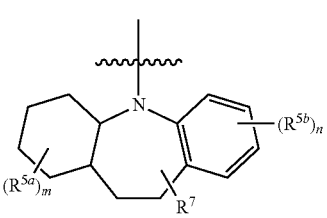
formula (2b-4)
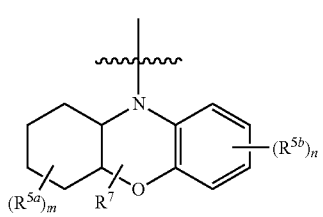
formula (2b-5)
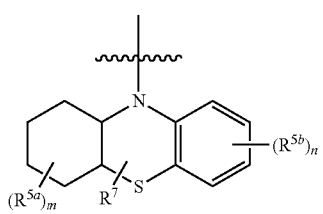
formula (2b-6)
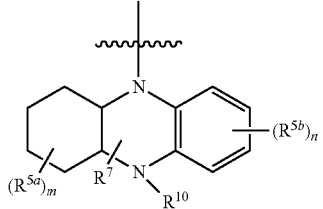
formula (2b-7)
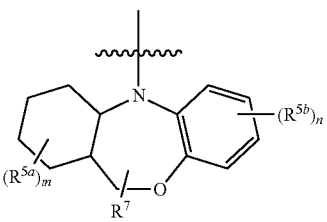
formula (2b-8)
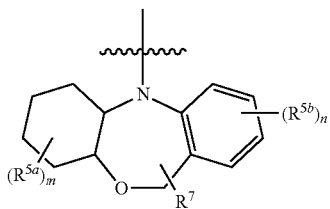
formula (2b-9)
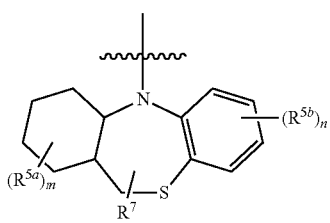
formula (2b-10)
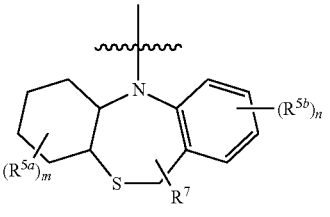
formula (2b-11)
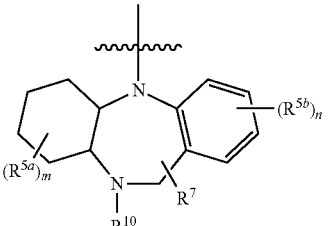
formula (2b-12)
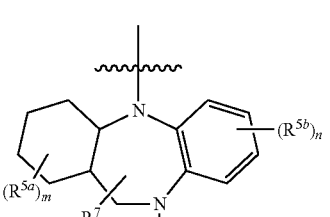
formula (2b-13)
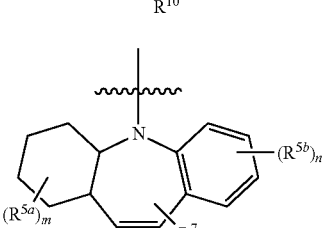
formula (2b-14)
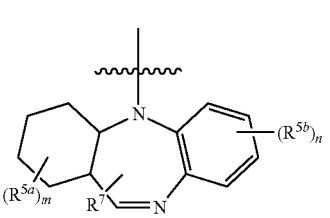

formula (2b-15)
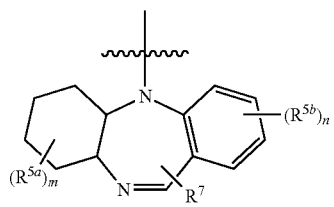
formula (2b-16)
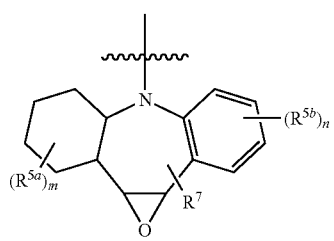
formula (2b-17)
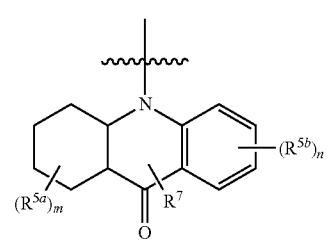
formula (2b-18)
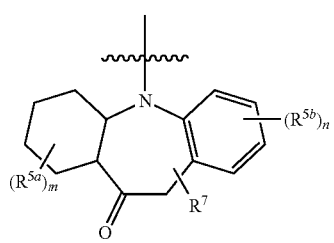
formula (2b-19)
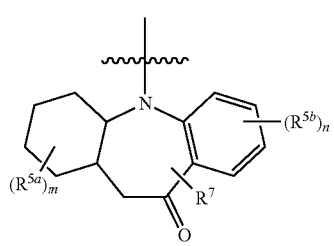
formula (2b-20)
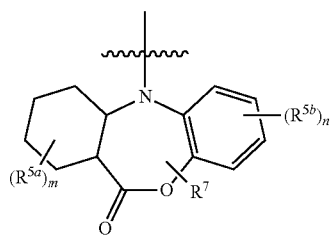
formula (2b-21)
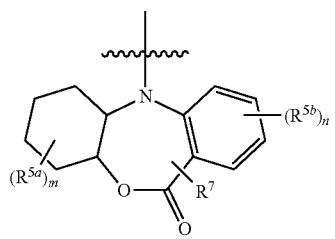
formula (2b-22)
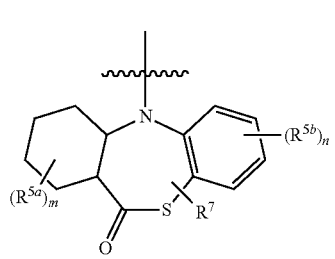
formula (2b-23)
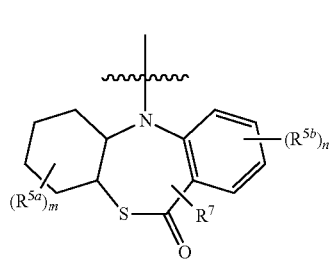
formula (2b-24)
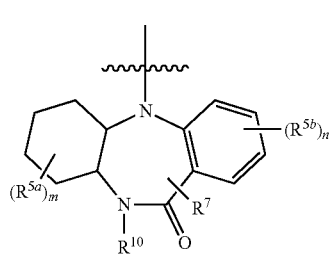
formula (2b-25)
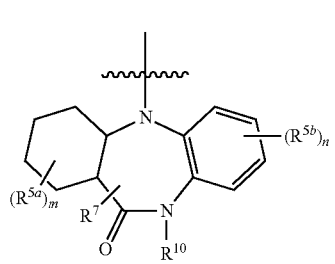
formula (2b-26)
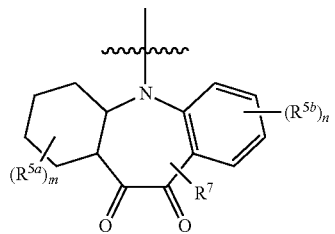

-continued
formula (2b-27)
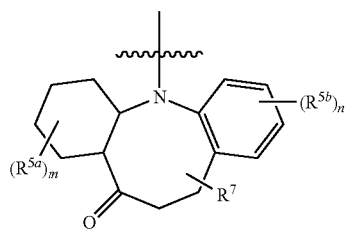
formula (2b-28)
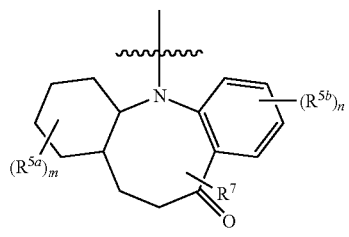
formula (2a-29)
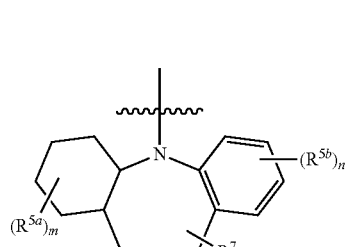
formula (2b-30)
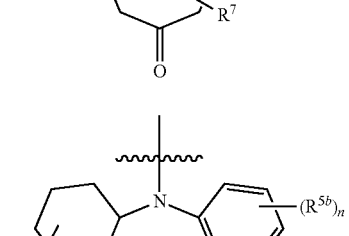
formula (2b-31)
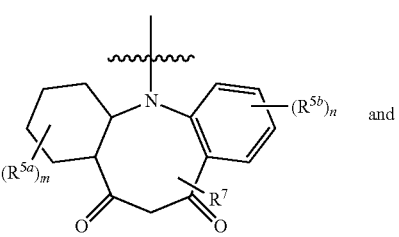
and
formula (2b-32)
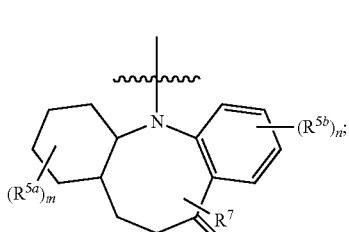;
and/or
the group of formula (3) has a structure selected from:
formula (3a-1)
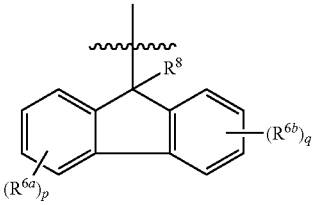
formula (3a-2)
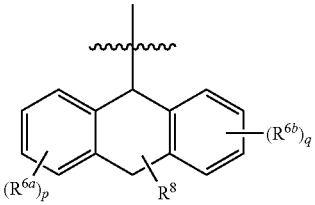
formula (3a-3)
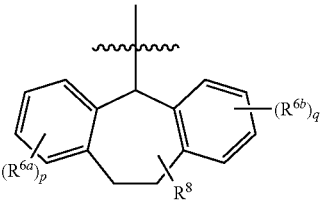
formula (3a-4)
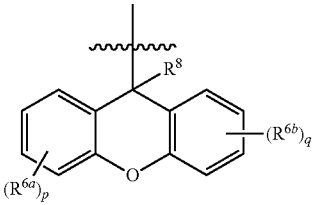
formula (3a-5)
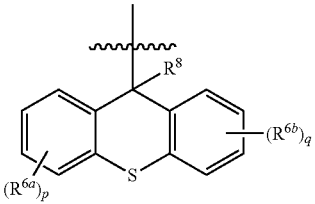
formula (3a-6)
formula (3a-7)
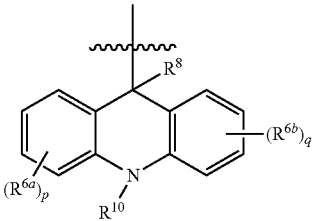

-continued
formula (3a-8)
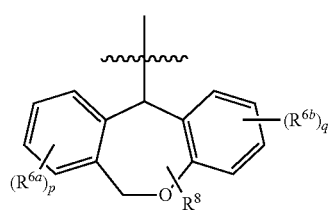
formula (3a-9)
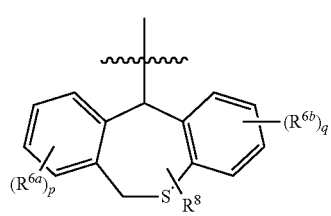
formula (3a-10)
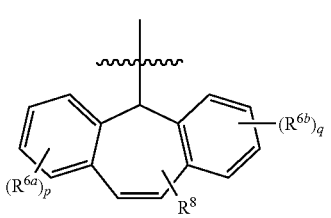
formula (3a-11)
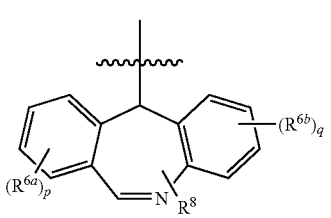
formula (3a-12)
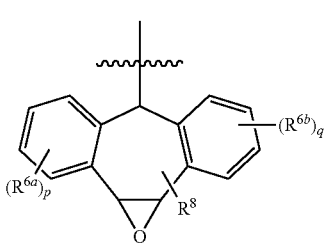
formula (3a-13)
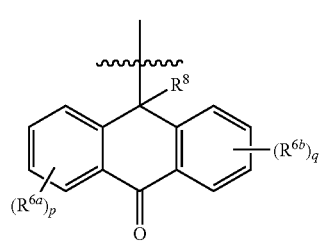
formula (3a-14)
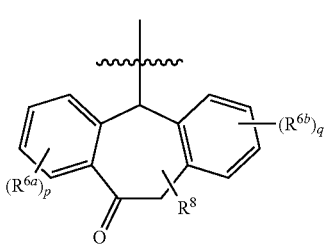
-continued
formula (3a-15)
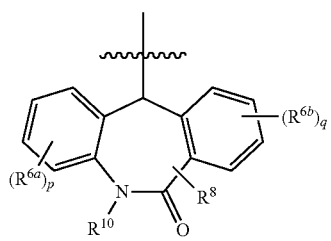
formula (3a-16)
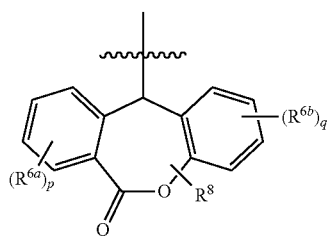
formula (3a-17)
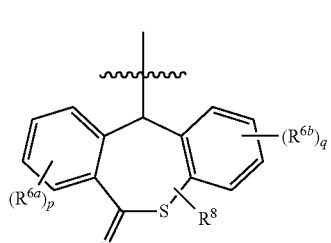
formula (3a-18)
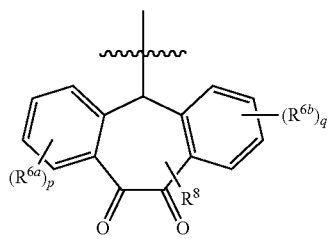
formula (3a-19)
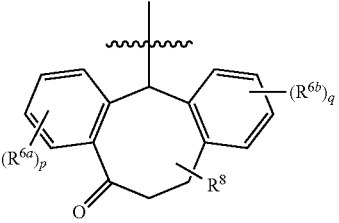
formula (3a-20)
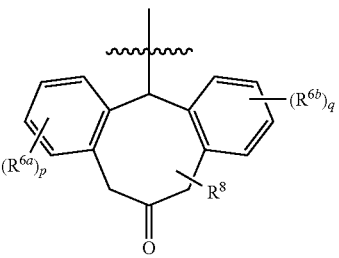

formula (3a-21)
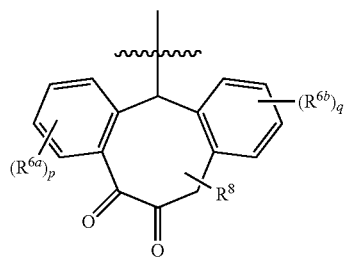
formula (3a-22)
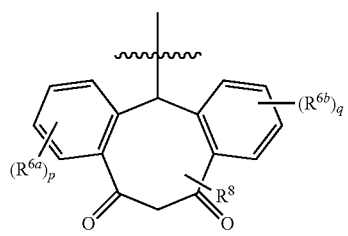
formula (3b-1)
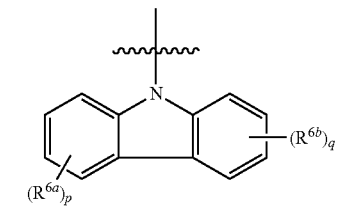
formula (3b-2)
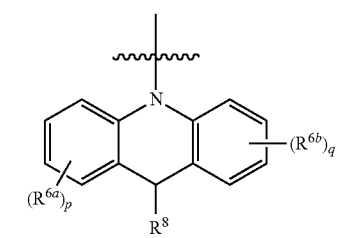
formula (3b-3)
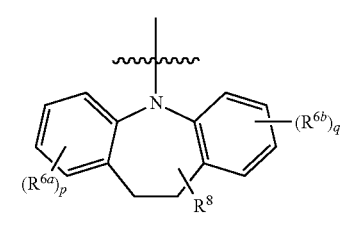
formula (3b-4)
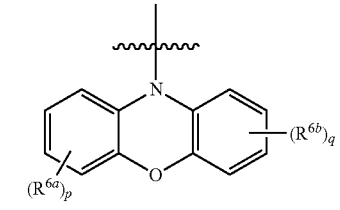
formula (3b-5)
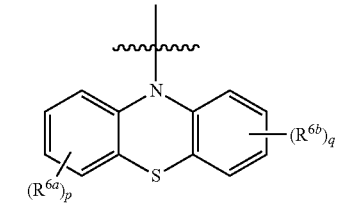
formula (3b-6)
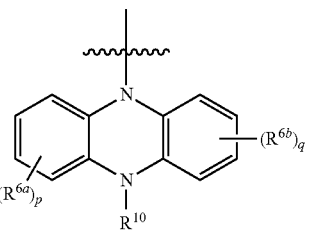
formula (3b-7)
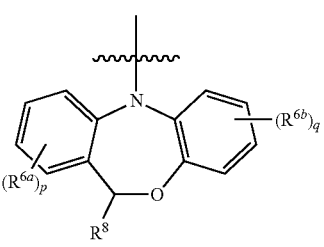
formula (3b-8)
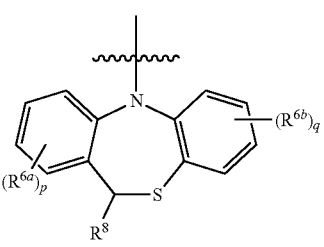
formula (3b-9)
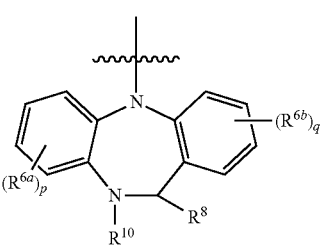
formula (3b-10)
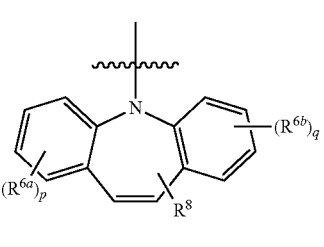
formula (3b-11)
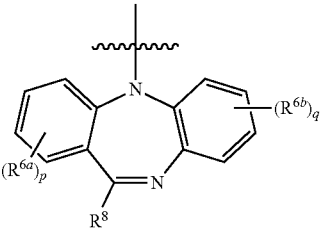

-continued
formula (3b-12)
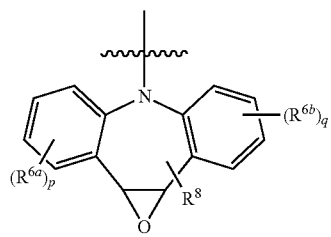
formula (3b-13)
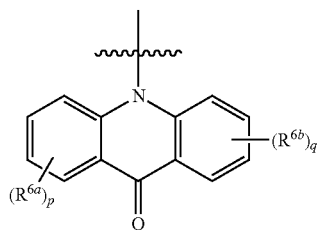
formula (3b-14)
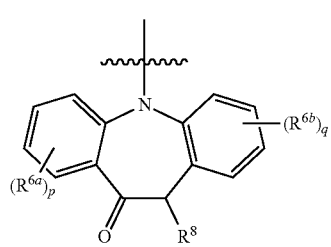
formula (3b-15)
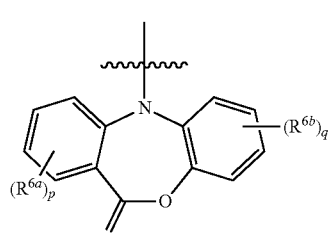
formula (3b-16)
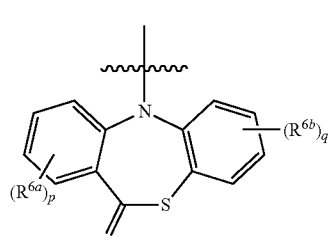
formula (3b-17)
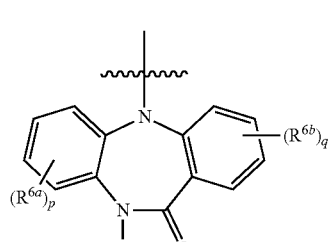
-continued
formula (3b-18)
formula (3b-19)
formula (3b-20)
formula (3b-21)
and
formula (3b-22)
;
or
the group of formula (4) has a structure selected from:
formula (4a-1)
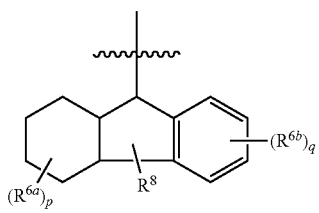

formula (4a-2)
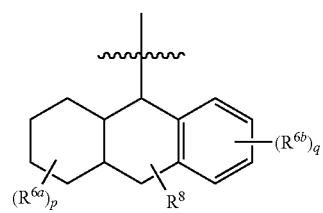
formula (4a-3)
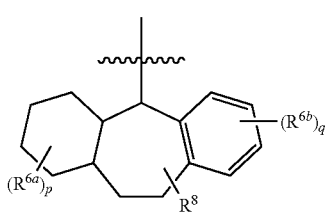
formula (4a-4)
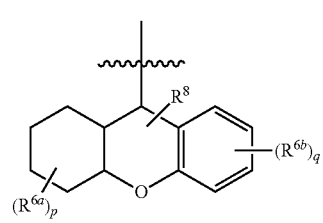
formula (4a-5)
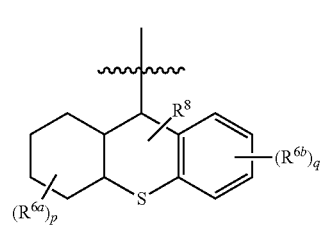
formula (4a-6)
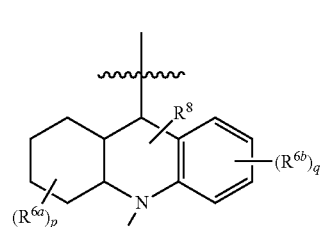
formula (4a-7)
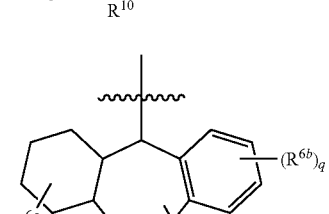
formula (4a-8)
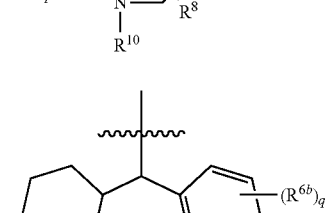
formula (4a-9)
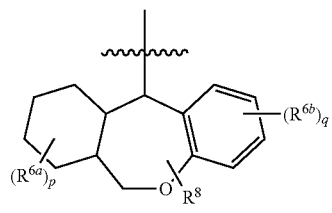
formula (4a-10)
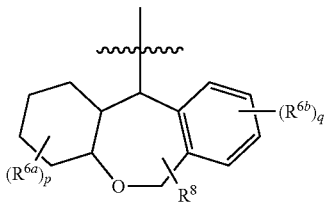
formula (4a-11)
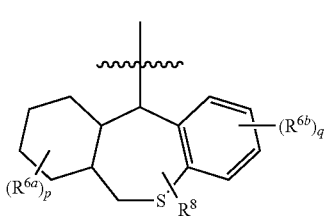
formula (4a-12)
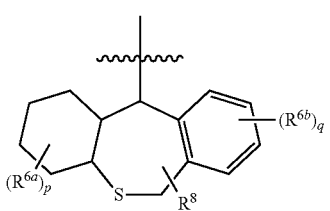
formula (4a-13)
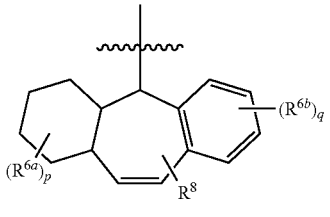
formula (4a-14)
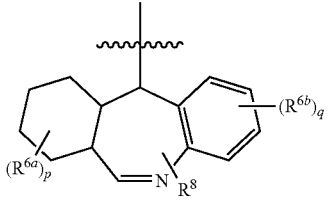
formula (4a-15)
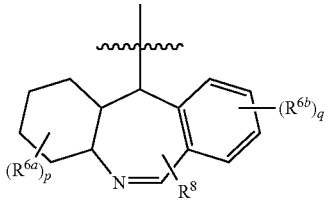

formula (4a-16)
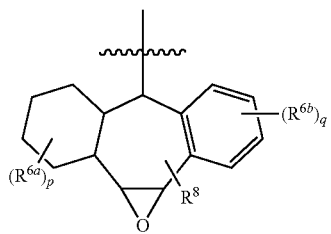
formula (4a-17)
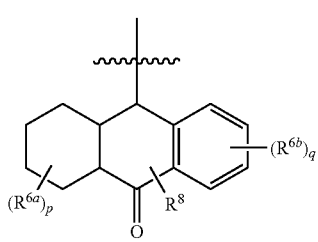
formula (4a-18)
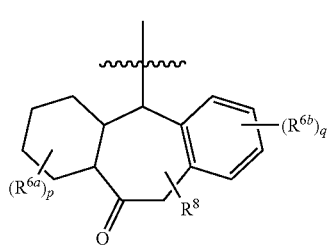
formula (4a-19)
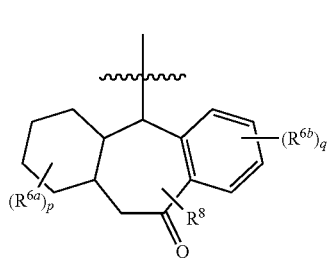
formula (4a-20)
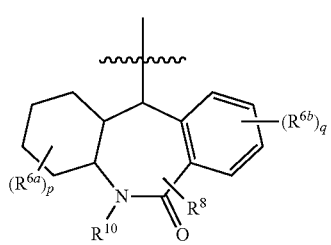
formula (4a-21)
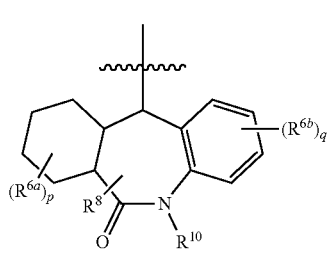
formula (4a-22)
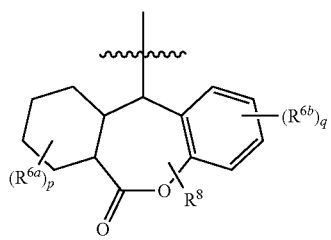
formula (4a-23)
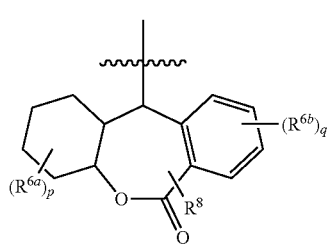
formula (4a-24)
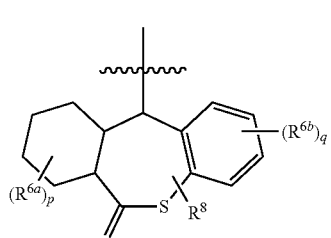
formula (4a-25)
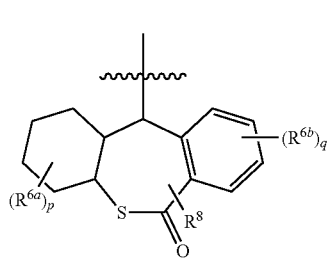
formula (4a-26)
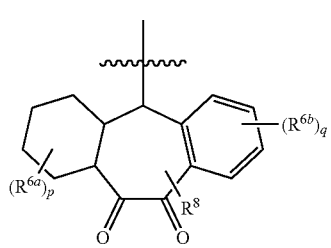
formula (4a-27)
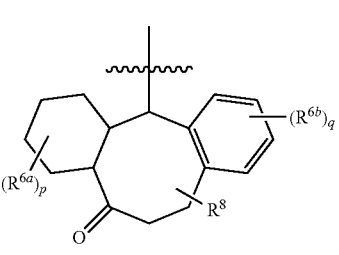

formula (4a-28)
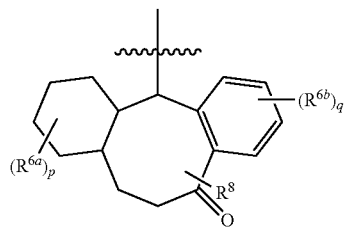
formula (4a-29)
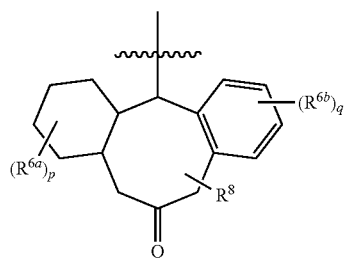
formula (4a-30)
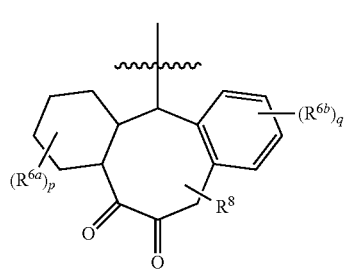
formula (4a-31)
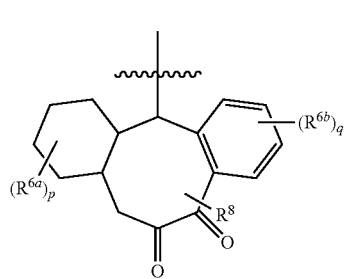
formula (4a-32)
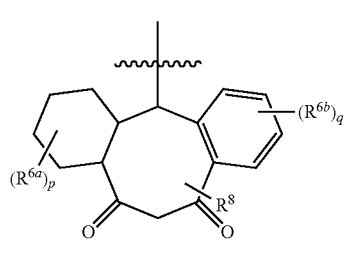
formula (4b-1)
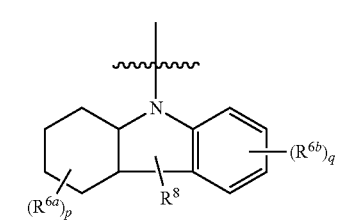
formula (4b-2)
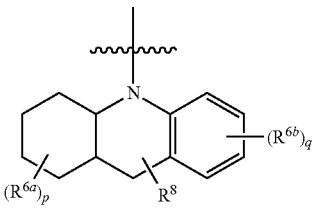
formula (4b-3)
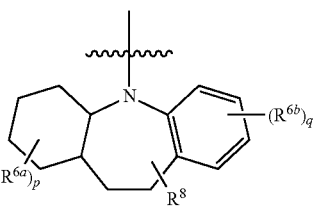
formula (4b-4)
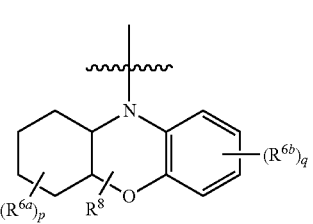
formula (4b-5)
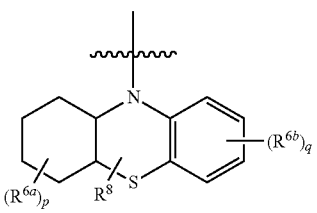
formula (4b-6)
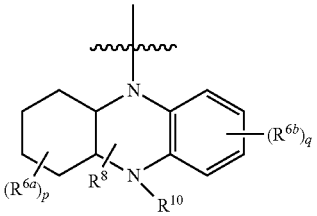
formula (4b-7)
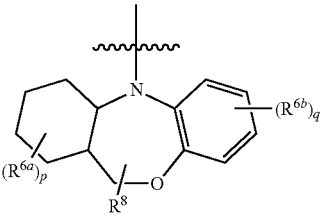
formula (4b-8)
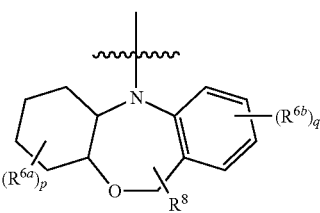

formula (4b-9)

formula (4b-10)

formula (4b-11)

formula (4b-12)

formula (4b-13)

formula (4b-14)

formula (4b-15)

或;

formula (4b-16)

formula (4b-17)

formula (4b-18)

formula (4b-19)

formula (4b-20)

formula (4b-21)

-continued formula (4b-22)
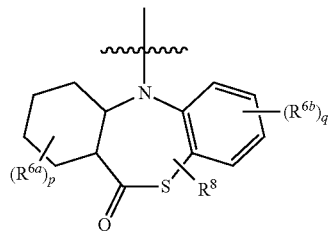

formula (4b-23)
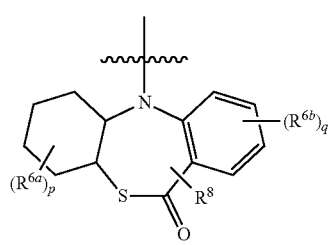

formula (4b-24)
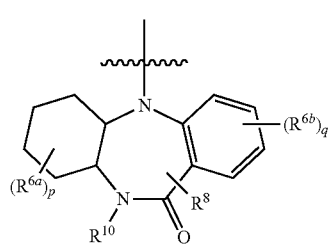

formula (4b-25)
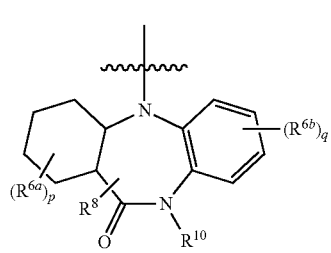

formula (4b-26)
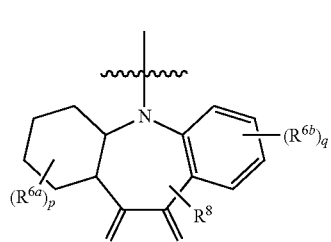

formula (4b-27)
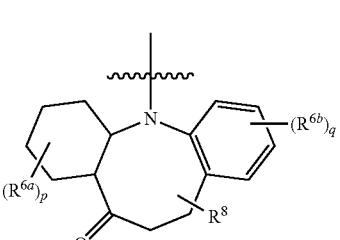

-continued formula (4b-28)
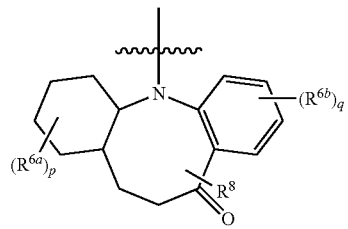

formula (4b-29)
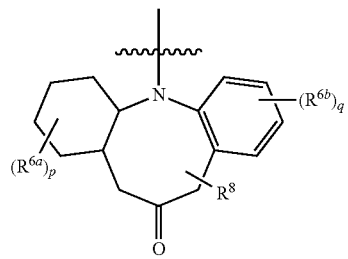

formula (4b-30)
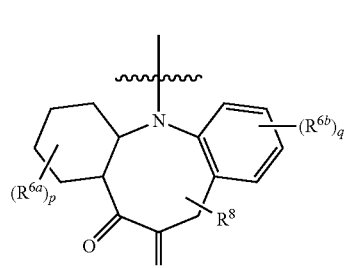

formula (4b-31)
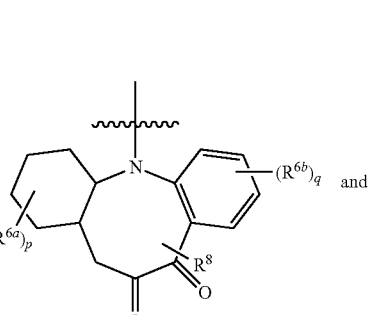
and formula (4b-32)
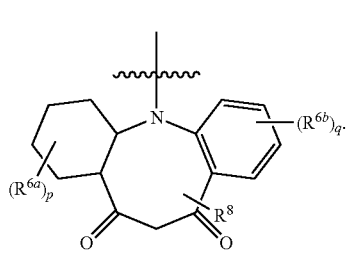

8. The compound according to claim 6, or a pharmaceutically acceptable salt, ester, stereoisomer, polymorph, solvate, N-oxide, isotopically labeled compound, or prodrug thereof, wherein the structure of formula (a) is a group having a structure of formula (5):

formula (5)

wherein, one or two of the bonds "=====" identified by a, b, and c represent a double bond, and the rest represent a single bond;

and/or the structure of formula (b) is a group having a structure of formula (6):

formula (6)

wherein, one or two of the bonds "=====" identified by t, u and v represent a double bond, and the rest represent a single bond.

9. The compound according to claim 1, or a pharmaceutically acceptable salt, ester, stereoisomer, polymorph, solvate, N-oxide, isotopically labeled compound, or prodrug thereof, wherein the compound has a structure of formula (IIa)

formula (IIb)

or formula (IId)

wherein the above $R^{1a}$, $R^{1b}$, $R^{2a}$, $R^{2b}$, $X^1$, $X^2$, $R^3$, $R^4$, $R^{10}$, Y and Z, at each occurrence, are each independently as defined in claim 1; and wherein the above $R^{5a}$, $R^{5b}$, $R^{6a}$, and $R^{6b}$ at each occurrence, are each independently $R^{10}$;

$R^7$ and $R^8$ are each independently absent or $R^{10}$; and m, n, p and q are each independently 0, 1, 2 or 3.

10. The compound according to claim 9, or a pharmaceutically acceptable salt, ester, stereoisomer, polymorph, solvate, N-oxide, isotopically labeled compound, or prodrug thereof, wherein:

$R^3$ is 5- to 6-membered heteroaryl which is optionally selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl; —C(=O)$OR^{11}$; —C(=O)$NR^{11S}$(=O)$_y NR^{11}R^{12}$; —C(=O)$NR^{11}S$(=O)$_y R^{12}$; or —S(=O)$_y NR^{11}C$(=O)$OR^{12}$; and wherein $R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl; and y, at each occurrence, is each independently 2.

11. The compound according to claim 9, or a pharmaceutically acceptable salt, ester, stereoisomer, polymorph, solvate, N-oxide, isotopically labeled compound, or prodrug thereof, wherein $R^3$ is —C(=O)$NR^{11}$—OH; and wherein $R^{11}$ is H, $C_{1-6}$ alkyl, $C_{3-10}$ cyclic hydrocarbyl group, 3- to 10-membered heterocyclic group, $C_{6-10}$ aryl, 5- to 14-membered heteroaryl or $C_{6-12}$ aralkyl.

12. The compound according to claim 9, or a pharmaceutically acceptable salt, ester, stereoisomer, polymorph, solvate, N-oxide, isotopically labeled compound, or prodrug thereof, wherein $R^{10}$ is H, $C_{1-4}$ alkyl, $C_{3-7}$ cyclic hydrocarbyl group, —$OR^{11}$, —$SR^{11}$, —C(=O)$OR^{11}$, or $NR^{11}R^{12}$; and wherein $R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl; and y, at each occurrence, is each independently 2.

13. The compound according to claim 12, or a pharmaceutically acceptable salt, ester, stereoisomer, polymorph, solvate, N-oxide, isotopically labeled compound, or prodrug thereof, wherein $R^{11}$ and $R^{12}$, at each occurrence, are each independently selected from the group consisting of H, $C_{1-4}$ alkyl, $C_{5-7}$ cyclic hydrocarbyl group, 5- to 7-membered monocyclic heterocyclic group, phenyl, and 5- to 6-membered heteroaryl.

14. The compound according to claim 13, or a pharmaceutically acceptable salt, ester, stereoisomer, polymorph, solvate, N-oxide, isotopically labeled compound, or prodrug thereof, wherein $R^{13}$, at each occurrence, is independently selected from the group consisting of F, Cl, Br, I, amino, cyano, nitro, $C_{1-4}$ alkyl, $C_{5-7}$ cyclic hydrocarbyl group, 5- to 7-membered monocyclic heterocyclic group, phenyl, 5- to 6-membered heteroaryl, —$OR^{11}$, —$SR^{11}$, —$OC(=O)R^{11}$, —$C(=O)OR^{11}$, —$C(=O)NR^{11}R^{12}$, —$C(=O)NR^{11}S(=O)_y NR^{11}R^{12}$, —$C(=O)NR^{11}S(=O)_y R^{12}$, —$S(=O)_y OR^{11}$, —$S(=O)_y NR^{11}R^{12}$, —$S(=O)_y NR^{11}C(=O)R^{12}$, —$S(=O)_y NR^{11}C(=O)OR^{12}$, —$C_{1-4}$ alkylene-$OR^{11}$, —$C_{1-4}$ alkylene-$OC(=O)R^{11}$, —$C_{1-4}$ alkylene-$C(=O)OR^{11}$, —$C_{1-4}$ alkylene-$S(=O)_y OR^{11}$, —$C_{1-4}$ alkylene-$OC(=O)NR^{11}R^{12}$, —$C_{1-4}$ alkylene-$C(=O)NR^{11}R^{12}$, —$C_{1-4}$ alkylene-$OS(=O)_y R^{11}$ and —$C_{1-4}$ alkylene-$S(=O)_y NR^{11}R^{12}$; and wherein the alkyl, alkylene, cyclic hydrocarbyl group, heterocyclic group, phenyl and heteroaryl as defined for the substituent $R^{13}$ are optionally further substituted by 1, 2, 3 or more substituents independently selected from the group consisting of F, Cl, Br, I, OH, oxo, amino, cyano, nitro, $C_{1-4}$ alkyl, halogenated $C_{1-4}$ alkyl, $C_{5-6}$ cyclic hydrocarbyl group, 5- to 7-membered monocyclic heterocyclic group, phenyl, and 5- to 6-membered heteroaryl;

wherein $R^{11}$, and $R^{12}$ are as defined in claim 13; and y at each occurrence is 2.

15. The compound according to claim 14, or a pharmaceutically acceptable salt, ester, stereoisomer, polymorph, solvate, N-oxide, isotopically labeled compound, or prodrug thereof, wherein $R^{5a}$, $R^{5b}$, $R^{6a}$ and $R^{6b}$ as well as $R^7$ and $R^8$ are each independently selected from the group consisting of H, $C_{1-6}$ alkyl, $C_{3-10}$ cyclic hydrocarbyl group, $C_{6-10}$ aryl, $OR^{11}$ and —$NR^{11}R^{12}$.

16. The compound according to claim 1, or a pharmaceutically acceptable salt, ester, stereoisomer, polymorph, solvate, N-oxide, isotopically labeled compound, or prodrug thereof, wherein the compound has a structure of

| No. | Structure |
|---|---|
| C1 | |
| C2 | 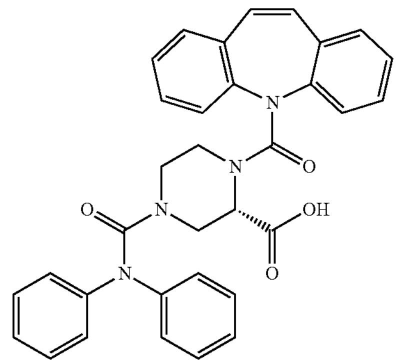 [SMILES: O=C(O)[C@@H]1CN(C(=O)N(c2ccccc2)c2ccccc2)CCN1C(=O)N1c2ccccc2C=Cc2ccccc21] |
| C3 | 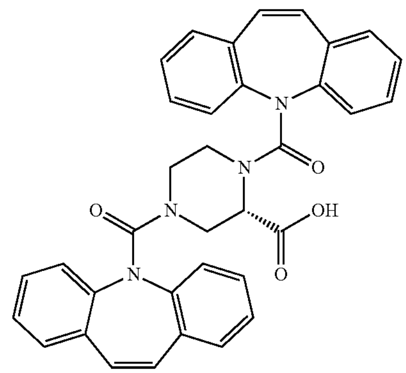 [SMILES: O=C(O)[C@@H]1CN(C(=O)N2c3ccccc3C=Cc3ccccc32)CCN1C(=O)N1c2ccccc2C=Cc2ccccc21] |
| C4 | 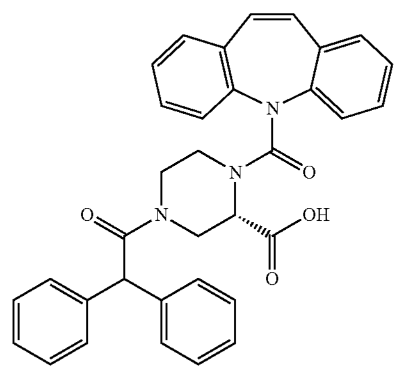 [SMILES: O=C(O)[C@@H]1CN(C(=O)C(c2ccccc2)c2ccccc2)CCN1C(=O)N1c2ccccc2C=Cc2ccccc21] |
| C5 | 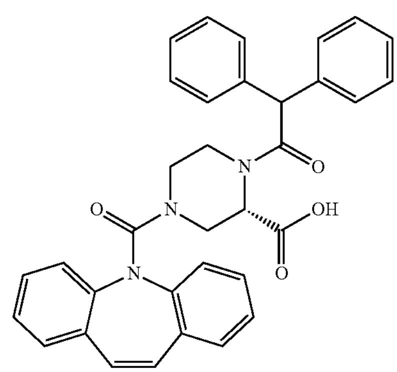 [SMILES: O=C(O)[C@@H]1CN(C(=O)N2c3ccccc3C=Cc3ccccc32)CCN1C(=O)C(c1ccccc1)c1ccccc1] |

| No. | Structure |
|---|---|
| C6 | 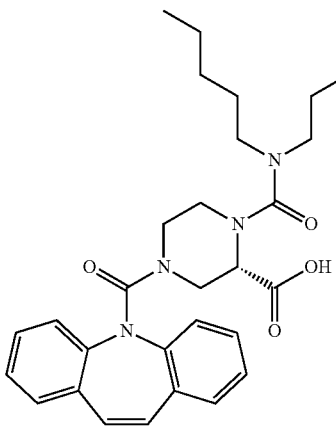 |
| C7 | 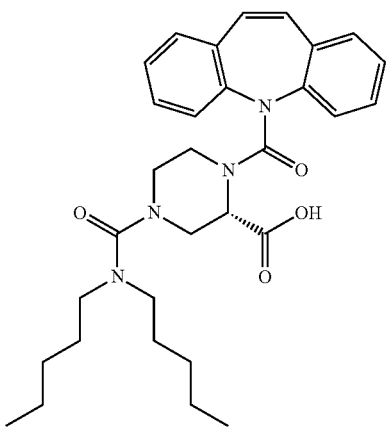 [SMILES: CCCCCN(CCCCC)C(=O)N1CCN(C(=O)N2c3ccccc3C=Cc3ccccc32)[C@H](C(=O)O)C1] |
| C8 | 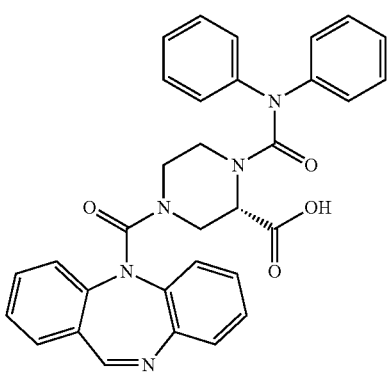 [SMILES: O=C(O)[C@@H]1CN(C(=O)N2c3ccccc3C=Nc3ccccc32)CCN1C(=O)N(c1ccccc1)c1ccccc1] |
| C9 | 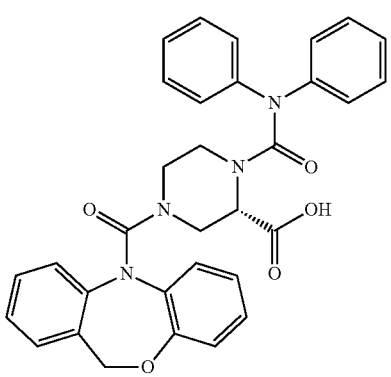 [SMILES: O=C(O)[C@@H]1CN(C(=O)N2c3ccccc3COc3ccccc32)CCN1C(=O)N(c1ccccc1)c1ccccc1] |
| No. | Structure |
|---|---|
| C10 | 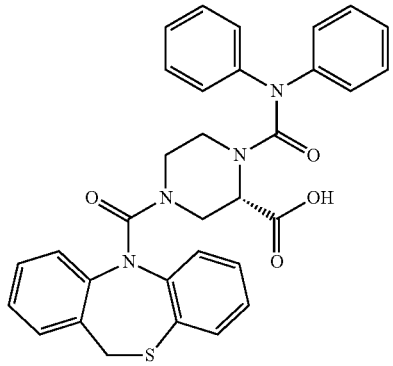 |
| C11 | 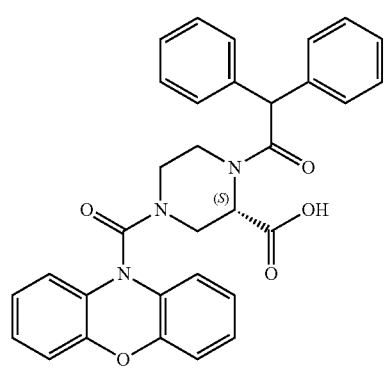 |
| C12 | 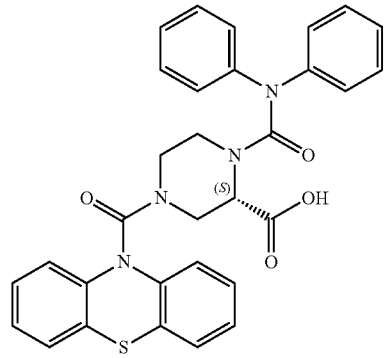 |
| C13 | 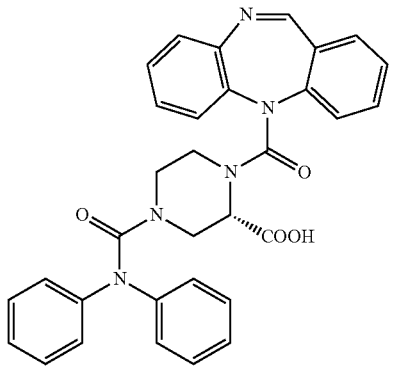 [SMILES: O=C(O)[C@@H]1CN(C(=O)N(c2ccccc2)c2ccccc2)CCN1C(=O)N1c2ccccc2C=Nc2ccccc21] |

| No. | Structure |
|---|---|
| C14 | 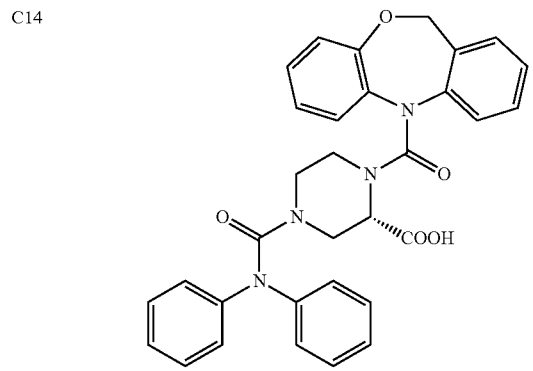 |
| C15 | 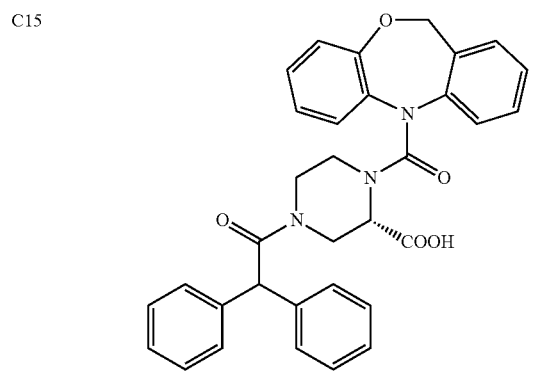 |
| C16 | 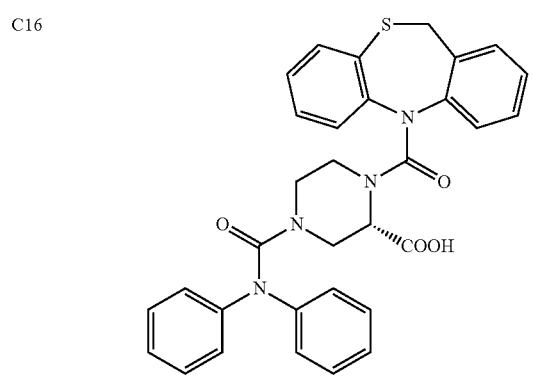 |
| C17 | 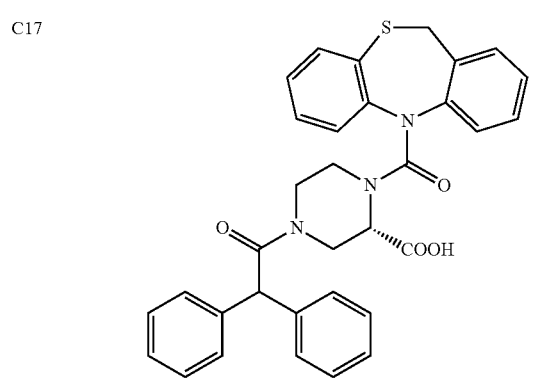 |
| No. | Structure |
|---|---|
| C18 | 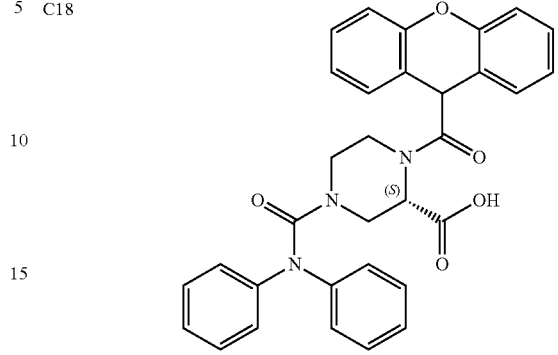 |
| C19 | 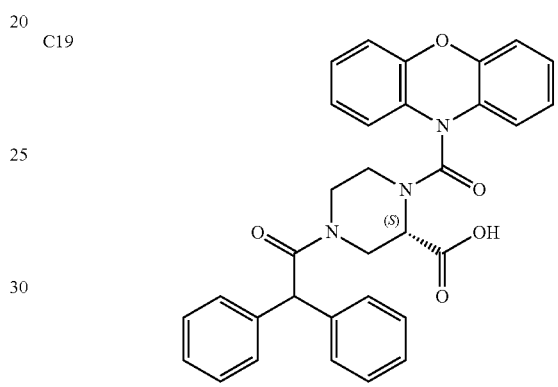 |
| C20 | 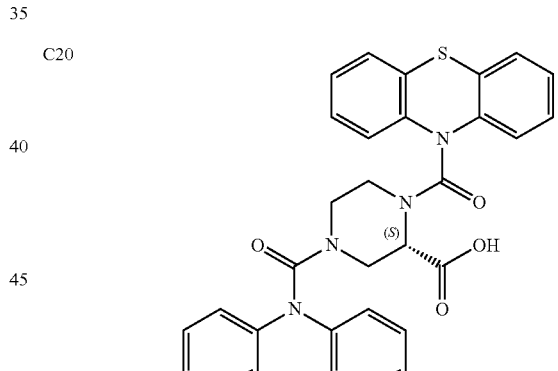 |
| C21 | 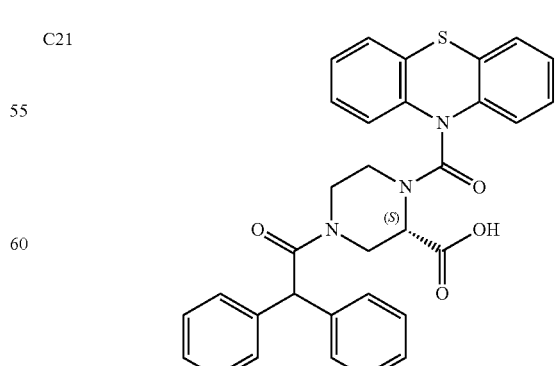 |

| No. | Structure |
|---|---|
| C22 | 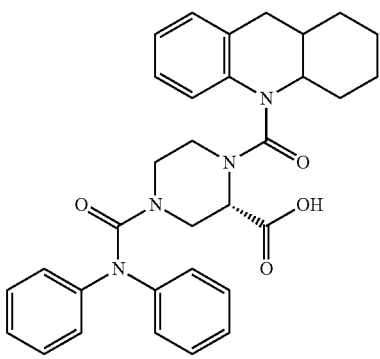 |
| C23 | 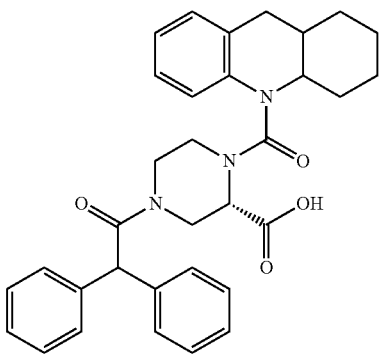 [SMILES: O=C(O)[C@@H]1CN(C(=O)C(c2ccccc2)c2ccccc2)CCN1C(=O)N1c2ccccc2CC2CCCCC21] |
| C24 | 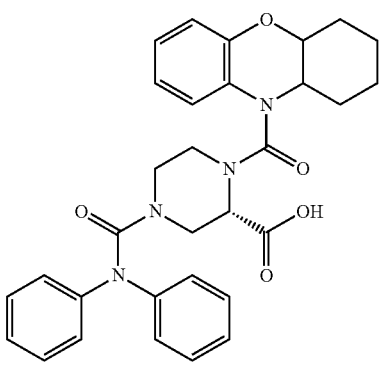 |
| C25 | 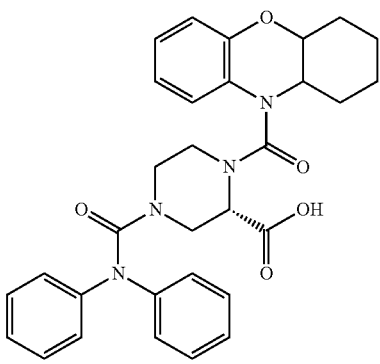 |
| No. | Structure |
|---|---|
| C26 | 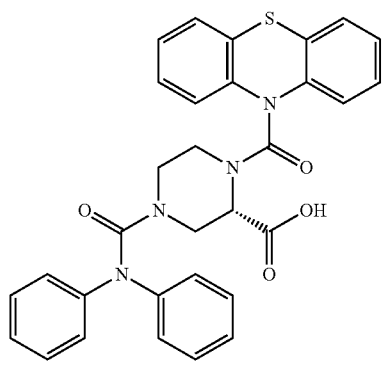 [SMILES: O=C(O)[C@@H]1CN(C(=O)N(c2ccccc2)c2ccccc2)CCN1C(=O)N1c2ccccc2Sc2ccccc21] |
| C27 | 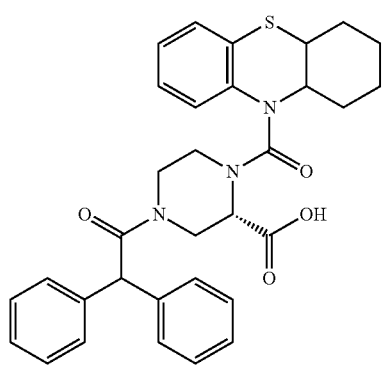 |
| C28 | 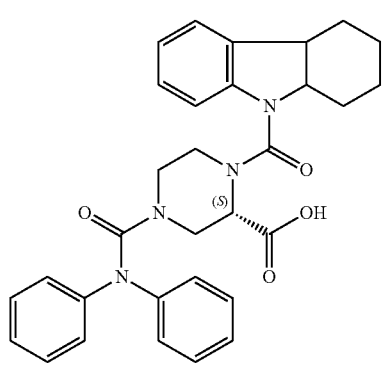 |
| C29 | 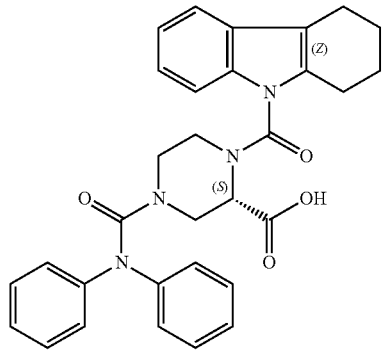 |

-continued
| No. | Structure |
|---|---|
| C30 | 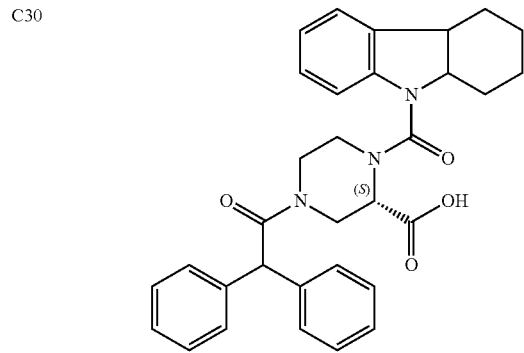 |
| C31 | 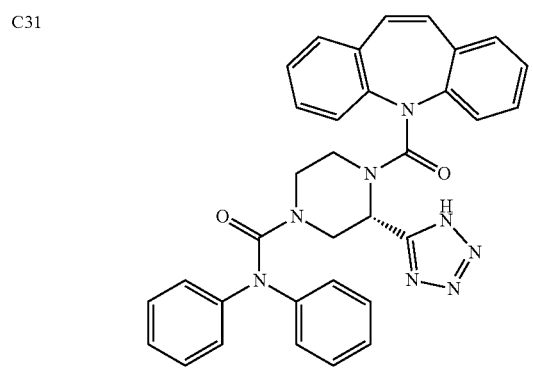 |
| C32 | 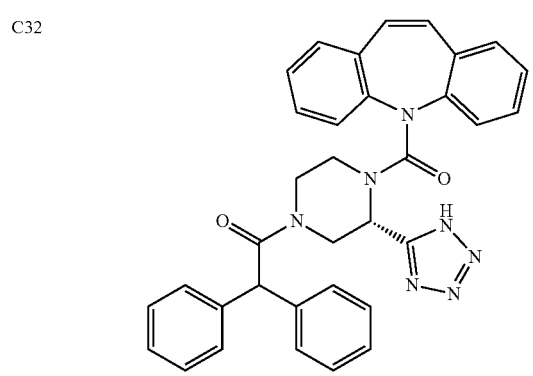 |
| C33 | 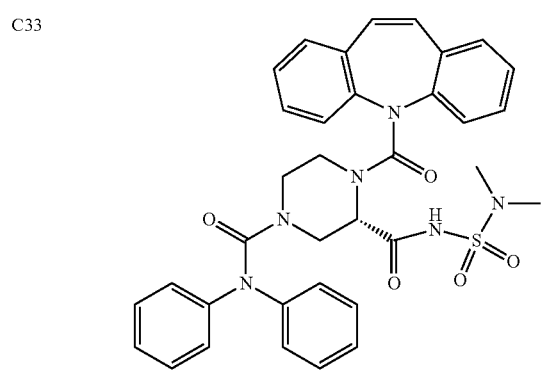 |
-continued
| No. | Structure |
|---|---|
| C34 | 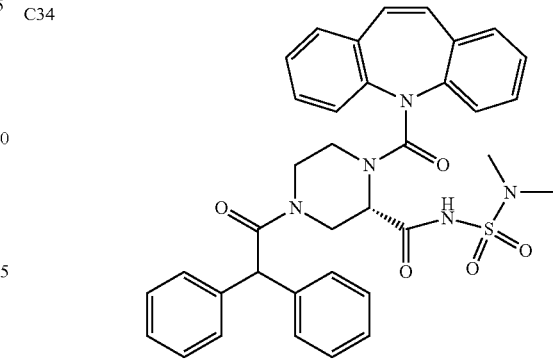 |
| C35 | 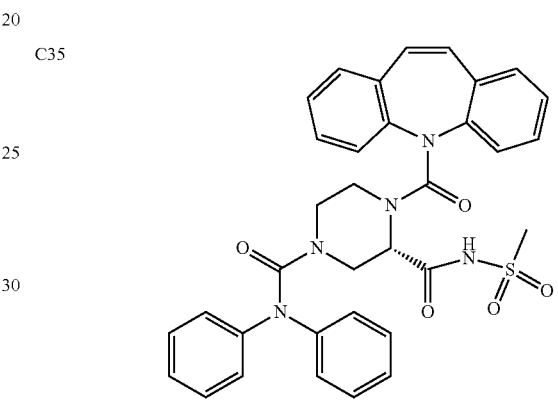 |
| C36 | 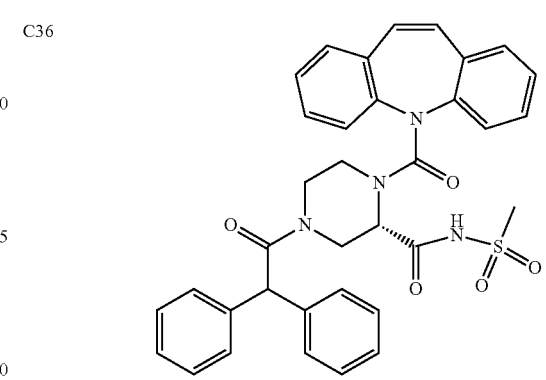 |
| C37 | 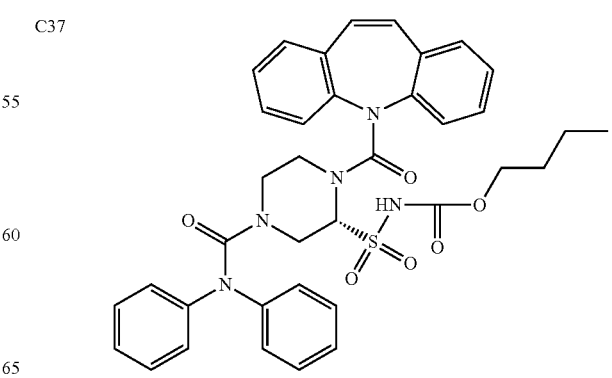 |

| No. | Structure |
|---|---|
| C38 | 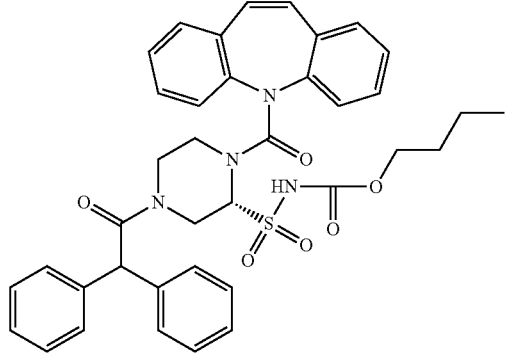 [SMILES: CCCCOC(=O)NS(=O)(=O)[C@@H]1CN(C(=O)C(c2ccccc2)c2ccccc2)CCN1C(=O)N1c2ccccc2C=Cc2ccccc21] |
| C39 | 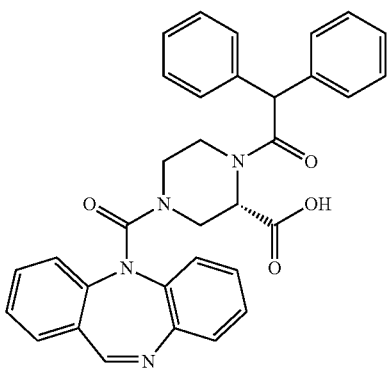 [SMILES: O=C(O)[C@@H]1CN(C(=O)N2c3ccccc3C=Nc3ccccc32)CCN1C(=O)C(c1ccccc1)c1ccccc1] |
| C40 | 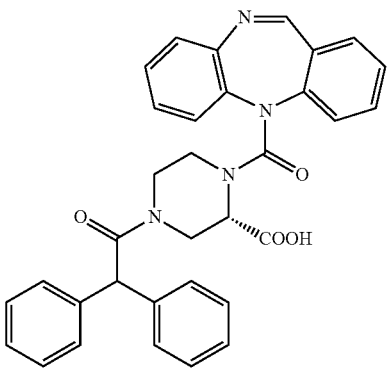 [SMILES: O=C(O)[C@@H]1CN(C(=O)C(c2ccccc2)c2ccccc2)CCN1C(=O)N1c2ccccc2C=Nc2ccccc21] |
| C41 | 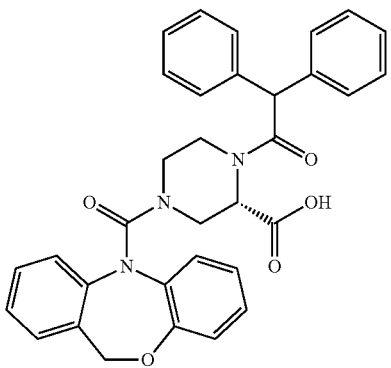 |
| No. | Structure |
|---|---|
| C42 | 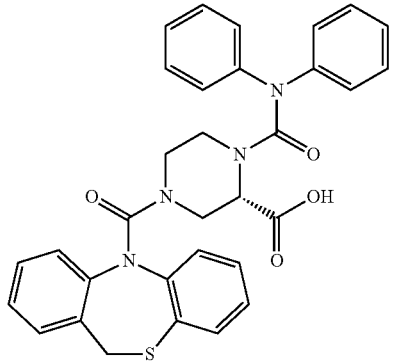 |
| C43 | 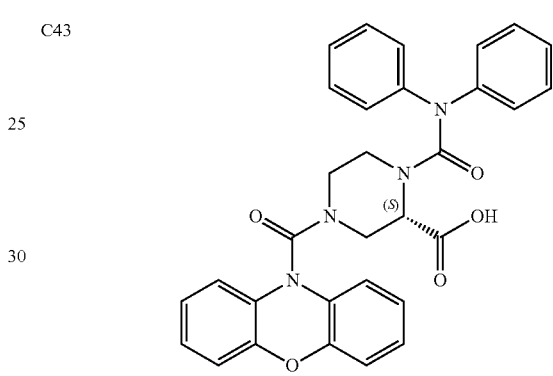 |
| C44 | 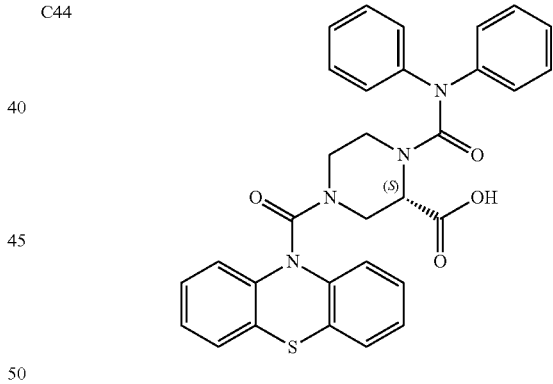 |
| C45 | 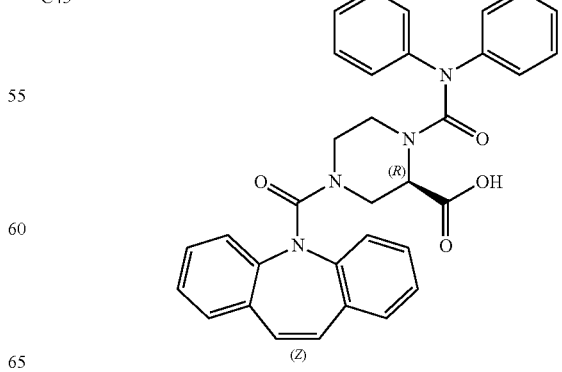 |

-continued

| No. | Structure |
|---|---|
| C46 | (structure: dibenzazepine-N-C(=O)-piperazine(R)-COOH with N'-C(=O)-N(phenyl)₂, (Z)) |
| C47 | (structure: dibenzazepine-N-C(=O)-piperazine-COOH with N'-Cbz (benzyloxycarbonyl)) |
| C48 | (structure: 2-phenylpropanoyl-piperazine-COOH with N'-C(=O)-N-dibenzazepine) |
| C49 | (structure: dibenzazepine-N-C(=O)-piperazine-COOH with N'-C(=O)-NH-CH₂-phenyl) |
| C50 | (structure: 10-OMe-dibenzazepine-N-C(=O)-piperazine-COOH with N'-C(=O)-N(phenyl)₂) |
| C51 | (structure: 10-Cl-dibenzazepine-N-C(=O)-piperazine-COOH with N'-C(=O)-N(phenyl)₂) |
| C52 | (structure: dibenzazepine-epoxide-N-C(=O)-piperazine-COOH with N'-C(=O)-N(phenyl)₂) |

| No. | Structure |
|---|---|
| C53 | 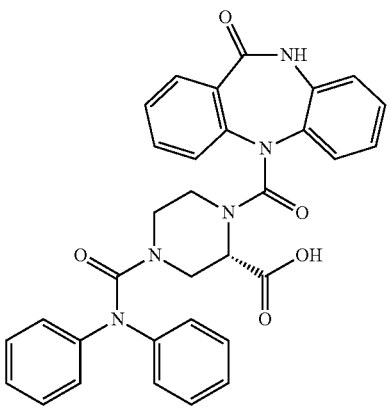 [SMILES: O=C1Nc2ccccc2N(C(=O)N2CCN(C(=O)N(c3ccccc3)c3ccccc3)C[C@H]2C(=O)O)c2ccccc21] |
| C54 | 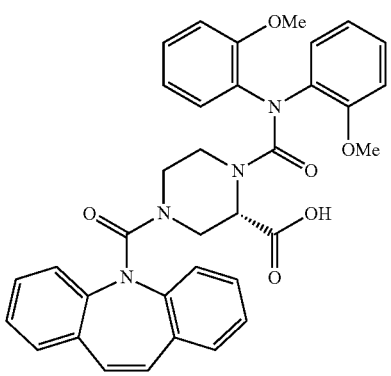 [SMILES: COc1ccccc1N(C(=O)N1CCN(C(=O)N2c3ccccc3C=Cc3ccccc32)C[C@H]1C(=O)O)c1ccccc1OC] |
| C55 | 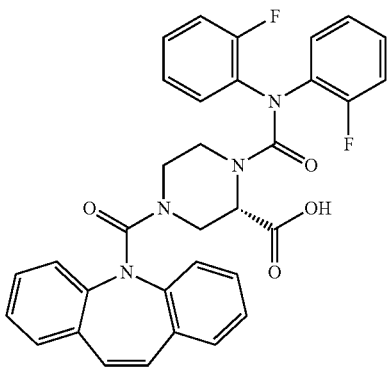 [SMILES: O=C(O)[C@@H]1CN(C(=O)N2c3ccccc3C=Cc3ccccc32)CCN1C(=O)N(c1ccccc1F)c1ccccc1F] |
| C56 | 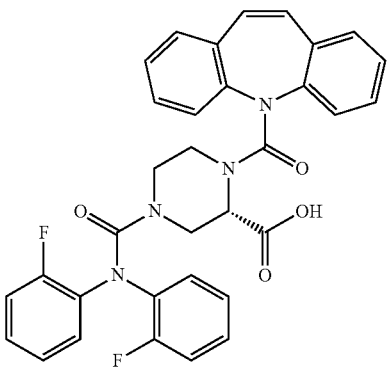 [SMILES: O=C(O)[C@@H]1CN(C(=O)N(c2ccccc2F)c2ccccc2F)CCN1C(=O)N1c2ccccc2C=Cc2ccccc21] |
| C57 | 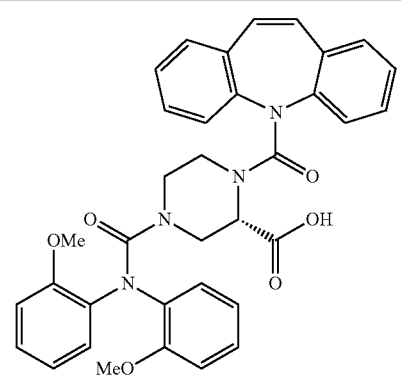 [SMILES: COc1ccccc1N(C(=O)N1CCN(C(=O)N2c3ccccc3C=Cc3ccccc32)[C@H](C(=O)O)C1)c1ccccc1OC] |
| C58 | 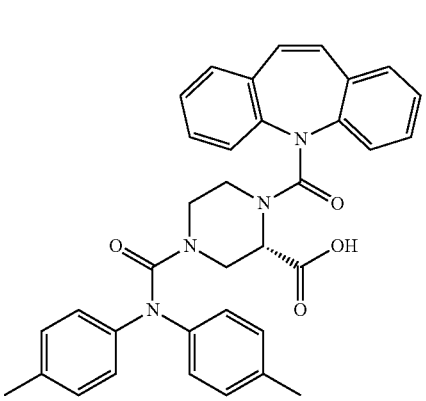 [SMILES: Cc1ccc(N(C(=O)N2CCN(C(=O)N3c4ccccc4C=Cc4ccccc43)[C@H](C(=O)O)C2)c2ccc(C)cc2)cc1] |
| C59 | 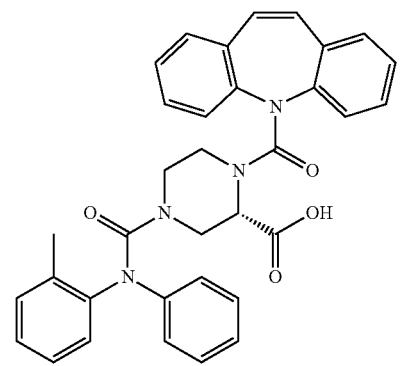 [SMILES: Cc1ccccc1N(C(=O)N1CCN(C(=O)N2c3ccccc3C=Cc3ccccc32)[C@H](C(=O)O)C1)c1ccccc1] |
| C60 | 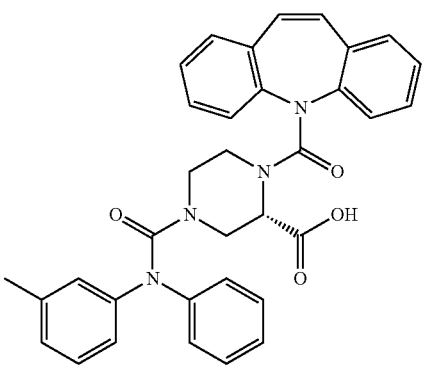 [SMILES: Cc1cccc(N(C(=O)N2CCN(C(=O)N3c4ccccc4C=Cc4ccccc43)[C@H](C(=O)O)C2)c2ccccc2)c1] |

| No. | Structure |
|---|---|
| C61 | 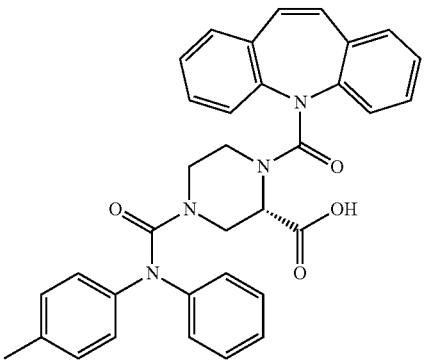 [SMILES: Cc1ccc(N(C(=O)N2CCN(C(=O)N3c4ccccc4C=Cc4ccccc43)[C@H](C(=O)O)C2)c2ccccc2)cc1] |
| C62 | 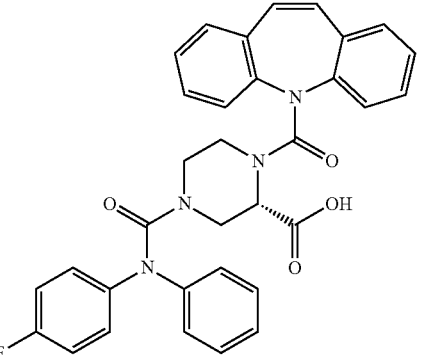 |
| C63 | 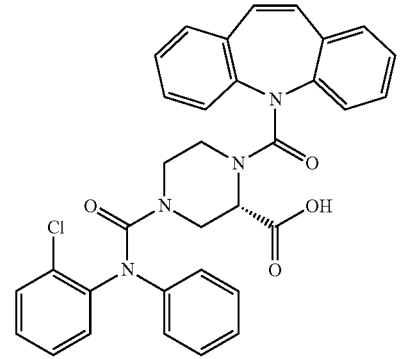 [SMILES: O=C(O)[C@@H]1CN(C(=O)N(c2ccccc2)c2ccccc2Cl)CCN1C(=O)N1c2ccccc2C=Cc2ccccc21] |
| C64 | 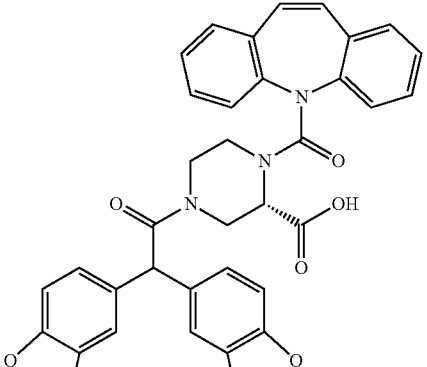 |
| C65 | 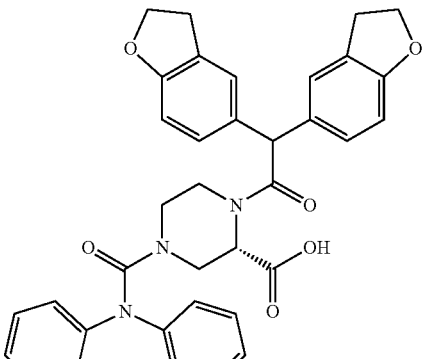 |
| C66 | 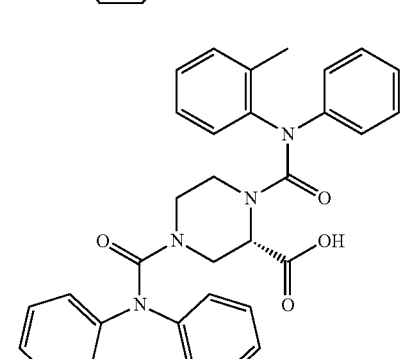 |
| C67 | 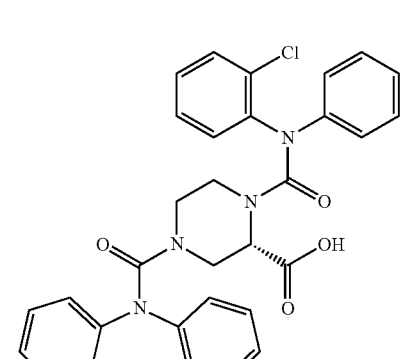 |
| C68 | 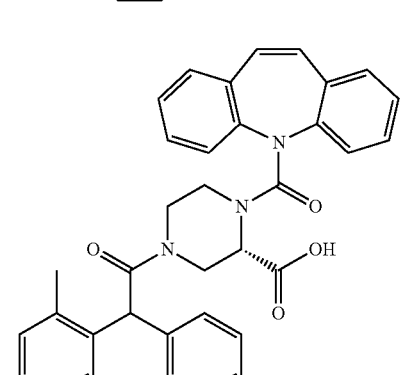 |

-continued
| No. | Structure |
|---|---|
| C69 | 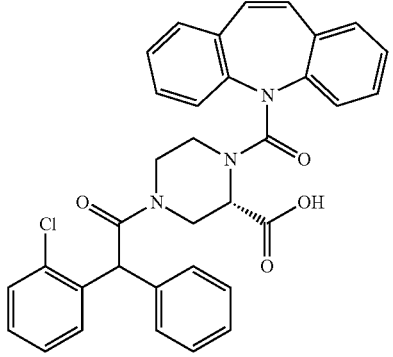 [SMILES: O=C(O)[C@@H]1CN(C(=O)C(c2ccccc2)c2ccccc2Cl)CCN1C(=O)N1c2ccccc2C=Cc2ccccc21] |
| C70 | 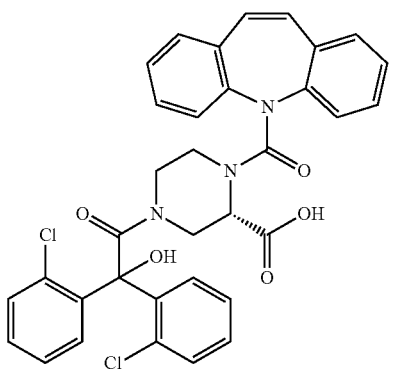 [SMILES: O=C(O)[C@@H]1CN(C(=O)C(O)(c2ccccc2Cl)c2ccccc2Cl)CCN1C(=O)N1c2ccccc2C=Cc2ccccc21] |
| C71 | 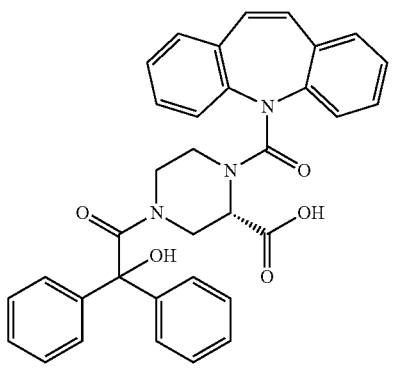 |
| C72 | 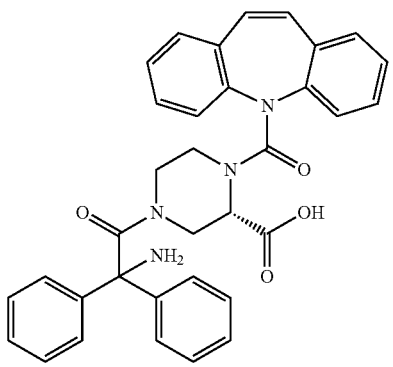 |
-continued
| No. | Structure |
|---|---|
| C73 | 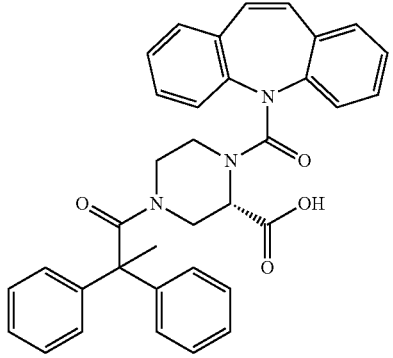 [SMILES: CC(C(=O)N1CCN(C(=O)N2c3ccccc3C=Cc3ccccc32)[C@H](C(=O)O)C1)(c1ccccc1)c1ccccc1] |
| C74 | 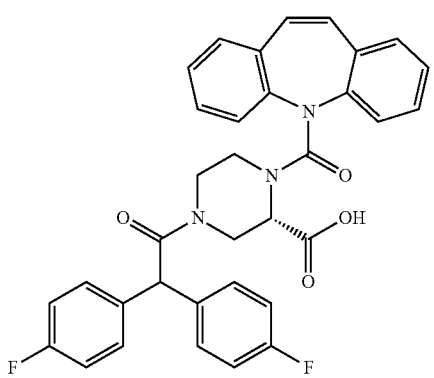 [SMILES: O=C(O)[C@@H]1CN(C(=O)C(c2ccc(F)cc2)c2ccc(F)cc2)CCN1C(=O)N1c2ccccc2C=Cc2ccccc21] |
| C75 | 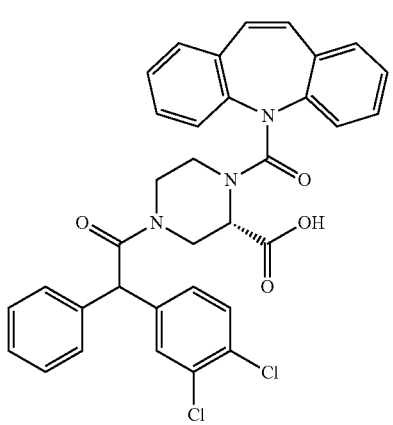 [SMILES: O=C(O)[C@@H]1CN(C(=O)C(c2ccccc2)c2ccc(Cl)c(Cl)c2)CCN1C(=O)N1c2ccccc2C=Cc2ccccc21] |
| C76 | 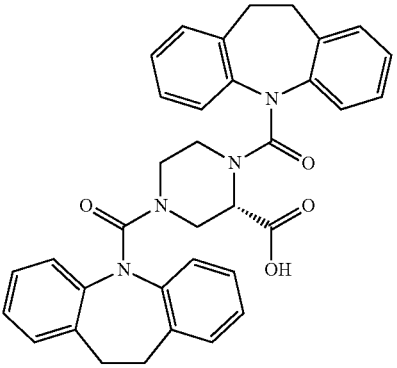 [SMILES: O=C(O)[C@@H]1CN(C(=O)N2c3ccccc3CCc3ccccc32)CCN1C(=O)N1c2ccccc2CCc2ccccc21] |

-continued
| No. | Structure |
|---|---|
| C77 | 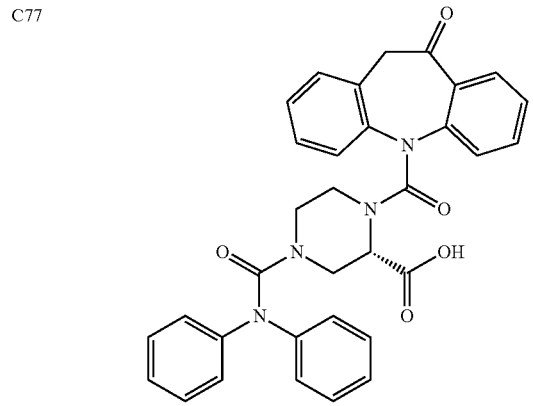 |
| C78 | 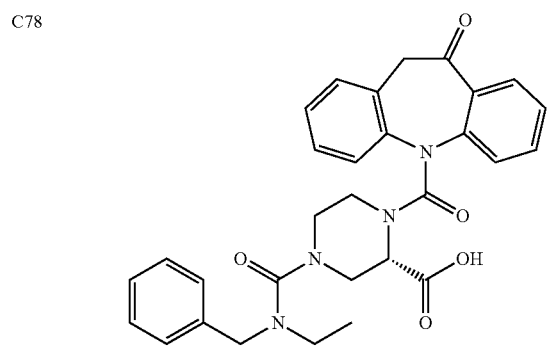 |
| C79 | 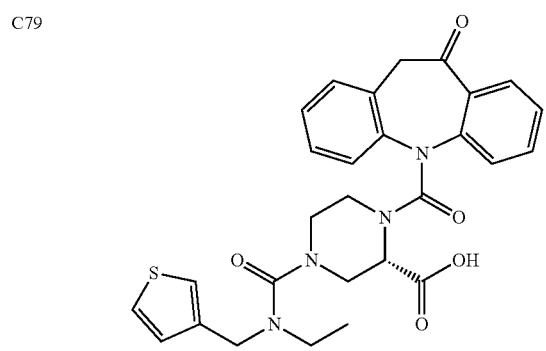 |
| C80 | 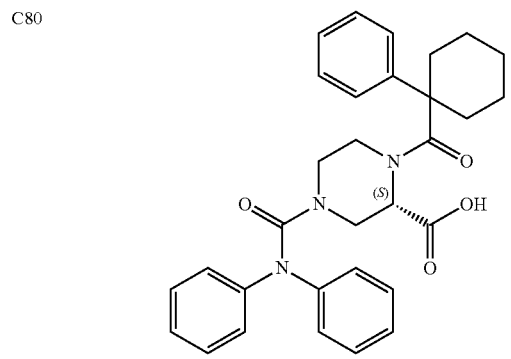 |
-continued
| No. | Structure |
|---|---|
| C81 | 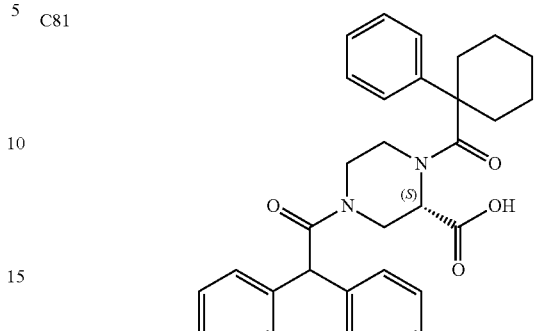 |
| C82 | 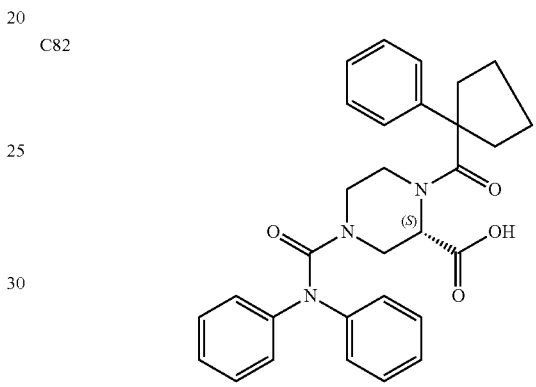 |
| C83 | 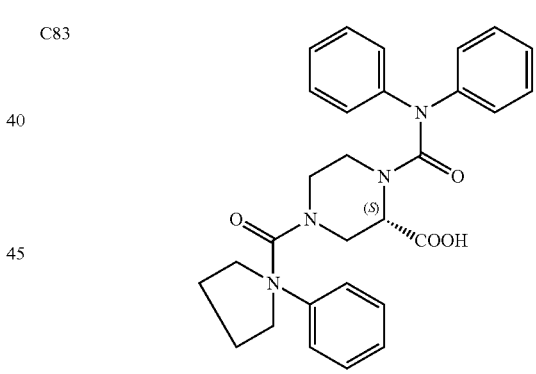 |
| C84 | 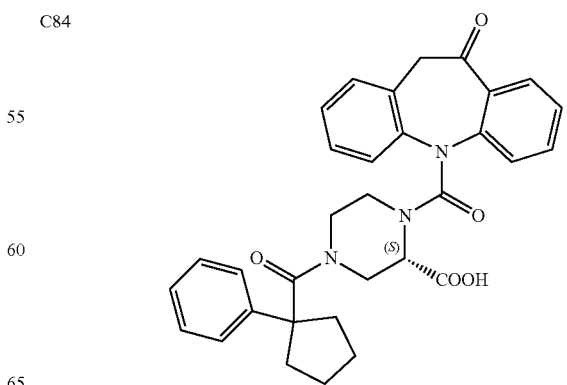 |

| No. | Structure |
|---|---|
| C85 | 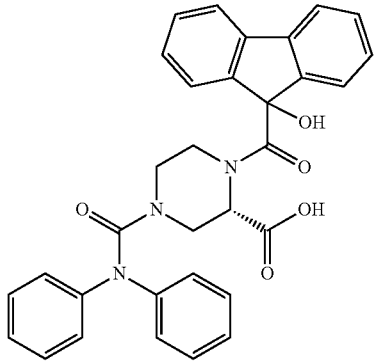 [SMILES: O=C(O)[C@@H]1CN(C(=O)N(c2ccccc2)c2ccccc2)CCN1C(=O)C1(O)c2ccccc2-c2ccccc21] |
| C86 | 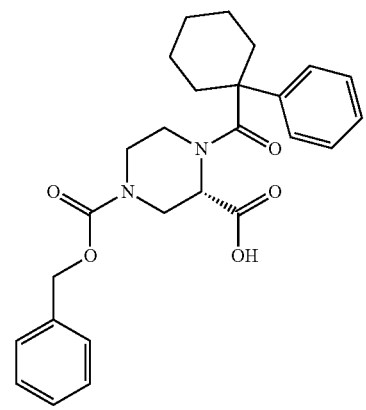 [SMILES: O=C(O)[C@@H]1CN(C(=O)OCc2ccccc2)CCN1C(=O)C1(c2ccccc2)CCCCC1] |
| C87 | 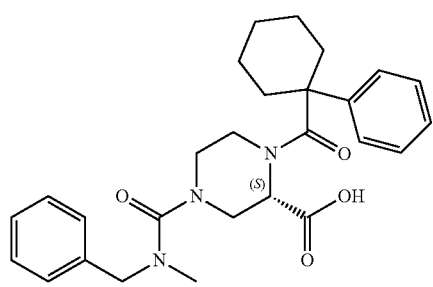 |
| C88 | 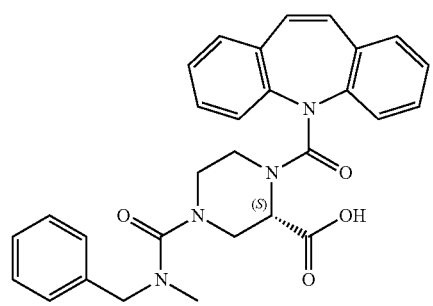 |
| No. | Structure |
|---|---|
| C89 | 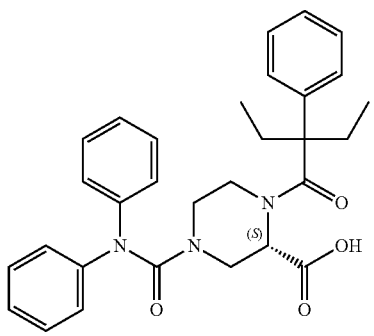 |
| C90 | 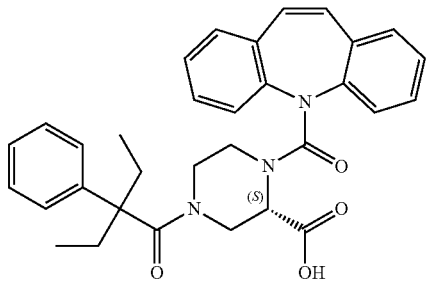 |
| C91 | 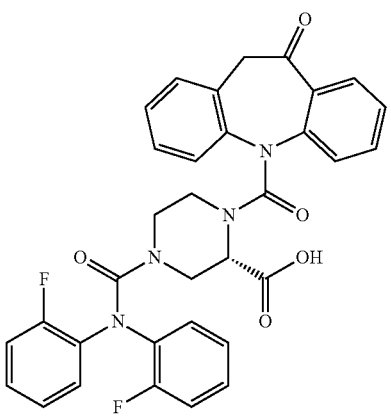 [SMILES: O=C1Cc2ccccc2N(C(=O)N2CCN(C(=O)N(c3ccccc3F)c3ccccc3F)C[C@H]2C(=O)O)c2ccccc21] |
| C92 | 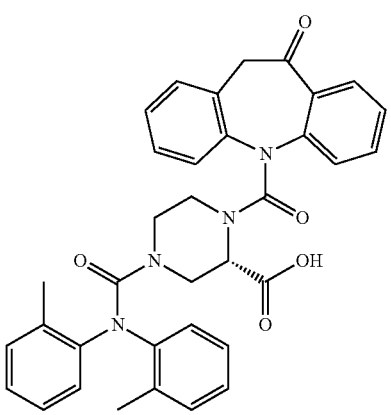 [SMILES: Cc1ccccc1N(C(=O)N1CCN(C(=O)N2c3ccccc3CC(=O)c3ccccc32)[C@H](C(=O)O)C1)c1ccccc1C] |

TABLE-continued
| No. | Structure |
|---|---|
| C93 | 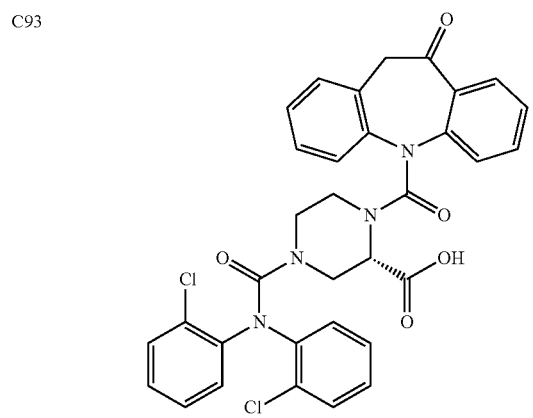 |
| C94 | 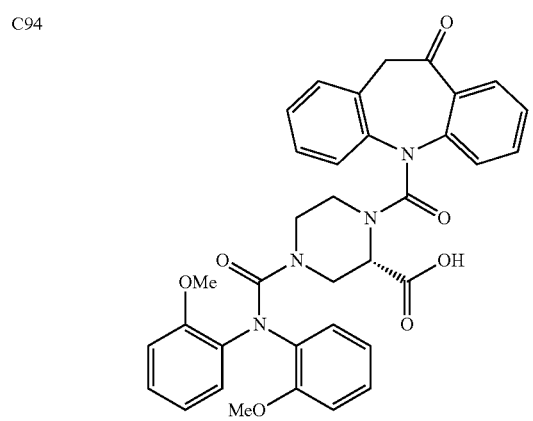 |
| C95 | 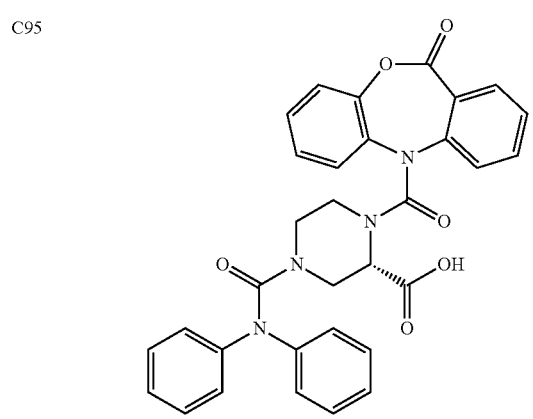 |
| C96 | 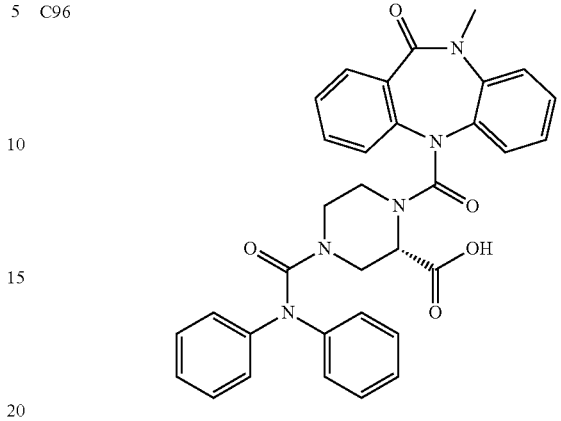 |
| C97 | 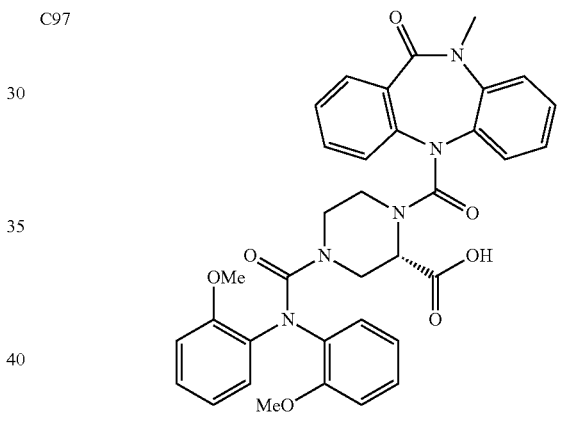 |
| C98 | 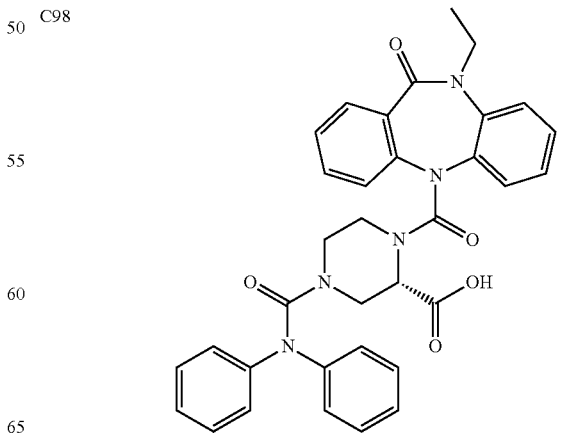 |

-continued
| No. | Structure |
|---|---|
| C99 | 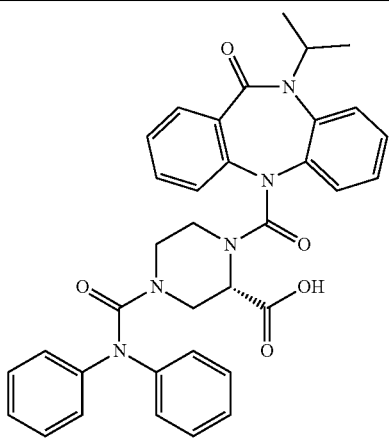 |
| C100 | 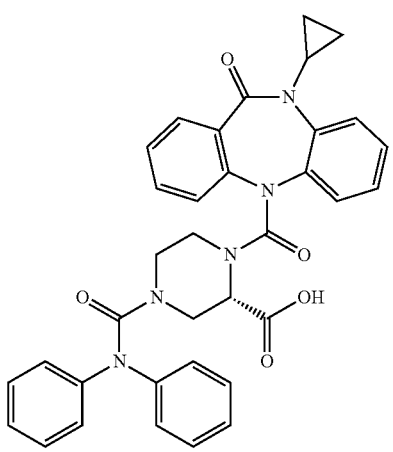 [SMILES: O=C(O)[C@@H]1CN(C(=O)N(c2ccccc2)c2ccccc2)CCN1C(=O)N1c2ccccc2C(=O)N(C2CC2)c2ccccc21] |
| C101 | 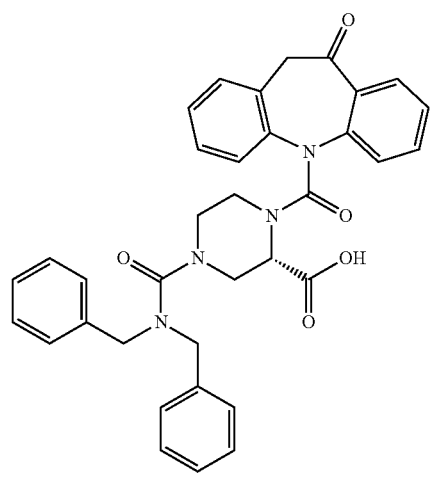 [SMILES: O=C1Cc2ccccc2N(C(=O)N2CCN(C(=O)N(Cc3ccccc3)Cc3ccccc3)C[C@H]2C(=O)O)c2ccccc21] |
-continued
| No. | Structure |
|---|---|
| C102 | 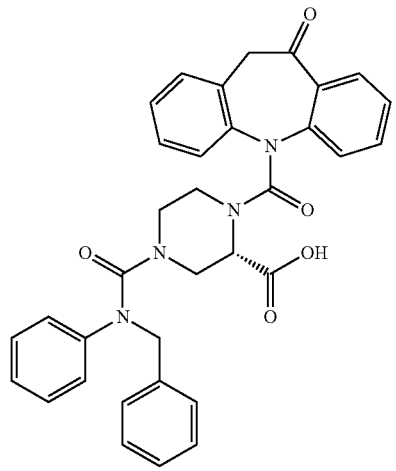 [SMILES: O=C1Cc2ccccc2N(C(=O)N2CCN(C(=O)N(Cc3ccccc3)c3ccccc3)C[C@H]2C(=O)O)c2ccccc21] |
| C103 | 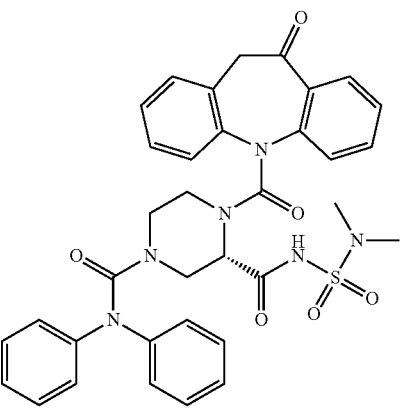 [SMILES: CN(C)S(=O)(=O)NC(=O)[C@@H]1CN(C(=O)N(c2ccccc2)c2ccccc2)CCN1C(=O)N1c2ccccc2CC(=O)c2ccccc21] |
| C104 | 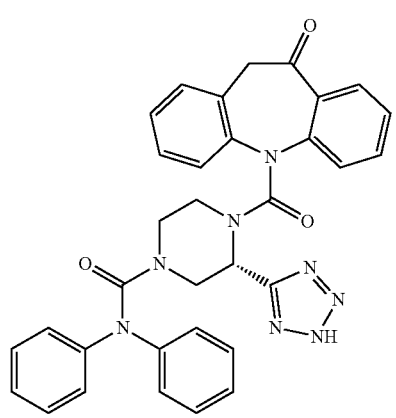 [SMILES: O=C1Cc2ccccc2N(C(=O)N2CCN(C(=O)N(c3ccccc3)c3ccccc3)C[C@H]2c2nn[nH]n2)c2ccccc21] |

-continued
| No. | Structure |
|---|---|
| C105 | 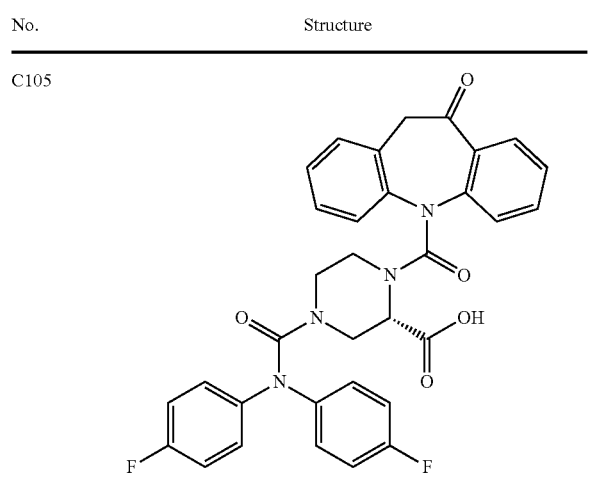 |
| C106 | 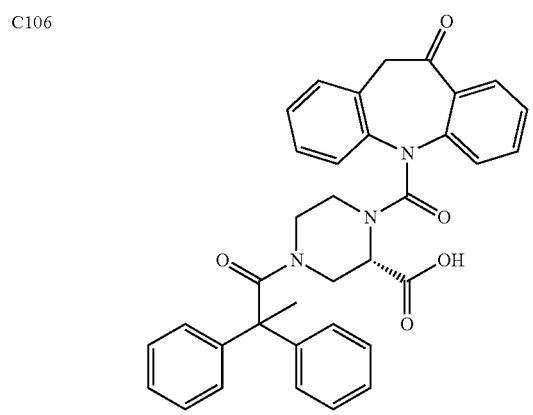 |
| C107 | 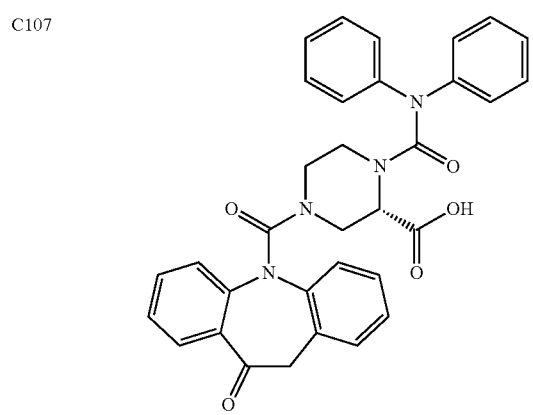 |
-continued
| No. | Structure |
|---|---|
| C108 | 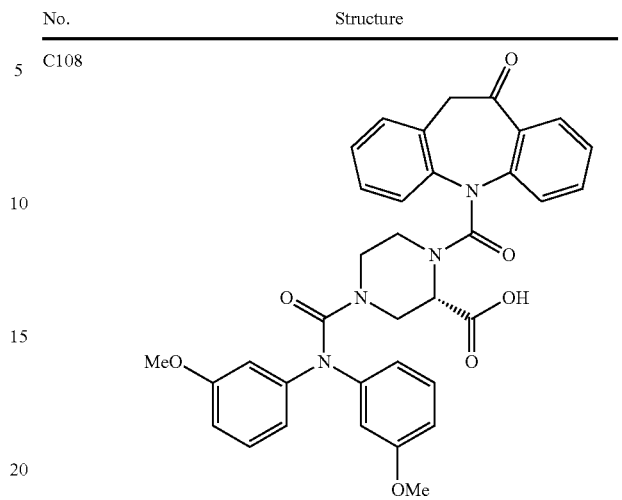 |
| C109 | 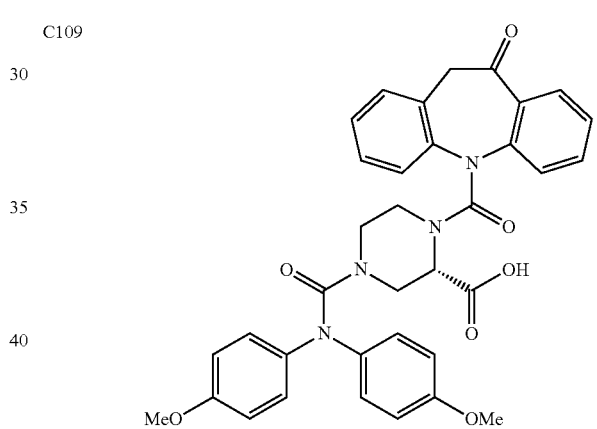 |
| C110 | 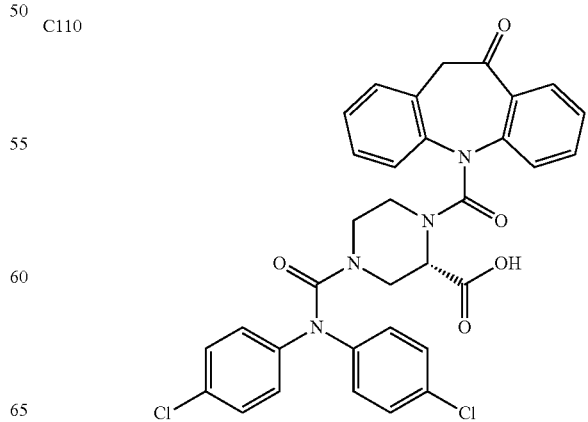 |

-continued
| No. | Structure |
|---|---|
| C111 | 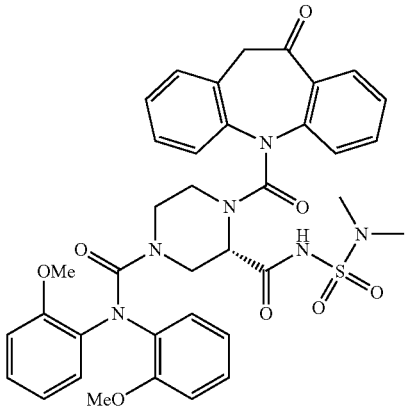 [SMILES: COc1ccccc1N(C(=O)N1CCN(C(=O)N2c3ccccc3CC(=O)c3ccccc32)[C@H](C(=O)NS(=O)(=O)N(C)C)C1)c1ccccc1OC] |
| C112 | 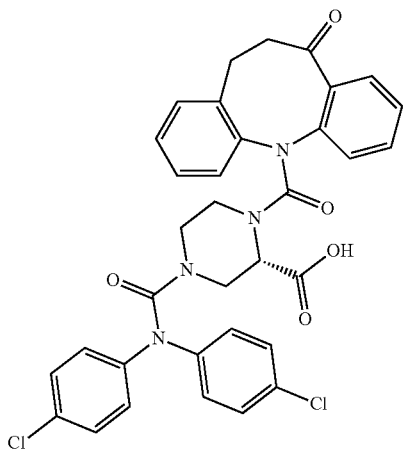 [SMILES: O=C1CCc2ccccc2N(C(=O)N2CCN(C(=O)N(c3ccc(Cl)cc3)c3ccc(Cl)cc3)C[C@H]2C(=O)O)c2ccccc21] |
| C113 | 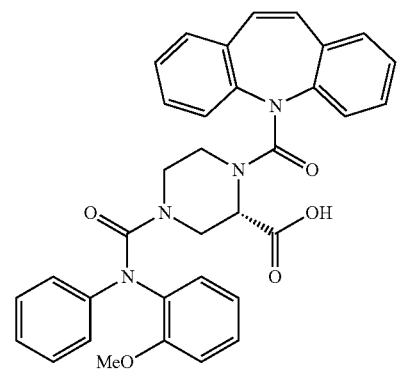 [SMILES: COc1ccccc1N(C(=O)N1CCN(C(=O)N2c3ccccc3C=Cc3ccccc32)[C@H](C(=O)O)C1)c1ccccc1] |
-continued
| No. | Structure |
|---|---|
| C114 | 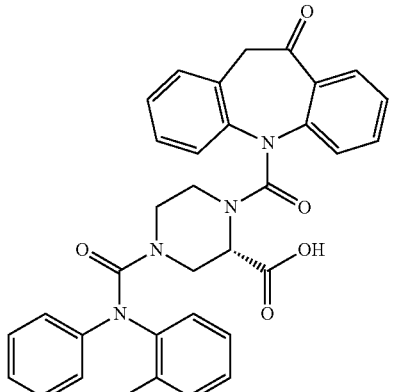 |
| C115 | 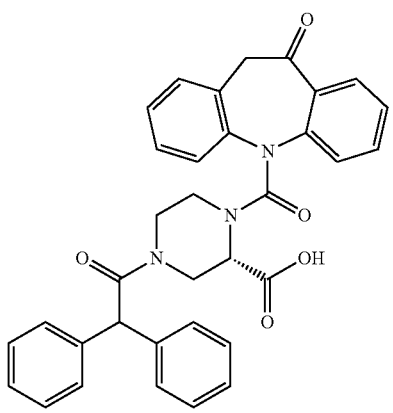 |
| C116 | 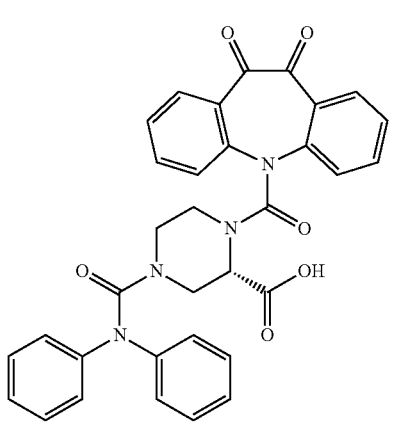 [SMILES: O=C(O)[C@@H]1CN(C(=O)N(c2ccccc2)c2ccccc2)CCN1C(=O)n1c2ccccc2c(=O)c(=O)c2ccccc21] |

-continued
| No. | Structure |
|---|---|
| C117 | 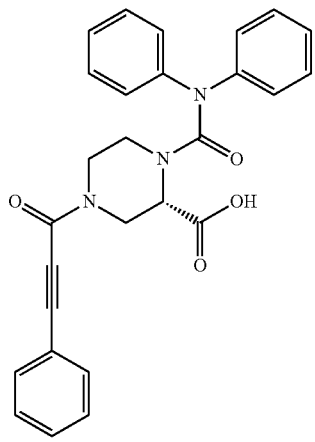 [SMILES: O=C(O)[C@@H]1CN(C(=O)C#Cc2ccccc2)CCN1C(=O)N(c1ccccc1)c1ccccc1] |
| C118 | 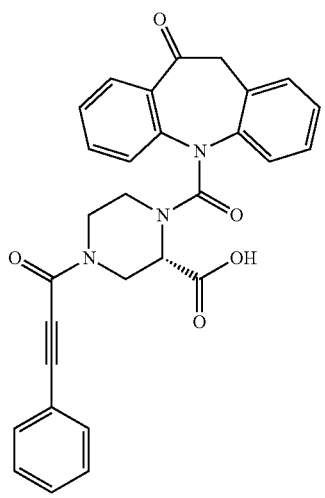 [SMILES: O=C1Cc2ccccc2N(C(=O)N2CCN(C(=O)C#Cc3ccccc3)C[C@H]2C(=O)O)c2ccccc21] |
| C119 | 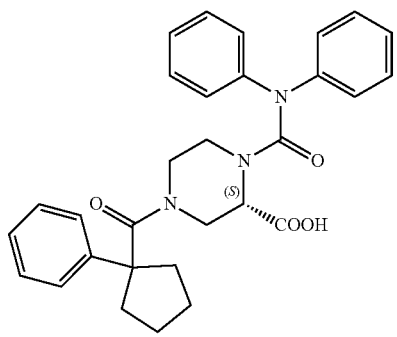 |
-continued
| No. | Structure |
|---|---|
| C120 | 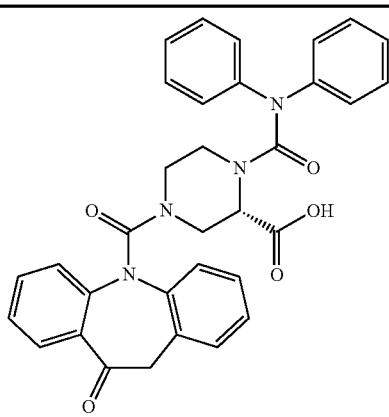 |
| C121 | 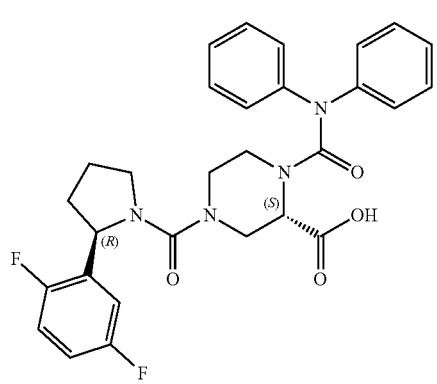 |
| C122 | 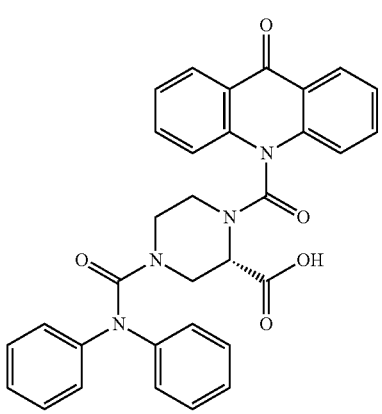 [SMILES: O=C(O)[C@@H]1CN(C(=O)N(c2ccccc2)c2ccccc2)CCN1C(=O)n1c2ccccc2c(=O)c2ccccc21] |
| C123 | 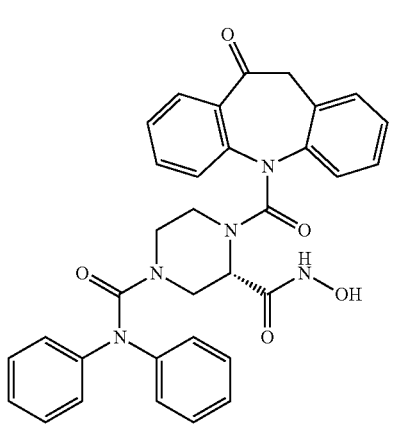 [SMILES: O=C1Cc2ccccc2N(C(=O)N2CCN(C(=O)N(c3ccccc3)c3ccccc3)C[C@H]2C(=O)NO)c2ccccc21] |

| No. | Structure |
|---|---|
| C124 | 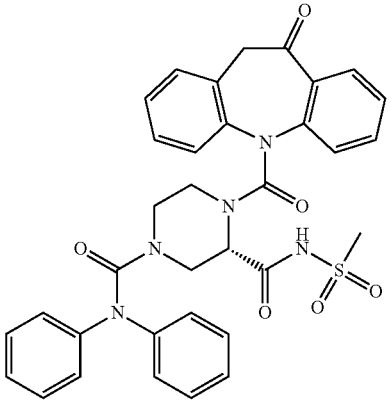 [SMILES: CS(=O)(=O)NC(=O)[C@@H]1CN(C(=O)N(c2ccccc2)c2ccccc2)CCN1C(=O)N1c2ccccc2CC(=O)c2ccccc21] |
| C125 | 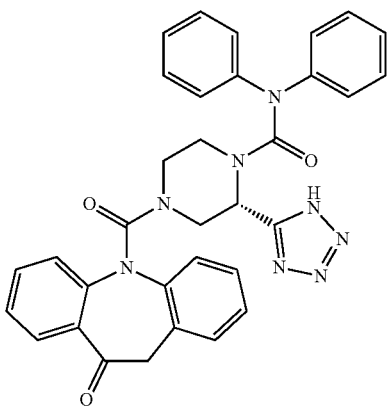 [SMILES: O=C1Cc2ccccc2N(C(=O)N2CCN(C(=O)N(c3ccccc3)c3ccccc3)[C@H](c3nnn[nH]3)C2)c2ccccc21] |
| C126 | 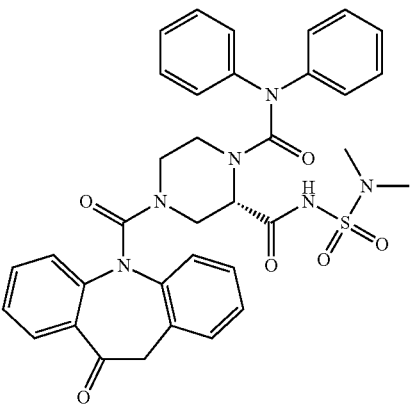 [SMILES: CN(C)S(=O)(=O)NC(=O)[C@@H]1CN(C(=O)N2c3ccccc3CC(=O)c3ccccc32)CCN1C(=O)N(c1ccccc1)c1ccccc1] |
| No. | Structure |
|---|---|
| C127 | 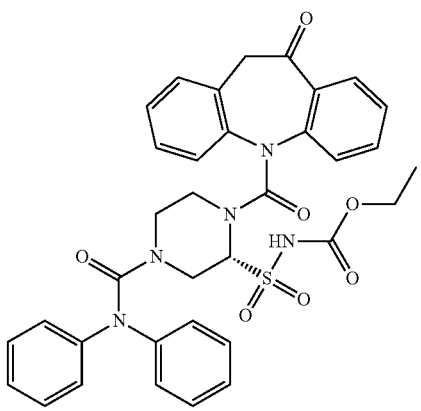 [SMILES: CCOC(=O)NS(=O)(=O)[C@@H]1CN(C(=O)N(c2ccccc2)c2ccccc2)CCN1C(=O)N1c2ccccc2CC(=O)c2ccccc21] |
| C128 | 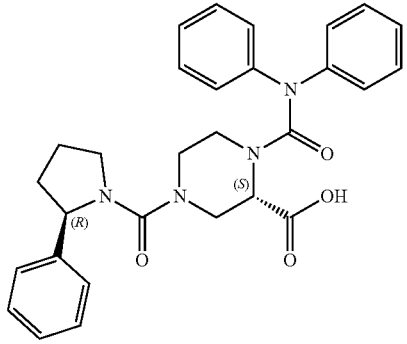 |
| C129 | 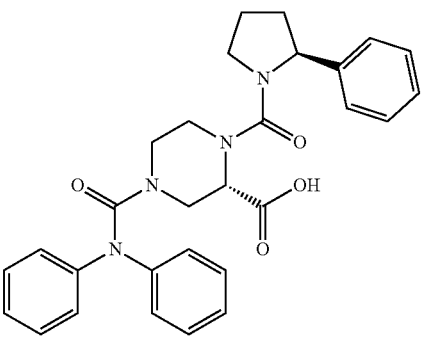 [SMILES: O=C(O)[C@@H]1CN(C(=O)N(c2ccccc2)c2ccccc2)CCN1C(=O)N1CCC[C@H]1c1ccccc1] |
| C130 | 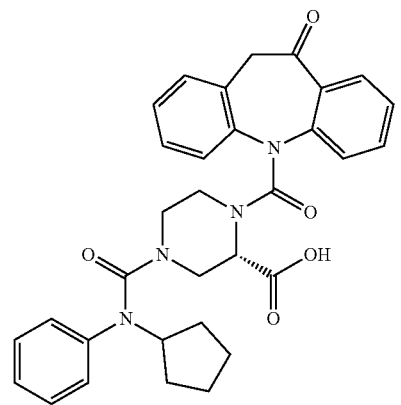 [SMILES: O=C1Cc2ccccc2N(C(=O)N2CCN(C(=O)N(c3ccccc3)C3CCCC3)C[C@H]2C(=O)O)c2ccccc21] |

-continued
| No. | Structure |
|---|---|
| C131 | 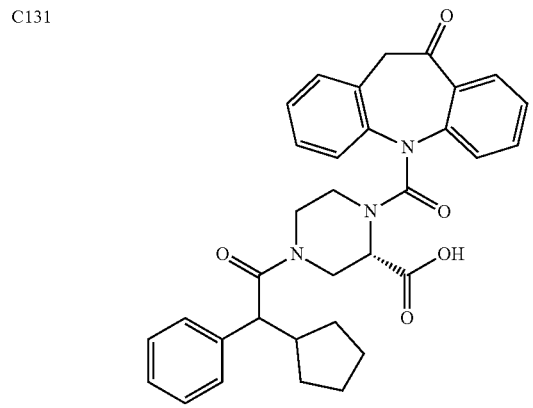 |
| C132 | 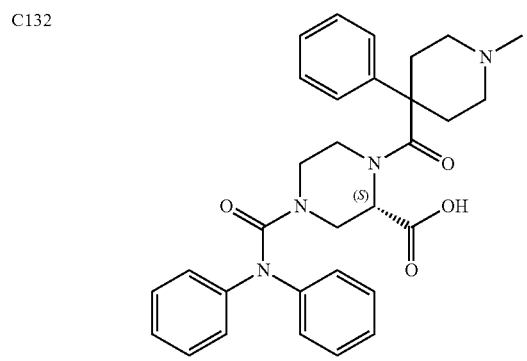 |
| C133 | 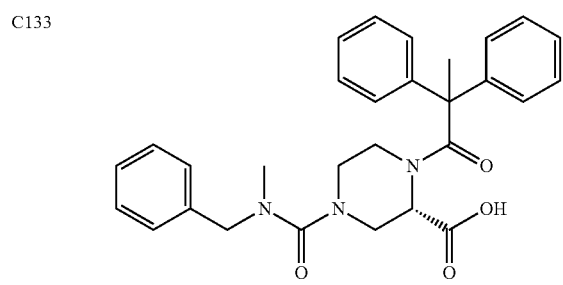 |
| C134 | 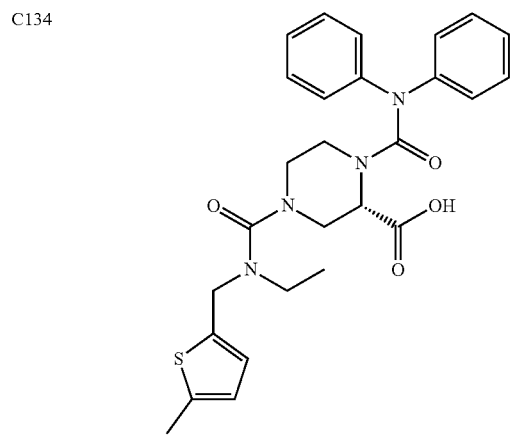 |
| C135 | 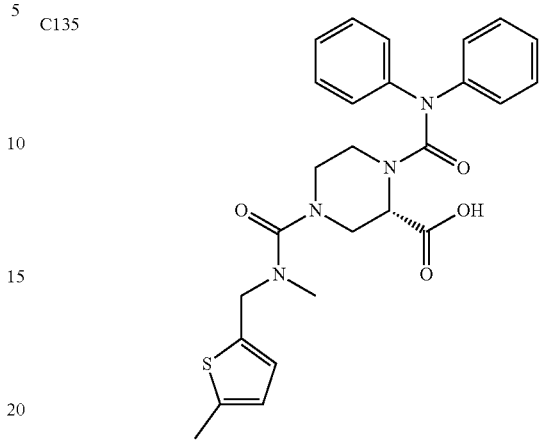 |
| C136 | 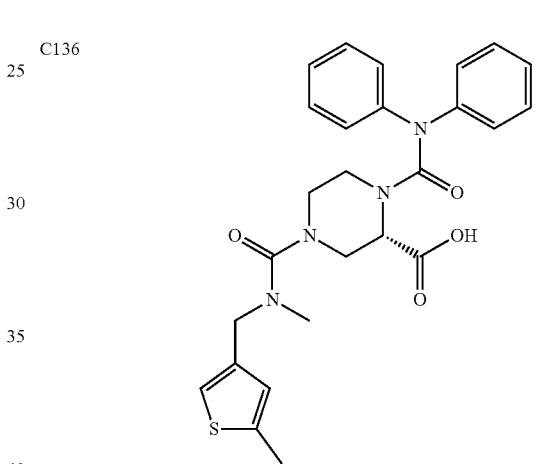 |
| C137 | 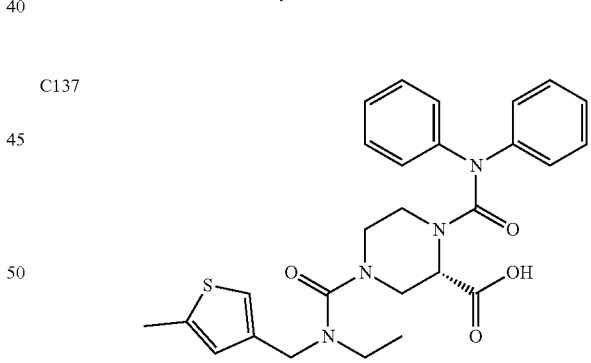 |
| C138 | 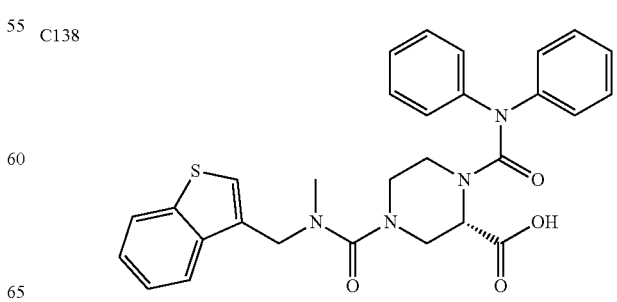 |

| No. | Structure |
|---|---|
| C139 | 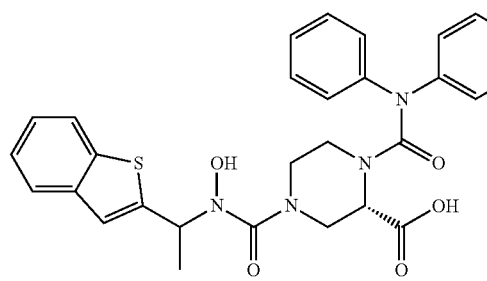 |
| C140 | 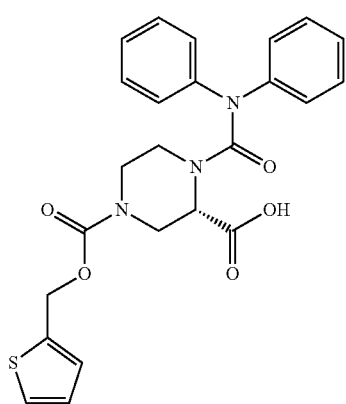 [SMILES: O=C(O)[C@@H]1CN(C(=O)OCc2cccs2)CCN1C(=O)N(c1ccccc1)c1ccccc1] |
| C141 | 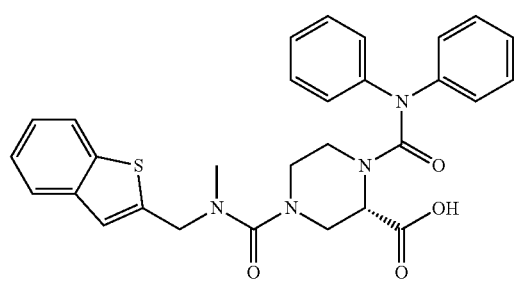 [SMILES: CN(Cc1cc2ccccc2s1)C(=O)N1CCN(C(=O)N(c2ccccc2)c2ccccc2)[C@H](C(=O)O)C1] |
| C142 | 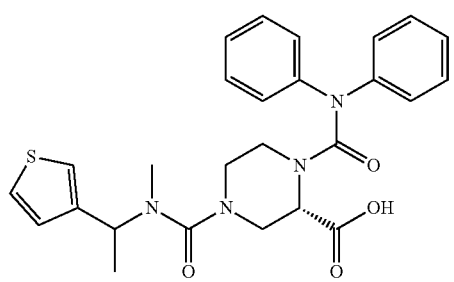 [SMILES: CC(c1ccsc1)N(C)C(=O)N1CCN(C(=O)N(c2ccccc2)c2ccccc2)[C@H](C(=O)O)C1] |
| No. | Structure |
|---|---|
| C144 | 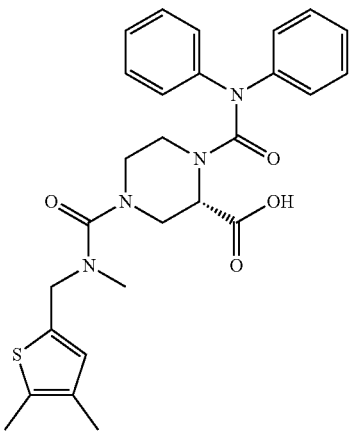 [SMILES: Cc1cc(CN(C)C(=O)N2CCN(C(=O)N(c3ccccc3)c3ccccc3)[C@H](C(=O)O)C2)sc1C] |
| C145 | 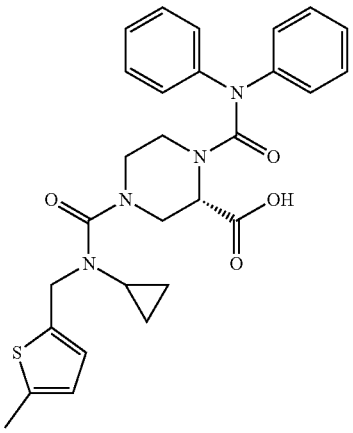 [SMILES: Cc1ccc(CN(C(=O)N2CCN(C(=O)N(c3ccccc3)c3ccccc3)[C@H](C(=O)O)C2)C2CC2)s1] |
| C146 | 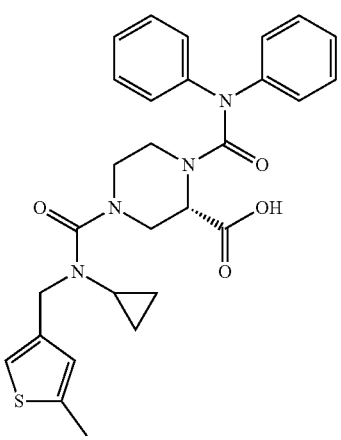 [SMILES: Cc1cc(CN(C(=O)N2CCN(C(=O)N(c3ccccc3)c3ccccc3)[C@H](C(=O)O)C2)C2CC2)cs1] |

| No. | Structure |
|---|---|
| C147 | 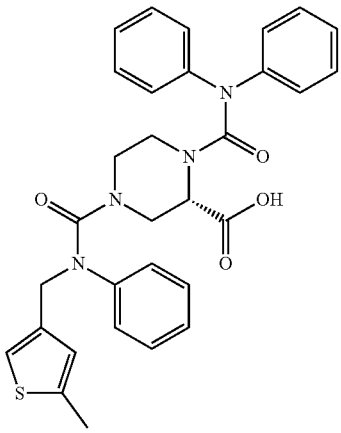 [SMILES: Cc1cc(CN(C(=O)N2CCN(C(=O)N(c3ccccc3)c3ccccc3)[C@H](C(=O)O)C2)c2ccccc2)cs1] |
| C148 | 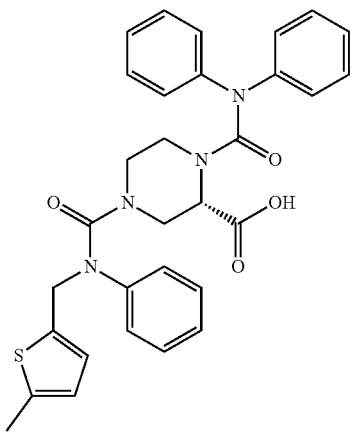 [SMILES: Cc1ccc(CN(C(=O)N2CCN(C(=O)N(c3ccccc3)c3ccccc3)[C@H](C(=O)O)C2)c2ccccc2)s1] |
| C149 | 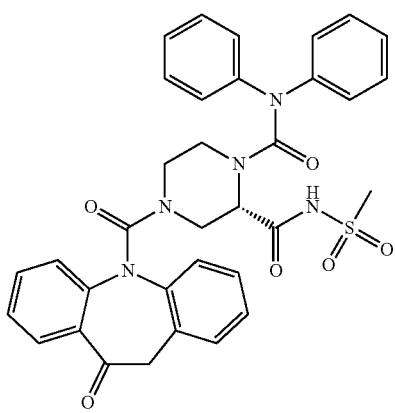 [SMILES: CS(=O)(=O)NC(=O)[C@@H]1CN(C(=O)N2c3ccccc3CC(=O)c3ccccc32)CCN1C(=O)N(c1ccccc1)c1ccccc1] |
| C150 | 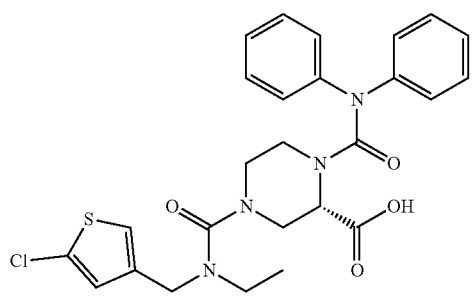 [SMILES: CCN(Cc1csc(Cl)c1)C(=O)N1CCN(C(=O)N(c2ccccc2)c2ccccc2)[C@H](C(=O)O)C1] |
| No. | Structure |
|---|---|
| C151 | 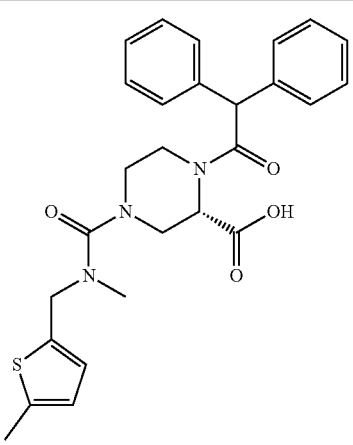 [SMILES: Cc1ccc(CN(C)C(=O)N2CCN(C(=O)C(c3ccccc3)c3ccccc3)[C@H](C(=O)O)C2)s1] |
| C152 | 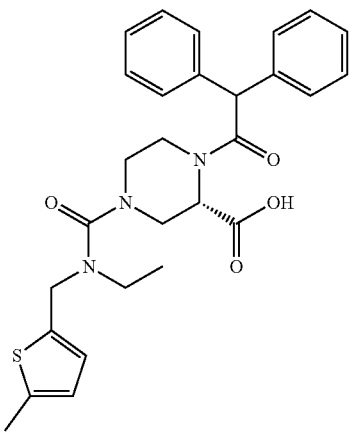 [SMILES: CCN(Cc1ccc(C)s1)C(=O)N1CCN(C(=O)C(c2ccccc2)c2ccccc2)[C@H](C(=O)O)C1] |
| C153 | 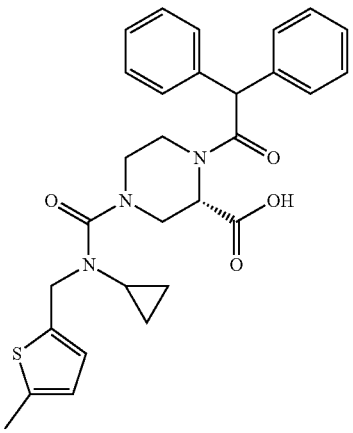 [SMILES: Cc1ccc(CN(C(=O)N2CCN(C(=O)C(c3ccccc3)c3ccccc3)[C@H](C(=O)O)C2)C2CC2)s1] |

329
-continued

| No. | Structure |
| --- | --- |
| C154 | 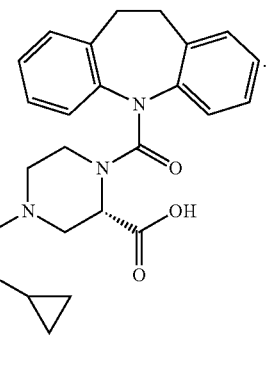 |

17. A pharmaceutical composition comprising a prophylactically or therapeutically effective amount of a compound according to claim 1 or a pharmaceutically acceptable salt, ester, stereoisomer, polymorph, solvate, N-oxide, isotopically labeled compound, or prodrug thereof, and a pharmaceutically acceptable carrier.

18. The compound according to claim 5, or a pharmaceutically acceptable salt, ester, stereoisomer, polymorph, solvate, N-oxide, isotopically labeled compound, or prodrug thereof, wherein:
said $C_{1-6}$ alkyl is selected from the group consisting of methyl, ethyl, n-propyl, isopropyl, n-butyl, isobutyl, sec-butyl, tert-butyl, n-pentyl, isopentyl, neopentyl, 1-hexyl, 1-heptyl, and 1-octyl; and/or
said $C_{2-6}$ alkenyl is selected from the group consisting of vinyl, 1-propenyl, 2-propenyl, 2-butenyl, 3-butenyl, 2-pentenyl, 3-pentenyl, 4-pentenyl, and 2-hexenyl; and/or
said $C_{2-6}$ alkynyl is selected from the group consisting of ethynyl, 1-propynyl, 2-propynyl, 2-butynyl, 3-butynyl, 2-pentynyl, 3-pentynyl, 4-pentynyl, 2-hexynyl, and 3-hexynyl; and/or
said $C_{3-7}$ cyclic hydrocarbyl group is selected from the group consisting of cyclopropyl, cyclopentyl, and cyclohexyl; and/or
said 8- to 10-membered benzo-fused heterocyclic group is selected from the group consisting of

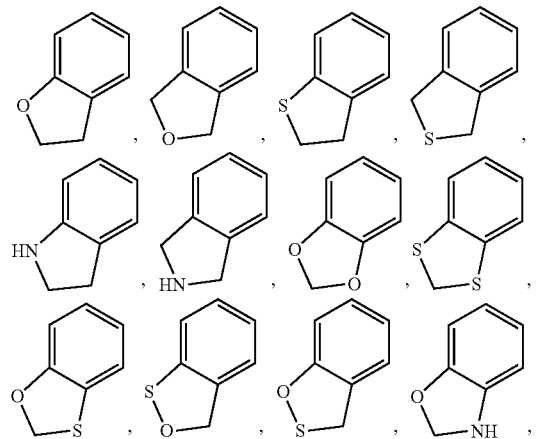

330
-continued

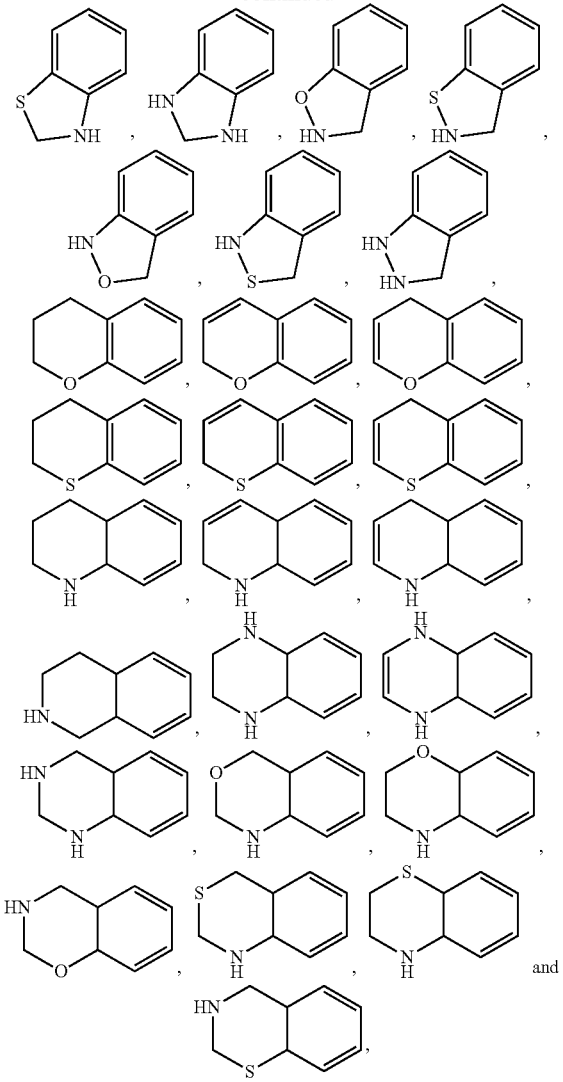

and/or
said 5- to 6-membered heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl; and/or
said —$C_{1-6}$ alkylene-$C_{6-10}$ aryl is —$C_{1-4}$ alkylene-$C_{6-10}$ aryl; and/or
said —$C_{1-6}$ alkylene-(5- to 14-membered heteroaryl) is —$C_{1-4}$ alkylene-(5- to 10-membered heteroaryl), wherein the heteroaryl is optionally selected from the group consisting of thienyl, furyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridyl, pyridazinyl, pyrimidinyl, pyrazinyl and triazinyl and their benzo derivatives.

19. The compound according to claim 18, or a pharmaceutically acceptable salt, ester, stereoisomer, polymorph, solvate, N-oxide, isotopically labeled compound, or prodrug thereof, wherein:
said 8- to 10-membered benzo-fused heterocyclic group is selected from the group consisting of

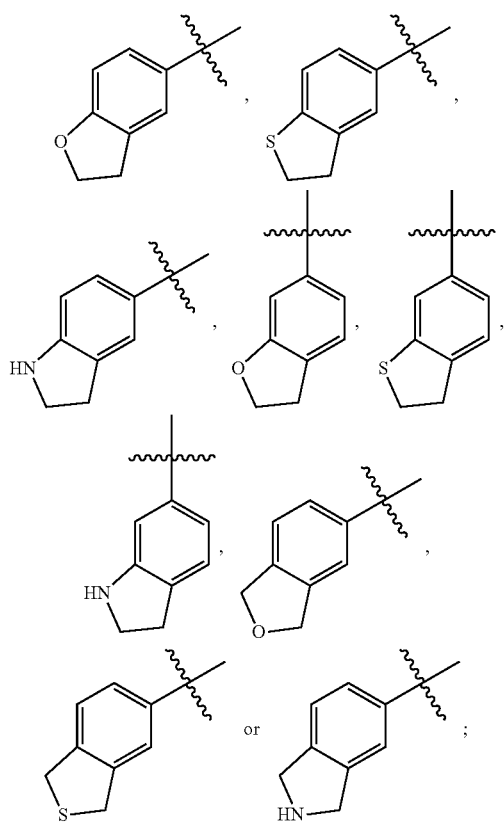

and/or
said 5- to 6-membered heteroaryl is selected from the group consisting of thienyl and furyl; and/or
said —$C_{1-4}$ alkylene-$C_{6-10}$ aryl is selected from the group consisting of phenylmethylene and phenylethylene; and/or
said —$C_{1-4}$ alkylene-(5- to 10-membered heteroaryl) is -methylene-(5- to 10-membered heteroaryl) or -ethylene-(5- to 10-membered heteroaryl), wherein the heteroaryl is optionally selected from the group consisting of thienyl, furanyl and their benzo derivatives.

20. The compound according to claim 19, or a pharmaceutically acceptable salt, ester, stereoisomer, polymorph, solvate, N-oxide, isotopically labeled compound, or prodrug thereof, wherein:
said 8- to 10-membered benzo-fused heterocyclic group is

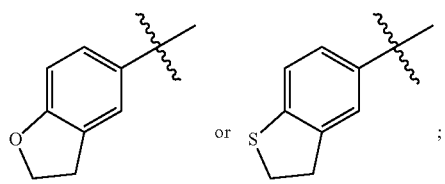 [SMILES: *c1ccc2c(c1)CCO2 ; *c1ccc2c(c1)CCS2]

and/or
said 5- to 6-membered heteroaryl is thienyl; and/or
said —$C_{1-4}$ alkylene-(5- to 10-membered heteroaryl) is -methylene-(5- to 10-membered heteroaryl) or -ethylene-(5- to 10-membered heteroaryl), wherein the heteroaryl is optionally selected from the group consisting of thienyl and the benzo derivatives thereof.

21. The compound according to claim 5, or a pharmaceutically acceptable salt, ester, stereoisomer, polymorph, solvate, N-oxide, isotopically labeled compound, or prodrug thereof, wherein $R^{1a}$ and $R^{1b}$ are each independently, or $R^{2a}$ and $R^{2b}$ are each independently selected from the group consisting of
methyl, ethyl, n-propyl, n-pentyl, cyclopropyl, cyclopentyl, cyclohexyl, phenyl,

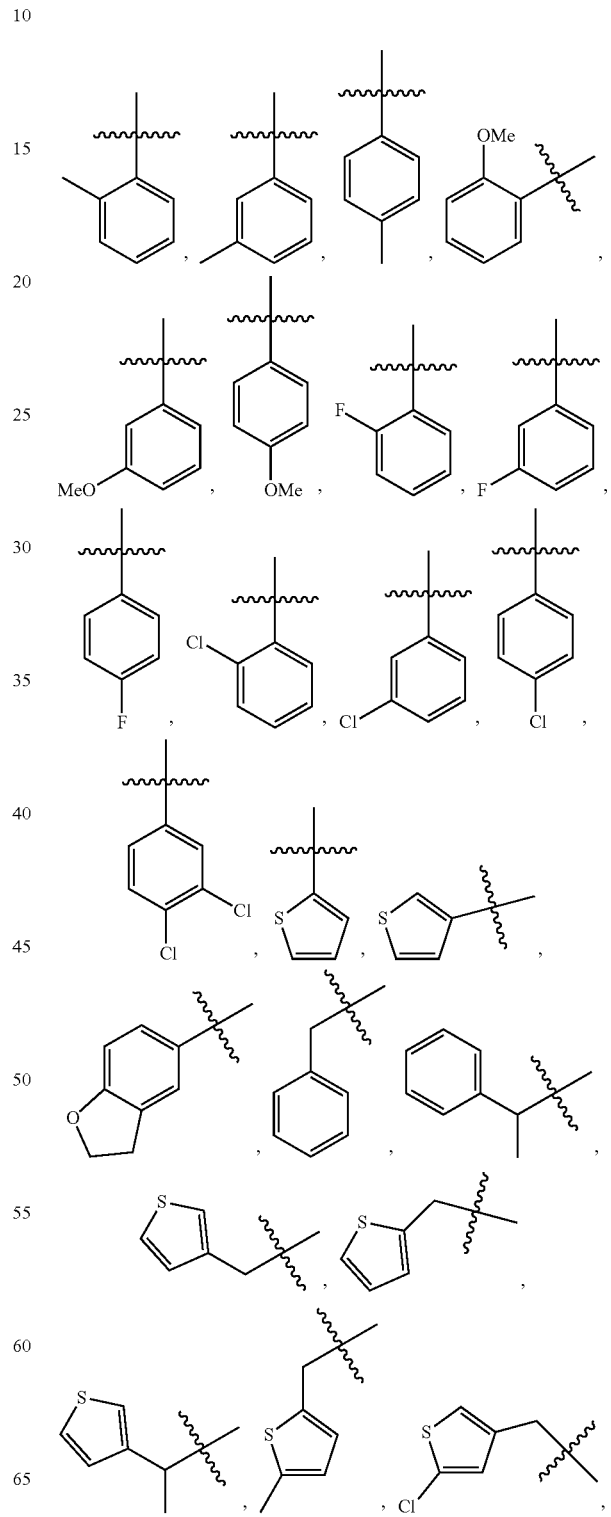

-continued

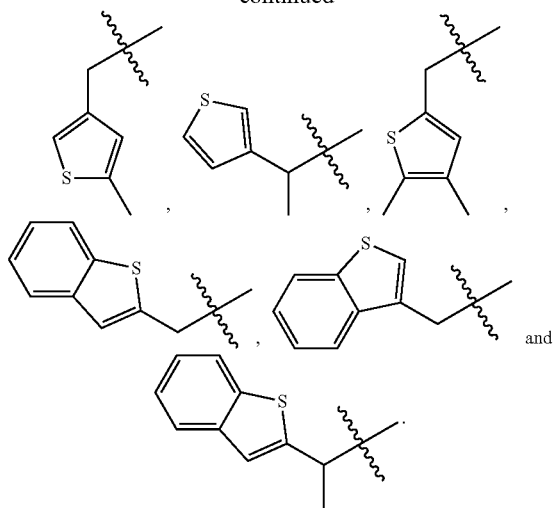
, and

22. The compound according to claim 6, or a pharmaceutically acceptable salt, ester, stereoisomer, polymorph, solvate, N-oxide, isotopically labeled compound, or prodrug thereof, wherein Y and Z, at each occurrence, are independently selected from the group consisting of a single bond; $NR^{10}$; O; S; and methylene, ethylene, $—CH_2—O—$, $—O—CH_2—$, $—CH_2—S—$, $—S—CH_2—$, $—CH_2—NR^{10}—$, $—NR^{10}—CH_2—$, $—CH=CH—$, $—CH=N—$ or $—N=CH—$, which are optionally substituted by 1, 2, 3 or more groups selected from the group consisting of halogen, OH, $—NR^{11}R^{12}$, cyano, nitro, $C_{1-6}$ alkyl, $C_{1-6}$ alkyl-O—, epoxy and oxo; and
    wherein $R^{10}$ is selected from the group consisting of H, $C_{1-6}$ alkyl, $C_{3-10}$ cyclic hydrocarbyl group, $—OR^{11}$, $—SR^{11}$, $—C(=O)OR^{11}$ and $—NR^{11}R^{12}$; and
    $R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl.

23. The compound according to claim 22, or a pharmaceutically acceptable salt, ester, stereoisomer, polymorph, solvate, N-oxide, isotopically labeled compound, or prodrug thereof, wherein the optional 1, 2, 3 or more substituting groups are selected from the group consisting of F, Cl, $C_{1-4}$ alkyl-O—, epoxy and oxo.

24. The compound according to claim 22, or a pharmaceutically acceptable salt, ester, stereoisomer, polymorph, solvate, N-oxide, isotopically labeled compound, or prodrug thereof, wherein Y and Z, at each occurrence, are each independently selected from the group consisting of $NR^{10}$; O; S; methylene and ethylene, which are optionally substituted by 1, 2, 3 or more epoxy or oxo groups; and $—CH_2—O—$, $—O—CH_2—$, $—CH_2—S—$, $—S—CH_2—$, $—CH_2—NR^{10}—$, $—NR^{10}—CH_2—$, $—CH=CH—$, $—CH=N—$ or $—N=CH—$, which are optionally substituted by 1, 2, 3 or more groups selected from the group consisting of halogen, OH, $—NR^{11}R^{12}$, cyano, nitro, $C_{1-6}$ alkyl, $C_{1-6}$ alkyl-O—, epoxy and oxo.

25. The compound according to claim 24, or a pharmaceutically acceptable salt, ester, stereoisomer, polymorph, solvate, N-oxide, isotopically labeled compound, or prodrug thereof, wherein the optional 1, 2, 3 or more substituting groups are selected from the group consisting of F, Cl, $C_{1-4}$ alkyl-O—, epoxy and oxo.

26. The compound according to claim 7, or a pharmaceutically acceptable salt, ester, stereoisomer, polymorph, solvate, N-oxide, isotopically labeled compound, or prodrug thereof, wherein the group of formula (1) and the group of formula (3) each have a structure selected from

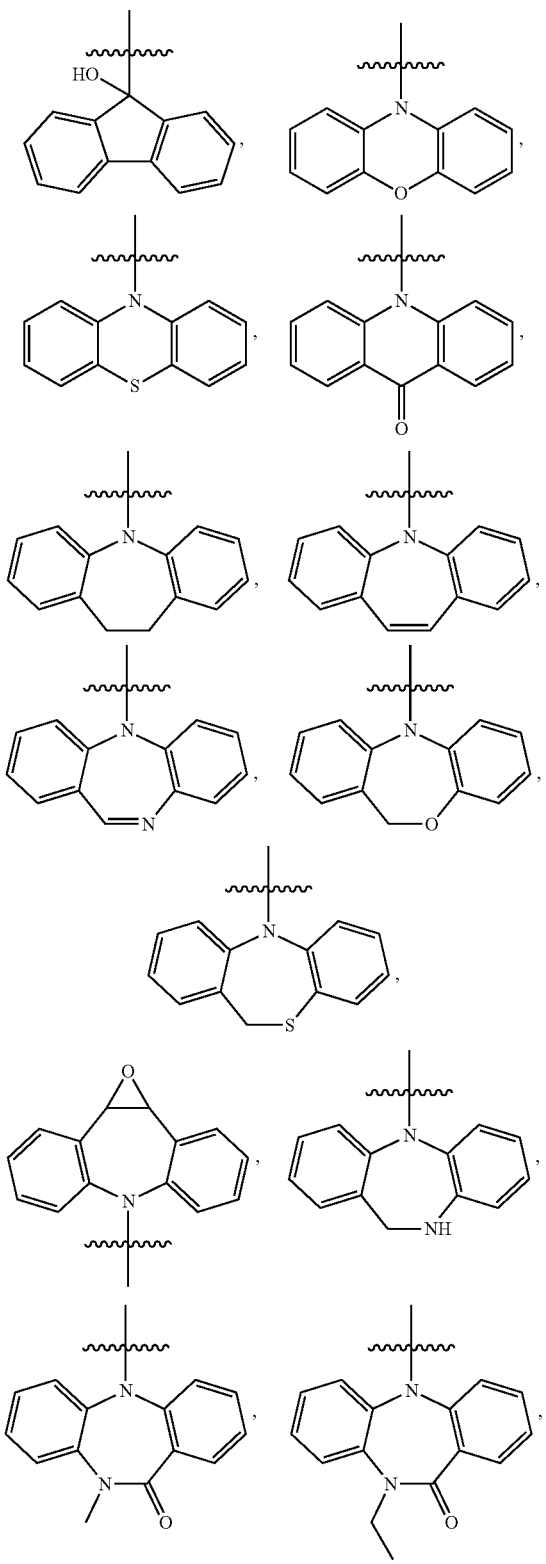

-continued

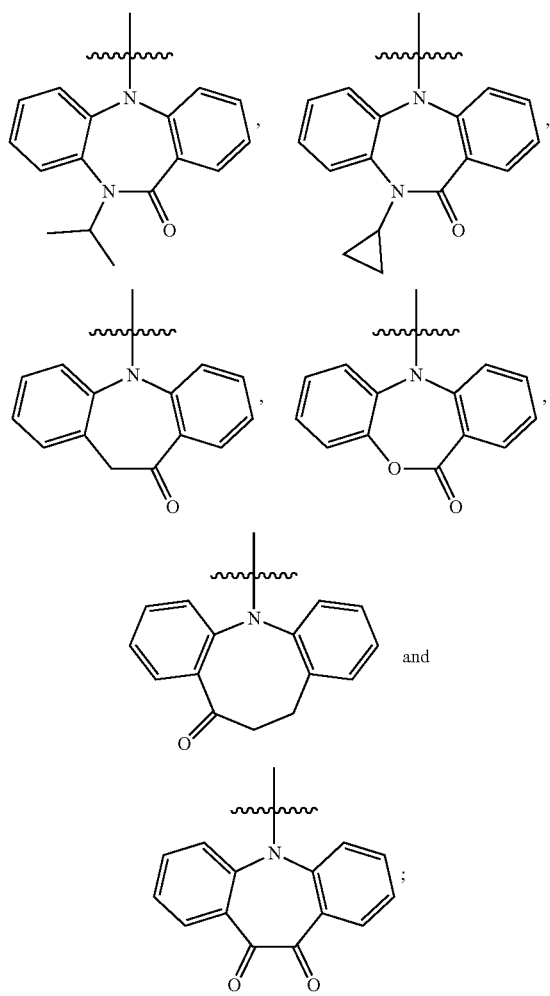

and/or
the group of formula (2) and the group of formula (4) each have a structure selected from 27. The compound according to claim 8, or a pharmaceutically acceptable salt, ester, stereoisomer, polymorph, solvate, N-oxide, isotopically labeled compound, or prodrug thereof, wherein the group with the structure of formula (5) is a group having a structure of formula (7):

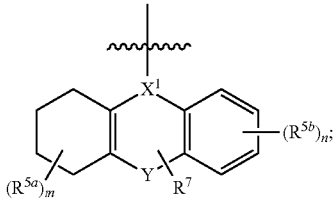

formula (7)

and/or
the group with the structure of formula (6) is a group having a structure of formula (8):

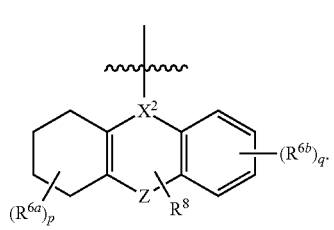

formula (8)

28. The compound according to claim 27, or a pharmaceutically acceptable salt, ester, stereoisomer, polymorph, solvate, N-oxide, isotopically labeled compound, or prodrug thereof, wherein the group of formula (7) has a structure selected from

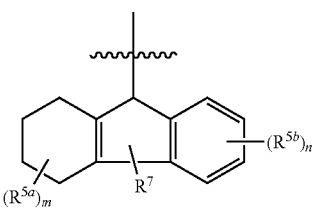

formula (7a-1)

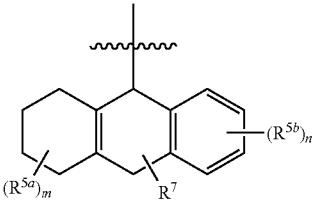

formula (7a-2)

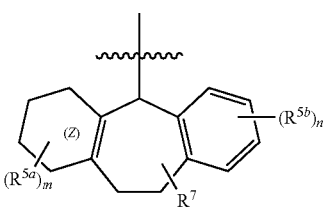

formula (7a-3)

formula (7a-4)

formula (7a-5)

formula (7a-6)

formula (7a-7)

formula (7a-8)

formula (7a-9)

formula (7a-10)

formula (7a-11)

formula (7a-12)

formula (7a-13)

formula (7a-14)

formula (7a-15)

formula (7a-16)

formula (7a-17)

formula (7a-18)
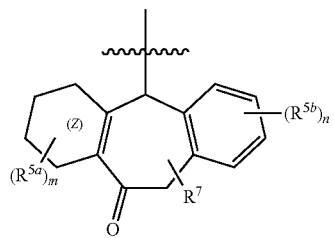
formula (7a-19)
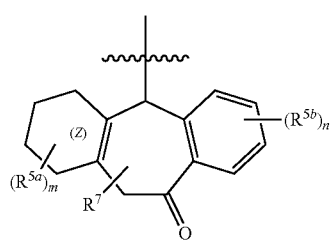
formula (7a-20)
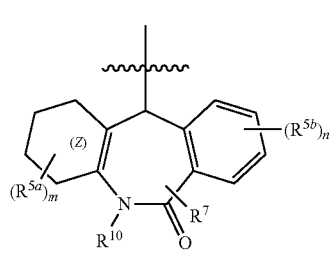
formula (7a-21)
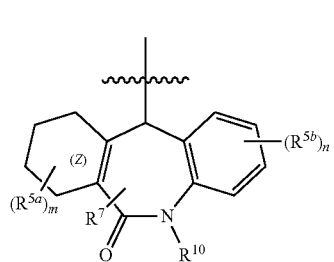
formula (7a-22)
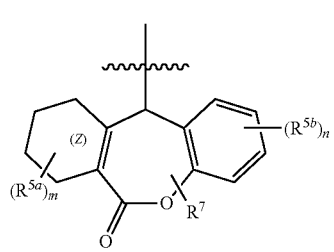
formula (7a-23)
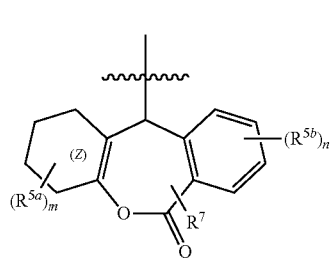
formula (7a-24)
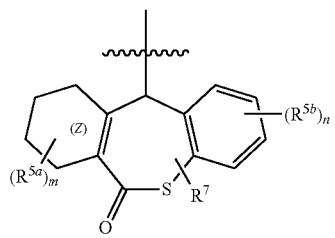
formula (7a-25)
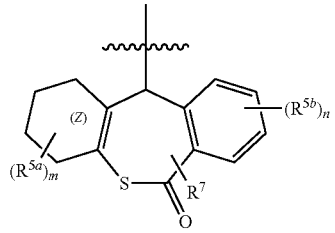
formula (7a-26)
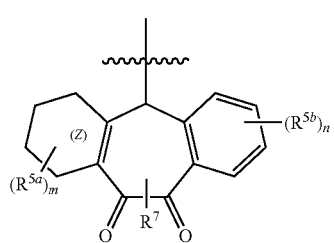
formula (7a-27)
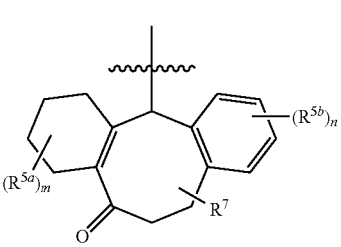
formula (7a-28)
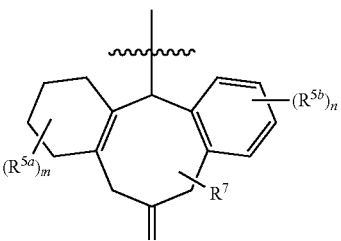
formula (7a-29)
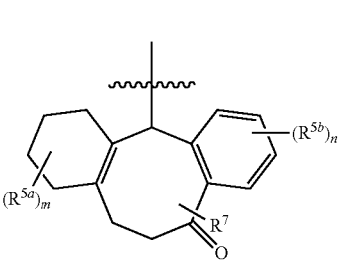

formula (7a-30)
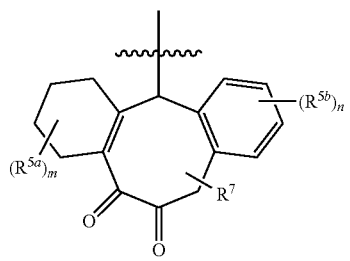
formula (7a-31)
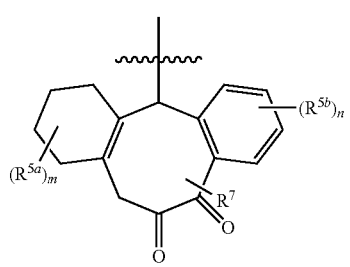
formula (7a-32)
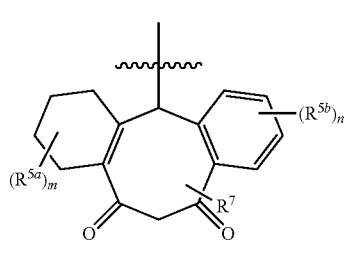
formula (7b-1)
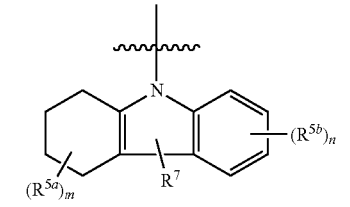
formula (7b-2)
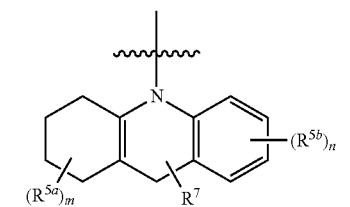
formula (7b-3)
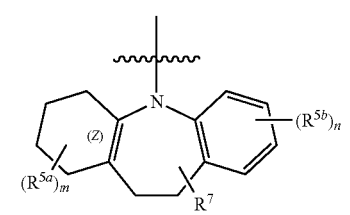
formula (7b-4)
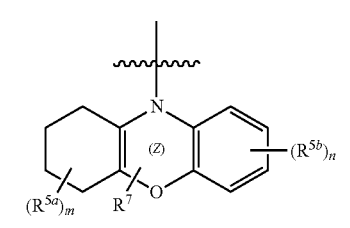
formula (7b-5)
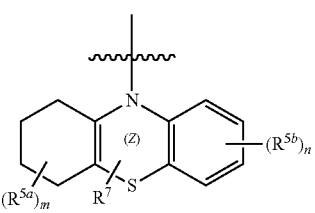
formula (7b-6)
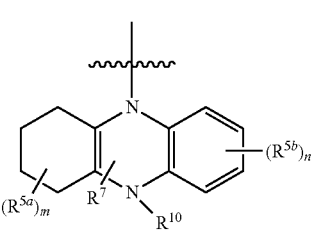
formula (7b-7)
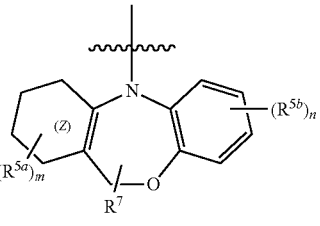
formula (7b-8)
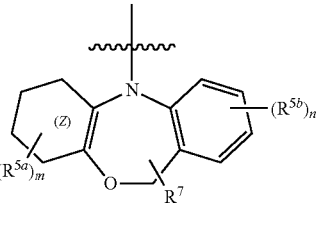
formula (7b-9)
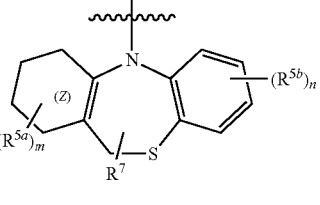
formula (7b-10)
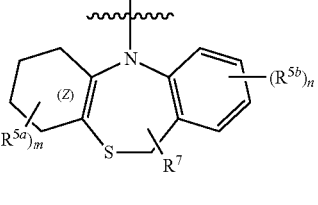
formula (7b-11)
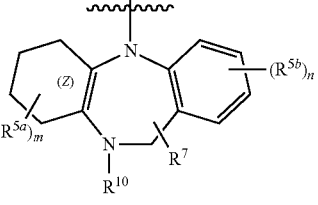

-continued
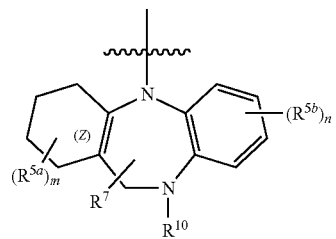
formula (7b-12)
formula (7b-13)
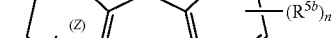
formula (7b-14)
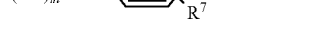
formula (7b-15)
formula (7b-16)
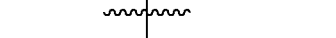
formula (7b-17)
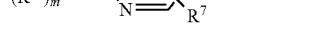
formula (7b-18)
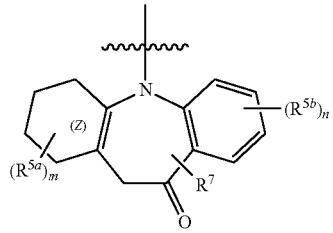
formula (7b-19)
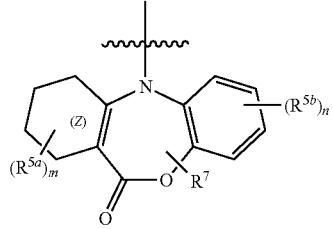
formula (7b-20)
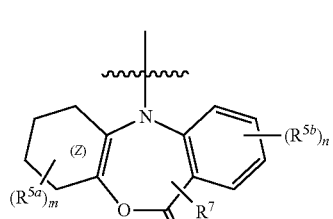
formula (7b-21)
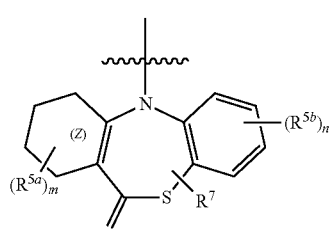
formula (7b-22)
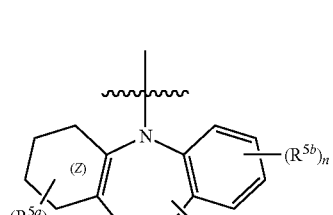
formula (7b-23)
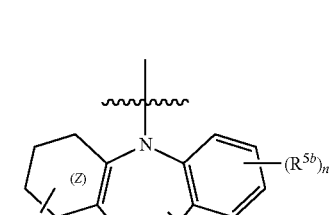
formula (7b-24)

formula (7b-25)
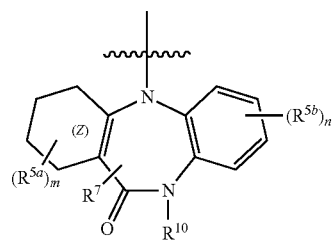
formula (7b-26)
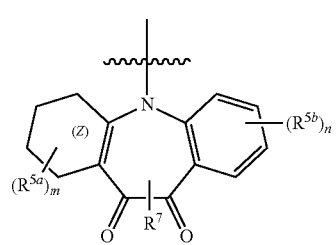
formula (7b-27)
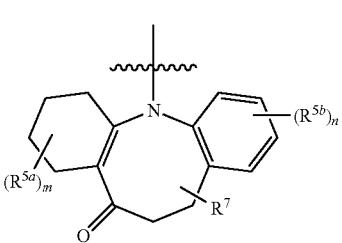
formula (7b-28)
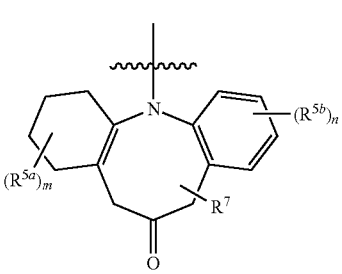
formula (7b-29)
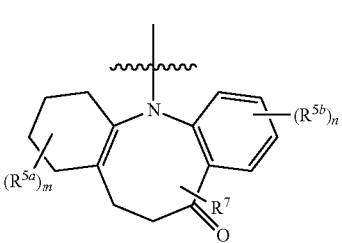
formula (7b-30)
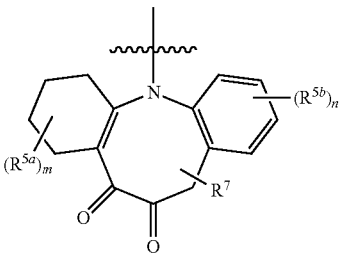
formula (7b-31)
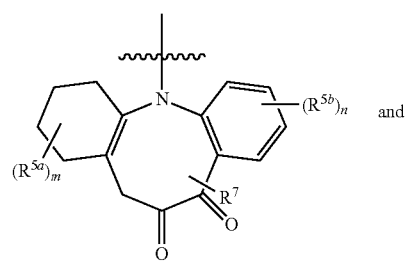 and
formula (7b-32)
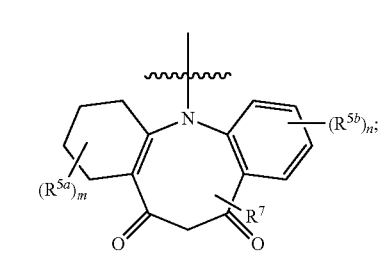;
and/or
the group of formula (8) has a structure selected from
formula (8a-1)
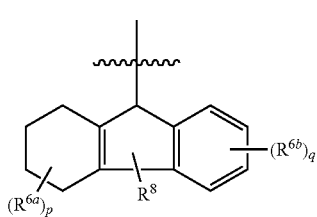
formula (8a-2)
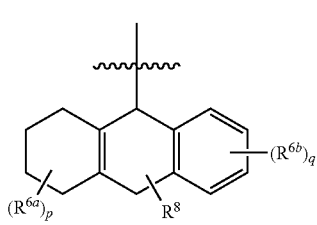
formula (8a-3)
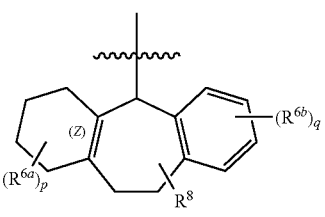
formula (8a-4)
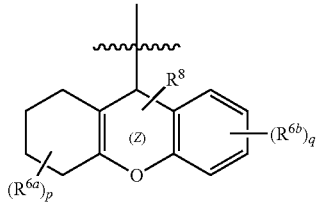

formula (8a-5)
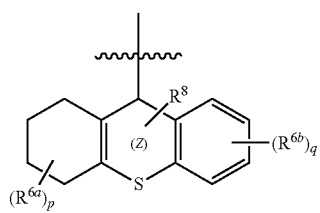
formula (8a-6)
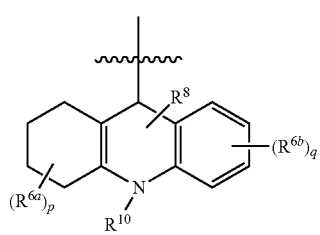
formula (8a-7)
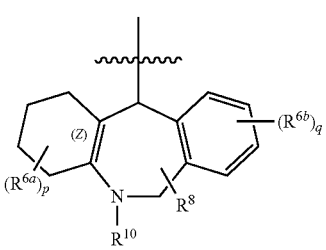
formula (8a-8)
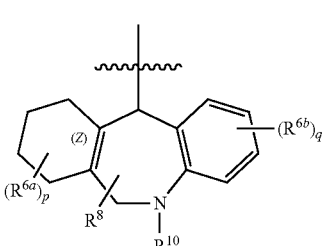
formula (8a-9)
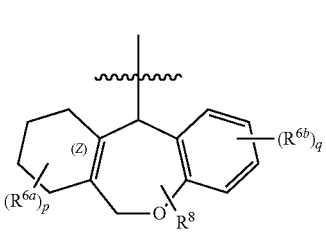
formula (8a-10)
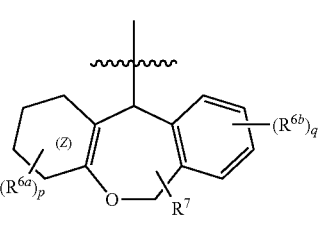
formula (8a-11)
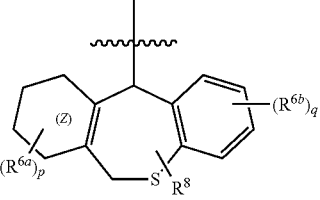
formula (8a-12)
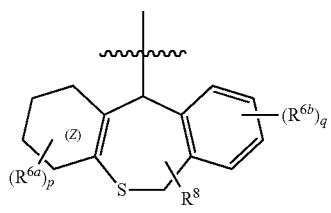
formula (8a-13)
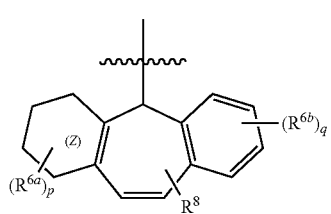
formula (8a-14)
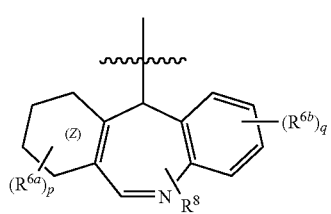
formula (8a-15)
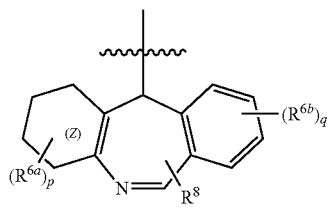
formula (8a-16)
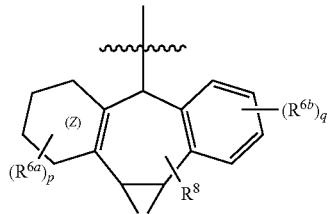
formula (8a-17)
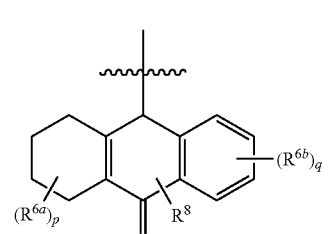
formula (8a-18)
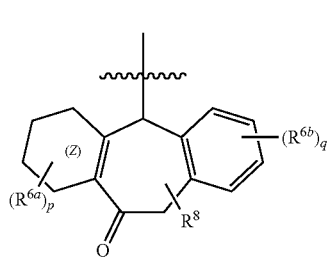

formula (8a-19)
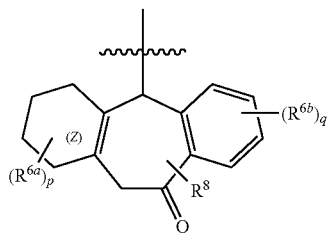
formula (8a-20)
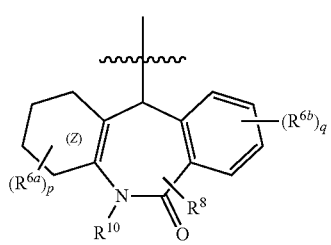
formula (8a-21)
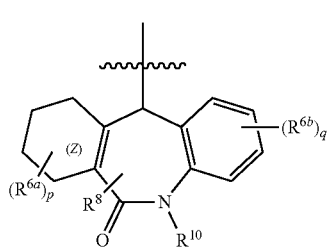
formula (8a-22)
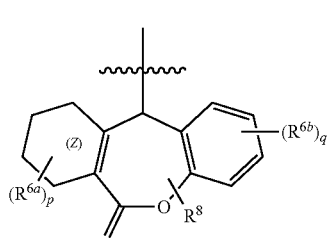
formula (8a-23)
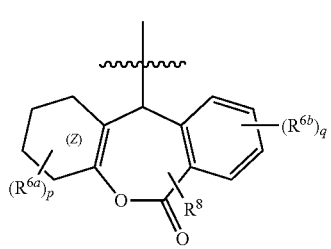
formula (8a-24)
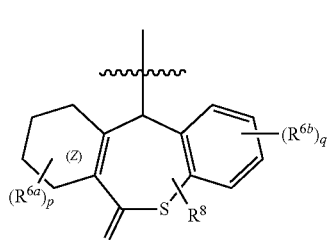
formula (8a-25)
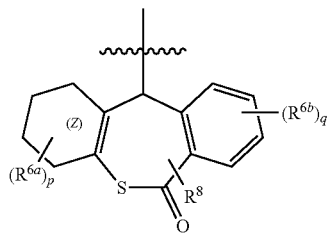
formula (8a-26)
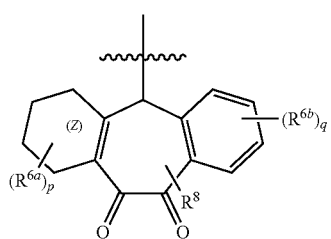
formula (8a-27)
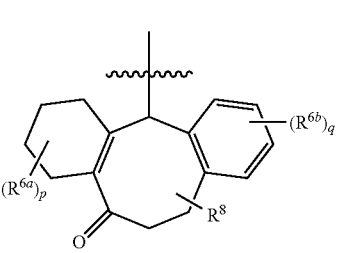
formula (8b-28)
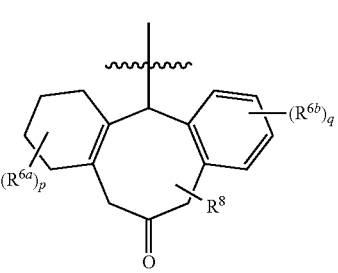
formula (8b-29)
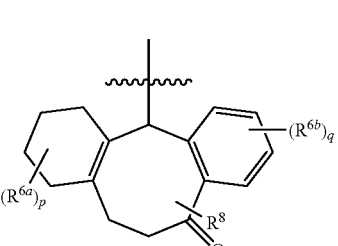
formula (8a-30)
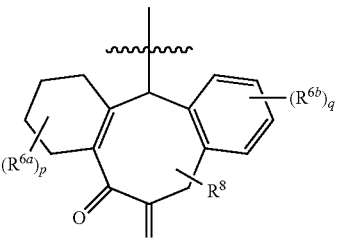

-continued
formula (8a-31)
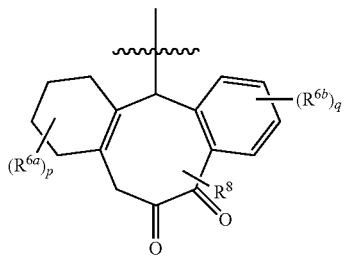
formula (8a-32)
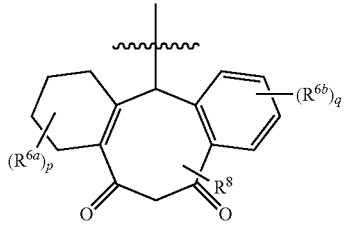
formula (8b-1)
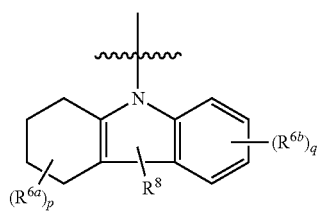
formula (8b-2)
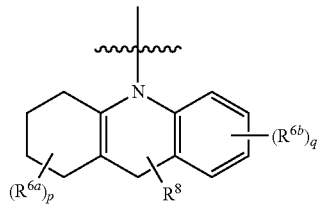
formula (8b-3)
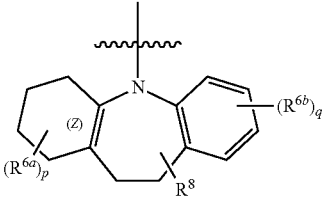
formula (8b-4)
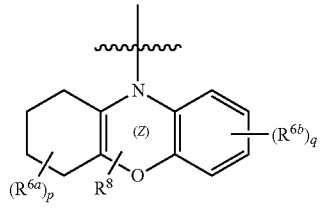
formula (8b-5)
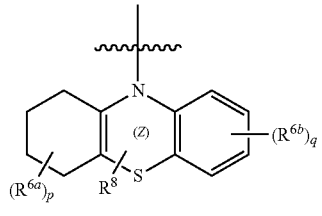
-continued
formula (8b-6)
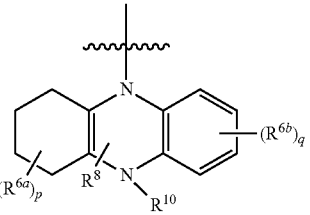
formula (8b-7)
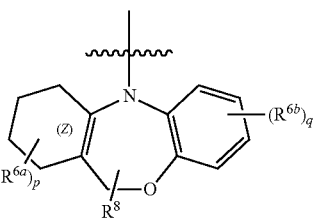
formula (8b-8)
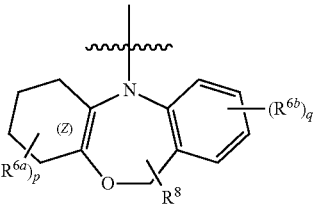
formula (8b-9)
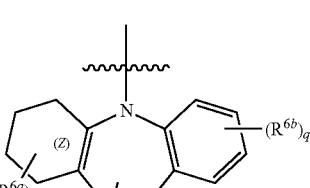
formula (8b-10)
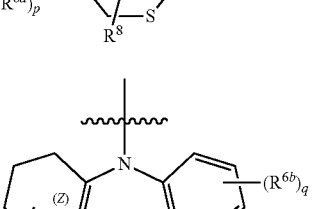
formula (8b-11)
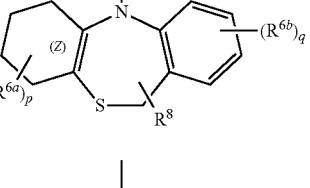
formula (8b-12)
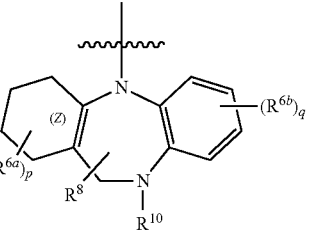

| | |
|---|---|
| formula (8b-13) 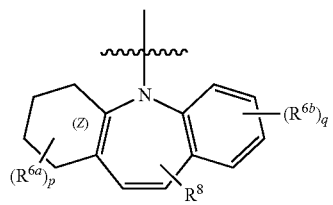 | formula (8b-20) 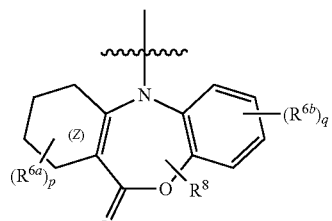 |
| formula (8b-14) 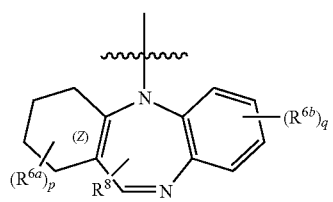 | formula (8b-21) 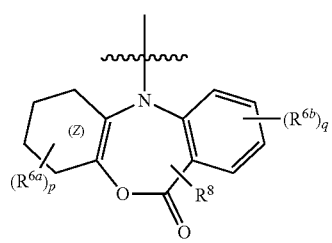 |
| formula (8b-15) 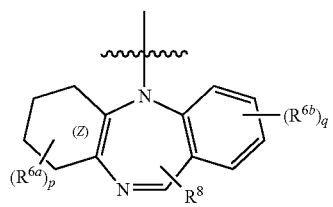 | formula (8b-22) 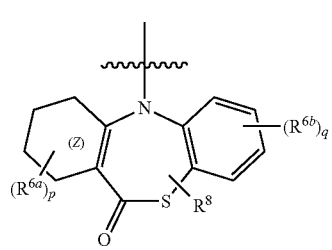 |
| formula (8b-16) 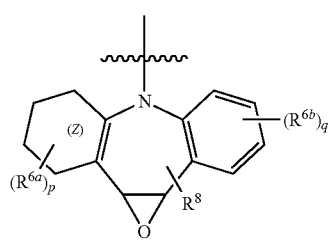 | formula (8b-23) 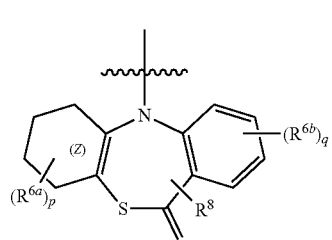 |
| formula (8b-17) 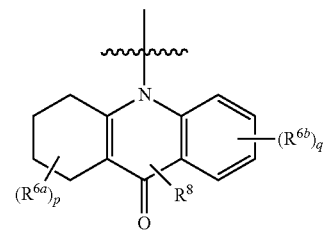 | formula (8b-24) 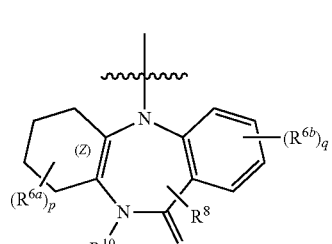 |
| formula (8b-18) 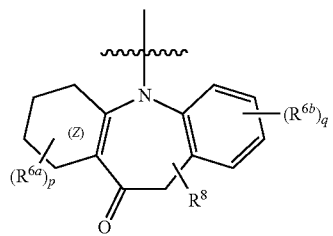 | formula (8b-25) 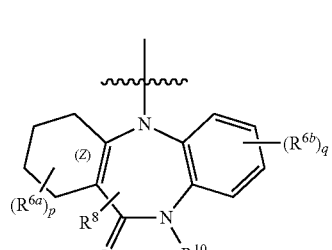 |
| formula (8b-19) 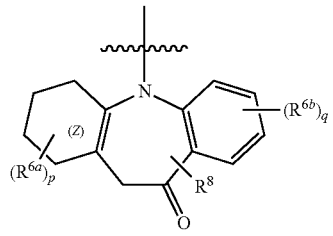 | | formula (8b-26)
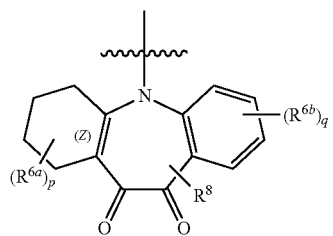

formula (8b-27)
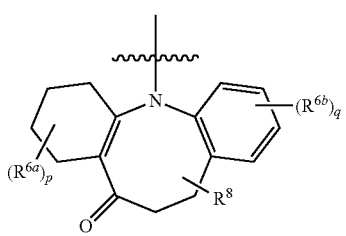

formula (8b-28)
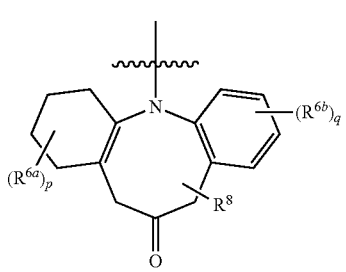

formula (8b-29)
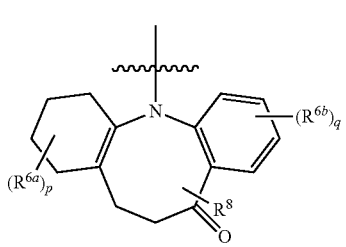

formula (8b-30)
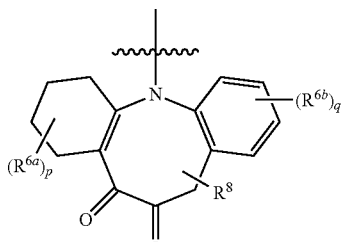

formula (8b-31)
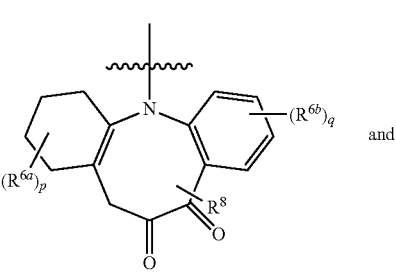
and formula (8b-32)
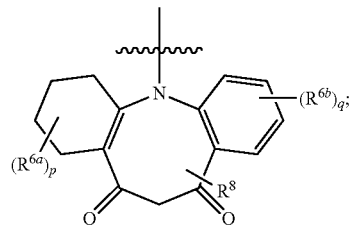;

29. The compound according to claim 27, or a pharmaceutically acceptable salt, ester, stereoisomer, polymorph, solvate, N-oxide, isotopically labeled compound, or prodrug thereof, wherein the group of formula (7) and the group of formula (8) are each

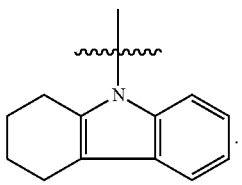 [SMILES: *n1c2c(c3ccccc31)CCCC2].

30. The compound according to claim 1, or a pharmaceutically acceptable salt, ester, stereoisomer, polymorph, solvate, N-oxide, isotopically labeled compound, or prodrug thereof, wherein the compound has a structure of formula (IIa-1)
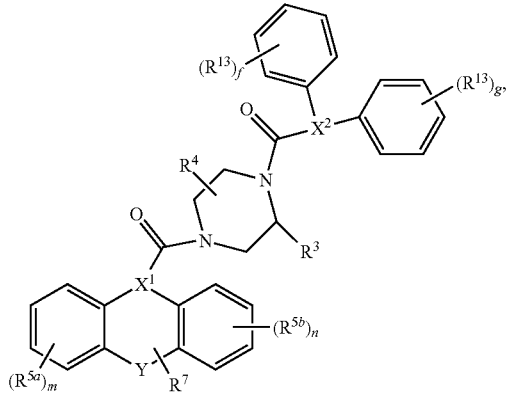

formula (IIa-2)
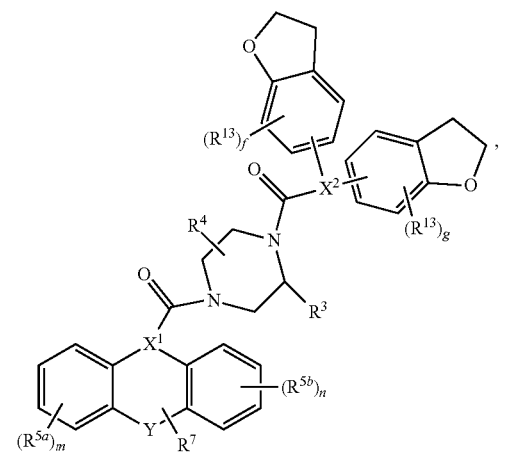, formula (IIa-3)

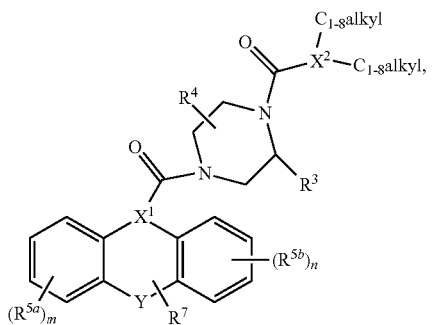

formula (IIa-4)

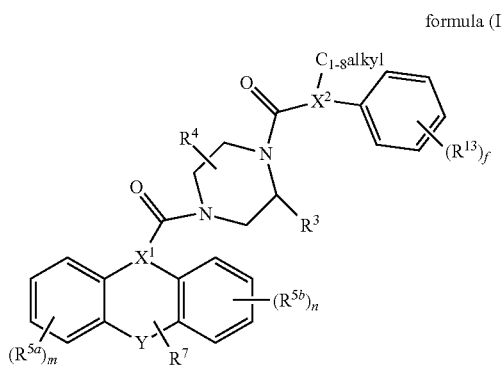

formula (IIb-1)

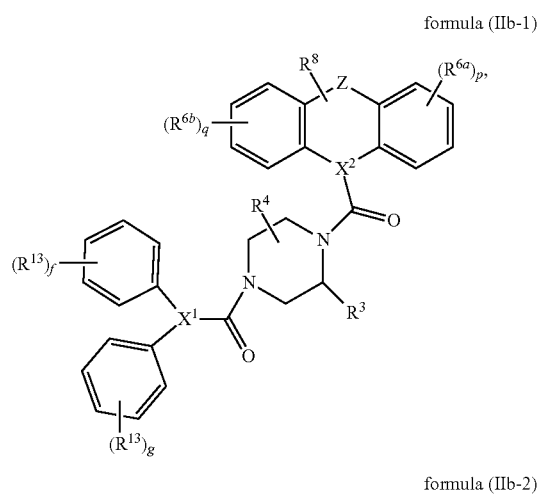

formula (IIb-2)

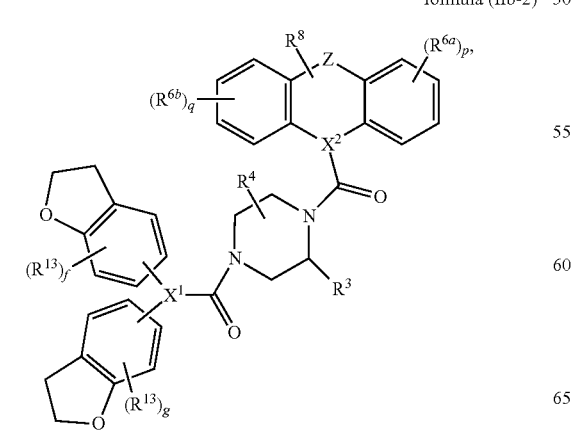

formula (IIb-3)

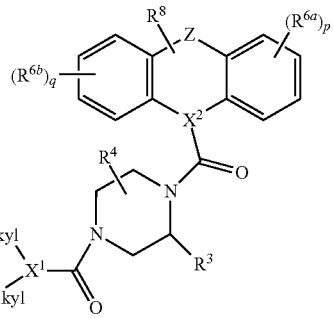

or formula (IIb-4)

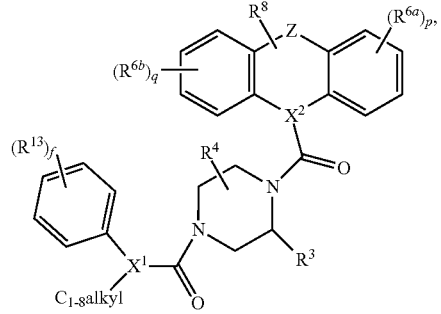

or formula (IId-1)

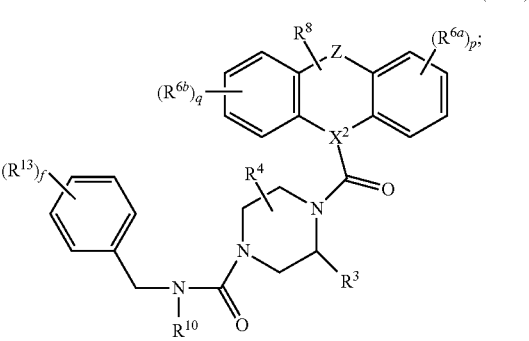

wherein f and g, at each occurrence, are each independently 0, 1, 2 or 3;

the $C_{1-8}$ alkyl, at each occurrence, is optionally substituted by 1, 2 or 3 $R^{13}$; and the above $X^1$, $X^2$, $R^3$, $R^4$, $R^{10}$, $R^{13}$, Y and Z, at each occurrence, are each independently as defined in claim 1;

wherein the above $R^{5a}$, $R^{5b}$, $R^{6a}$, and $R^{6b}$ at each occurrence, are each independently $R^{10}$;

$R^7$ and $R^8$ are each independently absent or $R^{10}$; and m, n, p and q are each independently 0, 1, 2 or 3.

31. The compound according to claim 9, or a pharmaceutically acceptable salt, ester, stereoisomer, polymorph, solvate, N-oxide, isotopically labeled compound, or prodrug thereof, wherein Y and Z, at each occurrence, are each independently selected from the group consisting of a single bond; $NR^{10}$; O; S; and methylene, ethylene, —$CH_2$—O—, —O—$CH_2$—, —$CH_2$—S—, —S—$CH_2$—, —$CH_2$—$NR^{10}$—, —$NR^{10}$—$CH_2$—, —CH═CH—, —CH═N— or —N═CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo; and wherein R[10] is selected from the group consisting of H, C$_{1-6}$ alkyl, C$_{3-10}$ cyclic hydrocarbyl group, —OR[11], —SR[11], —C(=O)OR[11] and —NR[11]R[12]; and R[11] and R[12], at each occurrence, are each independently selected from the group consisting of H, C$_{1-6}$ alkyl, C$_{3-10}$ cyclic hydrocarbyl group, 3- to 10-membered heterocyclic group, C$_{6-10}$ aryl, 5- to 14-membered heteroaryl and C$_{6-12}$ aralkyl.

32. The compound according to claim 9, or a pharmaceutically acceptable salt, ester, stereoisomer, polymorph, solvate, N-oxide, isotopically labeled compound, or prodrug thereof, wherein the optional 1, 2, 3 or more substituting groups defined for Y and Z are selected from the group consisting of F, Cl, C$_{1-4}$ alkyl-O—, epoxy and oxo.

33. The compound according to claim 10, or a pharmaceutically acceptable salt, ester, stereoisomer, polymorph, solvate, N-oxide, isotopically labeled compound, or prodrug thereof, wherein R[3] is 5-tetrazolyl, COOH,

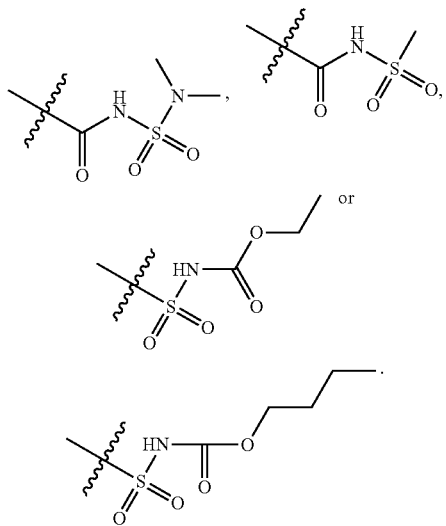

34. The compound according to claim 12, or a pharmaceutically acceptable salt, ester, stereoisomer, polymorph, solvate, N-oxide, isotopically labeled compound, or prodrug thereof, wherein R[10] is H, OH, amino, C$_{1-4}$ alkyl or C$_{3-7}$ cyclic hydrocarbyl group.

35. The compound according to claim 34, or a pharmaceutically acceptable salt, ester, stereoisomer, polymorph, solvate, N-oxide, isotopically labeled compound, or prodrug thereof, wherein R[10] is H, OH, amino, methyl, ethyl, isopropyl or cyclopropyl.

36. The compound according to claim 13, or a pharmaceutically acceptable salt, ester, stereoisomer, polymorph, solvate, N-oxide, isotopically labeled compound, or prodrug thereof, wherein R[11] and R[12], at each occurrence, are each independently selected from the group consisting of H and C$_{1-4}$ alkyl.

37. The compound according to claim 14, or a pharmaceutically acceptable salt, ester, stereoisomer, polymorph, solvate, N-oxide, isotopically labeled compound, or prodrug thereof, wherein R[13], at each occurrence, is independently selected from the group consisting of F, Cl, Br, I, amino, cyano, nitro, C$_{1-4}$ alkyl, —OR[11] and —SR[11].

38. The compound according to claim 14, or a pharmaceutically acceptable salt, ester, stereoisomer, polymorph, solvate, N-oxide, isotopically labeled compound, or prodrug thereof, wherein the alkyl, alkylene, cyclic hydrocarbyl group, heterocyclic group, phenyl and heteroaryl as defined for the substituent R[13] are optionally further substituted by 1, 2, 3 or more substitutes independently selected from the group consisting of F, Cl, OH, amino, cyano, nitro, C$_{1-4}$ alkyl and halogenated C$_{1-4}$ alkyl.

39. The compound according to claim 14, or a pharmaceutically acceptable salt, ester, stereoisomer, polymorph, solvate, N-oxide, isotopically labeled compound, or prodrug thereof, wherein R[5a], R[5b], R[6a] and R[6b] as well as R[7] and R[8] are each independently selected from the group consisting of H, OH, —OC$_{1-6}$ alkyl, amino, C$_{1-4}$ alkyl, C$_{3-7}$ cyclic hydrocarbyl group, and phenyl.

40. The compound according to claim 39, or a pharmaceutically acceptable salt, ester, stereoisomer, polymorph, solvate, N-oxide, isotopically labeled compound, or prodrug thereof, wherein R[5a], R[5b], R[6a] and R[6b] as well as R[7] and R[8] are each independently selected from the group consisting of H, OH, methoxy, ethoxy, isopropoxy, amino, methyl, ethyl, isopropyl or cyclopropyl.

41. The compound according to claim 40, or a pharmaceutically acceptable salt, ester, stereoisomer, polymorph, solvate, N-oxide, isotopically labeled compound, or prodrug thereof, wherein R[5a], R[5b], R[6a] and R[6b] as well as R[7] and R[8] are each independently selected from the group consisting of OH, methoxy, ethoxy, amino, methyl, ethyl, isopropyl or cyclopropyl.

42. The compound according to claim 8, or a pharmaceutically acceptable salt, ester, stereoisomer, polymorph, solvate, N-oxide, isotopically labeled compound, or prodrug thereof, wherein Y and Z, at each occurrence, are each independently selected from the group consisting of a single bond; NR[10]; O; S; and methylene, ethylene, —CH$_2$—O—, —O—CH$_2$—, —CH$_2$—S—, —S—CH$_2$—, —CH$_2$—NR[10]—, —NR[10]—CH$_2$—, —CH=CH—, —CH=N— or —N=CH—, which are optionally substituted by 1, 2, 3 or more groups selected from the group consisting of halogen, OH, —NR[11]R[12], cyano, nitro, C$_{1-6}$ alkyl, C$_{1-6}$ alkyl-O—, epoxy and oxo; and wherein R[10] is selected from the group consisting of H, C$_{1-6}$ alkyl, C$_{3-10}$ cyclic hydrocarbyl group, —OR[11], —SR[11], —C(=O)OR[11] and —NR[11]R[12]; and R[11] and R[12], at each occurrence, are each independently selected from the group consisting of H, C$_{1-6}$ alkyl, C$_{3-10}$ cyclic hydrocarbyl group, 3- to 10-membered heterocyclic group, C$_{6-10}$ aryl, 5- to 14-membered heteroaryl and C$_{6-12}$ aralkyl.

43. The compound according to claim 27, or a pharmaceutically acceptable salt, ester, stereoisomer, polymorph, solvate, N-oxide, isotopically labeled compound, or prodrug thereof, wherein Y and Z, at each occurrence, are each independently selected from the group consisting of a single bond; NR[10]; O; S; and methylene, ethylene, —CH$_2$—O—, —O—CH$_2$—, —CH$_2$—S—, —S—CH$_2$—, —CH$_2$—NR[10]—, —NR[10]—CH$_2$—, —CH=CH—, —CH=N— or —N=CH—, which are optionally substituted by 1, 2, 3 or more groups selected from the group consisting of F, Cl, C$_{1-4}$ alkyl-O—, epoxy and oxo; and wherein R[10] is selected from the group consisting of H, C$_{1-6}$ alkyl, C$_{3-10}$ cyclic hydrocarbyl group, —OR[11], —SR[11], —C(=O)OR[11] and —NR[11]R[12]; and R[11] and R[12], at each occurrence, are each independently selected from the group consisting of H, C$_{1-6}$ alkyl, C$_{3-10}$ cyclic hydrocarbyl group, 3- to 10-membered heterocyclic group, C$_{6-10}$ aryl, 5- to 14-membered heteroaryl and C$_{6-12}$ aralkyl.

44. The compound according to claim 30, or a pharmaceutically acceptable salt, ester, stereoisomer, polymorph, solvate, N-oxide, isotopically labeled compound, or prodrug thereof, wherein Y and Z, at each occurrence, are each independently selected from the group consisting of $NR^{10}$; O; S; methylene and ethylene, which are optionally substituted by 1, 2, 3 or more epoxy or oxo groups; and —$CH_2$—O—, —O—$CH_2$—, —$CH_2$—S—, —S—$CH_2$—, —$CH_2$—$NR^{10}$—, —$NR^{10}$—$CH_2$—, —CH=CH—, —CH=N— or —N=CH—, which are optionally substituted by 1, 2, 3 or more groups selected from the group consisting of halogen, OH, —$NR^{11}R^{12}$, cyano, nitro, $C_{1-6}$ alkyl, $C_{1-6}$ alkyl-O—, epoxy and oxo; and wherein $R^{10}$ is selected from the group consisting of H, $C_{1-6}$ alkyl, $C_{3-10}$ cyclic hydrocarbyl group, —$OR^{11}$, —$SR^{11}$, —C(=O)$OR^{11}$ and —$NR^{11}R^{12}$; and $R^{11}$ and $R^{12}$, at each occurrence, are each independently selected from the group consisting of H, $C_{1-6}$ alkyl, $C_{3-10}$ cyclic hydrocarbyl group, 3- to 10-membered heterocyclic group, $C_{6-10}$ aryl, 5- to 14-membered heteroaryl and $C_{6-12}$ aralkyl.

\* \* \* \* \*